US005874236A

United States Patent [19]
Harpold et al.

[11] Patent Number: 5,874,236
[45] Date of Patent: *Feb. 23, 1999

[54] DNA ENCODING HUMAN CALCIUM CHANNEL $\alpha_{-1A}$, $\beta_1$, $\beta_{-2}$, AND $\beta_{-4}$ SUBUNITS, AND ASSAYS USING CELLS THAT EXPRESS THE SUBUNITS

[75] Inventors: Michael M. Harpold, El Cajon; Steven B. Ellis, San Diego; Mark E. Williams, Carlsbad, all of Calif.; Daniel H. Feldman, Gainesville, Fla.; Ann F. McCue, La Mesa, Calif.; Robert Brenner, Austin, Tex.

[73] Assignee: Sibia Neurosciences. Inc., La Jolla, Calif.

[*] Notice: The portion of the term of this patent subsequent to Feb. 7, 2014, has been disclaimed.

[21] Appl. No.: 149,097

[22] Filed: Nov. 5, 1993

Related U.S. Application Data

[63] Continuation-in-part of Ser. No. 105,536, Aug. 11, 1993, which is a continuation-in-part of PCT/US92/06903, filed Aug. 14, 1992, Ser. No. 482,384, Feb. 20, 1990, Pat. No. 5,386,025, and Ser. No. 914,231, Jul. 13, 1992, Pat. No. 5,407,820, which is a continuation of Ser. No. 603,751, Nov. 8, 1990, abandoned, said Ser. No. 105,536, is a continuation-in-part of Ser. No. 868,354, Apr. 10, 1992, abandoned, which is a continuation-in-part of Ser. No. 745,206, Aug. 15, 1991, Pat. No. 5,429,921, which is a continuation-in-part of Ser. No. 620,250, Nov. 30, 1990, abandoned, which is a continuation-in-part of Ser. No. 176,899, filed as PCT/US89/01408, Apr. 4, 1989, abandoned.

[51] Int. Cl.$^6$ .............................. C12N 15/12; C12Q 1/02; C07K 14/705
[52] U.S. Cl. ..................... 435/29; 536/23.5; 435/69.1; 435/325; 435/254.11; 435/4; 514/44
[58] Field of Search ....................... 536/23.5; 435/240.2, 435/69.1, 4, 29, 325, 252.3, 254.11; 514/44

[56] References Cited

U.S. PATENT DOCUMENTS

| | | | |
|---|---|---|---|
| 4,788,135 | 11/1988 | Davis et al. | 435/6 |
| 4,912,202 | 3/1990 | Campbell et al. | 530/388.22 |
| 4,954,436 | 9/1990 | Froehner et al. | 424/1.49 |
| 5,024,939 | 6/1991 | Gorman | 435/69.1 |
| 5,051,403 | 9/1991 | Mijanich et al. | 514/12 |
| 5,189,020 | 2/1993 | Mijanich et al. | 514/12 |
| 5,264,371 | 11/1993 | Mijanich et al. | 436/503 |
| 5,424,218 | 6/1995 | Mijanich et al. | 436/503 |

FOREIGN PATENT DOCUMENTS

| | | |
|---|---|---|
| 2085502 | 8/1993 | Canada . |
| 0507170 A2 | 3/1992 | European Pat. Off. . |
| 0556651 A2 | 4/1993 | European Pat. Off. . |
| 4222126 | 8/1993 | Germany . |
| 8907608 | 8/1989 | WIPO . |
| 8909834 | 10/1989 | WIPO . |
| 9113077 | 9/1991 | WIPO . |
| 9202639 | 2/1992 | WIPO . |
| 9308469 | 4/1993 | WIPO . |
| 93/14098 | 7/1993 | WIPO . |
| 9402511 | 2/1994 | WIPO . |
| 9504144 | 2/1995 | WIPO . |

OTHER PUBLICATIONS

Powers, et al., "Assignment of the human gene for the $\alpha_1$ subunit of the cardiac DHP–sensitive $Ca^{2+}$ channel (CCHL1A1) to Chromosome 12p12–pter," *Genomics*, 10: 835–839 (1991).

Kim, et al., "IgG from patients with Lambert–Eaton syndrome blocks voltage–dependent calcium channels," *Science*, 239: 405–408 (1988).

Claudio, et al., "Genetic reconstitution of functional acetylcholine receptor channels in mouse fibroblasts," *Science*, 238: 1688–1694 (1987).

Tanabe, et al., "Primary structure of the receptor for calcium channel blockers from skeletal muscle," *Nature*, 328:313–318 (1987).

Nakayama, et al., "Purification of a putative $Ca^{2+}$ channel protein from rabbit skeletal muscle," *J.Biol.Chem.*, 262:6572–6576 (1987).

Vaghy, et al., "Identification of a novel 1,4–dihydropyridine– and phenylalkylamine–binding polypeptide in calcium channel preparations," *J.Biol.Chem.*, 262(29): 14337–14342 (1987).

Leung, et al., "Structural characterization of the 1,4–dihydropyridine receptor of the voltage–dependent $Ca^{2+}$ channel from rabbit skeletal muscle," *J.Biol.Chem.*, 262(17): 7943–7946 (1987).

Sharp, et al., "Identification and characterization of the dihydropyridine–binding subunit of the skeletal muscle dihydropyridine receptor," *J.Biol.Chem.*, 62(25): 12309–12315 (1987).

Takahashi, et al., "Subunit structure of dihydropyridine–sensitive calcium channels from skeletal muscle," *Proc.Natl.Acad.Sci. (USA)*, 84: 5478–5482 (1987).

Morton et al. "Monoclonal antibody identifies a 200–kDA subunit of the dihydropyridine–sensitive calcium channel," *J.Biol.Chem.*, 262(25): 11904–11907 (1987).

Barhanin, et al., "The calcium channel antagonists receptor from rabbit skeletal muscle: reconstitution after purification and subunit characterization," *Eur.J.Biochem.*, 164: 525–531 (1987).

Sieber, et al., "The 165–kDa peptide of the purified skeletal muscle dihydropyridine receptor contains the known regulatory sites of the calcium channel," *Eur.J.Biochem.*, 167: 117–122 (1987).

Lang, et al., "The effect of myasthenic syndrome antibody on presynaptic calcium channels in the mouse," *J.Physiol.*, 390: 257–270 (1987).

(List continued on next page.)

*Primary Examiner*—David L. Fitzgerald
*Attorney, Agent, or Firm*—Stephanie L. Seidman; Brown, Martin, Haller & McClain

[57] ABSTRACT

Isolated DNA encoding each of human calcium channel $\alpha_1$-, $\alpha_2$-, $\beta$-and $\gamma$-subunits, including subunits that arise as splice variants of primary transcripts, is provided. Cells and vectors containing the DNA and methods for identifying compounds that modulate the activity of human calcium channels are also provided.

37 Claims, No Drawings

OTHER PUBLICATIONS

Curran and Morgan, "Barium modules c–fos expression and post–translational modification," *Proc.Natl.Acad.Sci.,* 83: 3521–8524 (1986).

Fisch, et al., "c–fos sequences necessary for basal expression and induction by epidermal growth factor, 12–O–tetradecanoyl phorbol–13–acetate, and the calcium inophore," *Mol.Cell.Biol.,* 7(10): 3490–3502 (1987).

Noda, et al., "Existence of distinct sodium channel messenger RNAs in rat brain," *Nature,* 320: 188–192 (1986).

Noda, et al., "Expression of functional sodium channels from cloned cDNA," *Nature,* 322: 826–828 (1986).

Mierendorf, et al., "Gene isolation by screening kgtll libraries with antibodies," *Methods in Enz.,* 152: 458–469 (1986).

Gustin, et al., "Ion channels in yeast," *Science,* 233: 1195–1197 (1986).

Striessnig, et al., "Photoaffinity labelling of the phenylalkylamine receptor of the skeletal muscle transverse–tubule calcium channel," *FEBS Letters,* 212(2):247–253 (1987).

Froehner, "New insights into the molecular structure of the dihydropyridine–sensitive calcium channel," *TINS,* 11(3): 90–92 (1988).

Catterall, et al., "Molecular properties of dihydropyridine–sensitive calcium channels in skeletal muscle," *J.Biol.Chem.,* 263(8): 3535–3538 (1988).

Curtis, et al., "Purification fo the calcium antagonist receptor of the voltage–sensitive calcium channel from skeletal muscle transverse tubules," *Biochemistry,* 23(10): 2113–2118 (1984).

Borsotto, et al., "The 1,4–dihydropyridine receptor associated with the skeletal muscle voltage–dependent $Ca^{2+}$ channel," *J.Biol.Chem.,* 260(26): 14255–14263 (1985).

Cooper, et al., "Purification and characterization of the dihydropyridine–sensitive voltage–dependent calcium channel from cardiac tissue," *J.Biol.Chem.,* 262(2): 509–512 (1987).

Wood, "Gene cloning based on long oligonucleotide probes," *Methods in Enzymology,* 152: 443–447 (1987).

Schmid, et al., "Immunochemical analysis of subunit structure of 1,4–dihydropyridine receptors associated with voltage–dependent $Ca^{2+}$ channels in skeletal, cardiac, and smooth muscles," *Biochemistry,* 25:3492–3495 (1986).

Mishina, et al., "Location of functional regions of acetylcholine receptor α–subunit by site–directed mutagenesis," *Nature,* 313: 364–369 (1985).

Hamill, et al., "Improved patch–clamp techniques for high–resolution current recording from cells and cell–free membrane patches," *Pfluger Archiv.European Journal of Physiology,* 391: 85–100 (1981).

Hess, et al., "Different modes of Ca channel gating behavior favored by dihydropyridine Ca agonist and antagonists," *Nature,* 311: 538–544 (1984).

Leung, et al., "Biochemical and ultrastructural characterization of the 1,4–dihydropyridine receptor from rabbit skeletal muscle," *J. of Biol.Chem.,* 263(2): 994–1001 (1988).

Imagawa, et al., "Phosphorylation of the 1,4–dihydropyridine receptor of the voltage–dependent $Ca^{2+}$ channel by an intrinsic protein kinase in isolated triads from rabbit skeletal muscle," *J. of Biol.Chem.,* 262(17): 8333–8339 (1987).

Miller, "Multiple calcium channels and neuronal function," *Science,* 235: 46–52 (1987).

Kozak, "An analysis of 5'–noncoding sequences from 699 vertebrate messenger RNAs," *Nucleic Acids Research,* 15(20): 8125–8148 (1987).

Von Heijne, "Signal sequences: the limits of variation," *Jour. of Mol.Biol.,* 184: 99–105 (1985).

Hubbard, et al., "Synthesis and processing of asparagine–linked oligosaccharides$^{1,2}$," *Ann.Rev.Biochem.,* 50:555–583 (1981).

Feramisco, et al., "Optimal spatial requirements for the location of basic residues in peptide substrates for the cyclic AMP–dependent protein kinase," *Journal of Biological Chemistry,* 255(9): 4240–4245 (1980).

Takahashi, et al., "Identification of an α subunit of dihydropyridine–sensitive brain calcium channels," *Science,* 236: 88–91 (1987).

Hofmann, et al., "Regulation of the L–type calcium channel," *TINS,* 8: 393–398 (1987).

Curtis, et al., "Reconstitution of the voltage–sensitive calcium channel purified from skeletal muscle transverse tubules," *Biochemistry,* 25: 3077–3083 (1986).

Smith, et al., "Calcium channel activity in a purified dihydropyridine–receptor preparation of skeletal muscle," *Biochemistry,* 26: 7182–7188 (1987).

Meshi, et al., "Nucleotide sequence of the 30K protein cistron of cowpea strain of tobacco mosaic virus," *Nucleic Acids Research,* 10(19): 6111–6117 (1982).

Nikaido, et al., "Molecular cloning of cDNA encoding human interleukin–2 receptor," *Nature,* 311: 631–636 (1984).

Roberts, et al., "Paraneoplastic myasthenic syndrome IgG inhibits $^{45}Ca^{2+}$ flux in a human small cell carcinoma line," *Nature,* 317: 737–739 (1985).

Starr, et al., "Primary structure of a calcium channel that is highly expressed in rat cerebellum, " *Proc.Natl.Acad.Sci. USA,* 88: 5621–5625 (1991).

Snutch, et al., "Distinct calcium channels are generated by alternative splicing and are differentially expressed in the mammalian CNS," *Neuron,* 7: 45–57 (1991).

Hui, et al., "Molecular cloning of multiple sybtypes of a novel rat brain isoform of the $a_1$ subunit of the voltage–dependent calcium channel," *Neuron,* 7: 35–44 (1991).

Bean et al., "Classes of calcium channels in vertebrate cells," *Annu.Rev. Physiol.,* 51: 367–384 (1989).

Swandulla, et al., "Do calcium channel classifications account for neuronal calcium channel diversity?" *TINS,* 14(2): 46–51 (1991).

Ruth, et al., "Primary structure of the α subunit of the DHP–sensitive calcium channel from skeletal muscle," *Science,* 245: 1115–1118 (1989).

Mikami, et al., "Primary structure and functional expression of the cardiac dihydropyridine–sensitive calcium channel," *Nature,* 340: 230–233 (1989).

Biel, et al., "Primary structure and functional expression of a high voltage activiated calcium channel from rabbit lung," *FEBS Letters,* 269(2): 409–412 (1990).

Mori, et al., "Primary structure and functional expression from complementary DNA of a brain calcium channel," *Nature,* 350: 398–402 (1991).

Snutch, et al., "Rat brain expresses a heterogeneous family of calcium channels," *Proc.Natl.Acad.Sci. USA,* 87: 3391–3395 (1990).

Perez–Reyes, et al., "Molecular diversity of L–type calcium channels," *J. of Biol.Chem.,* 265(33): 20430–20436 (1990).

Perez–Reyes, et al., "Induction of calcium currents by the expression of the $α_1$–subunit of the dihydropyridine receptor from skeletal muscle," *Nature,* 340: 233–236 (1989).

Koch, et al., "Characterization of cDNA clones encoding two putative isoforms of the $\alpha_1$–subunit of the dihydropyridine–sensitive voltage–dependent calcium channel isolated from rat brain and rat aorta," *FEBS Letters,* 250(2): 386–388 (1989).

Slish, et al., "Evidence for the existence of a cardiac specific isoform of the $\alpha_1$–subunit of the voltage dependent calcium channel," *FEBS Letters,* 250(2): 509–514 (1989).

Varadi, et al., "Development regulation of expression of the $\alpha_1$ and $\alpha_2$ subunits mRNAs of the voltage–dependent calcium channel in a differentiating myogenic cell line," *FEBS Letters,* 250(2)CE: 515–518 (1989).

Jongh, et al., "Subunits of purified calcium channels: a 212–kDa form of $\alpha_1$ and partial amino acid sequence of a phosphorylation site of an independent $\beta$–subunit," *Proc.Natl.Acad.Sci. USA,* 86: 8585–8589 (1989).

Hamilton, et al., "Subunit composition of the purified dihydropyridine binding protein from skeletal muscle," *Biochemistry,* 28: 7820–7828 (1989).

Nunoki, et al., "Activation of purified calcium channels by stoichiometric protein phosphorylation," *Proc.Natl.Acad.Sci. USA,* 86: 6816–6820 (1989).

Ichida, et al., "Photoaffinity labeling with dihydropyridine derivatives of crude membranes from rat skeletal, cardiac, ileal, and uterine muscles and whole brain," *J.Biochem.,* 105: 767–774 (1989).

Sharp and Campbell, "Characterization of the 1,4–dihydropyridine receptor using subunit–specific polyclonal antibodies," *J.Biol.Chem.,* 264(5): 2816–2825 (1989).

Campbell, et al., "The biochemistry and molecular biology of the dihydropyridine–sensitive calcium channel," *TINS,* 11(10): 425–430 (1988).

Pelzer, et al., "Properties and regulation of calcium channels in muscle cells," *Rev.Physiol.Biochem.Pharmacol.,* 114: 107–207 (1990).

Kim, et al., "Studies on the structural requirements for the activity of the skeletal muscle dihydropyridine receptor/ slow $Ca^{2+}$ channel," *J.Biol.Chem.,* 11858–11863 (1990).

Lotan, et al., "Specific block of calcium channel expression by a fragment of dihydropyridine receptor cDNA," *Science,* 243: 666–669 (1989).

Rampe, et al., "[$^3$H]Pn200–110 binding in a fibroblast cell line transformed with the $\alpha_1$ subunit of the skeletal muscle L–type $Ca^{2+}$ channel," *Biochem. and Biophys.Research Communications,* 169(3): 825–831 (1990).

Adams, et al., "Intramembrane charge movement restored in dysgenic skeletal muscle by injection of dihydropyridine receptor cDNAs," *Nature,* 346: 569–572 (1990).

Tanabe, et al., "Cardiac–type excitation–contraction coupling in dysgenic skeletal muscle injected with cardiac dihydropyridine receptor cDNA," *Nature,* 344: 451–453 (1990).

Tanabe, et al., "Regions of the skeletal muscle dihydropyridine receptor critical for excitation–contraction coupling," *Nature,* 346: 567–569 (1991).

Regulla, et al., "Identification of the site of interaction of the dihydropyridine channel blockers nitrendipine and azidopine with the calcium–channel $\alpha_1$ subunit," *EMBO Journal,* 10(1): 45–49 (1991).

Williams, et al., "Structure and functional expression of $\alpha_1$, $\alpha_2$ and $\beta$ subunits of a novel human neuronal calcium channel subtype," *Neuron,* 8:71–84 (1992).

Olivera, et al., "Conotoxins," *J. of Biol.Chem.,* 266(33): 22067–22070 (1991).

Seino, et al., "Cloning of $\alpha_1$ subunit of a voltage–dependent calcium channel expressed in pancreatic $\beta$ cells," *Proc.Natl.Acad.Sci. USA,* 89: 584–588 (1992).

Perez–Reyes, et al., "Cloning and expression of a cardiac/ brain $\beta$ subunit of the L–type calcium channel," *J. of Biol.Chem.,* 267(3): 1792–1797 (1992).

Miller, R., "Voltage–sensitive $Ca^{2+}$ channels," *J. of Biol.Chem.,* 267(3): 1403–1406 (1992).

Artalejo, et al., "w–Conotoxin GVIA blocks a $Ca^{2+}$ current in bovine chromaffin cells that is not of the 'classic' N type," *Neuron,* 8: 85–95 (1992).

Kasai, H., "Tonic inhibition and rebound facilitation of a neuronal calcium channel by a GTP–binding protein," *Proc.Natl.Acad.Sci. USA,* 88: 8855–8859 (1991).

Sher, et al., "Voltage–operated calcium channels in small cell lung carcinoma cell lines: pharmacological, functional, and immunological properties," *Cancer Research,* 5: 3892–3896 (1990).

Sher, et al., "w–Conotoxin binding and effects on calcium channel function in human neuroblastoma and rat pheochromocytoma cell lines," *FEBS Letters,* 235: (1,2): 178–182 (1988).

Koch, et al., "cDNA cloning of a dihydropyridine–sensitive calcium channel from rat aorta," *J. of Biol.Chem.,* 265(29): 17786–17791 (1990).

Cohen, et al., "Distribution of $Ca^{2+}$ channels on frog motor nerve terminals revealed by fluorescent w–conotoxin," *J. of Neuroscience,* 11(4): 1032–1039 (1991).

Bosse, et al., "The cDNA and deduced amino acid sequence of the $\gamma$ subunit of the L–type calcium channel from rabbit skeletal muscle," *FEBS,* 267(1): 153–156 (1990).

Burns, et al., "Calcium channel activity of purified human synexin and structure of the human synexin gene," *Proc.Natl.Acad.Sci.,* 86: 3798–3802 (1989).

Campbell, et al., "32,000–Dalton subunit of the 1,4–dihydropyridine receptor," *Ann.N.Y.Acad.Sci.,* 560: 251–257 (1989).

Dascal, N., "The use of Xenopus oocytes for the study of ion channels," *CRC Critical Rev.Biochem.,* 22(4): 317–387 (1987).

DeJongh, et al., "Subunits of purified calcium channels," *J.Biol.Chem.,* 265(25): 14738–14741 (1990) (best available copy submitted).

Jay, et al., "Primary Structure of the $\gamma$ subunit of the DHP–sensitive calcium channel from skeletal muscle," *Science,* 248: 490–492 (1990).

Jay, et al., "Structural characterization of the dihydropyridine–sensitive calcium channel $\alpha_2$–subunit and the associated $\delta$ peptides," *J.Biol.Chem.,* 266(5): 3287–3293 (1991).

Leung, et al., "Monoclonal antibody characterization of the 1,4–dihydropyridine receptor of rabbit skeletal muscle," *Ann.N.Y.Acad.Sci.,* 522: 43–46 (1988).

Starr, et al., "Primary structure of a calcium channel that is highly expressed in the rat cerebellum," *Proc.Natl.Acad.Sci.,* 88: 5621–5625 (1991).

Vaghy, et al., "Mechanism of action of calcium channel modulator drugs," *Ann.N.Y.Acad.Sci.,* 522: 176–186 (1988).

Ahlijanian, et al., "Subunit structure and localization of dihydropyridine–sensitive calcium channels in mammalian brain, spinal cord, and retina," *Neuron,* 4: 819–832 (1990).

Blount, et al., "Assembly intermediates of the mouse muscle nicotinic Acetylcholine receptor in stably transfected fibroblasts," *J.Cell.Biol.,* 111: 2601 (1990).

Carbone, et al.,"Ca currents in human neuroblastoma IMR32 cells: kinetics, permeability and pharmacology," *Pfluegers Arch.* 416: 170–179 (1990) (best available copy submitted).

Dascal, et al., "Expression of modulation of voltage–gated calcium channels after RNA injection in Xenopus oocytes," *Science,* 231: 1147–1150 (1986).

Hess, et al., "Calcium channels in vertebrate cells," *Ann.Rev.Neurosci.,* 13: 337–356 (1990).

Stanley, et al., "Characterization of a calcium current in a vertebrate cholinergic presynaptic nerve terminal," *J. Neurosci.,* 11: 985 (1991).

Wei, et al., "Heterologous regulation of the cardiac $Ca^{2+}$ channel $\alpha_1$ subunit by skeletal muscle $\beta$ and $\gamma$ subunits," *J.Biol.Chem.,* 266: 21943–21947 (1991).

Ahlijanian, et al., "Phosphorylation of an $\alpha 1$–like subunit of an w–conotoxin–sensitive brain calcium channel by cAMP–dependent protein kinase and protein kinase C," *J.Biol.Chem.,* 266: 20192 (1991).

Claudio, T., "Stable expression of transfected Torpedo acetylcholine receptor $\alpha$ subunits in mouse fibroblast L cells," *Proc.Natl.Acad.Sci.,* 84: 5967–5971 (1987).

Hullin, et al., "Calcium channel $\beta$ subunit heterogeneity: functional expression of cloned cDNA from heart, aorta and brain," *EMBO J.,* 11: 885 (1992).

Kim, et al., "Rat brain expresses an alternatively spliced form of the dihydropyridine–sensitive L–type calcium channel $\alpha 2$ subunit," *Proc.Natl.Acad.Sci.,* 89:3251 (1992).

Pragnell, et al., "Cloning and tissue–specific expression of the brain calcium channel $\beta$–subunit," *FEBS Letters,* 291: 253 (1991).

Sakamoto, et al., "A monoclonal antibody to the $\beta$ subunit of the skeletal muscle dihydropyridine receptor immunoprecipitates the brain w–conotoxin GVIA receptor," *J.Biol.Chem.,* 266: 18914 (1991).

Seagar, et al., "Molecular properties of dehydropyrine–sensitive calcium channels," *Ann.N.Y.Acad.Sci.,* 552: 162–175 (1988).

Tsien, et al., "Molecular diversity of voltage–dependent $Ca^{2+}$ channels, " *Trends in Pharmacol.Sci.,* 12: 349 (1991).

Takahashi and Catterall, "Dihydropyridine–sensitive calcium channels in cardiac and skeletal muscle membranes: studies with antibodies against the $\alpha$–subunits," *Biochemistry,* 26(17): 1518–1526 (1987).

Cruz et al., "Characterization of w–Conotoxin Target. Evidence for Tissue–Specific Heterogeneity ion Calcium Channel Types", *Biochem. J.* 26:820 (1987).

Breitbart et al.,, "Alternatvie Splicing: A Ubiquitous Mechanism for the Generation of Multiple Protein Isoforms From Single Genes", *Ann. Rev. Biochem. 56*:467–495.

Williams et al. , "Structure and Functional Expression of an w–Conotoxin–Sensitive Human N–Type Calcium Channel", *Science 257*:389–395 (1992).

Rosenfield et al. , "Cloning and Characterization of a Lambert–Eaton Myasthenic Syndrome Antigen", *Annals of Neurology 33*:113–120 (1993).

Powers et al., "Skeletal Muscle and Brain Isoforms of a $\beta$–Subunit of Human Voltage–dependent Calcium Channels Are Encoded by a Single Gene", *J. Biol. Chem. 267*:22967–22972 (1992).

Wah et al. ,"Structure and Functional Expression of a Member of the Low–Voltage–Activated Calcium channel Family", *Science 260*:1133–1136.

Horne et al., "Molecular diversity of $Ca^{2+}$ channel $\alpha_1$ subunits from the marine ray *Discopyge ommata*", *Proc.Natl.Acad.Sci. 90*:3787–3791 (1993).

Yu et al., "Molecular characterization and nephron distribution of a family of transcripts encoding the pore–forming subunit of $Ca^{2+}$ channels in the kidney", *Proc.Natl.Acad.Sci. 89*:10494–10498 (1992).

Dubel et al., "Molecular cloning of the $\alpha$–1 subunit of an w–conotoxin–sensitive calcium channel", *Proc.Natl.Acad.Sci. 89*:5058–5062 (1992).

Soldatov, "Molecular diversity of L–type $Ca^{2+}$ channel transcripts in human fibroblasts", *Proc.Natl.Acad.Sci. 89*:4628–4632 (1992).

Leveque et al., "The synaptic vesicle protein synaptotagmim associates with calcium channels and is a putative Lambert–Eaton myasthenic syndrome antigen", *Proc.Natl.Acad.Sci. 89*:3625–3629 (1992).

Niidome et al., "Molecular cloning and characterization of a novel calcium channel from rabbit brain", *FEBS LTTRS 308*:7–13 (1992).

Elinor et al., "Functional expression of a rapidly inactivating neuronal calcium channel", *Nature 363*:455–458 (1993).

Spedding et al., Calcium Antgonists': A Class of Drugs with a Bright Future. Part II. Determination of Basic Pharmacological Properties, *Life Sciences 35*:575–587 (1984).

Castellano, A., et al. (1993) J. Biol. Chem. 268: 3450–55.

Castellano, A., et al. (1993) J. Biol. Chem. 268: 12359–66.

Scharf, S.J., (1990) in *PCR Protocols,* Innis, M.A., et al., eds ; New York: Academic.

Brust et al., "Human Neuronal Voltage–Dependent Calcium Channels: Studies on Subunit Structure and Role in Channel Assembly", *Neuropharmacology* 32(11):1089–1102 (1993).

Williams, et al., "Structure and Functional Characterization of Neuronal $\alpha_{1E}$ Calcium Channel Subtypes,"*J. Biol. Chem.* 269(35):22347–22357 (1994).

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 7635 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 511..6996

( i x ) FEATURE:
        ( A ) NAME/KEY: 5'UTR
        ( B ) LOCATION: 1..510

( i x ) FEATURE:
        ( A ) NAME/KEY: 3'UTR
        ( B ) LOCATION: 6994..7635

( x i ) SEQUENCE DESCRIPTION: SEQ ID NO:1:

```
GGGCGAGCGC   CTCCGTCCCC   GGATGTGAGC   TCCGGCTGCC   CGCGGTCCCG   AGCCAGCGGC        60

GCGCGGGCGG   CGGCGGCGGG   CACCGGGCAC   CGCGGCGGGC   GGGCAGACGG   GCGGGCATGG       120

GGGGAGCGCC   GAGCGGCCCC   GGCGGCCGGG   CCGGCATCAC   CGCGGCGTCT   CTCCGCTAGA       180

GGAGGGGACA   AGCCAGTTCT   CCTTTGCAGC   AAAAAATTAC   ATGTATATAT   TATTAAGATA       240

ATATATACAT   TGGATTTTAT   TTTTTAAAA    AGTTTATTTT   GCTCCATTTT   TGAAAAAGAG       300

AGAGCTTGGG   TGGCGAGCGG   TTTTTTTTA    AAATCAATTA   TCCTTATTTT   CTGTTATTTG       360
```

| | | | | | | | | | | |
|---|---|---|---|---|---|---|---|---|---|---|
| TCCCCGTCCC | TCCCCACCCC | CCTGCTGAAG | CGAGAATAAG | GGCAGGGACC | GCGGCTCCTA | | | | | 420 |
| CCTCTTGGTG | ATCCCCTTCC | CCATTCCGCC | CCCGCCCCAA | CGCCCAGCAC | AGTGCCCTGC | | | | | 480 |
| ACACAGTAGT | CGCTCAATAA | ATGTTCGTGG | ATG ATG | ATG ATG | ATG ATG | ATG AAA | | | | 534 |
| | | | Met Met | Met Met | Met Met | Met Lys | | | | |
| | | | 1 | | 5 | | | | | |

```
AAA  ATG  CAG  CAT  CAA  CGG  CAG  CAG  CAA  GCG  GAC  CAC  GCG  AAC  GAG  GCA      582
Lys  Met  Gln  His  Gln  Arg  Gln  Gln  Gln  Ala  Asp  His  Ala  Asn  Glu  Ala
     10                  15                       20

AAC  TAT  GCA  AGA  GGC  ACC  AGA  CTT  CCT  CTT  TCT  GGT  GAA  GGA  CCA  ACT      630
Asn  Tyr  Ala  Arg  Gly  Thr  Arg  Leu  Pro  Leu  Ser  Gly  Glu  Gly  Pro  Thr
 25                 30                       35                            40

TCT  CAG  CCG  AAT  AGC  TCC  AAG  CAA  ACT  GTC  CTG  TCT  TGG  CAA  GCT  GCA      678
Ser  Gln  Pro  Asn  Ser  Ser  Lys  Gln  Thr  Val  Leu  Ser  Trp  Gln  Ala  Ala
                    45                       50                       55

ATC  GAT  GCT  GCT  AGA  CAG  GCC  AAG  GCT  GCC  CAA  ACT  ATG  AGC  ACC  TCT      726
Ile  Asp  Ala  Ala  Arg  Gln  Ala  Lys  Ala  Ala  Gln  Thr  Met  Ser  Thr  Ser
                         60                       65                       70

GCA  CCC  CCA  CCT  GTA  GGA  TCT  CTC  TCC  CAA  AGA  AAA  CGT  CAG  CAA  TAC      774
Ala  Pro  Pro  Pro  Val  Gly  Ser  Leu  Ser  Gln  Arg  Lys  Arg  Gln  Gln  Tyr
          75                       80                       85

GCC  AAG  AGC  AAA  AAA  CAG  GGT  AAC  TCG  TCC  AAC  AGC  CGA  CCT  GCC  CGC      822
Ala  Lys  Ser  Lys  Lys  Gln  Gly  Asn  Ser  Ser  Asn  Ser  Arg  Pro  Ala  Arg
     90                  95                       100

GCC  CTT  TTC  TGT  TTA  TCA  CTC  AAT  AAC  CCC  ATC  CGA  AGA  GCC  TGC  ATT      870
Ala  Leu  Phe  Cys  Leu  Ser  Leu  Asn  Asn  Pro  Ile  Arg  Arg  Ala  Cys  Ile
105                      110                      115                      120

AGT  ATA  GTG  GAA  TGG  AAA  CCA  TTT  GAC  ATA  TTT  ATA  TTG  GCT  ATT           918
Ser  Ile  Val  Glu  Trp  Lys  Pro  Phe  Asp  Ile  Phe  Ile  Leu  Leu  Ala  Ile
                         125                      130                      135

TTT  GCC  AAT  TGT  GTG  GCC  TTA  GCT  ATT  TAC  ATC  CCA  TTC  CCT  GAA  GAT      966
Phe  Ala  Asn  Cys  Val  Ala  Leu  Ala  Ile  Tyr  Ile  Pro  Phe  Pro  Glu  Asp
               140                      145                      150

GAT  TCT  AAT  TCA  ACA  AAT  CAT  AAC  TTG  GAA  AAA  GTA  GAA  TAT  GCC  TTC     1014
Asp  Ser  Asn  Ser  Thr  Asn  His  Asn  Leu  Glu  Lys  Val  Glu  Tyr  Ala  Phe
                    155                      160                      165

CTG  ATT  ATT  TTT  ACA  GTC  GAG  ACA  TTT  TTG  AAG  ATT  ATA  GCG  TAT  GGA     1062
Leu  Ile  Ile  Phe  Thr  Val  Glu  Thr  Phe  Leu  Lys  Ile  Ile  Ala  Tyr  Gly
170                      175                      180

TTA  TTG  CTA  CAT  CCT  AAT  GCT  TAT  GTT  AGG  AAT  GGA  TGG  AAT  TTA  CTG     1110
Leu  Leu  Leu  His  Pro  Asn  Ala  Tyr  Val  Arg  Asn  Gly  Trp  Asn  Leu  Leu
185                      190                      195                      200

GAT  TTT  GTT  ATA  GTA  ATA  GTA  GGA  TTG  TTT  AGT  GTA  ATT  TTG  GAA  CAA     1158
Asp  Phe  Val  Ile  Val  Ile  Val  Gly  Leu  Phe  Ser  Val  Ile  Leu  Glu  Gln
                         205                      210                      215

TTA  ACC  AAA  GAA  ACA  GAA  GGC  GGG  AAC  CAC  TCA  AGC  GGC  AAA  TCT  GGA     1206
Leu  Thr  Lys  Glu  Thr  Glu  Gly  Gly  Asn  His  Ser  Ser  Gly  Lys  Ser  Gly
                    220                      225                      230

GGC  TTT  GAT  GTC  AAA  GCC  CTC  CGT  GCC  TTT  CGA  GTG  TTG  CGA  CCA  CTT     1254
Gly  Phe  Asp  Val  Lys  Ala  Leu  Arg  Ala  Phe  Arg  Val  Leu  Arg  Pro  Leu
               235                      240                      245

CGA  CTA  GTG  TCA  GGA  GTG  CCC  AGT  TTA  CAA  GTT  GTC  CTG  AAC  TCC  ATT     1302
Arg  Leu  Val  Ser  Gly  Val  Pro  Ser  Leu  Gln  Val  Val  Leu  Asn  Ser  Ile
250                      255                      260

ATA  AAA  GCC  ATG  GTT  CCC  CTC  CTT  CAC  ATA  GCC  CTT  TGT  GTA  TTA  TTT     1350
Ile  Lys  Ala  Met  Val  Pro  Leu  Leu  His  Ile  Ala  Leu  Cys  Val  Leu  Phe
265                      270                      275                      280

GTA  ATC  ATA  ATC  TAT  GCT  ATT  ATA  GGA  TTG  GAA  CTT  TTT  ATT  GGA  AAA     1398
Val  Ile  Ile  Ile  Tyr  Ala  Ile  Ile  Gly  Leu  Glu  Leu  Phe  Ile  Gly  Lys
                         285                      290                      295
```

| | | | | | | | | | | | | | | | | |
|---|---|---|---|---|---|---|---|---|---|---|---|---|---|---|---|---|
| ATG | CAC | AAA | ACA | TGT | TTT | TTT | GCT | GAC | TCA | GAT | ATC | GTA | GCT | GAA | GAG | 1446 |
| Met | His | Lys | Thr 300 | Cys | Phe | Phe | Ala | Asp 305 | Ser | Asp | Ile | Val 310 | Ala | Glu | Glu | |
| GAC | CCA | GCT | CCA | TGT | GCG | TTC | TCA | GGG | AAT | GGA | CGC | CAG | TGT | ACT | GCC | 1494 |
| Asp | Pro | Ala 315 | Pro | Cys | Ala | Phe | Ser 320 | Gly | Asn | Gly | Arg | Gln 325 | Cys | Thr | Ala | |
| AAT | GGC | ACG | GAA | TGT | AGG | AGT | GGC | TGG | GTT | GGC | CCG | AAC | GGA | GGC | ATC | 1542 |
| Asn | Gly 330 | Thr | Glu | Cys | Arg | Ser 335 | Gly | Trp | Val | Gly | Pro 340 | Asn | Gly | Gly | Ile | |
| ACC | AAC | TTT | GAT | AAC | TTT | GCC | TTT | GCC | ATG | CTT | ACT | GTG | TTT | CAG | TGC | 1590 |
| Thr 345 | Asn | Phe | Asp | Asn | Phe 350 | Ala | Phe | Ala | Met | Leu 355 | Thr | Val | Phe | Gln | Cys 360 | |
| ATC | ACC | ATG | GAG | GGC | TGG | ACA | GAC | GTG | CTC | TAC | TGG | ATG | AAT | GAT | GCT | 1638 |
| Ile | Thr | Met | Glu | Gly 365 | Trp | Thr | Asp | Val | Leu 370 | Tyr | Trp | Met | Asn | Asp 375 | Ala | |
| ATG | GGA | TTT | GAA | TTG | CCC | TGG | GTG | TAT | TTT | GTC | AGT | CTC | GTC | ATC | TTT | 1686 |
| Met | Gly | Phe | Glu 380 | Leu | Pro | Trp | Val | Tyr 385 | Phe | Val | Ser | Leu | Val 390 | Ile | Phe | |
| GGG | TCA | TTT | TTC | GTA | CTA | AAT | CTT | GTA | CTT | GGT | GTA | TTG | AGC | GGA | GAA | 1734 |
| Gly | Ser | Phe 395 | Phe | Val | Leu | Asn | Leu 400 | Val | Leu | Gly | Val | Leu 405 | Ser | Gly | Glu | |
| TTC | TCA | AAG | GAA | AGA | GAG | AAG | GCA | AAA | GCA | CGG | GGA | GAT | TTC | CAG | AAG | 1782 |
| Phe | Ser | Lys 410 | Glu | Arg | Glu | Lys | Ala 415 | Lys | Ala | Arg | Gly | Asp 420 | Phe | Gln | Lys | |
| CTC | CGG | GAG | AAG | CAG | CAG | CTG | GAG | GAG | GAT | CTA | AAG | GGC | TAC | TTG | GAT | 1830 |
| Leu 425 | Arg | Glu | Lys | Gln | Gln 430 | Leu | Glu | Glu | Asp | Leu 435 | Lys | Gly | Tyr | Leu | Asp 440 | |
| TGG | ATC | ACC | CAA | GCT | GAG | GAC | ATC | GAT | CCG | GAG | AAT | GAG | GAA | GAA | GGA | 1878 |
| Trp | Ile | Thr | Gln | Ala 445 | Glu | Asp | Ile | Asp | Pro 450 | Glu | Asn | Glu | Glu | Glu 455 | Gly | |
| GGA | GAG | GAA | GGC | AAA | CGA | AAT | ACT | AGC | ATG | CCC | ACC | AGC | GAG | ACT | GAG | 1926 |
| Gly | Glu | Glu | Gly 460 | Lys | Arg | Asn | Thr | Ser 465 | Met | Pro | Thr | Ser | Glu 470 | Thr | Glu | |
| TCT | GTG | AAC | ACA | GAG | AAC | GTC | AGC | GGT | GAA | GGC | GAG | AAC | CGA | GGC | TGC | 1974 |
| Ser | Val | Asn | Thr 475 | Glu | Asn | Val | Ser | Gly 480 | Glu | Gly | Glu | Asn | Arg 485 | Gly | Cys | |
| TGT | GGA | AGT | CTC | TGT | CAA | GCC | ATC | TCA | AAA | TCC | AAA | CTC | AGC | CGA | CGC | 2022 |
| Cys | Gly | Ser 490 | Leu | Cys | Gln | Ala | Ile 495 | Ser | Lys | Ser | Lys | Leu 500 | Ser | Arg | Arg | |
| TGG | CGT | CGC | TGG | AAC | CGA | TTC | AAT | CGC | AGA | AGA | TGT | AGG | GCC | GCC | GTG | 2070 |
| Trp 505 | Arg | Arg | Trp | Asn | Arg 510 | Phe | Asn | Arg | Arg | Arg 515 | Cys | Arg | Ala | Ala | Val 520 | |
| AAG | TCT | GTC | ACG | TTT | TAC | TGG | CTG | GTT | ATC | GTC | CTG | GTG | TTT | CTG | AAC | 2118 |
| Lys | Ser | Val | Thr | Phe 525 | Tyr | Trp | Leu | Val | Ile 530 | Val | Leu | Val | Phe | Leu 535 | Asn | |
| ACC | TTA | ACC | ATT | TCC | TCT | GAG | CAC | TAC | AAT | CAG | CCA | GAT | TGG | TTG | ACA | 2166 |
| Thr | Leu | Thr | Ile 540 | Ser | Ser | Glu | His | Tyr 545 | Asn | Gln | Pro | Asp | Trp 550 | Leu | Thr | |
| CAG | ATT | CAA | GAT | ATT | GCC | AAC | AAA | GTC | CTC | TTG | GCT | CTG | TTC | ACC | TGC | 2214 |
| Gln | Ile | Gln | Asp | Ile 555 | Ala | Asn | Lys | Val | Leu 560 | Leu | Ala | Leu | Phe | Thr 565 | Cys | |
| GAG | ATG | CTG | GTA | AAA | ATG | TAC | AGC | TTG | GGC | CTC | CAA | GCA | TAT | TTC | GTC | 2262 |
| Glu | Met | Leu 570 | Val | Lys | Met | Tyr | Ser 575 | Leu | Gly | Leu | Gln | Ala 580 | Tyr | Phe | Val | |
| TCT | CTT | TTC | AAC | CGG | TTT | GAT | TGC | TTC | GTG | GTG | TGT | GGT | GGA | ATC | ACT | 2310 |
| Ser | Leu 585 | Phe | Asn | Arg | Phe | Asp 590 | Cys | Phe | Val | Val | Cys 595 | Gly | Gly | Ile | Thr 600 | |
| GAG | ACG | ATC | TTG | GTG | GAA | CTG | GAA | ATC | ATG | TCT | CCC | CTG | GGG | ATC | TCT | 2358 |
| Glu | Thr | Ile | Leu | Val 605 | Glu | Leu | Glu | Ile | Met 610 | Ser | Pro | Leu | Gly | Ile 615 | Ser | |

| | | | | | | | | | | | | | | | | |
|---|---|---|---|---|---|---|---|---|---|---|---|---|---|---|---|---|
| GTG | TTT | CGG | TGT | GTG | CGC | CTC | TTA | AGA | ATC | TTC | AAA | GTG | ACC | AGG | CAC | 2406 |
| Val | Phe | Arg | Cys 620 | Val | Arg | Leu | Leu | Arg 625 | Ile | Phe | Lys | Val | Thr 630 | Arg | His | |
| TGG | ACT | TCC | CTG | AGC | AAC | TTA | GTG | GCA | TCC | TTA | TTA | AAC | TCC | ATG | AAG | 2454 |
| Trp | Thr | Ser 635 | Leu | Ser | Asn | Leu | Val 640 | Ala | Ser | Leu | Leu | Asn 645 | Ser | Met | Lys | |
| TCC | ATC | GCT | TCG | CTG | TTG | CTT | CTG | CTT | TTT | CTC | TTC | ATT | ATC | ATC | TTT | 2502 |
| Ser | Ile | Ala 650 | Ser | Leu | Leu | Leu 655 | Leu | Leu | Phe | Leu | Phe 660 | Ile | Ile | Ile | Phe | |
| TCC | TTG | CTT | GGG | ATG | CAG | CTG | TTT | GGC | GGC | AAG | TTT | AAT | TTT | GAT | GAA | 2550 |
| Ser | Leu | Leu 665 | Gly | Met | Gln | Leu 670 | Phe | Gly | Gly | Lys 675 | Phe | Asn | Phe | Asp | Glu 680 | |
| ACG | CAA | ACC | AAG | CGG | AGC | ACC | TTT | GAC | AAT | TTC | CCT | CAA | GCA | CTT | CTC | 2598 |
| Thr | Gln | Thr | Lys | Arg 685 | Ser | Thr | Phe | Asp | Asn 690 | Phe | Pro | Gln | Ala | Leu 695 | Leu | |
| ACA | GTG | TTC | CAG | ATC | CTG | ACA | GGC | GAA | GAC | TGG | AAT | GCT | GTG | ATG | TAC | 2646 |
| Thr | Val | Phe | Gln 700 | Ile | Leu | Thr | Gly | Glu 705 | Asp | Trp | Asn | Ala | Val 710 | Met | Tyr | |
| GAT | GGC | ATC | ATG | GCT | TAC | GGG | GGC | CCA | TCC | TCT | TCA | GGA | ATG | ATC | GTC | 2694 |
| Asp | Gly | Ile | Met 715 | Ala | Tyr | Gly | Gly | Pro 720 | Ser | Ser | Ser | Gly | Met 725 | Ile | Val | |
| TGC | ATC | TAC | TTC | ATC | ATC | CTC | TTC | ATT | TGT | GGT | AAC | TAT | ATT | CTA | CTG | 2742 |
| Cys | Ile 730 | Tyr | Phe | Ile | Ile | Leu 735 | Phe | Ile | Cys | Gly | Asn 740 | Tyr | Ile | Leu | Leu | |
| AAT | GTC | TTC | TTG | GCC | ATC | GCT | GTA | GAC | AAT | TTG | GCT | GAT | GCT | GAA | AGT | 2790 |
| Asn 745 | Val | Phe | Leu | Ala | Ile 750 | Ala | Val | Asp | Asn | Leu 755 | Ala | Asp | Ala | Glu | Ser 760 | |
| CTG | AAC | ACT | GCT | CAG | AAA | GAA | GAA | GCG | GAA | GAA | AAG | GAG | AGG | AAA | AAG | 2838 |
| Leu | Asn | Thr | Ala | Gln 765 | Lys | Glu | Glu | Ala | Glu 770 | Glu | Lys | Glu | Arg | Lys 775 | Lys | |
| ATT | GCC | AGA | AAA | GAG | AGC | CTA | GAA | AAT | AAA | AAG | AAC | AAC | AAA | CCA | GAA | 2886 |
| Ile | Ala | Arg | Lys 780 | Glu | Ser | Leu | Glu | Asn 785 | Lys | Lys | Asn | Asn | Lys 790 | Pro | Glu | |
| GTC | AAC | CAG | ATA | GCC | AAC | AGT | GAC | AAC | AAG | GTT | ACA | ATT | GAT | GAC | TAT | 2934 |
| Val | Asn | Gln | Ile 795 | Ala | Asn | Ser | Asp | Asn 800 | Lys | Val | Thr | Ile | Asp 805 | Asp | Tyr | |
| AGA | GAA | GAG | GAT | GAA | GAC | AAG | GAC | CCC | TAT | CCG | CCT | TGC | GAT | GTG | CCA | 2982 |
| Arg | Glu | Glu 810 | Asp | Glu | Asp | Lys | Asp 815 | Pro | Tyr | Pro | Pro | Cys 820 | Asp | Val | Pro | |
| GTA | GGG | GAA | GAG | GAA | GAG | GAA | GAG | GAG | GAG | GAT | GAA | CCT | GAG | GTT | CCT | 3030 |
| Val 825 | Gly | Glu | Glu | Glu | Glu 830 | Glu | Glu | Glu | Glu | Asp 835 | Glu | Pro | Glu | Val | Pro 840 | |
| GCC | GGA | CCC | CGT | CCT | CGA | AGG | ATC | TCG | GAG | TTG | AAC | ATG | AAG | GAA | AAA | 3078 |
| Ala | Gly | Pro | Arg | Pro 845 | Arg | Arg | Ile | Ser | Glu 850 | Leu | Asn | Met | Lys | Glu 855 | Lys | |
| ATT | GCC | CCC | ATC | CCT | GAA | GGG | AGC | GCT | TTC | TTC | ATT | CTT | AGC | AAG | ACC | 3126 |
| Ile | Ala | Pro | Ile | Pro 860 | Glu | Gly | Ser | Ala | Phe 865 | Phe | Ile | Leu | Ser | Lys 870 | Thr | |
| AAC | CCG | ATC | CGC | GTA | GGC | TGC | CAC | AAG | CTC | ATC | AAC | CAC | CAC | ATC | TTC | 3174 |
| Asn | Pro | Ile | Arg 875 | Val | Gly | Cys | His | Lys 880 | Leu | Ile | Asn | His | His 885 | Ile | Phe | |
| ACC | AAC | CTC | ATC | CTT | GTC | TTC | ATC | ATG | CTG | AGC | AGT | GCT | GCC | CTG | GCC | 3222 |
| Thr | Asn | Leu | Ile 890 | Leu | Val | Phe | Ile | Met 895 | Leu | Ser | Ser | Ala | Ala 900 | Leu | Ala | |
| GCA | GAG | GAC | CCC | ATC | CGC | AGC | CAC | TCC | TTC | CGG | AAC | ACG | ATA | CTG | GGT | 3270 |
| Ala | Glu | Asp | Pro | Ile 905 | Arg | Ser | His | Ser 910 | Phe | Arg | Asn | Thr | Ile 915 | Leu | Gly 920 | |
| TAC | TTT | GAC | TAT | GCC | TTC | ACA | GCC | ATC | TTT | ACT | GTT | GAG | ATC | CTG | TTG | 3318 |
| Tyr | Phe | Asp | Tyr | Ala 925 | Phe | Thr | Ala | Ile | Phe 930 | Thr | Val | Glu | Ile | Leu 935 | Leu | |

```
AAG  ATG  ACA  ACT  TTT  GGA  GCT  TTC  CTC  CAC  AAA  GGG  GCC  TTC  TGC  AGG    3366
Lys  Met  Thr  Thr  Phe  Gly  Ala  Phe  Leu  His  Lys  Gly  Ala  Phe  Cys  Arg
               940                 945                      950

AAC  TAC  TTC  AAT  TTG  CTG  GAT  ATG  CTG  GTG  GTT  GGG  GTG  TCT  CTG  GTG    3414
Asn  Tyr  Phe  Asn  Leu  Leu  Asp  Met  Leu  Val  Val  Gly  Val  Ser  Leu  Val
               955                 960                      965

TCA  TTT  GGG  ATT  CAA  TCC  AGT  GCC  ATC  TCC  GTT  GTG  AAG  ATT  CTG  AGG    3462
Ser  Phe  Gly  Ile  Gln  Ser  Ser  Ala  Ile  Ser  Val  Val  Lys  Ile  Leu  Arg
     970                 975                      980

GTC  TTA  AGG  GTC  CTG  CGT  CCC  CTC  AGG  GCC  ATC  AAC  AGA  GCA  AAA  GGA    3510
Val  Leu  Arg  Val  Leu  Arg  Pro  Leu  Arg  Ala  Ile  Asn  Arg  Ala  Lys  Gly
985                 990                      995                           1000

CTT  AAG  CAC  GTG  GTC  CAG  TGC  GTC  TTC  GTG  GCC  ATC  CGG  ACC  ATC  GGC    3558
Leu  Lys  His  Val  Val  Gln  Cys  Val  Phe  Val  Ala  Ile  Arg  Thr  Ile  Gly
                         1005                     1010                     1015

AAC  ATC  ATG  ATC  GTC  ACC  ACC  CTC  CTG  CAG  TTC  ATG  TTT  GCC  TGT  ATC    3606
Asn  Ile  Met  Ile  Val  Thr  Thr  Leu  Leu  Gln  Phe  Met  Phe  Ala  Cys  Ile
                    1020                     1025                     1030

GGG  GTC  CAG  TTG  TTC  AAG  GGG  AAG  TTC  TAT  CGC  TGT  ACG  GAT  GAA  GCC    3654
Gly  Val  Gln  Leu  Phe  Lys  Gly  Lys  Phe  Tyr  Arg  Cys  Thr  Asp  Glu  Ala
                    1035                     1040                     1045

AAA  AGT  AAC  CCT  GAA  GAA  TGC  AGG  GGA  CTT  TTC  ATC  CTC  TAC  AAG  GAT    3702
Lys  Ser  Asn  Pro  Glu  Glu  Cys  Arg  Gly  Leu  Phe  Ile  Leu  Tyr  Lys  Asp
     1050                     1055                     1060

GGG  GAT  GTT  GAC  AGT  CCT  GTG  GTC  CGT  GAA  CGG  ATC  TGG  CAA  AAC  AGT    3750
Gly  Asp  Val  Asp  Ser  Pro  Val  Val  Arg  Glu  Arg  Ile  Trp  Gln  Asn  Ser
1065                1070                     1075                          1080

GAT  TTC  AAC  TTC  GAC  AAC  GTC  CTC  TCT  GCT  ATG  ATG  GCG  CTC  TTC  ACA    3798
Asp  Phe  Asn  Phe  Asp  Asn  Val  Leu  Ser  Ala  Met  Met  Ala  Leu  Phe  Thr
               1085                     1090                     1095

GTC  TCC  ACG  TTT  GAG  GGC  TGG  CCT  GCG  TTG  CTG  TAT  AAA  GCC  ATC  GAC    3846
Val  Ser  Thr  Phe  Glu  Gly  Trp  Pro  Ala  Leu  Leu  Tyr  Lys  Ala  Ile  Asp
               1100                     1105                     1110

TCG  AAT  GGA  GAG  AAC  ATC  GGC  CCA  ATC  TAC  AAC  CAC  CGC  GTG  GAG  ATC    3894
Ser  Asn  Gly  Glu  Asn  Ile  Gly  Pro  Ile  Tyr  Asn  His  Arg  Val  Glu  Ile
               1115                     1120                     1125

TCC  ATC  TTC  TTC  ATC  ATC  TAC  ATC  ATC  ATT  GTA  GCT  TTC  TTC  ATG  ATG    3942
Ser  Ile  Phe  Phe  Ile  Ile  Tyr  Ile  Ile  Ile  Val  Ala  Phe  Phe  Met  Met
               1130                     1135                     1140

AAC  ATC  TTT  GTG  GGC  TTT  GTC  ATC  GTT  ACA  TTT  CAG  GAA  CAA  GGA  GAA    3990
Asn  Ile  Phe  Val  Gly  Phe  Val  Ile  Val  Thr  Phe  Gln  Glu  Gln  Gly  Glu
1145                1150                     1155                          1160

AAA  GAG  TAT  AAG  AAC  TGT  GAG  CTG  GAC  AAA  AAT  CAG  CGT  CAG  TGT  GTT    4038
Lys  Glu  Tyr  Lys  Asn  Cys  Glu  Leu  Asp  Lys  Asn  Gln  Arg  Gln  Cys  Val
               1165                     1170                     1175

GAA  TAC  GCC  TTG  AAA  GCA  CGT  CCC  TTG  CGG  AGA  TAC  ATC  CCC  AAA  AAC    4086
Glu  Tyr  Ala  Leu  Lys  Ala  Arg  Pro  Leu  Arg  Arg  Tyr  Ile  Pro  Lys  Asn
               1180                     1185                     1190

CCC  TAC  CAG  TAC  AAG  TTC  TGG  TAC  GTG  GTG  AAC  TCT  TCG  CCT  TTC  GAA    4134
Pro  Tyr  Gln  Tyr  Lys  Phe  Trp  Tyr  Val  Val  Asn  Ser  Ser  Pro  Phe  Glu
               1195                     1200                     1205

TAC  ATG  ATG  TTT  GTC  CTC  ATC  ATG  CTC  AAC  ACA  CTC  TGC  TTG  GCC  ATG    4182
Tyr  Met  Met  Phe  Val  Leu  Ile  Met  Leu  Asn  Thr  Leu  Cys  Leu  Ala  Met
               1210                     1215                     1220

CAG  CAC  TAC  GAG  CAG  TCC  AAG  ATG  TTC  AAT  GAT  GCC  ATG  GAC  ATT  CTG    4230
Gln  His  Tyr  Glu  Gln  Ser  Lys  Met  Phe  Asn  Asp  Ala  Met  Asp  Ile  Leu
1225                1230                     1235                          1240

AAC  ATG  GTC  TTC  ACC  GGG  GTG  TTC  ACC  GTC  GAG  ATG  GTT  TTG  AAA  GTC    4278
Asn  Met  Val  Phe  Thr  Gly  Val  Phe  Thr  Val  Glu  Met  Val  Leu  Lys  Val
               1245                     1250                     1255
```

```
ATC GCA TTT AAG CCT AAG GGG TAT TTT AGT GAC GCC TGG AAC ACG TTT       4326
Ile Ala Phe Lys Pro Lys Gly Tyr Phe Ser Asp Ala Trp Asn Thr Phe
        1260                1265                1270

GAC TCC CTC ATC GTA ATC GGC AGC ATT ATA GAC GTG GCC CTC AGC GAA       4374
Asp Ser Leu Ile Val Ile Gly Ser Ile Ile Asp Val Ala Leu Ser Glu
    1275                1280                1285

GCA GAC CCA ACT GAA AGT GAA AAT GTC CCT GTC CCA ACT GCT ACA CCT       4422
Ala Asp Pro Thr Glu Ser Glu Asn Val Pro Val Pro Thr Ala Thr Pro
1290                1295                1300

GGG AAC TCT GAA GAG AGC AAT AGA ATC TCC ATC ACC TTT TTC CGT CTT       4470
Gly Asn Ser Glu Glu Ser Asn Arg Ile Ser Ile Thr Phe Phe Arg Leu
1305                1310                1315                1320

TTC CGA GTG ATG CGA TTG GTG AAG CTT CTC AGC AGG GGG GAA GGC ATC       4518
Phe Arg Val Met Arg Leu Val Lys Leu Leu Ser Arg Gly Glu Gly Ile
                1325                1330                1335

CGG ACA TTG CTG TGG ACT TTT ATT AAG TTC TTT CAG GCG CTC CCG TAT       4566
Arg Thr Leu Leu Trp Thr Phe Ile Lys Phe Phe Gln Ala Leu Pro Tyr
            1340                1345                1350

GTG GCC CTC CTC ATA GCC ATG CTG TTC TTC ATC TAT GCG GTC ATT GGC       4614
Val Ala Leu Leu Ile Ala Met Leu Phe Phe Ile Tyr Ala Val Ile Gly
        1355                1360                1365

ATG CAG ATG TTT GGG AAA GTT GCC ATG AGA GAT AAC AAC CAG ATC AAT       4662
Met Gln Met Phe Gly Lys Val Ala Met Arg Asp Asn Asn Gln Ile Asn
    1370                1375                1380

AGG AAC AAT AAC TTC CAG ACG TTT CCC CAG GCG GTG CTG CTG CTC TTC       4710
Arg Asn Asn Asn Phe Gln Thr Phe Pro Gln Ala Val Leu Leu Leu Phe
1385                1390                1395                1400

AGG TGT GCA ACA GGT GAG GCC TGG CAG GAG ATC ATG CTG GCC TGT CTC       4758
Arg Cys Ala Thr Gly Glu Ala Trp Gln Glu Ile Met Leu Ala Cys Leu
                1405                1410                1415

CCA GGG AAG CTC TGT GAC CCT GAG TCA GAT TAC AAC CCC GGG GAG GAG       4806
Pro Gly Lys Leu Cys Asp Pro Glu Ser Asp Tyr Asn Pro Gly Glu Glu
            1420                1425                1430

CAT ACA TGT GGG AGC AAC TTT GCC ATT GTC TAT TTC ATC AGT TTT TAC       4854
His Thr Cys Gly Ser Asn Phe Ala Ile Val Tyr Phe Ile Ser Phe Tyr
        1435                1440                1445

ATG CTC TGT GCA TTT CTG ATC ATC AAT CTG TTT GTG GCT GTC ATC ATG       4902
Met Leu Cys Ala Phe Leu Ile Ile Asn Leu Phe Val Ala Val Ile Met
    1450                1455                1460

GAT AAT TTC GAC TAT CTG ACC CGG GAC TGG TCT ATT TTG GGG CCT CAC       4950
Asp Asn Phe Asp Tyr Leu Thr Arg Asp Trp Ser Ile Leu Gly Pro His
1465                1470                1475                1480

CAT TTA GAT GAA TTC AAA AGA ATA TGG TCA GAA TAT GAC CCT GAG GCA       4998
His Leu Asp Glu Phe Lys Arg Ile Trp Ser Glu Tyr Asp Pro Glu Ala
                1485                1490                1495

AAG GGA AGG ATA AAA CAC CTT GAT GTG GTC ACT CTG CTT CGA CGC ATC       5046
Lys Gly Arg Ile Lys His Leu Asp Val Val Thr Leu Leu Arg Arg Ile
            1500                1505                1510

CAG CCT CCC CTG GGG TTT GGG AAG TTA TGT CCA CAC AGG GTA GCG TGC       5094
Gln Pro Pro Leu Gly Phe Gly Lys Leu Cys Pro His Arg Val Ala Cys
        1515                1520                1525

AAG AGA TTA GTT GCC ATG AAC ATG CCT CTC AAC AGT GAC GGG ACA GTC       5142
Lys Arg Leu Val Ala Met Asn Met Pro Leu Asn Ser Asp Gly Thr Val
    1530                1535                1540

ATG TTT AAT GCA ACC CTG TTT GCT TTG GTT CGA ACG GCT CTT AAG ATC       5190
Met Phe Asn Ala Thr Leu Phe Ala Leu Val Arg Thr Ala Leu Lys Ile
1545                1550                1555                1560

AAG ACC GAA GGG AAC CTG GAG CAA GCT AAT GAA GAA CTT CGG GCT GTG       5238
Lys Thr Glu Gly Asn Leu Glu Gln Ala Asn Glu Glu Leu Arg Ala Val
                1565                1570                1575
```

| | |
|---|---|
| ATA AAG AAA ATT TGG AAG AAA ACC AGC ATG AAA TTA CTT GAC CAA GTT<br>Ile Lys Lys Ile Trp Lys Lys Thr Ser Met Lys Leu Leu Asp Gln Val<br>        1580                    1585                    1590 | 5286 |
| GTC CCT CCA GCT GGT GAT GAT GAG GTA ACC GTG GGG AAG TTC TAT GCC<br>Val Pro Pro Ala Gly Asp Asp Glu Val Thr Val Gly Lys Phe Tyr Ala<br>1595                    1600                    1605 | 5334 |
| ACT TTC CTG ATA CAG GAC TAC TTT AGG AAA TTC AAG AAA CGG AAA GAA<br>Thr Phe Leu Ile Gln Asp Tyr Phe Arg Lys Phe Lys Lys Arg Lys Glu<br>    1610                    1615                    1620 | 5382 |
| CAA GGA CTG GTG GGA AAG TAC CCT GCG AAG AAC ACC ACA ATT GCC CTA<br>Gln Gly Leu Val Gly Lys Tyr Pro Ala Lys Asn Thr Thr Ile Ala Leu<br>1625                    1630                    1635                    1640 | 5430 |
| CAG GCG GGA TTA AGG ACA CTG CAT GAC ATT GGG CCA GAA ATC CGG CGT<br>Gln Ala Gly Leu Arg Thr Leu His Asp Ile Gly Pro Glu Ile Arg Arg<br>                    1645                    1650                    1655 | 5478 |
| GCT ATA TCG TGT GAT TTG CAA GAT GAC GAG CCT GAG GAA ACA AAA CGA<br>Ala Ile Ser Cys Asp Leu Gln Asp Asp Glu Pro Glu Glu Thr Lys Arg<br>1660                    1665                    1670 | 5526 |
| GAA GAA GAA GAT GAT GTG TTC AAA AGA AAT GGT GCC CTG CTT GGA AAC<br>Glu Glu Glu Asp Asp Val Phe Lys Arg Asn Gly Ala Leu Leu Gly Asn<br>    1675                    1680                    1685 | 5574 |
| CAT GTC AAT CAT GTT AAT AGT GAT AGG AGA GAT TCC CTT CAG CAG ACC<br>His Val Asn His Val Asn Ser Asp Arg Arg Asp Ser Leu Gln Gln Thr<br>1690                    1695                    1700 | 5622 |
| AAT ACC ACC CAC CGT CCC CTG CAT GTC CAA AGG CCT TCA ATT CCA CCT<br>Asn Thr Thr His Arg Pro Leu His Val Gln Arg Pro Ser Ile Pro Pro<br>1705                    1710                    1715                    1720 | 5670 |
| GCA AGT GAT ACT GAG AAA CCG CTG TTT CCT CCA GCA GGA AAT TCG GTG<br>Ala Ser Asp Thr Glu Lys Pro Leu Phe Pro Pro Ala Gly Asn Ser Val<br>                    1725                    1730                    1735 | 5718 |
| TGT CAT AAC CAT CAT AAC CAT AAT TCC ATA GGA AAG CAA GTT CCC ACC<br>Cys His Asn His His Asn His Asn Ser Ile Gly Lys Gln Val Pro Thr<br>1740                    1745                    1750 | 5766 |
| TCA ACA AAT GCC AAT CTC AAT AAT GCC AAT ATG TCC AAA GCT GCC CAT<br>Ser Thr Asn Ala Asn Leu Asn Asn Ala Asn Met Ser Lys Ala Ala His<br>    1755                    1760                    1765 | 5814 |
| GGA AAG CGG CCC AGC ATT GGG AAC CTT GAG CAT GTG TCT GAA AAT GGG<br>Gly Lys Arg Pro Ser Ile Gly Asn Leu Glu His Val Ser Glu Asn Gly<br>1770                    1775                    1780 | 5862 |
| CAT CAT TCT TCC CAC AAG CAT GAC CGG GAG CCT CAG AGA AGG TCC AGT<br>His His Ser Ser His Lys His Asp Arg Glu Pro Gln Arg Arg Ser Ser<br>1785                    1790                    1795                    1800 | 5910 |
| GTG AAA AGA ACC CGC TAT TAT GAA ACT TAC ATT AGG TCC GAC TCA GGA<br>Val Lys Arg Thr Arg Tyr Tyr Glu Thr Tyr Ile Arg Ser Asp Ser Gly<br>                    1805                    1810                    1815 | 5958 |
| GAT GAA CAG CTC CCA ACT ATT TGC CGG GAA GAC CCA GAG ATA CAT GGC<br>Asp Glu Gln Leu Pro Thr Ile Cys Arg Glu Asp Pro Glu Ile His Gly<br>1820                    1825                    1830 | 6006 |
| TAT TTC AGG GAC CCC CAC TGC TTG GGG GAG CAG GAG TAT TTC AGT AGT<br>Tyr Phe Arg Asp Pro His Cys Leu Gly Glu Gln Glu Tyr Phe Ser Ser<br>    1835                    1840                    1845 | 6054 |
| GAG GAA TGC TAC GAG GAT GAC AGC TCG CCC ACC TGG AGC AGG CAA AAC<br>Glu Glu Cys Tyr Glu Asp Asp Ser Ser Pro Thr Trp Ser Arg Gln Asn<br>1850                    1855                    1860 | 6102 |
| TAT GGC TAC TAC AGC AGA TAC CCA GGC AGA AAC ATC GAC TCT GAG AGG<br>Tyr Gly Tyr Tyr Ser Arg Tyr Pro Gly Arg Asn Ile Asp Ser Glu Arg<br>1865                    1870                    1875                    1880 | 6150 |
| CCC CGA GGC TAC CAT CAT CCC CAA GGA TTC TTG GAG GAC GAT GAC TCG<br>Pro Arg Gly Tyr His His Pro Gln Gly Phe Leu Glu Asp Asp Asp Ser<br>                    1885                    1890                    1895 | 6198 |

```
CCC GTT TGC TAT GAT TCA CGG AGA TCT CCA AGG AGA CGC CTA CTA CCT     6246
Pro Val Cys Tyr Asp Ser Arg Arg Ser Pro Arg Arg Arg Leu Leu Pro
            1900                1905                1910

CCC ACC CCA GCA TCC CAC CGG AGA TCC TCC TTC AAC TTT GAG TGC CTG     6294
Pro Thr Pro Ala Ser His Arg Arg Ser Ser Phe Asn Phe Glu Cys Leu
            1915                1920                1925

CGC CGG CAG AGC AGC CAG GAA GAG GTC CCG TCG TCT CCC ATC TTC CCC     6342
Arg Arg Gln Ser Ser Gln Glu Glu Val Pro Ser Ser Pro Ile Phe Pro
        1930                1935                1940

CAT CGC ACG GCC CTG CCT CTG CAT CTA ATG CAG CAA CAG ATC ATG GCA     6390
His Arg Thr Ala Leu Pro Leu His Leu Met Gln Gln Gln Ile Met Ala
1945                1950                1955                1960

GTT GCC GGC CTA GAT TCA AGT AAA GCC CAG AAG TAC TCA CCG AGT CAC     6438
Val Ala Gly Leu Asp Ser Ser Lys Ala Gln Lys Tyr Ser Pro Ser His
                1965                1970                1975

TCG ACC CGG TCG TGG GCC ACC CCT CCA GCA ACC CCT CCC TAC CGG GAC     6486
Ser Thr Arg Ser Trp Ala Thr Pro Pro Ala Thr Pro Pro Tyr Arg Asp
            1980                1985                1990

TGG ACA CCG TGC TAC ACC CCC CTG ATC CAA GTG GAG CAG TCA GAG GCC     6534
Trp Thr Pro Cys Tyr Thr Pro Leu Ile Gln Val Glu Gln Ser Glu Ala
            1995                2000                2005

CTG GAC CAG GTG AAC GGC AGC CTG CCG TCC CTG CAC CGC AGC TCC TGG     6582
Leu Asp Gln Val Asn Gly Ser Leu Pro Ser Leu His Arg Ser Ser Trp
        2010                2015                2020

TAC ACA GAC GAG CCC GAC ATC TCC TAC CGG ACT TTC ACA CCA GCC AGC     6630
Tyr Thr Asp Glu Pro Asp Ile Ser Tyr Arg Thr Phe Thr Pro Ala Ser
2025                2030                2035                2040

CTG ACT GTC CCC AGC AGC TTC CGG AAC AAA AAC AGC GAC AAG CAG AGG     6678
Leu Thr Val Pro Ser Ser Phe Arg Asn Lys Asn Ser Asp Lys Gln Arg
                2045                2050                2055

AGT GCG GAC AGC TTG GTG GAG GCA GTC CTG ATA TCC GAA GGC TTG GGA     6726
Ser Ala Asp Ser Leu Val Glu Ala Val Leu Ile Ser Glu Gly Leu Gly
            2060                2065                2070

CGC TAT GCA AGG GAC CCA AAA TTT GTG TCA GCA ACA AAA CAC GAA ATC     6774
Arg Tyr Ala Arg Asp Pro Lys Phe Val Ser Ala Thr Lys His Glu Ile
            2075                2080                2085

GCT GAT GCC TGT GAC CTC ACC ATC GAC GAG ATG GAG AGT GCA GCC AGC     6822
Ala Asp Ala Cys Asp Leu Thr Ile Asp Glu Met Glu Ser Ala Ala Ser
        2090                2095                2100

ACC CTG CTT AAT GGG AAC GTG CGT CCC CGA GCC AAC GGG GAT GTG GGC     6870
Thr Leu Leu Asn Gly Asn Val Arg Pro Arg Ala Asn Gly Asp Val Gly
2105                2110                2115                2120

CCC CTC TCA CAC CGG CAG GAC TAT GAG CTA CAG GAC TTT GGT CCT GGC     6918
Pro Leu Ser His Arg Gln Asp Tyr Glu Leu Gln Asp Phe Gly Pro Gly
            2125                2130                2135

TAC AGC GAC GAA GAG CCA GAC CCT GGG AGG GAT GAG GAG GAC CTG GCG     6966
Tyr Ser Asp Glu Glu Pro Asp Pro Gly Arg Asp Glu Glu Asp Leu Ala
            2140                2145                2150

GAT GAA ATG ATA TGC ATC ACC ACC TTG TAGCCCCCAG CGAGGGGCAG           7013
Asp Glu Met Ile Cys Ile Thr Thr Leu
        2155                2160

ACTGGCTCTG GCCTCAGGTG GGGCGCAGGA GAGCCAGGGG AAAAGTGCCT CATAGTTAGG   7073

AAAGTTTAGG CACTAGTTGG GAGTAATATT CAATTAATTA GACTTTTGTA TAAGAGATGT   7133

CATGCCTCAA GAAAGCCATA AACCTGGTAG GAACAGGTCC CAAGCGGTTG AGCCTGGCAG   7193

AGTACCATGC GCTCGGCCCC AGCTGCAGGA AACAGCAGGC CCCGCCCTCT CACAGAGGAT   7253

GGGTGAGGAG GCCAGACCTG CCCTGCCCCA TTGTCCAGAT GGGCACTGCT GTGGAGTCTG   7313

CTTCTCCCAT GTACCAGGGC ACCAGGCCCA CCCAACTGAA GGCATGGCGG CGGGGTGCAG   7373
```

```
GGGAAAGTTA  AAGGTGATGA  CGATCATCAC  ACCTGTGTCG  TTACCTCAGC  CATCGGTCTA      7433

GCATATCAGT  CACTGGGCCC  AACATATCCA  TTTTTAAACC  CTTTCCCCCA  AATACACTGC      7493

GTCCTGGTTC  CTGTTTAGCT  GTTCTGAAAT  ACGGTGTGTA  AGTAAGTCAG  AACCCAGCTA      7553

CCAGTGATTA  TTGCGAGGGC  AATGGGACCT  CATAAATAAG  GTTTTCTGTG  ATGTGACGCC      7613

AGTTTACATA  AGAGAATATC  AC                                                  7635
```

( 2 ) INFORMATION FOR SEQ ID NO:2:

( i ) SEQUENCE CHARACTERISTICS:
        ( A ) LENGTH: 104 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..102

( i x ) FEATURE:
        ( A ) NAME/KEY: misc_feature
        ( B ) LOCATION: 1..104
        ( D ) OTHER INFORMATION: /note= "A 104-nucleotide
        alternative exon of alpha-1D."

( x i ) SEQUENCE DESCRIPTION: SEQ ID NO:2:

```
GTA  AAT  GAT  GCG  ATA  GGA  TGG  GAA  TGG  CCA  TGG  GTG  TAT  TTT  GTT  AGT      48
Val  Asn  Asp  Ala  Ile  Gly  Trp  Glu  Trp  Pro  Trp  Val  Tyr  Phe  Val  Ser
 1                    5                        10                       15

CTG  ATC  ATC  CTT  GGC  TCA  TTT  TTC  GTC  CTT  AAC  CTG  GTT  CTT  GGT  GTC      96
Leu  Ile  Ile  Leu  Gly  Ser  Phe  Phe  Val  Leu  Asn  Leu  Val  Leu  Gly  Val
              20                        25                       30

CTT  AGT  GG                                                                        104
Leu  Ser
```

( 2 ) INFORMATION FOR SEQ ID NO:3:

( i ) SEQUENCE CHARACTERISTICS:
        ( A ) LENGTH: 5904 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..5904

( x i ) SEQUENCE DESCRIPTION: SEQ ID NO:3:

```
ATG  GTC  AAT  GAG  AAT  ACG  AGG  ATG  TAC  ATT  CCA  GAG  GAA  AAC  CAC  CAA      48
Met  Val  Asn  Glu  Asn  Thr  Arg  Met  Tyr  Ile  Pro  Glu  Glu  Asn  His  Gln
 1                    5                        10                       15

GGT  TCC  AAC  TAT  GGG  AGC  CCA  CGC  CCC  GCC  CAT  GCC  AAC  ATG  AAT  GCC      96
Gly  Ser  Asn  Tyr  Gly  Ser  Pro  Arg  Pro  Ala  His  Ala  Asn  Met  Asn  Ala
              20                        25                       30

AAT  GCG  GCA  GCG  GGG  CTG  GCC  CCT  GAG  CAC  ATC  CCC  ACC  CCG  GGG  GCT     144
Asn  Ala  Ala  Ala  Gly  Leu  Ala  Pro  Glu  His  Ile  Pro  Thr  Pro  Gly  Ala
              35                        40                       45

GCC  CTG  TCG  TGG  CAG  GCG  GCC  ATC  GAC  GCA  GCC  CGG  CAG  GCT  AAG  CTG     192
Ala  Leu  Ser  Trp  Gln  Ala  Ala  Ile  Asp  Ala  Ala  Arg  Gln  Ala  Lys  Leu
              50                        55                       60

ATG  GGC  AGC  GCT  GGC  AAT  GCG  ACC  ATC  TCC  ACA  GTC  AGC  TCC  ACG  CAG     240
Met  Gly  Ser  Ala  Gly  Asn  Ala  Thr  Ile  Ser  Thr  Val  Ser  Ser  Thr  Gln
```

```
                65                              70                              75                              80
CGG  AAG  CGC  CAG  CAA  TAT  GGG  AAA  CCC  AAG  AAG  CAG  GGC  AGC  ACC  ACG      288
Arg  Lys  Arg  Gln  Gln  Tyr  Gly  Lys  Pro  Lys  Lys  Gln  Gly  Ser  Thr  Thr
                         85                         90                         95

GCC  ACA  CGC  CCG  CCC  CGA  GCC  CTG  CTC  TGC  CTG  ACC  CTG  AAG  AAC  CCC      336
Ala  Thr  Arg  Pro  Pro  Arg  Ala  Leu  Leu  Cys  Leu  Thr  Leu  Lys  Asn  Pro
               100                        105                        110

ATC  CGG  AGG  GCC  TGC  ATC  AGC  ATT  GTC  GAA  TGG  AAA  CCA  TTT  GAA  ATA      384
Ile  Arg  Arg  Ala  Cys  Ile  Ser  Ile  Val  Glu  Trp  Lys  Pro  Phe  Glu  Ile
          115                        120                        125

ATT  ATT  TTA  CTG  ACT  ATT  TTT  GCC  AAT  TGT  GTG  GCC  TTA  GCG  ATC  TAT      432
Ile  Ile  Leu  Leu  Thr  Ile  Phe  Ala  Asn  Cys  Val  Ala  Leu  Ala  Ile  Tyr
     130                        135                        140

ATT  CCC  TTT  CCA  GAA  GAT  GAT  TCC  AAC  GCC  ACC  AAT  TCC  AAC  CTG  GAA      480
Ile  Pro  Phe  Pro  Glu  Asp  Asp  Ser  Asn  Ala  Thr  Asn  Ser  Asn  Leu  Glu
145                       150                        155                        160

CGA  GTG  GAA  TAT  CTC  TTT  CTC  ATA  ATT  TTT  ACG  GTG  GAA  GCG  TTT  TTA      528
Arg  Val  Glu  Tyr  Leu  Phe  Leu  Ile  Ile  Phe  Thr  Val  Glu  Ala  Phe  Leu
                    165                        170                        175

AAA  GTA  ATC  GCC  TAT  GGA  CTC  CTC  TTT  CAC  CCC  AAT  GCC  TAC  CTC  CGC      576
Lys  Val  Ile  Ala  Tyr  Gly  Leu  Leu  Phe  His  Pro  Asn  Ala  Tyr  Leu  Arg
               180                        185                        190

AAC  GGC  TGG  AAC  CTA  CTA  GAT  TTT  ATA  ATT  GTG  GTT  GTG  GGG  CTT  TTT      624
Asn  Gly  Trp  Asn  Leu  Leu  Asp  Phe  Ile  Ile  Val  Val  Val  Gly  Leu  Phe
          195                        200                        205

AGT  GCA  ATT  TTA  GAA  CAA  GCA  ACC  AAA  GCA  GAT  GGG  GCA  AAC  GCT  CTC      672
Ser  Ala  Ile  Leu  Glu  Gln  Ala  Thr  Lys  Ala  Asp  Gly  Ala  Asn  Ala  Leu
     210                        215                        220

GGA  GGG  AAA  GGG  GCC  GGA  TTT  GAT  GTG  AAG  GCG  CTG  AGG  GCC  TTC  CGC      720
Gly  Gly  Lys  Gly  Ala  Gly  Phe  Asp  Val  Lys  Ala  Leu  Arg  Ala  Phe  Arg
225                       230                        235                        240

GTG  CTG  CGC  CCC  CTG  CGG  CTG  GTG  TCC  GGA  GTC  CCA  AGT  CTC  CAG  GTG      768
Val  Leu  Arg  Pro  Leu  Arg  Leu  Val  Ser  Gly  Val  Pro  Ser  Leu  Gln  Val
                    245                        250                        255

GTC  CTG  AAT  TCC  ATC  ATC  AAG  GCC  ATG  GTC  CCC  CTG  CTG  CAC  ATC  GCC      816
Val  Leu  Asn  Ser  Ile  Ile  Lys  Ala  Met  Val  Pro  Leu  Leu  His  Ile  Ala
               260                        265                        270

CTG  CTT  GTG  CTG  TTT  GTC  ATC  ATC  ATC  TAC  GCC  ATC  ATC  GGC  TTG  GAG      864
Leu  Leu  Val  Leu  Phe  Val  Ile  Ile  Ile  Tyr  Ala  Ile  Ile  Gly  Leu  Glu
          275                        280                        285

CTC  TTC  ATG  GGG  AAG  ATG  CAC  AAG  ACC  TGC  TAC  AAC  CAG  GAG  GGC  ATA      912
Leu  Phe  Met  Gly  Lys  Met  His  Lys  Thr  Cys  Tyr  Asn  Gln  Glu  Gly  Ile
     290                        295                        300

GCA  GAT  GTT  CCA  GCA  GAA  GAT  GAC  CCT  TCC  CCT  TGT  GCG  CTG  GAA  ACG      960
Ala  Asp  Val  Pro  Ala  Glu  Asp  Asp  Pro  Ser  Pro  Cys  Ala  Leu  Glu  Thr
305                       310                        315                        320

GGC  CAC  GGG  CGG  CAG  TGC  CAG  AAC  GGC  ACG  GTG  TGC  AAG  CCC  GGC  TGG     1008
Gly  His  Gly  Arg  Gln  Cys  Gln  Asn  Gly  Thr  Val  Cys  Lys  Pro  Gly  Trp
                    325                        330                        335

GAT  GGT  CCC  AAG  CAC  GGC  ATC  ACC  AAC  TTT  GAC  AAC  TTT  GCC  TTC  GCC     1056
Asp  Gly  Pro  Lys  His  Gly  Ile  Thr  Asn  Phe  Asp  Asn  Phe  Ala  Phe  Ala
               340                        345                        350

ATG  CTC  ACG  GTG  TTC  CAG  TGC  ATC  ACC  ATG  GAG  GGC  TGG  ACG  GAC  GTG     1104
Met  Leu  Thr  Val  Phe  Gln  Cys  Ile  Thr  Met  Glu  Gly  Trp  Thr  Asp  Val
          355                        360                        365

CTG  TAC  TGG  GTC  AAT  GAT  GCC  GTA  GGA  AGG  GAC  TGG  CCC  TGG  ATC  TAT     1152
Leu  Tyr  Trp  Val  Asn  Asp  Ala  Val  Gly  Arg  Asp  Trp  Pro  Trp  Ile  Tyr
     370                        375                        380

TTT  GTT  ACA  CTA  ATC  ATC  ATA  GGG  TCA  TTT  TTT  GTA  CTT  AAC  TTG  GTT     1200
Phe  Val  Thr  Leu  Ile  Ile  Ile  Gly  Ser  Phe  Phe  Val  Leu  Asn  Leu  Val
```

-continued

| 385 | | | | | 390 | | | | | 395 | | | | | 400 | | |
|---|---|---|---|---|---|---|---|---|---|---|---|---|---|---|---|---|---|

```
CTC  GGT  GTG  CTT  AGC  GGA  GAG  TTT  TCC  AAA  GAG  AGG  GAG  AAG  GCC  AAG        1248
Leu  Gly  Val  Leu  Ser  Gly  Glu  Phe  Ser  Lys  Glu  Arg  Glu  Lys  Ala  Lys
               405                      410                     415

GCC  CGG  GGA  GAT  TTC  CAG  AAG  CTG  CGG  GAG  AAG  CAG  CAG  CTA  GAA  GAG        1296
Ala  Arg  Gly  Asp  Phe  Gln  Lys  Leu  Arg  Glu  Lys  Gln  Gln  Leu  Glu  Glu
               420                      425                     430

GAT  CTC  AAA  GGC  TAC  CTG  GAT  TGG  ATC  ACT  CAG  GCC  GAA  GAC  ATC  GNT        1344
Asp  Leu  Lys  Gly  Tyr  Leu  Asp  Trp  Ile  Thr  Gln  Ala  Glu  Asp  Ile  Xaa
               435                      440                     445

CCT  GAG  AAT  GAG  GAC  GAA  GGC  ATG  GAT  GAG  GAG  AAG  CCC  CGA  AAC  AGA        1392
Pro  Glu  Asn  Glu  Asp  Glu  Gly  Met  Asp  Glu  Glu  Lys  Pro  Arg  Asn  Arg
               450                      455                     460

GGC  ACT  CCG  GCG  GGC  ATG  CTT  GAT  CAG  AAG  AAA  GGG  AAG  TTT  GCT  TGG        1440
Gly  Thr  Pro  Ala  Gly  Met  Leu  Asp  Gln  Lys  Lys  Gly  Lys  Phe  Ala  Trp
465                      470                     475                     480

TTT  AGT  CAC  TCC  ACA  GAA  ACC  CAT  GTG  AGC  ATG  CCC  ACC  AGT  GAG  ACC        1488
Phe  Ser  His  Ser  Thr  Glu  Thr  His  Val  Ser  Met  Pro  Thr  Ser  Glu  Thr
                         485                     490                     495

GAG  TCC  GTC  AAC  ACC  GAA  AAC  GTG  GCT  GGA  GGT  GAC  ATC  GAG  GGA  GAA        1536
Glu  Ser  Val  Asn  Thr  Glu  Asn  Val  Ala  Gly  Gly  Asp  Ile  Glu  Gly  Glu
               500                      505                     510

AAC  TGC  GGG  GCC  AGG  CTG  GCC  CAC  CGG  ATC  TCC  AAG  TCA  AAG  TTC  AGC        1584
Asn  Cys  Gly  Ala  Arg  Leu  Ala  His  Arg  Ile  Ser  Lys  Ser  Lys  Phe  Ser
               515                      520                     525

CGC  TAC  TGG  CGC  CGG  TGG  AAT  CGG  TTC  TGC  AGA  AGG  AAG  TGC  CGC  GCC        1632
Arg  Tyr  Trp  Arg  Arg  Trp  Asn  Arg  Phe  Cys  Arg  Arg  Lys  Cys  Arg  Ala
               530                      535                     540

GCA  GTC  AAG  TCT  AAT  GTC  TTC  TAC  TGG  CTG  GTG  ATT  TTC  CTG  GTG  TTC        1680
Ala  Val  Lys  Ser  Asn  Val  Phe  Tyr  Trp  Leu  Val  Ile  Phe  Leu  Val  Phe
545                      550                     555                     560

CTC  AAC  ACG  CTC  ACC  ATT  GCC  TCT  GAG  CAC  TAC  AAC  CAG  CCC  AAC  TGG        1728
Leu  Asn  Thr  Leu  Thr  Ile  Ala  Ser  Glu  His  Tyr  Asn  Gln  Pro  Asn  Trp
                         565                     570                     575

CTC  ACA  GAA  GTC  CAA  GAC  ACG  GCA  AAC  AAG  GCC  CTG  CTG  GCC  CTG  TTC        1776
Leu  Thr  Glu  Val  Gln  Asp  Thr  Ala  Asn  Lys  Ala  Leu  Leu  Ala  Leu  Phe
               580                      585                     590

ACG  GCA  GAG  ATG  CTC  CTG  AAG  ATG  TAC  AGC  CTG  GGC  CTG  CAG  GCC  TAC        1824
Thr  Ala  Glu  Met  Leu  Leu  Lys  Met  Tyr  Ser  Leu  Gly  Leu  Gln  Ala  Tyr
               595                      600                     605

TTC  GTG  TCC  CTC  TTC  AAC  CGC  TTT  GAC  TGC  TTC  GTC  GTG  TGT  GGC  GGC        1872
Phe  Val  Ser  Leu  Phe  Asn  Arg  Phe  Asp  Cys  Phe  Val  Val  Cys  Gly  Gly
               610                      615                     620

ATC  CTG  GAG  ACC  ATC  CTG  GTG  GAG  ACC  AAG  ATC  ATG  TCC  CCA  CTG  GGC        1920
Ile  Leu  Glu  Thr  Ile  Leu  Val  Glu  Thr  Lys  Ile  Met  Ser  Pro  Leu  Gly
625                      630                     635                     640

ATC  TCC  GTG  CTC  AGA  TGC  GTC  CGG  CTG  CTG  AGG  ATT  TTC  AAG  ATC  ACG        1968
Ile  Ser  Val  Leu  Arg  Cys  Val  Arg  Leu  Leu  Arg  Ile  Phe  Lys  Ile  Thr
                         645                     650                     655

AGG  TAC  TGG  AAC  TCC  TTG  AGC  AAC  CTG  GTG  GCA  TCC  TTG  CTG  AAC  TCT        2016
Arg  Tyr  Trp  Asn  Ser  Leu  Ser  Asn  Leu  Val  Ala  Ser  Leu  Leu  Asn  Ser
               660                      665                     670

GTG  CGC  TCC  ATC  GCC  TCC  CTG  CTC  CTT  CTC  CTC  TTC  CTC  TTC  ATC  ATC        2064
Val  Arg  Ser  Ile  Ala  Ser  Leu  Leu  Leu  Leu  Leu  Phe  Leu  Phe  Ile  Ile
               675                      680                     685

ATC  TTC  TCC  CTC  CTG  GGG  ATG  CAG  CTC  TTT  GGA  GGA  AAG  TTC  AAC  TTT        2112
Ile  Phe  Ser  Leu  Leu  Gly  Met  Gln  Leu  Phe  Gly  Gly  Lys  Phe  Asn  Phe
               690                      695                     700

GAT  GAG  ATG  CAG  ACC  CGG  AGG  AGC  ACA  TTC  GAT  AAC  TTC  CCC  CAG  TCC        2160
Asp  Glu  Met  Gln  Thr  Arg  Arg  Ser  Thr  Phe  Asp  Asn  Phe  Pro  Gln  Ser
```

| | | | | | | | | | | | | | | | | |
|---|---|---|---|---|---|---|---|---|---|---|---|---|---|---|---|---|
|705| | | | |710| | | | |715| | | | |720| |
|CTC|CTC|ACT|GTG|TTT|CAG|ATC|CTG|ACC|GGG|GAG|GAC|TGG|AAT|TCG|GTG|2208|
|Leu|Leu|Thr|Val|Phe|Gln|Ile|Leu|Thr|Gly|Glu|Asp|Trp|Asn|Ser|Val| |
| | | | |725| | | | |730| | | | |735| | |
|ATG|TAT|GAT|GGG|ATC|ATG|GCT|TAT|GGG|GGC|CCC|TCT|TTT|CCA|GGG|ATG|2256|
|Met|Tyr|Asp|Gly|Ile|Met|Ala|Tyr|Gly|Gly|Pro|Ser|Phe|Pro|Gly|Met| |
| | | |740| | | | |745| | | | |750| | | |
|TTA|GTC|TGT|ATT|TAC|TTC|ATC|ATC|CTC|TTC|ATC|TCT|GGA|AAC|TAT|ATC|2304|
|Leu|Val|Cys|Ile|Tyr|Phe|Ile|Ile|Leu|Phe|Ile|Ser|Gly|Asn|Tyr|Ile| |
| | |755| | | | |760| | | | |765| | | | |
|CTA|CTG|AAT|GTG|TTC|TTG|GCC|ATT|GCT|GTG|GAC|AAC|CTG|GCT|GAT|GCT|2352|
|Leu|Leu|Asn|Val|Phe|Leu|Ala|Ile|Ala|Val|Asp|Asn|Leu|Ala|Asp|Ala| |
| |770| | | | |775| | | | |780| | | | | |
|GAG|AGC|CTC|ACA|TCT|GCC|CTA|AAG|GAG|GAG|GAA|GAG|GAG|AAG|GAG|AGA|2400|
|Glu|Ser|Leu|Thr|Ser|Ala|Leu|Lys|Glu|Glu|Glu|Glu|Glu|Lys|Glu|Arg| |
|785| | | | |790| | | | |795| | | | |800| |
|AAG|AAG|CTG|GCC|AGG|ACT|GCC|AGC|CCA|GAG|AAG|AAA|CAA|GAG|TTG|GTG|2448|
|Lys|Lys|Leu|Ala|Arg|Thr|Ala|Ser|Pro|Glu|Lys|Lys|Gln|Glu|Leu|Val| |
| | | | |805| | | | |810| | | | |815| | |
|GAG|AAG|CCG|GCA|GTG|GGG|GAA|TCC|AAG|GAG|GAG|AAG|ATT|GAG|CTG|AAA|2496|
|Glu|Lys|Pro|Ala|Val|Gly|Glu|Ser|Lys|Glu|Glu|Lys|Ile|Glu|Leu|Lys| |
| | | |820| | | | |825| | | | |830| | | |
|TCC|ATC|ACG|GCT|GAC|GGA|GAG|TCT|CCA|CCC|GCC|ACC|AAG|ATC|AAC|ATG|2544|
|Ser|Ile|Thr|Ala|Asp|Gly|Glu|Ser|Pro|Pro|Ala|Thr|Lys|Ile|Asn|Met| |
| | |835| | | | |840| | | | |845| | | | |
|GAT|GAC|CTC|CAG|CCC|AAT|GAA|AAT|GAG|GAT|AAG|AGC|CCC|TAC|CCC|AAC|2592|
|Asp|Asp|Leu|Gln|Pro|Asn|Glu|Asn|Glu|Asp|Lys|Ser|Pro|Tyr|Pro|Asn| |
| |850| | | | |855| | | | |860| | | | | |
|CCA|GAA|ACT|ACA|GGA|GAA|GAG|GAT|GAG|GAG|GAG|CCA|GAG|ATG|CCT|GTC|2640|
|Pro|Glu|Thr|Thr|Gly|Glu|Glu|Asp|Glu|Glu|Glu|Pro|Glu|Met|Pro|Val| |
|865| | | | |870| | | | |875| | | | |880| |
|GGC|CCT|CGC|CCA|CGA|CCA|CTC|TCT|GAG|CTT|CAC|CTT|AAG|GAA|AAG|GCA|2688|
|Gly|Pro|Arg|Pro|Arg|Pro|Leu|Ser|Glu|Leu|His|Leu|Lys|Glu|Lys|Ala| |
| | | | |885| | | | |890| | | | |895| | |
|GTG|CCC|ATG|CCA|GAA|GCC|AGC|GCG|TTT|TTC|ATC|TTC|AGC|TCT|AAC|AAC|2736|
|Val|Pro|Met|Pro|Glu|Ala|Ser|Ala|Phe|Phe|Ile|Phe|Ser|Ser|Asn|Asn| |
| | | |900| | | | |905| | | | |910| | | |
|AGG|TTT|CGC|CTC|CAG|TGC|CAC|CGC|ATT|GTC|AAT|GAC|ACG|ATC|TTC|ACC|2784|
|Arg|Phe|Arg|Leu|Gln|Cys|His|Arg|Ile|Val|Asn|Asp|Thr|Ile|Phe|Thr| |
| | |915| | | | |920| | | | |925| | | | |
|AAC|CTG|ATC|CTC|TTC|TTC|ATT|CTG|CTC|AGC|AGC|ATT|TCC|CTG|GCT|GCT|2832|
|Asn|Leu|Ile|Leu|Phe|Phe|Ile|Leu|Leu|Ser|Ser|Ile|Ser|Leu|Ala|Ala| |
| |930| | | | |935| | | | |940| | | | | |
|GAG|GAC|CCG|GTC|CAG|CAC|ACC|TCC|TTC|AGG|AAC|CAT|ATT|CTG|TTT|TAT|2880|
|Glu|Asp|Pro|Val|Gln|His|Thr|Ser|Phe|Arg|Asn|His|Ile|Leu|Phe|Tyr| |
|945| | | | |950| | | | |955| | | | |960| |
|TTT|GAT|ATT|GTT|TTT|ACC|ACC|ATT|TTC|ACC|ATT|GAA|ATT|GCT|CTG|AAG|2928|
|Phe|Asp|Ile|Val|Phe|Thr|Thr|Ile|Phe|Thr|Ile|Glu|Ile|Ala|Leu|Lys| |
| | | | |965| | | | |970| | | | |975| | |
|ATG|ACT|GCT|TAT|GGG|GCT|TTC|TTG|CAC|AAG|GGT|TCT|TTC|TGC|CGG|AAC|2976|
|Met|Thr|Ala|Tyr|Gly|Ala|Phe|Leu|His|Lys|Gly|Ser|Phe|Cys|Arg|Asn| |
| | | |980| | | | |985| | | | |990| | | |
|TAC|TTC|AAC|ATC|CTG|GAC|CTG|CTG|GTG|GTC|AGC|GTG|TCC|CTC|ATC|TCC|3024|
|Tyr|Phe|Asn|Ile|Leu|Asp|Leu|Leu|Val|Val|Ser|Val|Ser|Leu|Ile|Ser| |
| | |995| | | | |1000| | | | |1005| | | | |
|TTT|GGC|ATC|CAG|TCC|AGT|GCA|ATC|AAT|GTC|GTG|AAG|ATC|TTG|CGA|GTC|3072|
|Phe|Gly|Ile|Gln|Ser|Ser|Ala|Ile|Asn|Val|Val|Lys|Ile|Leu|Arg|Val| |
| |1010| | | | |1015| | | | |1020| | | | | |
|CTG|CGA|GTA|CTC|AGG|CCC|CTG|AGG|GCC|ATC|AAC|AGG|GCC|AAG|GGG|CTA|3120|
|Leu|Arg|Val|Leu|Arg|Pro|Leu|Arg|Ala|Ile|Asn|Arg|Ala|Lys|Gly|Leu| |

|   |   |   |   |   |   |   |   |   |   |   |   |   |   |   |   |      |
|---|---|---|---|---|---|---|---|---|---|---|---|---|---|---|---|------|
| 1025 | | | | | 1030 | | | | | 1035 | | | | | 1040 | |

```
AAG  CAT  GTG  GTT  CAG  TGT  GTG  TTT  GTC  GCC  ATC  CGG  ACC  ATC  GGG  AAC        3168
Lys  His  Val  Val  Gln  Cys  Val  Phe  Val  Ala  Ile  Arg  Thr  Ile  Gly  Asn
               1045                     1050                     1055

ATC  GTG  ATT  GTC  ACC  ACC  CTG  CTG  CAG  TTC  ATG  TTT  GCC  TGC  ATC  GGG        3216
Ile  Val  Ile  Val  Thr  Thr  Leu  Leu  Gln  Phe  Met  Phe  Ala  Cys  Ile  Gly
               1060                     1065                     1070

GTC  CAG  CTC  TTC  AAG  GGA  AAG  CTG  TAC  ACC  TGT  TCA  GAC  AGT  TCC  AAG        3264
Val  Gln  Leu  Phe  Lys  Gly  Lys  Leu  Tyr  Thr  Cys  Ser  Asp  Ser  Ser  Lys
               1075                     1080                     1085

CAG  ACA  GAG  GCG  GAA  TGC  AAG  GGC  AAC  TAC  ATC  ACG  TAC  AAA  GAC  GGG        3312
Gln  Thr  Glu  Ala  Glu  Cys  Lys  Gly  Asn  Tyr  Ile  Thr  Tyr  Lys  Asp  Gly
     1090                     1095                     1100

GAG  GTT  GAC  CAC  CCC  ATC  ATC  CAA  CCC  CGC  AGC  TGG  GAG  AAC  AGC  AAG        3360
Glu  Val  Asp  His  Pro  Ile  Ile  Gln  Pro  Arg  Ser  Trp  Glu  Asn  Ser  Lys
1105                     1110                     1115                     1120

TTT  GAC  TTT  GAC  AAT  GTT  CTG  GCA  GCC  ATG  ATG  GCC  CTC  TTC  ACC  GTC        3408
Phe  Asp  Phe  Asp  Asn  Val  Leu  Ala  Ala  Met  Met  Ala  Leu  Phe  Thr  Val
                         1125                     1130                     1135

TCC  ACC  TTC  GAA  GGG  TGG  CCA  GAG  CTG  CTG  TAC  CGC  TCC  ATC  GAC  TCC        3456
Ser  Thr  Phe  Glu  Gly  Trp  Pro  Glu  Leu  Leu  Tyr  Arg  Ser  Ile  Asp  Ser
               1140                     1145                     1150

CAC  ACG  GAA  GAC  AAG  GGC  CCC  ATC  TAC  AAC  TAC  CGT  GTG  GAG  ATC  TCC        3504
His  Thr  Glu  Asp  Lys  Gly  Pro  Ile  Tyr  Asn  Tyr  Arg  Val  Glu  Ile  Ser
               1155                     1160                     1165

ATC  TTC  TTC  ATC  ATC  TAC  ATC  ATC  ATC  ATC  GCC  TTC  TTC  ATG  ATG  AAC        3552
Ile  Phe  Phe  Ile  Ile  Tyr  Ile  Ile  Ile  Ile  Ala  Phe  Phe  Met  Met  Asn
               1170                     1175                     1180

ATC  TTC  GTG  GGC  TTC  GTC  ATC  GTC  ACC  TTT  CAG  GAG  CAG  GGG  GAG  CAG        3600
Ile  Phe  Val  Gly  Phe  Val  Ile  Val  Thr  Phe  Gln  Glu  Gln  Gly  Glu  Gln
1185                     1190                     1195                     1200

GAG  TAC  AAG  AAC  TGT  GAG  CTG  GAC  AAG  AAC  CAG  CGA  CAG  TGC  GTG  GAA        3648
Glu  Tyr  Lys  Asn  Cys  Glu  Leu  Asp  Lys  Asn  Gln  Arg  Gln  Cys  Val  Glu
                         1205                     1210                     1215

TAC  GCC  CTC  AAG  GCC  CGG  CCC  CTG  CGG  AGG  TAC  ATC  CCC  AAG  AAC  CAG        3696
Tyr  Ala  Leu  Lys  Ala  Arg  Pro  Leu  Arg  Arg  Tyr  Ile  Pro  Lys  Asn  Gln
               1220                     1225                     1230

CAC  CAG  TAC  AAA  GTG  TGG  TAC  GTG  GTC  AAC  TCC  ACC  TAC  TTC  GAG  TAC        3744
His  Gln  Tyr  Lys  Val  Trp  Tyr  Val  Val  Asn  Ser  Thr  Tyr  Phe  Glu  Tyr
               1235                     1240                     1245

CTG  ATG  TTC  GTC  CTC  ATC  CTG  CTC  AAC  ACC  ATC  TGC  CTG  GCC  ATG  CAG        3792
Leu  Met  Phe  Val  Leu  Ile  Leu  Leu  Asn  Thr  Ile  Cys  Leu  Ala  Met  Gln
     1250                     1255                     1260

CAC  TAC  GGC  CAG  AGC  TGC  CTG  TTC  AAA  ATC  GCC  ATG  AAC  ATC  CTC  AAC        3840
His  Tyr  Gly  Gln  Ser  Cys  Leu  Phe  Lys  Ile  Ala  Met  Asn  Ile  Leu  Asn
1265                     1270                     1275                     1280

ATG  CTC  TTC  ACT  GGC  CTC  TTC  ACC  GTG  GAG  ATG  ATC  CTG  AAG  CTC  ATT        3888
Met  Leu  Phe  Thr  Gly  Leu  Phe  Thr  Val  Glu  Met  Ile  Leu  Lys  Leu  Ile
                         1285                     1290                     1295

GCC  TTC  AAA  CCC  AAG  GGT  TAC  TTT  AGT  GAT  CCC  TGG  AAT  GTT  TTT  GAC        3936
Ala  Phe  Lys  Pro  Lys  Gly  Tyr  Phe  Ser  Asp  Pro  Trp  Asn  Val  Phe  Asp
               1300                     1305                     1310

TTC  CTC  ATC  GTA  ATT  GGC  AGC  ATA  ATT  GAC  GTC  ATT  CTC  AGT  GAG  ACT        3984
Phe  Leu  Ile  Val  Ile  Gly  Ser  Ile  Ile  Asp  Val  Ile  Leu  Ser  Glu  Thr
               1315                     1320                     1325

AAT  CCA  GCT  GAA  CAT  ACC  CAA  TGC  TCT  CCC  TCT  ATG  AAC  GCA  GAG  GAA        4032
Asn  Pro  Ala  Glu  His  Thr  Gln  Cys  Ser  Pro  Ser  Met  Asn  Ala  Glu  Glu
     1330                     1335                     1340

AAC  TCC  CGC  ATC  TCC  ATC  ACC  TTC  TTC  CGC  CTG  TTC  CGG  GTC  ATG  CGT        4080
Asn  Ser  Arg  Ile  Ser  Ile  Thr  Phe  Phe  Arg  Leu  Phe  Arg  Val  Met  Arg
```

-continued

| | | | | |
|---|---|---|---|---|
| 1345 | | 1350 | 1355 | 1360 |

```
CTG  GTG  AAG  CTG  CTG  AGC  CGT  GGG  GAG  GGC  ATC  CGG  ACG  CTG  CTG  TGG    4128
Leu  Val  Lys  Leu  Leu  Ser  Arg  Gly  Glu  Gly  Ile  Arg  Thr  Leu  Leu  Trp
               1365                     1370                     1375

ACC  TTC  ATC  AAG  TCC  TTC  CAG  GCC  CTG  CCC  TAT  GTG  GCC  CTC  CTG  ATC    4176
Thr  Phe  Ile  Lys  Ser  Phe  Gln  Ala  Leu  Pro  Tyr  Val  Ala  Leu  Leu  Ile
               1380                     1385                     1390

GTG  ATG  CTG  TTC  TTC  ATC  TAC  GCG  GTG  ATC  GGG  ATG  CAG  GTG  TTT  GGG    4224
Val  Met  Leu  Phe  Phe  Ile  Tyr  Ala  Val  Ile  Gly  Met  Gln  Val  Phe  Gly
     1395                     1400                     1405

AAA  ATT  GCC  CTG  AAT  GAT  ACC  ACA  GAG  ATC  AAC  CGG  AAC  AAC  AAC  TTT    4272
Lys  Ile  Ala  Leu  Asn  Asp  Thr  Thr  Glu  Ile  Asn  Arg  Asn  Asn  Asn  Phe
     1410                     1415                     1420

CAG  ACC  TTC  CCC  CAG  GCC  GTG  CTG  CTC  CTC  TTC  AGG  TGT  GCC  ACC  GGG    4320
Gln  Thr  Phe  Pro  Gln  Ala  Val  Leu  Leu  Leu  Phe  Arg  Cys  Ala  Thr  Gly
1425                     1430                     1435                     1440

GAG  GCC  TGG  CAG  GAC  ATC  ATG  CTG  GCC  TGC  ATG  CCA  GGC  AAG  AAG  TGT    4368
Glu  Ala  Trp  Gln  Asp  Ile  Met  Leu  Ala  Cys  Met  Pro  Gly  Lys  Lys  Cys
               1445                     1450                     1455

GCC  CCA  GAG  TCC  GAG  CCC  AGC  AAC  AGC  ACG  GAG  GGT  GAA  ACA  CCC  TGT    4416
Ala  Pro  Glu  Ser  Glu  Pro  Ser  Asn  Ser  Thr  Glu  Gly  Glu  Thr  Pro  Cys
               1460                     1465                     1470

GGT  AGC  AGC  TTT  GCT  GTC  TTC  TAC  TTC  ATC  AGC  TTC  TAC  ATG  CGC  TGT    4464
Gly  Ser  Ser  Phe  Ala  Val  Phe  Tyr  Phe  Ile  Ser  Phe  Tyr  Met  Arg  Cys
               1475                     1480                     1485

GCC  TTC  CTG  ATC  ATC  AAC  CTC  TTT  GTA  GCT  GTC  ATC  ATG  GAC  AAC  TTT    4512
Ala  Phe  Leu  Ile  Ile  Asn  Leu  Phe  Val  Ala  Val  Ile  Met  Asp  Asn  Phe
               1490                     1495                     1500

GAC  TAC  CTG  ACA  AGG  GAC  TGG  TCC  ATC  CTT  GGT  CCC  CAC  CAC  CTG  GAT    4560
Asp  Tyr  Leu  Thr  Arg  Asp  Trp  Ser  Ile  Leu  Gly  Pro  His  His  Leu  Asp
1505                     1510                     1515                     1520

GAG  TTT  AAA  AGA  ATC  TGG  GCA  GAG  TAT  GAC  CCT  GAA  GCC  AAG  GGT  CGT    4608
Glu  Phe  Lys  Arg  Ile  Trp  Ala  Glu  Tyr  Asp  Pro  Glu  Ala  Lys  Gly  Arg
               1525                     1530                     1535

ATC  AAA  CAC  CTG  GAT  GTG  GTG  ACC  CTC  CTC  CGG  CGG  ATT  CAG  CCG  CCA    4656
Ile  Lys  His  Leu  Asp  Val  Val  Thr  Leu  Leu  Arg  Arg  Ile  Gln  Pro  Pro
               1540                     1545                     1550

CTA  GGT  TTT  GGG  AAG  CTG  TGC  CCT  CAC  CGC  GTG  GCT  TGC  AAA  CGC  CTG    4704
Leu  Gly  Phe  Gly  Lys  Leu  Cys  Pro  His  Arg  Val  Ala  Cys  Lys  Arg  Leu
               1555                     1560                     1565

GTC  TCC  ATG  AAC  ATG  CCT  CTG  AAC  AGC  GAC  GGG  ACA  GTC  ATG  TTC  AAT    4752
Val  Ser  Met  Asn  Met  Pro  Leu  Asn  Ser  Asp  Gly  Thr  Val  Met  Phe  Asn
1570                     1575                     1580

GCC  ACC  CTG  TTT  GCC  CTG  GTC  AGG  ACG  GCC  CTG  AGG  ATC  AAA  ACA  GAA    4800
Ala  Thr  Leu  Phe  Ala  Leu  Val  Arg  Thr  Ala  Leu  Arg  Ile  Lys  Thr  Glu
1585                     1590                     1595                     1600

GGG  AAC  CTA  GAA  CAA  GCC  AAT  GAG  GAG  CTG  CGG  GCG  ATC  ATC  AAG  AAG    4848
Gly  Asn  Leu  Glu  Gln  Ala  Asn  Glu  Glu  Leu  Arg  Ala  Ile  Ile  Lys  Lys
                         1605                    1610                    1615

ATC  TGG  AAG  CGG  ACC  AGC  ATG  AAG  CTG  CTG  GAC  CAG  GTG  GTG  CCC  CCT    4896
Ile  Trp  Lys  Arg  Thr  Ser  Met  Lys  Leu  Leu  Asp  Gln  Val  Val  Pro  Pro
               1620                     1625                     1630

GCA  GGT  GAT  GAT  GAG  GTC  ACC  GTT  GGC  AAG  TTC  TAC  GCC  ACG  TTC  CTG    4944
Ala  Gly  Asp  Asp  Glu  Val  Thr  Val  Gly  Lys  Phe  Tyr  Ala  Thr  Phe  Leu
               1635                     1640                     1645

ATC  CAG  GAG  TAC  TTC  CGG  AAG  TTC  AAG  AAG  CGC  AAA  GAG  CAG  GGC  CTT    4992
Ile  Gln  Glu  Tyr  Phe  Arg  Lys  Phe  Lys  Lys  Arg  Lys  Glu  Gln  Gly  Leu
     1650                     1655                     1660

GTG  GGC  AAG  CCC  TCC  CAG  AGG  AAC  GCG  CTG  TCT  CTG  CAG  GCT  GGC  TTG    5040
Val  Gly  Lys  Pro  Ser  Gln  Arg  Asn  Ala  Leu  Ser  Leu  Gln  Ala  Gly  Leu
```

|     |     |     |     |     |     |     |     |     |     |     |     |     |     |     |     |      |
|---|---|---|---|---|---|---|---|---|---|---|---|---|---|---|---|---|
| 1665 | | | | | 1670 | | | | | 1675 | | | | | 1680 | |
| CGC | ACA | CTG | CAT | GAC | ATC | GGG | CCT | GAG | ATC | CGA | CGG | GCC | ATC | TCT | GGA | 5088 |
| Arg | Thr | Leu | His | Asp | Ile | Gly | Pro | Glu | Ile | Arg | Arg | Ala | Ile | Ser | Gly | |
| | | | | 1685 | | | | | 1690 | | | | | 1695 | | |
| GAT | CTC | ACC | GCT | GAG | GAG | GAG | CTG | GAC | AAG | GCC | ATG | AAG | GAG | GCT | GTG | 5136 |
| Asp | Leu | Thr | Ala | Glu | Glu | Glu | Leu | Asp | Lys | Ala | Met | Lys | Glu | Ala | Val | |
| | | | | 1700 | | | | | 1705 | | | | | 1710 | | |
| TCC | GCT | GCT | TCT | GAA | GAT | GAC | ATC | TTC | AGG | AGG | GCC | GGT | GGC | CTG | TTC | 5184 |
| Ser | Ala | Ala | Ser | Glu | Asp | Asp | Ile | Phe | Arg | Arg | Ala | Gly | Gly | Leu | Phe | |
| | | | | 1715 | | | | | 1720 | | | | | 1725 | | |
| GGC | AAC | CAC | GTC | AGC | TAC | TAC | CAA | AGC | GAC | GGC | CGG | AGC | GCC | TTC | CCC | 5232 |
| Gly | Asn | His | Val | Ser | Tyr | Tyr | Gln | Ser | Asp | Gly | Arg | Ser | Ala | Phe | Pro | |
| | | | | 1730 | | | | | 1735 | | | | | 1740 | | |
| CAG | ACC | TTC | ACC | ACT | CAG | CGC | CCG | CTG | CAC | ATC | AAC | AAG | GCG | GGC | AGC | 5280 |
| Gln | Thr | Phe | Thr | Thr | Gln | Arg | Pro | Leu | His | Ile | Asn | Lys | Ala | Gly | Ser | |
| 1745 | | | | | 1750 | | | | | 1755 | | | | | 1760 | |
| AGC | CAG | GGC | GAC | ACT | GAG | TCG | CCA | TCC | CAC | GAG | AAG | CTG | GTG | GAC | TCC | 5328 |
| Ser | Gln | Gly | Asp | Thr | Glu | Ser | Pro | Ser | His | Glu | Lys | Leu | Val | Asp | Ser | |
| | | | | 1765 | | | | | 1770 | | | | | 1775 | | |
| ACC | TTC | ACC | CCG | AGC | AGC | TAC | TCG | TCC | ACC | GGC | TCC | AAC | GCC | AAC | ATC | 5376 |
| Thr | Phe | Thr | Pro | Ser | Ser | Tyr | Ser | Ser | Thr | Gly | Ser | Asn | Ala | Asn | Ile | |
| | | | | 1780 | | | | | 1785 | | | | | 1790 | | |
| AAC | AAC | GCC | AAC | AAC | ACC | GCC | CTG | GGT | CGC | CTC | CCT | CGC | CCC | GCC | GGC | 5424 |
| Asn | Asn | Ala | Asn | Asn | Thr | Ala | Leu | Gly | Arg | Leu | Pro | Arg | Pro | Ala | Gly | |
| | | | | 1795 | | | | | 1800 | | | | | 1805 | | |
| TAC | CCC | AGC | ACA | GTC | AGC | ACT | GTG | GAG | GGC | CAC | GGG | CCC | CCC | TTG | TCC | 5472 |
| Tyr | Pro | Ser | Thr | Val | Ser | Thr | Val | Glu | Gly | His | Gly | Pro | Pro | Leu | Ser | |
| | | | | 1810 | | | | | 1815 | | | | | 1820 | | |
| CCT | GCC | ATC | CGG | GTG | CAG | GAG | GTG | GCG | TGG | AAG | CTC | AGC | TCC | AAC | AGG | 5520 |
| Pro | Ala | Ile | Arg | Val | Gln | Glu | Val | Ala | Trp | Lys | Leu | Ser | Ser | Asn | Arg | |
| 1825 | | | | | 1830 | | | | | 1835 | | | | | 1840 | |
| TGC | CAC | TCC | CGG | GAG | AGC | CAG | GCA | GCC | ATG | GCG | CGT | CAG | GAG | GAG | ACG | 5568 |
| Cys | His | Ser | Arg | Glu | Ser | Gln | Ala | Ala | Met | Ala | Arg | Gln | Glu | Glu | Thr | |
| | | | | 1845 | | | | | 1850 | | | | | 1855 | | |
| TCT | CAG | GAT | GAG | ACC | TAT | GAA | GTG | AAG | ATG | AAC | CAT | GAC | ACG | GAG | GCC | 5616 |
| Ser | Gln | Asp | Glu | Thr | Tyr | Glu | Val | Lys | Met | Asn | His | Asp | Thr | Glu | Ala | |
| | | | | 1860 | | | | | 1865 | | | | | 1870 | | |
| TGC | AGT | GAG | CCC | AGC | CTG | CTC | TCC | ACA | GAG | ATG | CTC | TCC | TAC | CAG | GAT | 5664 |
| Cys | Ser | Glu | Pro | Ser | Leu | Leu | Ser | Thr | Glu | Met | Leu | Ser | Tyr | Gln | Asp | |
| | | | | 1875 | | | | | 1880 | | | | | 1885 | | |
| GAC | GAA | AAT | CGG | CAA | CTG | ACG | CTC | CCA | GAG | GAG | GAC | AAG | AGG | GAC | ATC | 5712 |
| Asp | Glu | Asn | Arg | Gln | Leu | Thr | Leu | Pro | Glu | Glu | Asp | Lys | Arg | Asp | Ile | |
| | | | | 1890 | | | | | 1895 | | | | | 1900 | | |
| CGG | CAA | TCT | CCG | AAG | AGG | GGT | TTC | CTC | CGC | TCT | TCC | TCA | CTA | GGT | CGA | 5760 |
| Arg | Gln | Ser | Pro | Lys | Arg | Gly | Phe | Leu | Arg | Ser | Ser | Ser | Leu | Gly | Arg | |
| 1905 | | | | | 1910 | | | | | 1915 | | | | | 1920 | |
| AGG | GCC | TCC | TTC | CAC | CTG | GAA | TGT | CTG | AAG | CGA | CAG | AAG | GAC | CGA | GGG | 5808 |
| Arg | Ala | Ser | Phe | His | Leu | Glu | Cys | Leu | Lys | Arg | Gln | Lys | Asp | Arg | Gly | |
| | | | | 1925 | | | | | 1930 | | | | | 1935 | | |
| GGA | GAC | ATC | TCT | CAG | AAG | ACA | GTC | CTG | CCC | TTG | CAT | CTG | GTT | CAT | CAT | 5856 |
| Gly | Asp | Ile | Ser | Gln | Lys | Thr | Val | Leu | Pro | Leu | His | Leu | Val | His | His | |
| | | | | 1940 | | | | | 1945 | | | | | 1950 | | |
| CAG | GCA | TTG | GCA | GTG | GCA | GGC | CTG | AGC | CCC | CTC | CTC | CAG | AGA | AGC | CAT | 5904 |
| Gln | Ala | Leu | Ala | Val | Ala | Gly | Leu | Ser | Pro | Leu | Leu | Gln | Arg | Ser | His | |
| | | | | 1955 | | | | | 1960 | | | | | 1965 | | |

( 2 ) INFORMATION FOR SEQ ID NO:4:

( i ) SEQUENCE CHARACTERISTICS:
        ( A ) LENGTH: 132 base pairs
        ( B ) TYPE: nucleic acid (C) STRANDEDNESS: double
(D) TOPOLOGY: linear (ii) MOLECULE TYPE: DNA (genomic)

(xi) SEQUENCE DESCRIPTION: SEQ ID NO:4:

AGACCACGGC TTCCTCGAAT CTTGCGCGAA GCCGCCGGCC TCGGAGGAGG GATTAATCCA  60

GACCCGCCGG GGGGTGTTTT CACATTTCTT CCTCTTCGTG GCTGCTCCTC CTATTAAAAC  120

CATTTTTGGT CC  132

(2) INFORMATION FOR SEQ ID NO:5:

(i) SEQUENCE CHARACTERISTICS:
(A) LENGTH: 89 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:5:

CGCTGAGGGC CTTCCGCGTG CTGCGCCCCC TGCGGCTGGT GTCCGGAGTC CCAAGTCTCC  60

AGGTGGTCCT GAATTCCATC ATCAAGGCC  89

(2) INFORMATION FOR SEQ ID NO:6:

(i) SEQUENCE CHARACTERISTICS:
(A) LENGTH: 84 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..84
(D) OTHER INFORMATION: /note= "An alternative exon of alpha-1C."

(xi) SEQUENCE DESCRIPTION: SEQ ID NO:6:

| CAC | TAT | TTC | TGT | GAT | GCA | TGG | AAT | ACA | TTT | GAC | GCC | TTG | ATT | GTT | GTG | 48 |
| His | Tyr | Phe | Cys | Asp | Ala | Trp | Asn | Thr | Phe | Asp | Ala | Leu | Ile | Val | Val | |
| 1 | | | | 5 | | | | | 10 | | | | | 15 | | |

| GGT | AGC | ATT | GTT | GAT | ATA | GCA | ATC | ACC | GAG | GTA | AAC | 84 |
| Gly | Ser | Ile | Val | Asp | Ile | Ala | Ile | Thr | Glu | Val | Asn | |
| | | | 20 | | | | | 25 | | | | |

(2) INFORMATION FOR SEQ ID NO:7:

(i) SEQUENCE CHARACTERISTICS:
(A) LENGTH: 7362 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 144..7163

(ix) FEATURE:
(A) NAME/KEY: 5'UTR
(B) LOCATION: 1..143

(ix) FEATURE:
(A) NAME/KEY: 3'UTR
(B) LOCATION: 7161..7362

( x i ) SEQUENCE DESCRIPTION: SEQ ID NO:7:

| | | | | | | |
|---|---|---|---|---|---|---|
| GCGGCGGCGG | CTGCGGCGGT | GGGGCCGGGC | GAGGTCCGTG | CGGTCCCGGC | GGCTCCGTGG | 60 |
| CTGCTCCGCT | CTGAGCGCCT | GCGCGCCCCG | CGCCCTCCCT | GCCGGGGCCG | CTGGGCCGGG | 120 |

| | | | | | | | | | | |
|---|---|---|---|---|---|---|---|---|---|---|
| GATGCACGCG | GGGCCCGGGA | GCC | ATG | GTC | CGC | TTC | GGG | GAC | GAG | CTG | GGC | 170 |
| | | | Met | Val | Arg | Phe | Gly | Asp | Glu | Leu | Gly |
| | | | 1 | | | | 5 | | | | |

| GGC | CGC | TAT | GGA | GGC | CCC | GGC | GGA | GAG | CGG | CCG | GGC | GGC | GGG | 218 |
|---|---|---|---|---|---|---|---|---|---|---|---|---|---|---|
| Gly | Arg | Tyr | Gly | Gly | Pro | Gly | Gly | Gly | Glu | Arg | Ala | Arg | Gly | Gly | Gly |
| 10 | | | | 15 | | | | | 20 | | | | | 25 |

| GCC | GGC | GGG | GCG | GGG | GGC | CCG | GGT | CCC | GGG | GGG | CTG | CAG | CCC | GGC | CAG | 266 |
|---|---|---|---|---|---|---|---|---|---|---|---|---|---|---|---|---|
| Ala | Gly | Gly | Ala | Gly | Gly | Pro | Gly | Pro | Gly | Gly | Leu | Gln | Pro | Gly | Gln |
| | | | | 30 | | | | | 35 | | | | | 40 | |

| CGG | GTC | CTC | TAC | AAG | CAA | TCG | ATC | GCG | CAG | CGC | GCG | CGG | ACC | ATG | GCG | 314 |
|---|---|---|---|---|---|---|---|---|---|---|---|---|---|---|---|---|
| Arg | Val | Leu | Tyr | Lys | Gln | Ser | Ile | Ala | Gln | Arg | Ala | Arg | Thr | Met | Ala |
| | | | | 45 | | | | | 50 | | | | | 55 | |

| CTG | TAC | AAC | CCC | ATC | CCG | GTC | AAG | CAG | AAC | TGC | TTC | ACC | GTC | AAC | CGC | 362 |
|---|---|---|---|---|---|---|---|---|---|---|---|---|---|---|---|---|
| Leu | Tyr | Asn | Pro | Ile | Pro | Val | Lys | Gln | Asn | Cys | Phe | Thr | Val | Asn | Arg |
| | | | 60 | | | | | 65 | | | | | 70 | | |

| TCG | CTC | TTC | GTC | TTC | AGC | GAG | GAC | AAC | GTC | GTC | CGC | AAA | TAC | GCG | AAG | 410 |
|---|---|---|---|---|---|---|---|---|---|---|---|---|---|---|---|---|
| Ser | Leu | Phe | Val | Phe | Ser | Glu | Asp | Asn | Val | Val | Arg | Lys | Tyr | Ala | Lys |
| | 75 | | | | | 80 | | | | | 85 | | | | | |

| CGC | ATC | ACC | GAG | TGG | CCT | CCA | TTC | GAG | AAT | ATG | ATC | CTG | GCC | ACC | ATC | 458 |
|---|---|---|---|---|---|---|---|---|---|---|---|---|---|---|---|---|
| Arg | Ile | Thr | Glu | Trp | Pro | Pro | Phe | Glu | Asn | Met | Ile | Leu | Ala | Thr | Ile |
| 90 | | | | | 95 | | | | | 100 | | | | | 105 | |

| ATC | GCC | AAC | TGC | ATC | GTG | CTG | GCC | CTG | GAG | CAG | CAC | CTC | CCT | GAT | GGG | 506 |
|---|---|---|---|---|---|---|---|---|---|---|---|---|---|---|---|---|
| Ile | Ala | Asn | Cys | Ile | Val | Leu | Ala | Leu | Glu | Gln | His | Leu | Pro | Asp | Gly |
| | | | | 110 | | | | | 115 | | | | | 120 | |

| GAC | AAA | ACG | CCC | ATG | TCC | GAG | CGG | CTG | GAC | GAC | ACG | GAG | CCC | TAT | TTC | 554 |
|---|---|---|---|---|---|---|---|---|---|---|---|---|---|---|---|---|
| Asp | Lys | Thr | Pro | Met | Ser | Glu | Arg | Leu | Asp | Asp | Thr | Glu | Pro | Tyr | Phe |
| | | | 125 | | | | | 130 | | | | | 135 | | |

| ATC | GGG | ATC | TTT | TGC | TTC | GAG | GCA | GGG | ATC | AAA | ATC | ATC | GCT | CTG | GGC | 602 |
|---|---|---|---|---|---|---|---|---|---|---|---|---|---|---|---|---|
| Ile | Gly | Ile | Phe | Cys | Phe | Glu | Ala | Gly | Ile | Lys | Ile | Ile | Ala | Leu | Gly |
| | | | 140 | | | | | 145 | | | | | 150 | | |

| TTT | GTC | TTC | CAC | AAG | GGC | TCT | TAC | CTG | CGG | AAC | GGC | TGG | AAC | GTC | ATG | 650 |
|---|---|---|---|---|---|---|---|---|---|---|---|---|---|---|---|---|
| Phe | Val | Phe | His | Lys | Gly | Ser | Tyr | Leu | Arg | Asn | Gly | Trp | Asn | Val | Met |
| | 155 | | | | | 160 | | | | | 165 | | | | | |

| GAC | TTC | GTG | GTC | GTC | CTC | ACA | GGG | ATC | CTT | GCC | ACG | GCT | GGA | ACT | GAC | 698 |
|---|---|---|---|---|---|---|---|---|---|---|---|---|---|---|---|---|
| Asp | Phe | Val | Val | Val | Leu | Thr | Gly | Ile | Leu | Ala | Thr | Ala | Gly | Thr | Asp |
| 170 | | | | | 175 | | | | | 180 | | | | | 185 | |

| TTC | GAC | CTG | CGA | ACA | CTG | AGG | GCT | GTG | CGT | GTG | CTG | AGG | CCC | CTG | AAG | 746 |
|---|---|---|---|---|---|---|---|---|---|---|---|---|---|---|---|---|
| Phe | Asp | Leu | Arg | Thr | Leu | Arg | Ala | Val | Arg | Val | Leu | Arg | Pro | Leu | Lys |
| | | | | 190 | | | | | 195 | | | | | 200 | | |

| CTG | GTG | TCT | GGG | ATT | CCA | AGT | TTG | CAG | GTG | GTG | CTC | AAG | TCC | ATC | ATG | 794 |
|---|---|---|---|---|---|---|---|---|---|---|---|---|---|---|---|---|
| Leu | Val | Ser | Gly | Ile | Pro | Ser | Leu | Gln | Val | Val | Leu | Lys | Ser | Ile | Met |
| | | | 205 | | | | | 210 | | | | | 215 | | |

| AAG | GCC | ATG | GTT | CCA | CTC | CTG | CAG | ATT | GGG | CTG | CTT | CTC | TTC | TTT | GCC | 842 |
|---|---|---|---|---|---|---|---|---|---|---|---|---|---|---|---|---|
| Lys | Ala | Met | Val | Pro | Leu | Leu | Gln | Ile | Gly | Leu | Leu | Leu | Phe | Phe | Ala |
| | | 220 | | | | | 225 | | | | | 230 | | | | |

| ATC | CTC | ATG | TTT | GCC | ATC | ATT | GGC | CTG | GAG | TTC | TAC | ATG | GGC | AAG | TTC | 890 |
|---|---|---|---|---|---|---|---|---|---|---|---|---|---|---|---|---|
| Ile | Leu | Met | Phe | Ala | Ile | Ile | Gly | Leu | Glu | Phe | Tyr | Met | Gly | Lys | Phe |
| | 235 | | | | | 240 | | | | | 245 | | | | | |

| CAC | AAG | GCC | TGT | TTC | CCC | AAC | AGC | ACA | GAT | GCG | GAG | CCC | GTG | GGT | GAC | 938 |
|---|---|---|---|---|---|---|---|---|---|---|---|---|---|---|---|---|
| His | Lys | Ala | Cys | Phe | Pro | Asn | Ser | Thr | Asp | Ala | Glu | Pro | Val | Gly | Asp |
| 250 | | | | 255 | | | | | 260 | | | | | 265 | | |

| TTC | CCC | TGT | GGC | AAG | GAG | GCC | CCA | GCC | CGG | CTG | TGC | GAG | GGC | GAC | ACT | 986 |
|---|---|---|---|---|---|---|---|---|---|---|---|---|---|---|---|---|
| Phe | Pro | Cys | Gly | Lys | Glu | Ala | Pro | Ala | Arg | Leu | Cys | Glu | Gly | Asp | Thr |
| | | | | 270 | | | | | 275 | | | | | 280 | | |

| GAG | TGC | CGG | GAG | TAC | TGG | CCA | GGA | CCC | AAC | TTT | GGC | ATC | ACC | AAC | TTT | 1034 |
|---|---|---|---|---|---|---|---|---|---|---|---|---|---|---|---|---|
| Glu | Cys | Arg | Glu | Tyr | Trp | Pro | Gly | Pro | Asn | Phe | Gly | Ile | Thr | Asn | Phe |

|     |     |     |     |     | 285 |     |     |     |     | 290 |     |     |     |     | 295 |     |      |
|-----|-----|-----|-----|-----|-----|-----|-----|-----|-----|-----|-----|-----|-----|-----|-----|-----|------|
| GAC | AAT | ATC | CTG | TTT | GCC | ATC | TTG | ACG | GTG | TTC | CAG | TGC | ATC | ACC | ATG |     | 1082 |
| Asp | Asn | Ile | Leu | Phe | Ala | Ile | Leu | Thr | Val | Phe | Gln | Cys | Ile | Thr | Met |     |      |
|     |     | 300 |     |     |     |     | 305 |     |     |     |     | 310 |     |     |     |     |      |
| GAG | GGC | TGG | ACT | GAC | ATC | CTC | TAT | AAT | ACA | AAC | GAT | GCG | GCC | GGC | AAC |     | 1130 |
| Glu | Gly | Trp | Thr | Asp | Ile | Leu | Tyr | Asn | Thr | Asn | Asp | Ala | Ala | Gly | Asn |     |      |
|     | 315 |     |     |     |     | 320 |     |     |     |     | 325 |     |     |     |     |     |      |
| ACC | TGG | AAC | TGG | CTC | TAC | TTC | ATC | CCT | CTC | ATC | ATC | ATC | GGC | TCC | TTC |     | 1178 |
| Thr | Trp | Asn | Trp | Leu | Tyr | Phe | Ile | Pro | Leu | Ile | Ile | Ile | Gly | Ser | Phe |     |      |
| 330 |     |     |     |     | 335 |     |     |     |     | 340 |     |     |     |     | 345 |     |      |
| TTC | ATG | CTC | AAC | CTG | GTG | CTG | GGC | GTG | CTC | TCG | GGG | GAG | TTT | GCC | AAG |     | 1226 |
| Phe | Met | Leu | Asn | Leu | Val | Leu | Gly | Val | Leu | Ser | Gly | Glu | Phe | Ala | Lys |     |      |
|     |     |     |     | 350 |     |     |     |     | 355 |     |     |     |     | 360 |     |     |      |
| GAG | CGA | GAG | AGG | GTG | GAG | AAC | CGC | CGC | GCC | TTC | CTG | AAG | CTG | CGC | CGG |     | 1274 |
| Glu | Arg | Glu | Arg | Val | Glu | Asn | Arg | Arg | Ala | Phe | Leu | Lys | Leu | Arg | Arg |     |      |
|     |     | 365 |     |     |     |     | 370 |     |     |     |     | 375 |     |     |     |     |      |
| CAG | CAG | CAG | ATC | GAG | CGA | GAG | CTC | AAC | GGG | TAC | CTG | GAG | TGG | ATC | TTC |     | 1322 |
| Gln | Gln | Gln | Ile | Glu | Arg | Glu | Leu | Asn | Gly | Tyr | Leu | Glu | Trp | Ile | Phe |     |      |
|     | 380 |     |     |     |     | 385 |     |     |     |     | 390 |     |     |     |     |     |      |
| AAG | GCG | GAG | GAA | GTC | ATG | CTG | GCC | GAG | GAG | GAC | AGG | AAT | GCA | GAG | GAG |     | 1370 |
| Lys | Ala | Glu | Glu | Val | Met | Leu | Ala | Glu | Glu | Asp | Arg | Asn | Ala | Glu | Glu |     |      |
| 395 |     |     |     |     | 400 |     |     |     |     | 405 |     |     |     |     |     |     |      |
| AAG | TCC | CCT | TTG | GAC | GTG | CTG | AAG | AGA | GCG | GCC | ACC | AAG | AAG | AGC | AGA |     | 1418 |
| Lys | Ser | Pro | Leu | Asp | Val | Leu | Lys | Arg | Ala | Ala | Thr | Lys | Lys | Ser | Arg |     |      |
| 410 |     |     |     |     | 415 |     |     |     |     | 420 |     |     |     |     | 425 |     |      |
| AAT | GAC | CTG | ATC | CAC | GCA | GAG | GAG | GGA | GAG | GAC | CGG | TTT | GCA | GAT | CTC |     | 1466 |
| Asn | Asp | Leu | Ile | His | Ala | Glu | Glu | Gly | Glu | Asp | Arg | Phe | Ala | Asp | Leu |     |      |
|     |     |     |     | 430 |     |     |     |     | 435 |     |     |     |     | 440 |     |     |      |
| TGT | GCT | GTT | GGA | TCC | CCC | TTC | GCC | CGC | GCC | AGC | CTC | AAG | AGC | GGG | AAG |     | 1514 |
| Cys | Ala | Val | Gly | Ser | Pro | Phe | Ala | Arg | Ala | Ser | Leu | Lys | Ser | Gly | Lys |     |      |
|     |     |     | 445 |     |     |     |     | 450 |     |     |     |     | 455 |     |     |     |      |
| ACA | GAG | AGC | TCG | TCA | TAC | TTC | CGG | AGG | AAG | GAG | AAG | ATG | TTC | CGG | TTT |     | 1562 |
| Thr | Glu | Ser | Ser | Ser | Tyr | Phe | Arg | Arg | Lys | Glu | Lys | Met | Phe | Arg | Phe |     |      |
|     |     | 460 |     |     |     |     | 465 |     |     |     |     | 470 |     |     |     |     |      |
| TTT | ATC | CGG | CGC | ATG | GTG | AAG | GCT | CAG | AGC | TTC | TAC | TGG | GTG | GTG | CTG |     | 1610 |
| Phe | Ile | Arg | Arg | Met | Val | Lys | Ala | Gln | Ser | Phe | Tyr | Trp | Val | Val | Leu |     |      |
|     | 475 |     |     |     |     | 480 |     |     |     |     | 485 |     |     |     |     |     |      |
| TGC | GTG | GTG | GCC | CTG | AAC | ACA | CTG | TGT | GTG | GCC | ATG | GTG | CAT | TAC | AAC |     | 1658 |
| Cys | Val | Val | Ala | Leu | Asn | Thr | Leu | Cys | Val | Ala | Met | Val | His | Tyr | Asn |     |      |
| 490 |     |     |     |     | 495 |     |     |     |     | 500 |     |     |     |     | 505 |     |      |
| CAG | CCG | CGG | CGG | CTT | ACC | ACG | ACC | CTG | TAT | TTT | GCA | GAG | TTT | GTT | TTC |     | 1706 |
| Gln | Pro | Arg | Arg | Leu | Thr | Thr | Thr | Leu | Tyr | Phe | Ala | Glu | Phe | Val | Phe |     |      |
|     |     |     |     | 510 |     |     |     |     | 515 |     |     |     |     | 520 |     |     |      |
| CTG | GGT | CTC | TTC | CTC | ACA | GAG | ATG | TCC | CTG | AAG | ATG | TAT | GGC | CTG | GGG |     | 1754 |
| Leu | Gly | Leu | Phe | Leu | Thr | Glu | Met | Ser | Leu | Lys | Met | Tyr | Gly | Leu | Gly |     |      |
|     |     |     | 525 |     |     |     |     | 530 |     |     |     |     | 535 |     |     |     |      |
| CCC | AGA | AGC | TAC | TTC | CGG | TCC | TCC | TTC | AAC | TGC | TTC | GAC | TTT | GGG | GTC |     | 1802 |
| Pro | Arg | Ser | Tyr | Phe | Arg | Ser | Ser | Phe | Asn | Cys | Phe | Asp | Phe | Gly | Val |     |      |
|     |     | 540 |     |     |     |     | 545 |     |     |     |     | 550 |     |     |     |     |      |
| ATC | GTG | GGG | AGC | GTC | TTT | GAA | GTG | GTC | TGG | GCG | GCC | ATC | AAG | CCG | GGA |     | 1850 |
| Ile | Val | Gly | Ser | Val | Phe | Glu | Val | Val | Trp | Ala | Ala | Ile | Lys | Pro | Gly |     |      |
|     | 555 |     |     |     |     | 560 |     |     |     |     | 565 |     |     |     |     |     |      |
| AGC | TCC | TTT | GGG | ATC | AGT | GTG | CTG | CGG | GCC | CTC | CGC | CTG | CTG | AGG | ATC |     | 1898 |
| Ser | Ser | Phe | Gly | Ile | Ser | Val | Leu | Arg | Ala | Leu | Arg | Leu | Leu | Arg | Ile |     |      |
| 570 |     |     |     |     | 575 |     |     |     |     | 580 |     |     |     |     | 585 |     |      |
| TTC | AAA | GTC | ACG | AAG | TAC | TGG | AGC | TCC | CTG | CGG | AAC | CTG | GTG | GTG | TCC |     | 1946 |
| Phe | Lys | Val | Thr | Lys | Tyr | Trp | Ser | Ser | Leu | Arg | Asn | Leu | Val | Val | Ser |     |      |
|     |     |     |     | 590 |     |     |     |     | 595 |     |     |     |     | 600 |     |     |      |
| CTG | CTG | AAC | TCC | ATG | AAG | TCC | ATC | ATC | AGC | CTG | CTC | TTC | TTG | CTC | TTC |     | 1994 |
| Leu | Leu | Asn | Ser | Met | Lys | Ser | Ile | Ile | Ser | Leu | Leu | Phe | Leu | Leu | Phe |     |      |

```
                          605                             610                            615
CTG  TTC  ATT  GTG  GTC  TTC  GCC  CTG  CTG  GGG  ATG  CAG  CTG  TTT  GGG  GGA      2042
Leu  Phe  Ile  Val  Val  Phe  Ala  Leu  Leu  Gly  Met  Gln  Leu  Phe  Gly  Gly
               620                 625                      630

CAG  TTC  AAC  TTC  CAG  GAT  GAG  ACT  CCC  ACA  ACC  AAC  TTC  GAC  ACC  TTC      2090
Gln  Phe  Asn  Phe  Gln  Asp  Glu  Thr  Pro  Thr  Thr  Asn  Phe  Asp  Thr  Phe
               635                 640                      645

CCT  GCC  GCC  ATC  CTC  ACT  GTC  TTC  CAG  ATC  CTG  ACG  GGA  GAG  GAC  TGG      2138
Pro  Ala  Ala  Ile  Leu  Thr  Val  Phe  Gln  Ile  Leu  Thr  Gly  Glu  Asp  Trp
650                      655                      660                      665

AAT  GCA  GTG  ATG  TAT  CAC  GGG  ATC  GAA  TCG  CAA  GGC  GGC  GTC  AGC  AAA      2186
Asn  Ala  Val  Met  Tyr  His  Gly  Ile  Glu  Ser  Gln  Gly  Gly  Val  Ser  Lys
                    670                      675                      680

GGC  ATG  TTC  TCG  TCC  TTT  TAC  TTC  ATT  GTC  CTG  ACA  CTG  TTC  GGA  AAC      2234
Gly  Met  Phe  Ser  Ser  Phe  Tyr  Phe  Ile  Val  Leu  Thr  Leu  Phe  Gly  Asn
               685                      690                      695

TAC  ACT  CTG  CTG  AAT  GTC  TTT  CTG  GCC  ATC  GCT  GTG  GAC  AAC  CTG  GCC      2282
Tyr  Thr  Leu  Leu  Asn  Val  Phe  Leu  Ala  Ile  Ala  Val  Asp  Asn  Leu  Ala
               700                 705                      710

AAC  GCC  CAA  GAG  CTG  ACC  AAG  GAT  GAA  GAG  GAG  ATG  GAA  GAA  GCA  GCC      2330
Asn  Ala  Gln  Glu  Leu  Thr  Lys  Asp  Glu  Glu  Glu  Met  Glu  Glu  Ala  Ala
     715                      720                      725

AAT  CAG  AAG  CTT  GCT  CTG  CAA  AAG  GCC  AAA  GAA  GTG  GCT  GAA  GTC  AGC      2378
Asn  Gln  Lys  Leu  Ala  Leu  Gln  Lys  Ala  Lys  Glu  Val  Ala  Glu  Val  Ser
730                      735                      740                      745

CCC  ATG  TCT  GCC  GCG  AAC  ATC  TCC  ATC  GCC  GCC  AGG  CAG  CAG  AAC  TCG      2426
Pro  Met  Ser  Ala  Ala  Asn  Ile  Ser  Ile  Ala  Ala  Arg  Gln  Gln  Asn  Ser
               750                      755                      760

GCC  AAG  GCG  CGC  TCG  GTG  TGG  GAG  CAG  CGG  GCC  AGC  CAG  CTA  CGG  CTG      2474
Ala  Lys  Ala  Arg  Ser  Val  Trp  Glu  Gln  Arg  Ala  Ser  Gln  Leu  Arg  Leu
               765                      770                      775

CAG  AAC  CTG  CGG  GCC  AGC  TGC  GAG  GCG  CTG  TAC  AGC  GAG  ATG  GAC  CCC      2522
Gln  Asn  Leu  Arg  Ala  Ser  Cys  Glu  Ala  Leu  Tyr  Ser  Glu  Met  Asp  Pro
               780                      785                      790

GAG  GAG  CGG  CTG  CGC  TTC  GCC  ACT  ACG  CGC  CAC  CTG  CGG  CCC  GAC  ATG      2570
Glu  Glu  Arg  Leu  Arg  Phe  Ala  Thr  Thr  Arg  His  Leu  Arg  Pro  Asp  Met
     795                      800                      805

AAG  ACG  CAC  CTG  GAC  CGG  CCG  CTG  GTG  GTG  GAG  CTG  GGC  CGC  GAC  GGC      2618
Lys  Thr  His  Leu  Asp  Arg  Pro  Leu  Val  Val  Glu  Leu  Gly  Arg  Asp  Gly
810                      815                      820                      825

GCG  CGG  GGG  CCC  GTG  GGA  GGC  AAA  GCC  CGA  CCT  GAG  GCT  GCG  GAG  GCC      2666
Ala  Arg  Gly  Pro  Val  Gly  Gly  Lys  Ala  Arg  Pro  Glu  Ala  Ala  Glu  Ala
               830                      835                      840

CCC  GAG  GGC  GTC  GAC  CCT  CCG  CGC  AGG  CAC  CAC  CGG  CAC  CGC  GAC  AAG      2714
Pro  Glu  Gly  Val  Asp  Pro  Pro  Arg  Arg  His  His  Arg  His  Arg  Asp  Lys
               845                      850                      855

GAC  AAG  ACC  CCC  GCG  GCG  GGG  GAC  CAG  GAC  CGA  GCA  GAG  GCC  CCG  AAG      2762
Asp  Lys  Thr  Pro  Ala  Ala  Gly  Asp  Gln  Asp  Arg  Ala  Glu  Ala  Pro  Lys
               860                      865                      870

GCG  GAG  AGC  GGG  GAG  CCC  GGT  GCC  CGG  GAG  GAG  CGG  CCG  CGG  CCG  CAC      2810
Ala  Glu  Ser  Gly  Glu  Pro  Gly  Ala  Arg  Glu  Glu  Arg  Pro  Arg  Pro  His
               875                      880                      885

CGC  AGC  CAC  AGC  AAG  GAG  GCC  GCG  GGG  CCG  CCG  GAG  GCG  CGG  AGC  GAG      2858
Arg  Ser  His  Ser  Lys  Glu  Ala  Ala  Gly  Pro  Pro  Glu  Ala  Arg  Ser  Glu
890                      895                      900                      905

CGC  GGC  CGA  GGC  CCA  GGC  CCC  GAG  GGC  GGC  CGG  CGG  CAC  CAC  CGG  CGC      2906
Arg  Gly  Arg  Gly  Pro  Gly  Pro  Glu  Gly  Gly  Arg  Arg  His  His  Arg  Arg
                    910                      915                      920

GGC  TCC  CCG  GAG  GAG  GCG  GCC  GAG  CGG  GAG  CCC  GAC  GCC  CAC  CGC  GCG      2954
Gly  Ser  Pro  Glu  Glu  Ala  Ala  Glu  Arg  Glu  Pro  Arg  Arg  His  Arg  Ala
```

```
                      925                      930                           935
CAC CGG CAC CAG GAT CCG AGC AAG GAG TGC GCC GGC GCC AAG GGC GAG        3002
His Arg His Gln Asp Pro Ser Lys Glu Cys Ala Gly Ala Lys Gly Glu
        940                 945                 950

CGG CGC GCG CGG CAC CGC GGC GGC CCC CGA GCG GGG CCC CGG GAG GCG        3050
Arg Arg Ala Arg His Arg Gly Gly Pro Arg Ala Gly Pro Arg Glu Ala
    955                 960                 965

GAG AGC GGG GAG GAG CCG GCG CGG CGG CAC CGG GCC CGG CAC AAG GCG        3098
Glu Ser Gly Glu Glu Pro Ala Arg Arg His Arg Ala Arg His Lys Ala
970                 975                 980                 985

CAG CCT GCT CAC GAG GCT GTG GAG AAG GAG ACC ACG GAG AAG GAG GCC        3146
Gln Pro Ala His Glu Ala Val Glu Lys Glu Thr Thr Glu Lys Glu Ala
            990                 995                 1000

ACG GAG AAG GAG GCT GAG ATA GTG GAA GCC GAC AAG GAA AAG GAG CTC        3194
Thr Glu Lys Glu Ala Glu Ile Val Glu Ala Asp Lys Glu Lys Glu Leu
        1005                1010                1015

CGG AAC CAC CAG CCC CGG GAG CCA CAC TGT GAC CTG GAG ACC AGT GGG        3242
Arg Asn His Gln Pro Arg Glu Pro His Cys Asp Leu Glu Thr Ser Gly
    1020                1025                1030

ACT GTG ACT GTG GGT CCC ATG CAC ACA CTG CCC AGC ACC TGT CTC CAG        3290
Thr Val Thr Val Gly Pro Met His Thr Leu Pro Ser Thr Cys Leu Gln
1035                1040                1045

AAG GTG GAG GAA CAG CCA GAG GAT GCA GAC AAT CAG CGG AAC GTC ACT        3338
Lys Val Glu Glu Gln Pro Glu Asp Ala Asp Asn Gln Arg Asn Val Thr
1050                1055                1060                1065

CGC ATG GGC AGT CAG CCC CCA GAC CCG AAC ACT ATT GTA CAT ATC CCA        3386
Arg Met Gly Ser Gln Pro Pro Asp Pro Asn Thr Ile Val His Ile Pro
        1070                1075                1080

GTG ATG CTG ACG GGC CCT CTT GGG GAA GCC ACG GTC GTT CCC AGT GGT        3434
Val Met Leu Thr Gly Pro Leu Gly Glu Ala Thr Val Val Pro Ser Gly
    1085                1090                1095

AAC GTG GAC CTG GAA AGC CAA GCA GAG GGG AAG AAG GAG GTG GAA GCG        3482
Asn Val Asp Leu Glu Ser Gln Ala Glu Gly Lys Lys Glu Val Glu Ala
        1100                1105                1110

GAT GAC GTG ATG AGG AGC GGC CCC CGG CCT ATC GTC CCA TAC AGC TCC        3530
Asp Asp Val Met Arg Ser Gly Pro Arg Pro Ile Val Pro Tyr Ser Ser
    1115                1120                1125

ATG TTC TGT TTA AGC CCC ACC AAC CTG CTC CGC CGC TTC TGC CAC TAC        3578
Met Phe Cys Leu Ser Pro Thr Asn Leu Leu Arg Arg Phe Cys His Tyr
1130                1135                1140                1145

ATC GTG ACC ATG AGG TAC TTC GAG GTG GTC ATT CTC GTG GTC ATC GCC        3626
Ile Val Thr Met Arg Tyr Phe Glu Val Val Ile Leu Val Val Ile Ala
                1150                1155                1160

TTG AGC AGC ATC GCC CTG GCT GCT GAG GAC CCA GTG CGC ACA GAC TCG        3674
Leu Ser Ser Ile Ala Leu Ala Ala Glu Asp Pro Val Arg Thr Asp Ser
            1165                1170                1175

CCC AGG AAC AAC GCT CTG AAA TAC CTG GAT TAC ATT TTC ACT GGT GTC        3722
Pro Arg Asn Asn Ala Leu Lys Tyr Leu Asp Tyr Ile Phe Thr Gly Val
        1180                1185                1190

TTT ACC TTT GAG ATG GTG ATA AAG ATG ATC GAC TTG GGA CTG CTG CTT        3770
Phe Thr Phe Glu Met Val Ile Lys Met Ile Asp Leu Gly Leu Leu Leu
    1195                1200                1205

CAC CCT GGA GCC TAT TTC CGG GAC TTG TGG AAC ATT CTG GAC TTC ATT        3818
His Pro Gly Ala Tyr Phe Arg Asp Leu Trp Asn Ile Leu Asp Phe Ile
1210                1215                1220                1225

GTG GTC AGT GGC GCC CTG GTG GCG TTT GCT TTC TCA GGA TCC AAA GGG        3866
Val Val Ser Gly Ala Leu Val Ala Phe Ala Phe Ser Gly Ser Lys Gly
                1230                1235                1240

AAA GAC ATC AAT ACC ATC AAG TCT CTG AGA GTC CTT CGT GTC CTG CGG        3914
Lys Asp Ile Asn Thr Ile Lys Ser Leu Arg Val Leu Arg Val Leu Arg
```

```
                   1245                    1250                    1255

CCC  CTC  AAG  ACC  ATC  AAA  CGG  CTG  CCC  AAG  CTC  AAG  GCT  GTG  TTT  GAC         3962
Pro  Leu  Lys  Thr  Ile  Lys  Arg  Leu  Pro  Lys  Leu  Lys  Ala  Val  Phe  Asp
               1260                    1265                    1270

TGT  GTG  GTG  AAC  TCC  CTG  AAG  AAT  GTC  CTC  AAC  ATC  TTG  ATT  GTC  TAC         4010
Cys  Val  Val  Asn  Ser  Leu  Lys  Asn  Val  Leu  Asn  Ile  Leu  Ile  Val  Tyr
          1275                    1280                    1285

ATG  CTC  TTC  ATG  TTC  ATA  TTT  GCC  GTC  ATT  GCG  GTG  CAG  CTC  TTC  AAA         4058
Met  Leu  Phe  Met  Phe  Ile  Phe  Ala  Val  Ile  Ala  Val  Gln  Leu  Phe  Lys
1290                    1295                    1300                    1305

GGG  AAG  TTT  TTC  TAC  TGC  ACA  GAT  GAA  TCC  AAG  GAG  CTG  GAG  AGG  GAC         4106
Gly  Lys  Phe  Phe  Tyr  Cys  Thr  Asp  Glu  Ser  Lys  Glu  Leu  Glu  Arg  Asp
                    1310                    1315                    1320

TGC  AGG  GGT  CAG  TAT  TTG  GAT  TAT  GAG  AAG  GAG  GAA  GTG  GAA  GCT  CAG         4154
Cys  Arg  Gly  Gln  Tyr  Leu  Asp  Tyr  Glu  Lys  Glu  Glu  Val  Glu  Ala  Gln
               1325                    1330                    1335

CCC  AGG  CAG  TGG  AAG  AAA  TAC  GAC  TTT  CAC  TAC  GAC  AAT  GTG  CTC  TGG         4202
Pro  Arg  Gln  Trp  Lys  Lys  Tyr  Asp  Phe  His  Tyr  Asp  Asn  Val  Leu  Trp
          1340                    1345                    1350

GCT  CTG  CTG  ACG  CTG  TTC  ACA  GTG  TCC  ACG  GGA  GAA  GGC  TGG  CCC  ATG         4250
Ala  Leu  Leu  Thr  Leu  Phe  Thr  Val  Ser  Thr  Gly  Glu  Gly  Trp  Pro  Met
     1355                    1360                    1365

GTG  CTG  AAA  CAC  TCC  GTG  GAT  GCC  ACC  TAT  GAG  GAG  CAG  GGT  CCA  AGC         4298
Val  Leu  Lys  His  Ser  Val  Asp  Ala  Thr  Tyr  Glu  Glu  Gln  Gly  Pro  Ser
1370                    1375                    1380                    1385

CCT  GGG  TAC  CGC  ATG  GAG  CTG  TCC  ATC  TTC  TAC  GTG  GTC  TAC  TTT  GTG         4346
Pro  Gly  Tyr  Arg  Met  Glu  Leu  Ser  Ile  Phe  Tyr  Val  Val  Tyr  Phe  Val
                    1390                    1395                    1400

GTC  TTT  CCC  TTC  TTC  TTC  GTC  AAC  ATC  TTT  GTG  GCT  TTG  ATC  ATC  ATC         4394
Val  Phe  Pro  Phe  Phe  Phe  Val  Asn  Ile  Phe  Val  Ala  Leu  Ile  Ile  Ile
               1405                    1410                    1415

ACC  TTC  CAG  GAG  CAG  GGG  GAC  AAG  GTG  ATG  TCT  GAA  TGC  AGC  CTG  GAG         4442
Thr  Phe  Gln  Glu  Gln  Gly  Asp  Lys  Val  Met  Ser  Glu  Cys  Ser  Leu  Glu
          1420                    1425                    1430

AAG  AAC  GAG  AGG  GCT  TGC  ATT  GAC  TTC  GCC  ATC  AGC  GCC  AAA  CCC  CTG         4490
Lys  Asn  Glu  Arg  Ala  Cys  Ile  Asp  Phe  Ala  Ile  Ser  Ala  Lys  Pro  Leu
     1435                    1440                    1445

ACA  CGG  TAC  ATG  CCC  CAA  AAC  CGG  CAG  TCG  TTC  CAG  TAT  AAG  ACG  TGG         4538
Thr  Arg  Tyr  Met  Pro  Gln  Asn  Arg  Gln  Ser  Phe  Gln  Tyr  Lys  Thr  Trp
1450                    1455                    1460                    1465

ACA  TTT  GTG  GTC  TCC  CCG  CCC  TTT  GAA  TAC  TTC  ATC  ATG  GCC  ATG  ATA         4586
Thr  Phe  Val  Val  Ser  Pro  Pro  Phe  Glu  Tyr  Phe  Ile  Met  Ala  Met  Ile
                    1470                    1475                    1480

GCC  CTC  AAC  ACT  GTG  GTG  CTG  ATG  ATG  AAG  TTC  TAT  GAT  GCA  CCC  TAT         4634
Ala  Leu  Asn  Thr  Val  Val  Leu  Met  Met  Lys  Phe  Tyr  Asp  Ala  Pro  Tyr
               1485                    1490                    1495

GAG  TAC  GAG  CTG  ATG  CTG  AAA  TGC  CTG  AAC  ATC  GTG  TTC  ACA  TCC  ATG         4682
Glu  Tyr  Glu  Leu  Met  Leu  Lys  Cys  Leu  Asn  Ile  Val  Phe  Thr  Ser  Met
          1500                    1505                    1510

TTC  TCC  ATG  GAA  TGC  GTG  CTG  AAG  ATC  ATC  GCC  TTT  GGG  GTG  CTG  AAC         4730
Phe  Ser  Met  Glu  Cys  Val  Leu  Lys  Ile  Ile  Ala  Phe  Gly  Val  Leu  Asn
     1515                    1520                    1525

TAT  TTC  AGA  GAT  GCC  TGG  AAT  GTC  TTT  GAC  TTT  GTC  ACT  GTG  TTG  GGA         4778
Tyr  Phe  Arg  Asp  Ala  Trp  Asn  Val  Phe  Asp  Phe  Val  Thr  Val  Leu  Gly
1530                    1535                    1540                    1545

AGT  ATT  ACT  GAT  ATT  TTA  GTA  ACA  GAG  ATT  GCG  GAA  ACG  AAC  AAT  TTC         4826
Ser  Ile  Thr  Asp  Ile  Leu  Val  Thr  Glu  Ile  Ala  Glu  Thr  Asn  Asn  Phe
                    1550                    1555                    1560

ATC  AAC  CTC  AGC  TTC  CTC  CGC  CTC  TTT  CGA  GCT  GCG  CGG  CTG  ATC  AAG         4874
Ile  Asn  Leu  Ser  Phe  Leu  Arg  Leu  Phe  Arg  Ala  Ala  Arg  Leu  Ile  Lys
```

```
                              1565                          1570                            1575
CTG  CTC  CGC  CAG  GGC  TAC  ACC  ATC  CGC  ATC  CTG  CTG  TGG  ACC  TTT  GTC           4922
Leu  Leu  Arg  Gln  Gly  Tyr  Thr  Ile  Arg  Ile  Leu  Leu  Trp  Thr  Phe  Val
          1580                     1585                          1590

CAG  TCC  TTC  AAG  GCC  CTG  CCC  TAC  GTG  TGT  CTG  CTC  ATT  GCC  ATG  CTG           4970
Gln  Ser  Phe  Lys  Ala  Leu  Pro  Tyr  Val  Cys  Leu  Leu  Ile  Ala  Met  Leu
1595                          1600                     1605

TTC  TTC  ATC  TAC  GCC  ATC  ATC  GGC  ATG  CAG  GTG  TTT  GGG  AAT  ATT  GCC           5018
Phe  Phe  Ile  Tyr  Ala  Ile  Ile  Gly  Met  Gln  Val  Phe  Gly  Asn  Ile  Ala
1610                          1615                     1620                     1625

CTG  GAT  GAT  GAC  ACC  AGC  ATC  AAC  CGC  CAC  AAC  AAC  TTC  CGG  ACG  TTT           5066
Leu  Asp  Asp  Asp  Thr  Ser  Ile  Asn  Arg  His  Asn  Asn  Phe  Arg  Thr  Phe
               1630                     1635                          1640

TTG  CAA  GCC  CTG  ATG  CTG  CTG  TTC  AGG  AGC  GCC  ACG  GGG  GAG  GCC  TGG           5114
Leu  Gln  Ala  Leu  Met  Leu  Leu  Phe  Arg  Ser  Ala  Thr  Gly  Glu  Ala  Trp
               1645                     1650                          1655

CAC  GAG  ATC  ATG  CTG  TCC  TGC  CTG  AGC  AAC  CAG  GCC  TGT  GAT  GAG  CAG           5162
His  Glu  Ile  Met  Leu  Ser  Cys  Leu  Ser  Asn  Gln  Ala  Cys  Asp  Glu  Gln
          1660                     1665                          1670

GCC  AAT  GCC  ACC  GAG  TGT  GGA  AGT  GAC  TTT  GCC  TAC  TTC  TAC  TTC  GTC           5210
Ala  Asn  Ala  Thr  Glu  Cys  Gly  Ser  Asp  Phe  Ala  Tyr  Phe  Tyr  Phe  Val
1675                          1680                     1685

TCC  TTC  ATC  TTC  CTG  TGC  TCC  TTT  CTG  ATG  TTG  AAC  CTC  TTT  GTG  GCT           5258
Ser  Phe  Ile  Phe  Leu  Cys  Ser  Phe  Leu  Met  Leu  Asn  Leu  Phe  Val  Ala
1690                          1695                     1700                     1705

GTG  ATC  ATG  GAC  AAT  TTT  GAG  TAC  CTC  ACG  CGG  GAC  TCT  TCC  ATC  CTA           5306
Val  Ile  Met  Asp  Asn  Phe  Glu  Tyr  Leu  Thr  Arg  Asp  Ser  Ser  Ile  Leu
               1710                     1715                          1720

GGT  CCT  CAC  CAC  TTG  GAT  GAG  TTC  ATC  CGG  GTC  TGG  GCT  GAA  TAC  GAC           5354
Gly  Pro  His  His  Leu  Asp  Glu  Phe  Ile  Arg  Val  Trp  Ala  Glu  Tyr  Asp
               1725                     1730                          1735

CCG  GCT  GCG  TGT  GGG  CGC  ATC  AGT  TAC  AAT  GAC  ATG  TTT  GAG  ATG  CTG           5402
Pro  Ala  Ala  Cys  Gly  Arg  Ile  Ser  Tyr  Asn  Asp  Met  Phe  Glu  Met  Leu
          1740                     1745                          1750

AAA  CAC  ATG  TCC  CCG  CCT  CTG  GGG  CTG  GGG  AAG  AAA  TGC  CCT  GCT  CGA           5450
Lys  His  Met  Ser  Pro  Pro  Leu  Gly  Leu  Gly  Lys  Lys  Cys  Pro  Ala  Arg
1755                          1760                     1765

GTT  GCT  TAC  AAG  CGC  CTG  GTT  CGC  ATG  AAC  ATG  CCC  ATC  TCC  AAC  GAG           5498
Val  Ala  Tyr  Lys  Arg  Leu  Val  Arg  Met  Asn  Met  Pro  Ile  Ser  Asn  Glu
1770                          1775                     1780                     1785

GAC  ATG  ACT  GTT  CAC  TTC  ACG  TCC  ACG  CTG  ATG  GCC  CTC  ATC  CGG  ACG           5546
Asp  Met  Thr  Val  His  Phe  Thr  Ser  Thr  Leu  Met  Ala  Leu  Ile  Arg  Thr
               1790                     1795                          1800

GCA  CTG  GAG  ATC  AAG  CTG  GCC  CCA  GCT  GGG  ACA  AAG  CAG  CAT  CAG  TGT           5594
Ala  Leu  Glu  Ile  Lys  Leu  Ala  Pro  Ala  Gly  Thr  Lys  Gln  His  Gln  Cys
                    1805                     1810                     1815

GAC  GCG  GAG  TTG  AGG  AAG  GAG  ATT  TCC  GTT  GTG  TGG  GCC  AAT  CTG  CCC           5642
Asp  Ala  Glu  Leu  Arg  Lys  Glu  Ile  Ser  Val  Val  Trp  Ala  Asn  Leu  Pro
               1820                     1825                          1830

CAG  AAG  ACT  TTG  GAC  TTG  CTG  GTA  CCA  CCC  CAT  AAG  CCT  GAT  GAG  ATG           5690
Gln  Lys  Thr  Leu  Asp  Leu  Leu  Val  Pro  Pro  His  Lys  Pro  Asp  Glu  Met
          1835                     1840                     1845

ACA  GTG  GGG  AAG  GTT  TAT  GCA  GCT  CTG  ATG  ATA  TTT  GAC  TTC  TAC  AAG           5738
Thr  Val  Gly  Lys  Val  Tyr  Ala  Ala  Leu  Met  Ile  Phe  Asp  Phe  Tyr  Lys
1850                          1855                     1860                     1865

CAG  AAC  AAA  ACC  ACC  AGA  GAC  CAG  ATG  CAG  CAG  GCT  CCT  GGA  GGC  CTC           5786
Gln  Asn  Lys  Thr  Thr  Arg  Asp  Gln  Met  Gln  Gln  Ala  Pro  Gly  Gly  Leu
               1870                     1875                          1880

TCC  CAG  ATG  GGT  CCT  GTG  TCC  CTG  TTC  CAC  CCT  CTG  AAG  GCC  ACC  CTG           5834
Ser  Gln  Met  Gly  Pro  Val  Ser  Leu  Phe  His  Pro  Leu  Lys  Ala  Thr  Leu
```

```
                    1885                            1890                            1895
GAG  CAG  ACA  CAG  CCG  GCT  GTG  CTC  CGA  GGA  GCC  CGG  GTT  TTC  CTT  CGA        5882
Glu  Gln  Thr  Gln  Pro  Ala  Val  Leu  Arg  Gly  Ala  Arg  Val  Phe  Leu  Arg
               1900                            1905                            1910

CAG  AAG  AGT  TCC  ACC  TCC  CTC  AGC  AAT  GGC  GGG  GCC  ATA  CAA  AAC  CAA        5930
Gln  Lys  Ser  Ser  Thr  Ser  Leu  Ser  Asn  Gly  Gly  Ala  Ile  Gln  Asn  Gln
               1915                            1920                            1925

GAG  AGT  GGC  ATC  AAA  GAG  TCT  GTC  TCC  TGG  GGC  ACT  CAA  AGG  ACC  CAG        5978
Glu  Ser  Gly  Ile  Lys  Glu  Ser  Val  Ser  Trp  Gly  Thr  Gln  Arg  Thr  Gln
1930                            1935                            1940                      1945

GAT  GCA  CCC  CAT  GAG  GCC  AGG  CCA  CCC  CTG  GAG  CGT  GGC  CAC  TCC  ACA        6026
Asp  Ala  Pro  His  Glu  Ala  Arg  Pro  Pro  Leu  Glu  Arg  Gly  His  Ser  Thr
                         1950                            1955                       1960

GAG  ATC  CCT  GTG  GGG  CGG  TCA  GGA  GCA  CTG  GCT  GTG  GAC  GTT  CAG  ATG        6074
Glu  Ile  Pro  Val  Gly  Arg  Ser  Gly  Ala  Leu  Ala  Val  Asp  Val  Gln  Met
                    1965                            1970                            1975

CAG  AGC  ATA  ACC  CGG  AGG  GGC  CCT  GAT  GGG  GAG  CCC  CAG  CCT  GGG  CTG        6122
Gln  Ser  Ile  Thr  Arg  Arg  Gly  Pro  Asp  Gly  Glu  Pro  Gln  Pro  Gly  Leu
               1980                            1985                            1990

GAG  AGC  CAG  GGT  CGA  GCG  GCC  TCC  ATG  CCC  CGC  CTT  GCG  GCC  GAG  ACT        6170
Glu  Ser  Gln  Gly  Arg  Ala  Ala  Ser  Met  Pro  Arg  Leu  Ala  Ala  Glu  Thr
          1995                            2000                            2005

CAG  CCC  GTC  ACA  GAT  GCC  AGC  CCC  ATG  AAG  CGC  TCC  ATC  TCC  ACG  CTG        6218
Gln  Pro  Val  Thr  Asp  Ala  Ser  Pro  Met  Lys  Arg  Ser  Ile  Ser  Thr  Leu
2010                            2015                            2020                      2025

GCC  CAG  CGG  CCC  CGT  GGG  ACT  CAT  CTT  TGC  AGC  ACC  ACC  CCG  GAC  CGC        6266
Ala  Gln  Arg  Pro  Arg  Gly  Thr  His  Leu  Cys  Ser  Thr  Thr  Pro  Asp  Arg
                         2030                            2035                       2040

CCA  CCC  CCT  AGC  CAG  GCG  TCG  TCG  CAC  CAC  CAC  CAC  CAC  CGC  TGC  CAC        6314
Pro  Pro  Pro  Ser  Gln  Ala  Ser  Ser  His  His  His  His  His  Arg  Cys  His
                    2045                            2050                            2055

CGC  CGC  AGG  GAC  AGG  AAG  CAG  AGG  TCC  CTG  GAG  AAG  GGG  CCC  AGC  CTG        6362
Arg  Arg  Arg  Asp  Arg  Lys  Gln  Arg  Ser  Leu  Glu  Lys  Gly  Pro  Ser  Leu
               2060                            2065                            2070

TCT  GCC  GAT  ATG  GAT  GGC  GCA  CCA  AGC  AGT  GCT  GTG  GGG  CCG  GGG  CTG        6410
Ser  Ala  Asp  Met  Asp  Gly  Ala  Pro  Ser  Ser  Ala  Val  Gly  Pro  Gly  Leu
               2075                            2080                            2085

CCC  CCG  GGA  GAG  GGG  CCT  ACA  GGC  TGC  CGG  CGG  GAA  CGA  GAG  CGC  CGG        6458
Pro  Pro  Gly  Glu  Gly  Pro  Thr  Gly  Cys  Arg  Arg  Glu  Arg  Glu  Arg  Arg
2090                            2095                            2100                      2105

CAG  GAG  CGG  GGC  CGG  TCC  CAG  GAG  CGG  AGG  CAG  CCC  TCA  TCC  TCC  TCC        6506
Gln  Glu  Arg  Gly  Arg  Ser  Gln  Glu  Arg  Arg  Gln  Pro  Ser  Ser  Ser  Ser
                         2110                            2115                       2120

TCG  GAG  AAG  CAG  CGC  TTC  TAC  TCC  TGC  GAC  CGC  TTT  GGG  GGC  CGT  GAG        6554
Ser  Glu  Lys  Gln  Arg  Phe  Tyr  Ser  Cys  Asp  Arg  Phe  Gly  Gly  Arg  Glu
                    2125                            2130                            2135

CCC  CCG  AAG  CCC  AAG  CCC  TCC  CTC  AGC  AGC  CAC  CCA  ACG  TCG  CCA  ACA        6602
Pro  Pro  Lys  Pro  Lys  Pro  Ser  Leu  Ser  Ser  His  Pro  Thr  Ser  Pro  Thr
               2140                            2145                            2150

GCT  GGC  CAG  GAG  CCG  GGA  CCC  CAC  CCA  CAG  GGC  AGT  GGT  TCC  GTG  AAT        6650
Ala  Gly  Gln  Glu  Pro  Gly  Pro  His  Pro  Gln  Gly  Ser  Gly  Ser  Val  Asn
          2155                            2160                            2165

GGG  AGC  CCC  TTG  CTG  TCA  ACA  TCT  GGT  GCT  AGC  ACC  CCC  GGC  CGC  GGT        6698
Gly  Ser  Pro  Leu  Leu  Ser  Thr  Ser  Gly  Ala  Ser  Thr  Pro  Gly  Arg  Gly
2170                            2175                            2180                      2185

GGG  CGG  AGG  CAG  CTC  CCC  CAG  ACG  CCC  CTG  ACT  CCC  CGC  CCC  AGC  ATC        6746
Gly  Arg  Arg  Gln  Leu  Pro  Gln  Thr  Pro  Leu  Thr  Pro  Arg  Pro  Ser  Ile
                         2190                            2195                       2200

ACC  TAC  AAG  ACG  GCC  AAC  TCC  TCA  CCC  ATC  CAC  TTC  GCC  GGG  GCT  CAG        6794
Thr  Tyr  Lys  Thr  Ala  Asn  Ser  Ser  Pro  Ile  His  Phe  Ala  Gly  Ala  Gln
```

|  |  |  |  |  |  |  |  |  |  |  |  |  |  |  |  |
|---|---|---|---|---|---|---|---|---|---|---|---|---|---|---|---|
|  | 2205 |  |  |  |  |  | 2210 |  |  |  |  |  | 2215 |  |  |
| ACC | AGC | CTC | CCT | GCC | TTC | TCC | CCA | GGC | CGG | CTC | AGC | CGT | GGG | CTT | TCC | 6842
| Thr | Ser | Leu | Pro | Ala | Phe | Ser | Pro | Gly | Arg | Leu | Ser | Arg | Gly | Leu | Ser |
|  |  | 2220 |  |  |  |  | 2225 |  |  |  |  | 2230 |  |  |  |
| GAA | CAC | AAC | GCC | CTG | CTG | CAG | AGA | GAC | CCC | CTC | AGC | CAG | CCC | CTG | GCC | 6890
| Glu | His | Asn | Ala | Leu | Leu | Gln | Arg | Asp | Pro | Leu | Ser | Gln | Pro | Leu | Ala |
|  |  | 2235 |  |  |  |  | 2240 |  |  |  |  | 2245 |  |  |  |
| CCT | GGC | TCT | CGA | ATT | GGC | TCT | GAC | CCT | TAC | CTG | GGG | CAG | CGT | CTG | GAC | 6938
| Pro | Gly | Ser | Arg | Ile | Gly | Ser | Asp | Pro | Tyr | Leu | Gly | Gln | Arg | Leu | Asp |
| 2250 |  |  |  |  | 2255 |  |  |  |  | 2260 |  |  |  |  | 2265 |
| AGT | GAG | GCC | TCT | GTC | CAC | GCC | CTG | CCT | GAG | GAC | ACG | CTC | ACT | TTC | GAG | 6986
| Ser | Glu | Ala | Ser | Val | His | Ala | Leu | Pro | Glu | Asp | Thr | Leu | Thr | Phe | Glu |
|  |  |  |  | 2270 |  |  |  |  | 2275 |  |  |  |  | 2280 |  |
| GAG | GCT | GTG | GCC | ACC | AAC | TCG | GGC | CGC | TCC | TCC | AGG | ACT | TCC | TAC | GTG | 7034
| Glu | Ala | Val | Ala | Thr | Asn | Ser | Gly | Arg | Ser | Ser | Arg | Thr | Ser | Tyr | Val |
|  |  |  |  | 2285 |  |  |  |  | 2290 |  |  |  |  | 2295 |  |
| TCC | TCC | CTG | ACC | TCC | CAG | TCT | CAC | CCT | CTC | CGC | CGC | GTG | CCC | AAC | GGT | 7082
| Ser | Ser | Leu | Thr | Ser | Gln | Ser | His | Pro | Leu | Arg | Arg | Val | Pro | Asn | Gly |
|  |  | 2300 |  |  |  |  | 2305 |  |  |  |  | 2310 |  |  |  |
| TAC | CAC | TGC | ACC | CTG | GGA | CTC | AGC | TCG | GGT | GGC | CGA | GCA | CGG | CAC | AGC | 7130
| Tyr | His | Cys | Thr | Leu | Gly | Leu | Ser | Ser | Gly | Gly | Arg | Ala | Arg | His | Ser |
|  |  | 2315 |  |  |  |  | 2320 |  |  |  |  | 2325 |  |  |  |
| TAC | CAC | CAC | CCT | GAC | CAA | GAC | CAC | TGG | TGC | TAGCTGCACC | GTGACCGCTC |  |  |  |  | 7180
| Tyr | His | His | Pro | Asp | Gln | Asp | His | Trp | Cys |  |  |  |  |  |  |
| 2330 |  |  |  |  | 2335 |  |  |  |  |  |  |  |  |  |  |

AGACGCCTGC ATGCAGCAGG CGTGTGTTCC AGTGGATGAG TTTTATCATC CACACGGGGC 7240

AGTCGGCCCT CGGGGGAGGC CTTGCCCACC TTGGTGAGGC TCCTGTGGCC CCTCCCTCCC 7300

CCTCCTCCCC TCTTTTACTC TAGACGACGA ATAAAGCCCT GTTGCTTGAG TGTACGTACC 7360

GC 7362

( 2 ) INFORMATION FOR SEQ ID NO:8:

( i ) SEQUENCE CHARACTERISTICS:
        ( A ) LENGTH: 7175 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 144..6857

( i x ) FEATURE:
        ( A ) NAME/KEY: 5'UTR
        ( B ) LOCATION: 1..143

( i x ) FEATURE:
        ( A ) NAME/KEY: 3'UTR
        ( B ) LOCATION: 6855..7175

( x i ) SEQUENCE DESCRIPTION: SEQ ID NO:8:

GCGGCGGCGG CTGCGGCGGT GGGGCCGGGC GAGGTCCGTG CGGTCCCGGC GGCTCCGTGG 60

CTGCTCCGCT CTGAGCGCCT GCGCGCCCCG CGCCCTCCCT GCCGGGGCCG CTGGGCCGGG 120

|  |  |  |  |  |  |  |  |  |  |  |  |  |  |  |  |
|---|---|---|---|---|---|---|---|---|---|---|---|---|---|---|---|
| GATGCACGCG | GGGCCCGGGA | GCC | ATG | GTC | CGC | TTC | GGG | GAC | GAG | CTG | GGC |  |  |  |  | 170
|  |  |  | Met | Val | Arg | Phe | Gly | Asp | Glu | Leu | Gly |  |  |  |  |
|  |  |  | 1 |  |  |  | 5 |  |  |  |  |  |  |  |  |
| GGC | CGC | TAT | GGA | GGC | CCC | GGC | GGA | GAG | CGG | GCC | CGG | GGC | GGC | GGG |  | 218
| Gly | Arg | Tyr | Gly | Gly | Pro | Gly | Gly | Glu | Arg | Ala | Arg | Gly | Gly | Gly |  |
| 10 |  |  |  | 15 |  |  |  |  | 20 |  |  |  |  | 25 |  |
| GCC | GGC | GGG | GCG | GGG | GGC | CCG | GGT | CCC | GGG | GGG | CTG | CAG | CCC | GGC | CAG | 266

|  |  |  |  |  |  |  |  |  |  |  |  |  |  |  |  |
|---|---|---|---|---|---|---|---|---|---|---|---|---|---|---|---|
| Ala | Gly | Gly | Ala | Gly | Gly | Pro | Gly | Pro | Gly | Gly | Leu | Gln | Pro | Gly | Gln |
|  |  |  | 30 |  |  |  |  | 35 |  |  |  |  | 40 |  |  |

| CGG | GTC | CTC | TAC | AAG | CAA | TCG | ATC | GCG | CAG | CGC | GCG | CGG | ACC | ATG | GCG | 314 |
| Arg | Val | Leu | Tyr | Lys | Gln | Ser | Ile | Ala | Gln | Arg | Ala | Arg | Thr | Met | Ala |  |
|  |  |  | 45 |  |  |  |  | 50 |  |  |  |  | 55 |  |  |  |

| CTG | TAC | AAC | CCC | ATC | CCG | GTC | AAG | CAG | AAC | TGC | TTC | ACC | GTC | AAC | CGC | 362 |
| Leu | Tyr | Asn | Pro | Ile | Pro | Val | Lys | Gln | Asn | Cys | Phe | Thr | Val | Asn | Arg |  |
|  |  | 60 |  |  |  |  | 65 |  |  |  |  | 70 |  |  |  |  |

| TCG | CTC | TTC | GTC | TTC | AGC | GAG | GAC | AAC | GTC | GTC | CGC | AAA | TAC | GCG | AAG | 410 |
| Ser | Leu | Phe | Val | Phe | Ser | Glu | Asp | Asn | Val | Val | Arg | Lys | Tyr | Ala | Lys |  |
|  | 75 |  |  |  |  | 80 |  |  |  |  | 85 |  |  |  |  |  |

| CGC | ATC | ACC | GAG | TGG | CCT | CCA | TTC | GAG | AAT | ATG | ATC | CTG | GCC | ACC | ATC | 458 |
| Arg | Ile | Thr | Glu | Trp | Pro | Pro | Phe | Glu | Asn | Met | Ile | Leu | Ala | Thr | Ile |  |
| 90 |  |  |  |  | 95 |  |  |  |  | 100 |  |  |  |  | 105 |  |

| ATC | GCC | AAC | TGC | ATC | GTG | CTG | GCC | CTG | GAG | CAG | CAC | CTC | CCT | GAT | GGG | 506 |
| Ile | Ala | Asn | Cys | Ile | Val | Leu | Ala | Leu | Glu | Gln | His | Leu | Pro | Asp | Gly |  |
|  |  |  |  | 110 |  |  |  |  | 115 |  |  |  |  | 120 |  |  |

| GAC | AAA | ACG | CCC | ATG | TCC | GAG | CGG | CTG | GAC | GAC | ACG | GAG | CCC | TAT | TTC | 554 |
| Asp | Lys | Thr | Pro | Met | Ser | Glu | Arg | Leu | Asp | Asp | Thr | Glu | Pro | Tyr | Phe |  |
|  |  |  | 125 |  |  |  |  | 130 |  |  |  |  | 135 |  |  |  |

| ATC | GGG | ATC | TTT | TGC | TTC | GAG | GCA | GGG | ATC | AAA | ATC | ATC | GCT | CTG | GGC | 602 |
| Ile | Gly | Ile | Phe | Cys | Phe | Glu | Ala | Gly | Ile | Lys | Ile | Ile | Ala | Leu | Gly |  |
|  |  | 140 |  |  |  |  | 145 |  |  |  |  | 150 |  |  |  |  |

| TTT | GTC | TTC | CAC | AAG | GGC | TCT | TAC | CTG | CGG | AAC | GGC | TGG | AAC | GTC | ATG | 650 |
| Phe | Val | Phe | His | Lys | Gly | Ser | Tyr | Leu | Arg | Asn | Gly | Trp | Asn | Val | Met |  |
|  | 155 |  |  |  |  | 160 |  |  |  |  | 165 |  |  |  |  |  |

| GAC | TTC | GTG | GTC | GTC | CTC | ACA | GGG | ATC | CTT | GCC | ACG | GCT | GGA | ACT | GAC | 698 |
| Asp | Phe | Val | Val | Val | Leu | Thr | Gly | Ile | Leu | Ala | Thr | Ala | Gly | Thr | Asp |  |
| 170 |  |  |  |  | 175 |  |  |  |  | 180 |  |  |  |  | 185 |  |

| TTC | GAC | CTG | CGA | ACA | CTG | AGG | GCT | GTG | CGT | GTG | CTG | AGG | CCC | CTG | AAG | 746 |
| Phe | Asp | Leu | Arg | Thr | Leu | Arg | Ala | Val | Arg | Val | Leu | Arg | Pro | Leu | Lys |  |
|  |  |  |  | 190 |  |  |  |  | 195 |  |  |  |  | 200 |  |  |

| CTG | GTG | TCT | GGG | ATT | CCA | AGT | TTG | CAG | GTG | GTG | CTC | AAG | TCC | ATC | ATG | 794 |
| Leu | Val | Ser | Gly | Ile | Pro | Ser | Leu | Gln | Val | Val | Leu | Lys | Ser | Ile | Met |  |
|  |  |  | 205 |  |  |  |  | 210 |  |  |  |  | 215 |  |  |  |

| AAG | GCC | ATG | GTT | CCA | CTC | CTG | CAG | ATT | GGG | CTG | CTT | CTC | TTC | TTT | GCC | 842 |
| Lys | Ala | Met | Val | Pro | Leu | Leu | Gln | Ile | Gly | Leu | Leu | Leu | Phe | Phe | Ala |  |
|  |  | 220 |  |  |  |  | 225 |  |  |  |  | 230 |  |  |  |  |

| ATC | CTC | ATG | TTT | GCC | ATC | ATT | GGC | CTG | GAG | TTC | TAC | ATG | GGC | AAG | TTC | 890 |
| Ile | Leu | Met | Phe | Ala | Ile | Ile | Gly | Leu | Glu | Phe | Tyr | Met | Gly | Lys | Phe |  |
|  | 235 |  |  |  |  | 240 |  |  |  |  | 245 |  |  |  |  |  |

| CAC | AAG | GCC | TGT | TTC | CCC | AAC | AGC | ACA | GAT | GCG | GAG | CCC | GTG | GGT | GAC | 938 |
| His | Lys | Ala | Cys | Phe | Pro | Asn | Ser | Thr | Asp | Ala | Glu | Pro | Val | Gly | Asp |  |
| 250 |  |  |  |  | 255 |  |  |  |  | 260 |  |  |  |  | 265 |  |

| TTC | CCC | TGT | GGC | AAG | GAG | GCC | CCA | GCC | CGG | CTG | TGC | GAG | GGC | GAC | ACT | 986 |
| Phe | Pro | Cys | Gly | Lys | Glu | Ala | Pro | Ala | Arg | Leu | Cys | Glu | Gly | Asp | Thr |  |
|  |  |  | 270 |  |  |  |  | 275 |  |  |  |  | 280 |  |  |  |

| GAG | TGC | CGG | GAG | TAC | TGG | CCA | GGA | CCC | AAC | TTT | GGC | ATC | ACC | AAC | TTT | 1034 |
| Glu | Cys | Arg | Glu | Tyr | Trp | Pro | Gly | Pro | Asn | Phe | Gly | Ile | Thr | Asn | Phe |  |
|  |  | 285 |  |  |  |  | 290 |  |  |  |  | 295 |  |  |  |  |

| GAC | AAT | ATC | CTG | TTT | GCC | ATC | TTG | ACG | GTG | TTC | CAG | TGC | ATC | ACC | ATG | 1082 |
| Asp | Asn | Ile | Leu | Phe | Ala | Ile | Leu | Thr | Val | Phe | Gln | Cys | Ile | Thr | Met |  |
|  |  | 300 |  |  |  |  | 305 |  |  |  |  | 310 |  |  |  |  |

| GAG | GGC | TGG | ACT | GAC | ATC | CTC | TAT | AAT | ACA | AAC | GAT | GCG | GCC | GGC | AAC | 1130 |
| Glu | Gly | Trp | Thr | Asp | Ile | Leu | Tyr | Asn | Thr | Asn | Asp | Ala | Ala | Gly | Asn |  |
|  | 315 |  |  |  |  | 320 |  |  |  |  | 325 |  |  |  |  |  |

| ACC | TGG | AAC | TGG | CTC | TAC | TTC | ATC | CCT | CTC | ATC | ATC | ATC | GGC | TCC | TTC | 1178 |
| Thr | Trp | Asn | Trp | Leu | Tyr | Phe | Ile | Pro | Leu | Ile | Ile | Ile | Gly | Ser | Phe |  |
| 330 |  |  |  |  | 335 |  |  |  |  | 340 |  |  |  |  | 345 |  |

| TTC | ATG | CTC | AAC | CTG | GTG | CTG | GGC | GTG | CTC | TCG | GGG | GAG | TTT | GCC | AAG | 1226 |

```
                Phe  Met  Leu  Asn  Leu  Val  Leu  Gly  Val  Leu  Ser  Gly  Glu  Phe  Ala  Lys
                               350                355                          360

GAG CGA GAG AGG GTG GAG AAC CGC CGC GCC TTC CTG AAG CTG CGC CGG                              1274
Glu Arg Glu Arg Val Glu Asn Arg Arg Ala Phe Leu Lys Leu Arg Arg
            365                370                     375

CAG CAG CAG ATC GAG CGA GAG CTC AAC GGG TAC CTG GAG TGG ATC TTC                              1322
Gln Gln Gln Ile Glu Arg Glu Leu Asn Gly Tyr Leu Glu Trp Ile Phe
        380                385                     390

AAG GCG GAG GAA GTC ATG CTG GCC GAG GAG GAC AGG AAT GCA GAG GAG                              1370
Lys Ala Glu Glu Val Met Leu Ala Glu Glu Asp Arg Asn Ala Glu Glu
    395                400                405

AAG TCC CCT TTG GAC GTG CTG AAG AGA GCG GCC ACC AAG AAG AGC AGA                              1418
Lys Ser Pro Leu Asp Val Leu Lys Arg Ala Ala Thr Lys Lys Ser Arg
410            415                420                     425

AAT GAC CTG ATC CAC GCA GAG GAG GGA GAG GAC CGG TTT GCA GAT CTC                              1466
Asn Asp Leu Ile His Ala Glu Glu Gly Glu Asp Arg Phe Ala Asp Leu
            430                435                     440

TGT GCT GTT GGA TCC CCC TTC GCC CGC GCC AGC CTC AAG AGC GGG AAG                              1514
Cys Ala Val Gly Ser Pro Phe Ala Arg Ala Ser Leu Lys Ser Gly Lys
        445                450                     455

ACA GAG AGC TCG TCA TAC TTC CGG AGG AAG GAG AAG ATG TTC CGG TTT                              1562
Thr Glu Ser Ser Ser Tyr Phe Arg Arg Lys Glu Lys Met Phe Arg Phe
    460                465                470

TTT ATC CGG CGC ATG GTG AAG GCT CAG AGC TTC TAC TGG GTG GTG CTG                              1610
Phe Ile Arg Arg Met Val Lys Ala Gln Ser Phe Tyr Trp Val Val Leu
475            480                485

TGC GTG GTG GCC CTG AAC ACA CTG TGT GTG GCC ATG GTG CAT TAC AAC                              1658
Cys Val Val Ala Leu Asn Thr Leu Cys Val Ala Met Val His Tyr Asn
490            495                500                     505

CAG CCG CGG CGG CTT ACC ACG ACC CTG TAT TTT GCA GAG TTT GTT TTC                              1706
Gln Pro Arg Arg Leu Thr Thr Thr Leu Tyr Phe Ala Glu Phe Val Phe
        510                515                     520

CTG GGT CTC TTC CTC ACA GAG ATG TCC CTG AAG ATG TAT GGC CTG GGG                              1754
Leu Gly Leu Phe Leu Thr Glu Met Ser Leu Lys Met Tyr Gly Leu Gly
            525                530                     535

CCC AGA AGC TAC TTC CGG TCC TCC TTC AAC TGC TTC GAC TTT GGG GTC                              1802
Pro Arg Ser Tyr Phe Arg Ser Ser Phe Asn Cys Phe Asp Phe Gly Val
        540                545                     550

ATC GTG GGG AGC GTC TTT GAA GTG GTC TGG GCG GCC ATC AAG CCG GGA                              1850
Ile Val Gly Ser Val Phe Glu Val Val Trp Ala Ala Ile Lys Pro Gly
555                560                     565

AGC TCC TTT GGG ATC AGT GTG CTG CGG GCC CTC CGC CTG CTG AGG ATC                              1898
Ser Ser Phe Gly Ile Ser Val Leu Arg Ala Leu Arg Leu Leu Arg Ile
570                575                580                     585

TTC AAA GTC ACG AAG TAC TGG AGC TCC CTG CGG AAC CTG GTG GTG TCC                              1946
Phe Lys Val Thr Lys Tyr Trp Ser Ser Leu Arg Asn Leu Val Val Ser
                590                595                     600

CTG CTG AAC TCC ATG AAG TCC ATC ATC AGC CTG CTC TTC TTG CTC TTC                              1994
Leu Leu Asn Ser Met Lys Ser Ile Ile Ser Leu Leu Phe Leu Leu Phe
            605                610                     615

CTG TTC ATT GTG GTC TTC GCC CTG CTG GGG ATG CAG CTG TTT GGG GGA                              2042
Leu Phe Ile Val Val Phe Ala Leu Leu Gly Met Gln Leu Phe Gly Gly
        620                625                     630

CAG TTC AAC TTC CAG GAT GAG ACT CCC ACA ACC AAC TTC GAC ACC TTC                              2090
Gln Phe Asn Phe Gln Asp Glu Thr Pro Thr Thr Asn Phe Asp Thr Phe
    635                640                645

CCT GCC GCC ATC CTC ACT GTC TTC CAG ATC CTG ACG GGA GAG GAC TGG                              2138
Pro Ala Ala Ile Leu Thr Val Phe Gln Ile Leu Thr Gly Glu Asp Trp
650            655                660                     665

AAT GCA GTG ATG TAT CAC GGG ATC GAA TCG CAA GGC GGC GTC AGC AAA                              2186
```

-continued

| | | | | | | | | | | | | | | | |
|---|---|---|---|---|---|---|---|---|---|---|---|---|---|---|---|
| Asn | Ala | Val | Met | Tyr | His | Gly | Ile | Glu | Ser | Gln | Gly | Gly | Val | Ser | Lys |
| | | | | 670 | | | | | 675 | | | | | | 680 |

| GGC | ATG | TTC | TCG | TCC | TTT | TAC | TTC | ATT | GTC | CTG | ACA | CTG | TTC | GGA | AAC | 2234 |
|---|---|---|---|---|---|---|---|---|---|---|---|---|---|---|---|---|
| Gly | Met | Phe | Ser | Ser | Phe | Tyr | Phe | Ile | Val | Leu | Thr | Leu | Phe | Gly | Asn | |
| | | | | 685 | | | | | 690 | | | | | 695 | | |

| TAC | ACT | CTG | CTG | AAT | GTC | TTT | CTG | GCC | ATC | GCT | GTG | GAC | AAC | CTG | GCC | 2282 |
|---|---|---|---|---|---|---|---|---|---|---|---|---|---|---|---|---|
| Tyr | Thr | Leu | Leu | Asn | Val | Phe | Leu | Ala | Ile | Ala | Val | Asp | Asn | Leu | Ala | |
| | | 700 | | | | | 705 | | | | | 710 | | | | |

| AAC | GCC | CAA | GAG | CTG | ACC | AAG | GAT | GAA | GAG | GAG | ATG | GAA | GAA | GCA | GCC | 2330 |
|---|---|---|---|---|---|---|---|---|---|---|---|---|---|---|---|---|
| Asn | Ala | Gln | Glu | Leu | Thr | Lys | Asp | Glu | Glu | Glu | Met | Glu | Glu | Ala | Ala | |
| | | 715 | | | | | 720 | | | | | 725 | | | | |

| AAT | CAG | AAG | CTT | GCT | CTG | CAA | AAG | GCC | AAA | GAA | GTG | GCT | GAA | GTC | AGC | 2378 |
|---|---|---|---|---|---|---|---|---|---|---|---|---|---|---|---|---|
| Asn | Gln | Lys | Leu | Ala | Leu | Gln | Lys | Ala | Lys | Glu | Val | Ala | Glu | Val | Ser | |
| 730 | | | | | 735 | | | | | 740 | | | | | 745 | |

| CCC | ATG | TCT | GCC | GCG | AAC | ATC | TCC | ATC | GCC | GCC | AGG | CAG | CAG | AAC | TCG | 2426 |
|---|---|---|---|---|---|---|---|---|---|---|---|---|---|---|---|---|
| Pro | Met | Ser | Ala | Ala | Asn | Ile | Ser | Ile | Ala | Ala | Arg | Gln | Gln | Asn | Ser | |
| | | | | 750 | | | | | 755 | | | | | 760 | | |

| GCC | AAG | GCG | CGC | TCG | GTG | TGG | GAG | CAG | CGG | GCC | AGC | CAG | CTA | CGG | CTG | 2474 |
|---|---|---|---|---|---|---|---|---|---|---|---|---|---|---|---|---|
| Ala | Lys | Ala | Arg | Ser | Val | Trp | Glu | Gln | Arg | Ala | Ser | Gln | Leu | Arg | Leu | |
| | | | 765 | | | | | 770 | | | | | 775 | | | |

| CAG | AAC | CTG | CGG | GCC | AGC | TGC | GAG | GCG | CTG | TAC | AGC | GAG | ATG | GAC | CCC | 2522 |
|---|---|---|---|---|---|---|---|---|---|---|---|---|---|---|---|---|
| Gln | Asn | Leu | Arg | Ala | Ser | Cys | Glu | Ala | Leu | Tyr | Ser | Glu | Met | Asp | Pro | |
| | | 780 | | | | | 785 | | | | | 790 | | | | |

| GAG | GAG | CGG | CTG | CGC | TTC | GCC | ACT | ACG | CGC | CAC | CTG | CGG | CCC | GAC | ATG | 2570 |
|---|---|---|---|---|---|---|---|---|---|---|---|---|---|---|---|---|
| Glu | Glu | Arg | Leu | Arg | Phe | Ala | Thr | Thr | Arg | His | Leu | Arg | Pro | Asp | Met | |
| 795 | | | | | 800 | | | | | 805 | | | | | | |

| AAG | ACG | CAC | CTG | GAC | CGG | CCG | CTG | GTG | GTG | GAG | CTG | GGC | CGC | GAC | GGC | 2618 |
|---|---|---|---|---|---|---|---|---|---|---|---|---|---|---|---|---|
| Lys | Thr | His | Leu | Asp | Arg | Pro | Leu | Val | Val | Glu | Leu | Gly | Arg | Asp | Gly | |
| 810 | | | | | 815 | | | | | 820 | | | | | 825 | |

| GCG | CGG | GGG | CCC | GTG | GGA | GGC | AAA | GCC | CGA | CCT | GAG | GCT | GCG | GAG | GCC | 2666 |
|---|---|---|---|---|---|---|---|---|---|---|---|---|---|---|---|---|
| Ala | Arg | Gly | Pro | Val | Gly | Gly | Lys | Ala | Arg | Pro | Glu | Ala | Ala | Glu | Ala | |
| | | | | 830 | | | | | 835 | | | | | 840 | | |

| CCC | GAG | GGC | GTC | GAC | CCT | CCG | CGC | AGG | CAC | CAC | CGG | CAC | CGC | GAC | AAG | 2714 |
|---|---|---|---|---|---|---|---|---|---|---|---|---|---|---|---|---|
| Pro | Glu | Gly | Val | Asp | Pro | Pro | Arg | Arg | His | His | Arg | His | Arg | Asp | Lys | |
| | | | 845 | | | | | 850 | | | | | 855 | | | |

| GAC | AAG | ACC | CCC | GCG | GCG | GGG | GAC | CAG | GAC | CGA | GCA | GAG | GCC | CCG | AAG | 2762 |
|---|---|---|---|---|---|---|---|---|---|---|---|---|---|---|---|---|
| Asp | Lys | Thr | Pro | Ala | Ala | Gly | Asp | Gln | Asp | Arg | Ala | Glu | Ala | Pro | Lys | |
| | | 860 | | | | | 865 | | | | | 870 | | | | |

| GCG | GAG | AGC | GGG | GAG | CCC | GGT | GCC | CGG | GAG | GAG | CGG | CCG | CGG | CCG | CAC | 2810 |
|---|---|---|---|---|---|---|---|---|---|---|---|---|---|---|---|---|
| Ala | Glu | Ser | Gly | Glu | Pro | Gly | Ala | Arg | Glu | Glu | Arg | Pro | Arg | Pro | His | |
| 875 | | | | | 880 | | | | | 885 | | | | | | |

| CGC | AGC | CAC | AGC | AAG | GAG | GCC | GCG | GGG | CCC | CCG | GAG | GCG | CGG | AGC | GAG | 2858 |
|---|---|---|---|---|---|---|---|---|---|---|---|---|---|---|---|---|
| Arg | Ser | His | Ser | Lys | Glu | Ala | Ala | Gly | Pro | Pro | Glu | Ala | Arg | Ser | Glu | |
| 890 | | | | | 895 | | | | | 900 | | | | | 905 | |

| CGC | GGC | CGA | GGC | CCA | GGC | CCC | GAG | GGC | GGC | CGG | CGG | CAC | CAC | CGG | CGC | 2906 |
|---|---|---|---|---|---|---|---|---|---|---|---|---|---|---|---|---|
| Arg | Gly | Arg | Gly | Pro | Gly | Pro | Glu | Gly | Gly | Arg | Arg | His | His | Arg | Arg | |
| | | | | 910 | | | | | 915 | | | | | 920 | | |

| GGC | TCC | CCG | GAG | GAG | GCG | GCC | GAG | CGG | GAG | CCC | CGA | CGC | CAC | CGC | GCG | 2954 |
|---|---|---|---|---|---|---|---|---|---|---|---|---|---|---|---|---|
| Gly | Ser | Pro | Glu | Glu | Ala | Ala | Glu | Arg | Glu | Pro | Arg | Arg | His | Arg | Ala | |
| | | | | 925 | | | | | 930 | | | | | 935 | | |

| CAC | CGG | CAC | CAG | GAT | CCG | AGC | AAG | GAG | TGC | GCC | GGC | GCC | AAG | GGC | GAG | 3002 |
|---|---|---|---|---|---|---|---|---|---|---|---|---|---|---|---|---|
| His | Arg | His | Gln | Asp | Pro | Ser | Lys | Glu | Cys | Ala | Gly | Ala | Lys | Gly | Glu | |
| | | 940 | | | | | 945 | | | | | 950 | | | | |

| CGG | CGC | GCG | CGG | CAC | CGC | GGC | GGC | CCC | CGA | GCG | GGG | CCC | CGG | GAG | GCG | 3050 |
|---|---|---|---|---|---|---|---|---|---|---|---|---|---|---|---|---|
| Arg | Arg | Ala | Arg | His | Arg | Gly | Gly | Pro | Arg | Ala | Gly | Pro | Arg | Glu | Ala | |
| | | 955 | | | | | 960 | | | | | 965 | | | | |

| GAG | AGC | GGG | GAG | GAG | CCG | GCG | CGG | CGG | CAC | CGG | GCC | CGG | CAC | AAG | GCG | 3098 |
|---|---|---|---|---|---|---|---|---|---|---|---|---|---|---|---|---|
| Glu | Ser | Gly | Glu | Glu | Pro | Ala | Arg | Arg | His | Arg | Ala | Arg | His | Lys | Ala | |
| 970 | | | | | 975 | | | | | 980 | | | | | 985 | |

| CAG | CCT | GCT | CAC | GAG | GCT | GTG | GAG | AAG | GAG | ACC | ACG | GAG | AAG | GAG | GCC | 3146 |
|---|---|---|---|---|---|---|---|---|---|---|---|---|---|---|---|---|

|  |  |  |  |  |  |  |  |  |  |  |  |  |  |  |  |
|---|---|---|---|---|---|---|---|---|---|---|---|---|---|---|---|
| Gln | Pro | Ala | His | Glu | Ala | Val | Glu | Lys | Glu | Thr | Thr | Glu | Lys | Glu | Ala |
|  |  |  |  | 990 |  |  |  | 995 |  |  |  |  | 1000 |  |  |

| ACG | GAG | AAG | GAG | GCT | GAG | ATA | GTG | GAA | GCC | GAC | AAG | GAA | AAG | GAG | CTC | 3194 |
|---|---|---|---|---|---|---|---|---|---|---|---|---|---|---|---|---|
| Thr | Glu | Lys | Glu | Ala | Glu | Ile | Val | Glu | Ala | Asp | Lys | Glu | Lys | Glu | Leu |  |
|  |  |  | 1005 |  |  |  | 1010 |  |  |  |  | 1015 |  |  |  |  |

| CGG | AAC | CAC | CAG | CCC | CGG | GAG | CCA | CAC | TGT | GAC | CTG | GAG | ACC | AGT | GGG | 3242 |
|---|---|---|---|---|---|---|---|---|---|---|---|---|---|---|---|---|
| Arg | Asn | His | Gln | Pro | Arg | Glu | Pro | His | Cys | Asp | Leu | Glu | Thr | Ser | Gly |  |
|  |  |  | 1020 |  |  |  | 1025 |  |  |  |  | 1030 |  |  |  |  |

| ACT | GTG | ACT | GTG | GGT | CCC | ATG | CAC | ACA | CTG | CCC | AGC | ACC | TGT | CTC | CAG | 3290 |
|---|---|---|---|---|---|---|---|---|---|---|---|---|---|---|---|---|
| Thr | Val | Thr | Val | Gly | Pro | Met | His | Thr | Leu | Pro | Ser | Thr | Cys | Leu | Gln |  |
|  |  |  | 1035 |  |  |  | 1040 |  |  |  |  | 1045 |  |  |  |  |

| AAG | GTG | GAG | GAA | CAG | CCA | GAG | GAT | GCA | GAC | AAT | CAG | CGG | AAC | GTC | ACT | 3338 |
|---|---|---|---|---|---|---|---|---|---|---|---|---|---|---|---|---|
| Lys | Val | Glu | Glu | Gln | Pro | Glu | Asp | Ala | Asp | Asn | Gln | Arg | Asn | Val | Thr |  |
| 1050 |  |  |  |  | 1055 |  |  |  |  | 1060 |  |  |  |  | 1065 |  |

| CGC | ATG | GGC | AGT | CAG | CCC | CCA | GAC | CCG | AAC | ACT | ATT | GTA | CAT | ATC | CCA | 3386 |
|---|---|---|---|---|---|---|---|---|---|---|---|---|---|---|---|---|
| Arg | Met | Gly | Ser | Gln | Pro | Pro | Asp | Pro | Asn | Thr | Ile | Val | His | Ile | Pro |  |
|  |  |  | 1070 |  |  |  | 1075 |  |  |  |  | 1080 |  |  |  |  |

| GTG | ATG | CTG | ACG | GGC | CCT | CTT | GGG | GAA | GCC | ACG | GTC | GTT | CCC | AGT | GGT | 3434 |
|---|---|---|---|---|---|---|---|---|---|---|---|---|---|---|---|---|
| Val | Met | Leu | Thr | Gly | Pro | Leu | Gly | Glu | Ala | Thr | Val | Val | Pro | Ser | Gly |  |
|  |  |  | 1085 |  |  |  | 1090 |  |  |  |  | 1095 |  |  |  |  |

| AAC | GTG | GAC | CTG | GAA | AGC | CAA | GCA | GAG | GGG | AAG | AAG | GAG | GTG | GAA | GCG | 3482 |
|---|---|---|---|---|---|---|---|---|---|---|---|---|---|---|---|---|
| Asn | Val | Asp | Leu | Glu | Ser | Gln | Ala | Glu | Gly | Lys | Lys | Glu | Val | Glu | Ala |  |
|  |  |  | 1100 |  |  |  | 1105 |  |  |  |  | 1110 |  |  |  |  |

| GAT | GAC | GTG | ATG | AGG | AGC | GGC | CCC | CGG | CCT | ATC | GTC | CCA | TAC | AGC | TCC | 3530 |
|---|---|---|---|---|---|---|---|---|---|---|---|---|---|---|---|---|
| Asp | Asp | Val | Met | Arg | Ser | Gly | Pro | Arg | Pro | Ile | Val | Pro | Tyr | Ser | Ser |  |
| 1115 |  |  |  |  | 1120 |  |  |  |  | 1125 |  |  |  |  |  |  |

| ATG | TTC | TGT | TTA | AGC | CCC | ACC | AAC | CTG | CTC | CGC | CGC | TTC | TGC | CAC | TAC | 3578 |
|---|---|---|---|---|---|---|---|---|---|---|---|---|---|---|---|---|
| Met | Phe | Cys | Leu | Ser | Pro | Thr | Asn | Leu | Leu | Arg | Arg | Phe | Cys | His | Tyr |  |
| 1130 |  |  |  |  | 1135 |  |  |  |  | 1140 |  |  |  |  | 1145 |  |

| ATC | GTG | ACC | ATG | AGG | TAC | TTC | GAG | GTG | GTC | ATT | CTC | GTG | GTC | ATC | GCC | 3626 |
|---|---|---|---|---|---|---|---|---|---|---|---|---|---|---|---|---|
| Ile | Val | Thr | Met | Arg | Tyr | Phe | Glu | Val | Val | Ile | Leu | Val | Val | Ile | Ala |  |
|  |  |  |  | 1150 |  |  |  |  | 1155 |  |  |  |  | 1160 |  |  |

| TTG | AGC | AGC | ATC | GCC | CTG | GCT | GCT | GAG | GAC | CCA | GTG | CGC | ACA | GAC | TCG | 3674 |
|---|---|---|---|---|---|---|---|---|---|---|---|---|---|---|---|---|
| Leu | Ser | Ser | Ile | Ala | Leu | Ala | Ala | Glu | Asp | Pro | Val | Arg | Thr | Asp | Ser |  |
|  |  |  | 1165 |  |  |  | 1170 |  |  |  |  | 1175 |  |  |  |  |

| CCC | AGG | AAC | AAC | GCT | CTG | AAA | TAC | CTG | GAT | TAC | ATT | TTC | ACT | GGT | GTC | 3722 |
|---|---|---|---|---|---|---|---|---|---|---|---|---|---|---|---|---|
| Pro | Arg | Asn | Asn | Ala | Leu | Lys | Tyr | Leu | Asp | Tyr | Ile | Phe | Thr | Gly | Val |  |
|  |  |  | 1180 |  |  |  | 1185 |  |  |  |  | 1190 |  |  |  |  |

| TTT | ACC | TTT | GAG | ATG | GTG | ATA | AAG | ATG | ATC | GAC | TTG | GGA | CTG | CTG | CTT | 3770 |
|---|---|---|---|---|---|---|---|---|---|---|---|---|---|---|---|---|
| Phe | Thr | Phe | Glu | Met | Val | Ile | Lys | Met | Ile | Asp | Leu | Gly | Leu | Leu | Leu |  |
|  |  |  | 1195 |  |  |  | 1200 |  |  |  |  | 1205 |  |  |  |  |

| CAC | CCT | GGA | GCC | TAT | TTC | CGG | GAC | TTG | TGG | AAC | ATT | CTG | GAC | TTC | ATT | 3818 |
|---|---|---|---|---|---|---|---|---|---|---|---|---|---|---|---|---|
| His | Pro | Gly | Ala | Tyr | Phe | Arg | Asp | Leu | Trp | Asn | Ile | Leu | Asp | Phe | Ile |  |
| 1210 |  |  |  |  | 1215 |  |  |  |  | 1220 |  |  |  |  | 1225 |  |

| GTG | GTC | AGT | GGC | GCC | CTG | GTG | GCG | TTT | GCT | TTC | TCA | GGA | TCC | AAA | GGG | 3866 |
|---|---|---|---|---|---|---|---|---|---|---|---|---|---|---|---|---|
| Val | Val | Ser | Gly | Ala | Leu | Val | Ala | Phe | Ala | Phe | Ser | Gly | Ser | Lys | Gly |  |
|  |  |  | 1230 |  |  |  | 1235 |  |  |  |  | 1240 |  |  |  |  |

| AAA | GAC | ATC | AAT | ACC | ATC | AAG | TCT | CTG | AGA | GTC | CTT | CGT | GTC | CTG | CGG | 3914 |
|---|---|---|---|---|---|---|---|---|---|---|---|---|---|---|---|---|
| Lys | Asp | Ile | Asn | Thr | Ile | Lys | Ser | Leu | Arg | Val | Leu | Arg | Val | Leu | Arg |  |
|  |  |  | 1245 |  |  |  | 1250 |  |  |  |  | 1255 |  |  |  |  |

| CCC | CTC | AAG | ACC | ATC | AAA | CGG | CTG | CCC | AAG | CTC | AAG | GCT | GTG | TTT | GAC | 3962 |
|---|---|---|---|---|---|---|---|---|---|---|---|---|---|---|---|---|
| Pro | Leu | Lys | Thr | Ile | Lys | Arg | Leu | Pro | Lys | Leu | Lys | Ala | Val | Phe | Asp |  |
|  |  |  | 1260 |  |  |  | 1265 |  |  |  |  | 1270 |  |  |  |  |

| TGT | GTG | GTG | AAC | TCC | CTG | AAG | AAT | GTC | CTC | AAC | ATC | TTG | ATT | GTC | TAC | 4010 |
|---|---|---|---|---|---|---|---|---|---|---|---|---|---|---|---|---|
| Cys | Val | Val | Asn | Ser | Leu | Lys | Asn | Val | Leu | Asn | Ile | Leu | Ile | Val | Tyr |  |
| 1275 |  |  |  |  | 1280 |  |  |  |  | 1285 |  |  |  |  |  |  |

| ATG | CTC | TTC | ATG | TTC | ATA | TTT | GCC | GTC | ATT | GCG | GTG | CAG | CTC | TTC | AAA | 4058 |
|---|---|---|---|---|---|---|---|---|---|---|---|---|---|---|---|---|
| Met | Leu | Phe | Met | Phe | Ile | Phe | Ala | Val | Ile | Ala | Val | Gln | Leu | Phe | Lys |  |
| 1290 |  |  |  |  | 1295 |  |  |  |  | 1300 |  |  |  |  | 1305 |  |

| GGG | AAG | TTT | TTC | TAC | TGC | ACA | GAT | GAA | TCC | AAG | GAG | CTG | GAG | AGG | GAC | 4106 |
|---|---|---|---|---|---|---|---|---|---|---|---|---|---|---|---|---|

-continued

| | | | | | | | | | | | | | | |
|---|---|---|---|---|---|---|---|---|---|---|---|---|---|---|
| Gly | Lys | Phe | Phe | Tyr | Cys | Thr | Asp | Glu | Ser | Lys | Glu | Leu | Glu | Arg | Asp |
| | | | 1310 | | | | | 1315 | | | | | 1320 | | |

| TGC | AGG | GGT | CAG | TAT | TTG | GAT | TAT | GAG | AAG | GAG | GAA | GTG | GAA | GCT | CAG | 4154 |
|---|---|---|---|---|---|---|---|---|---|---|---|---|---|---|---|---|
| Cys | Arg | Gly | Gln | Tyr | Leu | Asp | Tyr | Glu | Lys | Glu | Glu | Val | Glu | Ala | Gln | |
| | 1325 | | | | | 1330 | | | | | 1335 | | | | | |

| CCC | AGG | CAG | TGG | AAG | AAA | TAC | GAC | TTT | CAC | TAC | GAC | AAT | GTG | CTC | TGG | 4202 |
|---|---|---|---|---|---|---|---|---|---|---|---|---|---|---|---|---|
| Pro | Arg | Gln | Trp | Lys | Lys | Tyr | Asp | Phe | His | Tyr | Asp | Asn | Val | Leu | Trp | |
| | 1340 | | | | | 1345 | | | | | 1350 | | | | | |

| GCT | CTG | CTG | ACG | CTG | TTC | ACA | GTG | TCC | ACG | GGA | GAA | GGC | TGG | CCC | ATG | 4250 |
|---|---|---|---|---|---|---|---|---|---|---|---|---|---|---|---|---|
| Ala | Leu | Leu | Thr | Leu | Phe | Thr | Val | Ser | Thr | Gly | Glu | Gly | Trp | Pro | Met | |
| | 1355 | | | | | 1360 | | | | | 1365 | | | | | |

| GTG | CTG | AAA | CAC | TCC | GTG | GAT | GCC | ACC | TAT | GAG | GAG | CAG | GGT | CCA | AGC | 4298 |
|---|---|---|---|---|---|---|---|---|---|---|---|---|---|---|---|---|
| Val | Leu | Lys | His | Ser | Val | Asp | Ala | Thr | Tyr | Glu | Glu | Gln | Gly | Pro | Ser | |
| 1370 | | | | | 1375 | | | | | 1380 | | | | | 1385 | |

| CCT | GGG | TAC | CGC | ATG | GAG | CTG | TCC | ATC | TTC | TAC | GTG | GTC | TAC | TTT | GTG | 4346 |
|---|---|---|---|---|---|---|---|---|---|---|---|---|---|---|---|---|
| Pro | Gly | Tyr | Arg | Met | Glu | Leu | Ser | Ile | Phe | Tyr | Val | Val | Tyr | Phe | Val | |
| | | | 1390 | | | | | 1395 | | | | | 1400 | | | |

| GTC | TTT | CCC | TTC | TTC | TTC | GTC | AAC | ATC | TTT | GTG | GCT | TTG | ATC | ATC | ATC | 4394 |
|---|---|---|---|---|---|---|---|---|---|---|---|---|---|---|---|---|
| Val | Phe | Pro | Phe | Phe | Phe | Val | Asn | Ile | Phe | Val | Ala | Leu | Ile | Ile | Ile | |
| | | | 1405 | | | | | 1410 | | | | | 1415 | | | |

| ACC | TTC | CAG | GAG | CAG | GGG | GAC | AAG | GTG | ATG | TCT | GAA | TGC | AGC | CTG | GAG | 4442 |
|---|---|---|---|---|---|---|---|---|---|---|---|---|---|---|---|---|
| Thr | Phe | Gln | Glu | Gln | Gly | Asp | Lys | Val | Met | Ser | Glu | Cys | Ser | Leu | Glu | |
| | | 1420 | | | | | 1425 | | | | | 1430 | | | | |

| AAG | AAC | GAG | AGG | GCT | TGC | ATT | GAC | TTC | GCC | ATC | AGC | GCC | AAA | CCC | CTG | 4490 |
|---|---|---|---|---|---|---|---|---|---|---|---|---|---|---|---|---|
| Lys | Asn | Glu | Arg | Ala | Cys | Ile | Asp | Phe | Ala | Ile | Ser | Ala | Lys | Pro | Leu | |
| | 1435 | | | | | 1440 | | | | | 1445 | | | | | |

| ACA | CGG | TAC | ATG | CCC | CAA | AAC | CGG | CAG | TCG | TTC | CAG | TAT | AAG | ACG | TGG | 4538 |
|---|---|---|---|---|---|---|---|---|---|---|---|---|---|---|---|---|
| Thr | Arg | Tyr | Met | Pro | Gln | Asn | Arg | Gln | Ser | Phe | Gln | Tyr | Lys | Thr | Trp | |
| 1450 | | | | | 1455 | | | | | 1460 | | | | | 1465 | |

| ACA | TTT | GTG | GTC | TCC | CCG | CCC | TTT | GAA | TAC | TTC | ATC | ATG | GCC | ATG | ATA | 4586 |
|---|---|---|---|---|---|---|---|---|---|---|---|---|---|---|---|---|
| Thr | Phe | Val | Val | Ser | Pro | Pro | Phe | Glu | Tyr | Phe | Ile | Met | Ala | Met | Ile | |
| | | | 1470 | | | | | 1475 | | | | | 1480 | | | |

| GCC | CTC | AAC | ACT | GTG | GTG | CTG | ATG | ATG | AAG | TTC | TAT | GAT | GCA | CCC | TAT | 4634 |
|---|---|---|---|---|---|---|---|---|---|---|---|---|---|---|---|---|
| Ala | Leu | Asn | Thr | Val | Val | Leu | Met | Met | Lys | Phe | Tyr | Asp | Ala | Pro | Tyr | |
| | | | 1485 | | | | | 1490 | | | | | 1495 | | | |

| GAG | TAC | GAG | CTG | ATG | CTG | AAA | TGC | CTG | AAC | ATC | GTG | TTC | ACA | TCC | ATG | 4682 |
|---|---|---|---|---|---|---|---|---|---|---|---|---|---|---|---|---|
| Glu | Tyr | Glu | Leu | Met | Leu | Lys | Cys | Leu | Asn | Ile | Val | Phe | Thr | Ser | Met | |
| | | 1500 | | | | | 1505 | | | | | 1510 | | | | |

| TTC | TCC | ATG | GAA | TGC | GTG | CTG | AAG | ATC | ATC | GCC | TTT | GGG | GTG | CTG | AAC | 4730 |
|---|---|---|---|---|---|---|---|---|---|---|---|---|---|---|---|---|
| Phe | Ser | Met | Glu | Cys | Val | Leu | Lys | Ile | Ile | Ala | Phe | Gly | Val | Leu | Asn | |
| | 1515 | | | | | 1520 | | | | | 1525 | | | | | |

| TAT | TTC | AGA | GAT | GCC | TGG | AAT | GTC | TTT | GAC | TTT | GTC | ACT | GTG | TTG | GGA | 4778 |
|---|---|---|---|---|---|---|---|---|---|---|---|---|---|---|---|---|
| Tyr | Phe | Arg | Asp | Ala | Trp | Asn | Val | Phe | Asp | Phe | Val | Thr | Val | Leu | Gly | |
| 1530 | | | | | 1535 | | | | | 1540 | | | | | 1545 | |

| AGT | ATT | ACT | GAT | ATT | TTA | GTA | ACA | GAG | ATT | GCG | GAA | ACG | AAC | AAT | TTC | 4826 |
|---|---|---|---|---|---|---|---|---|---|---|---|---|---|---|---|---|
| Ser | Ile | Thr | Asp | Ile | Leu | Val | Thr | Glu | Ile | Ala | Glu | Thr | Asn | Asn | Phe | |
| | | | 1550 | | | | | 1555 | | | | | 1560 | | | |

| ATC | AAC | CTC | AGC | TTC | CTC | CGC | CTC | TTT | CGA | GCT | GCG | CGG | CTG | ATC | AAG | 4874 |
|---|---|---|---|---|---|---|---|---|---|---|---|---|---|---|---|---|
| Ile | Asn | Leu | Ser | Phe | Leu | Arg | Leu | Phe | Arg | Ala | Ala | Arg | Leu | Ile | Lys | |
| | | | 1565 | | | | | 1570 | | | | | 1575 | | | |

| CTG | CTC | CGC | CAG | GGC | TAC | ACC | ATC | CGC | ATC | CTG | CTG | TGG | ACC | TTT | GTC | 4922 |
|---|---|---|---|---|---|---|---|---|---|---|---|---|---|---|---|---|
| Leu | Leu | Arg | Gln | Gly | Tyr | Thr | Ile | Arg | Ile | Leu | Leu | Trp | Thr | Phe | Val | |
| | | | 1580 | | | | | 1585 | | | | | 1590 | | | |

| CAG | TCC | TTC | AAG | GCC | CTG | CCC | TAC | GTG | TGT | CTG | CTC | ATT | GCC | ATG | CTG | 4970 |
|---|---|---|---|---|---|---|---|---|---|---|---|---|---|---|---|---|
| Gln | Ser | Phe | Lys | Ala | Leu | Pro | Tyr | Val | Cys | Leu | Leu | Ile | Ala | Met | Leu | |
| | | | 1595 | | | | | 1600 | | | | | 1605 | | | |

| TTC | TTC | ATC | TAC | GCC | ATC | ATC | GGC | ATG | CAG | GTG | TTT | GGG | AAT | ATT | GCC | 5018 |
|---|---|---|---|---|---|---|---|---|---|---|---|---|---|---|---|---|
| Phe | Phe | Ile | Tyr | Ala | Ile | Ile | Gly | Met | Gln | Val | Phe | Gly | Asn | Ile | Ala | |
| 1610 | | | | | 1615 | | | | | 1620 | | | | | 1625 | |

| CTG | GAT | GAT | GAC | ACC | AGC | ATC | AAC | CGC | CAC | AAC | AAC | TTC | CGG | ACG | TTT | 5066 |

```
        Leu  Asp  Asp  Asp  Thr  Ser  Ile  Asn  Arg  His  Asn  Asn  Phe  Arg  Thr  Phe
                       1630                    1635                    1640

TTG  CAA  GCC  CTG  ATG  CTG  CTG  TTC  AGG  AGC  GCC  ACG  GGG  GAG  GCC  TGG        5114
        Leu  Gln  Ala  Leu  Met  Leu  Leu  Phe  Arg  Ser  Ala  Thr  Gly  Glu  Ala  Trp
                       1645                    1650                    1655

CAC  GAG  ATC  ATG  CTG  TCC  TGC  CTG  AGC  AAC  CAG  GCC  TGT  GAT  GAG  CAG        5162
        His  Glu  Ile  Met  Leu  Ser  Cys  Leu  Ser  Asn  Gln  Ala  Cys  Asp  Glu  Gln
                       1660                    1665                    1670

GCC  AAT  GCC  ACC  GAG  TGT  GGA  AGT  GAC  TTT  GCC  TAC  TTC  TAC  TTC  GTC        5210
        Ala  Asn  Ala  Thr  Glu  Cys  Gly  Ser  Asp  Phe  Ala  Tyr  Phe  Tyr  Phe  Val
                       1675                    1680                    1685

TCC  TTC  ATC  TTC  CTG  TGC  TCC  TTT  CTG  ATG  TTG  AAC  CTC  TTT  GTG  GCT        5258
        Ser  Phe  Ile  Phe  Leu  Cys  Ser  Phe  Leu  Met  Leu  Asn  Leu  Phe  Val  Ala
        1690                 1695                    1700                    1705

GTG  ATC  ATG  GAC  AAT  TTT  GAG  TAC  CTC  ACG  CGG  GAC  TCT  TCC  ATC  CTA        5306
        Val  Ile  Met  Asp  Asn  Phe  Glu  Tyr  Leu  Thr  Arg  Asp  Ser  Ser  Ile  Leu
                            1710                    1715                    1720

GGT  CCT  CAC  CAC  TTG  GAT  GAG  TTC  ATC  CGG  GTC  TGG  GCT  GAA  TAC  GAC        5354
        Gly  Pro  His  His  Leu  Asp  Glu  Phe  Ile  Arg  Val  Trp  Ala  Glu  Tyr  Asp
                       1725                    1730                    1735

CCG  GCT  GCG  TGT  GGG  CGC  ATC  AGT  TAC  AAT  GAC  ATG  TTT  GAG  ATG  CTG        5402
        Pro  Ala  Ala  Cys  Gly  Arg  Ile  Ser  Tyr  Asn  Asp  Met  Phe  Glu  Met  Leu
                       1740                    1745                    1750

AAA  CAC  ATG  TCC  CCG  CCT  CTG  GGG  CTG  GGG  AAG  AAA  TGC  CCT  GCT  CGA        5450
        Lys  His  Met  Ser  Pro  Pro  Leu  Gly  Leu  Gly  Lys  Lys  Cys  Pro  Ala  Arg
                       1755                    1760                    1765

GTT  GCT  TAC  AAG  CGC  CTG  GTT  CGC  ATG  AAC  ATG  CCC  ATC  TCC  AAC  GAG        5498
        Val  Ala  Tyr  Lys  Arg  Leu  Val  Arg  Met  Asn  Met  Pro  Ile  Ser  Asn  Glu
        1770                 1775                    1780                    1785

GAC  ATG  ACT  GTT  CAC  TTC  ACG  TCC  ACG  CTG  ATG  GCC  CTC  ATC  CGG  ACG        5546
        Asp  Met  Thr  Val  His  Phe  Thr  Ser  Thr  Leu  Met  Ala  Leu  Ile  Arg  Thr
                       1790                    1795                    1800

GCA  CTG  GAG  ATC  AAG  CTG  GCC  CCA  GCT  GGG  ACA  AAG  CAG  CAT  CAG  TGT        5594
        Ala  Leu  Glu  Ile  Lys  Leu  Ala  Pro  Ala  Gly  Thr  Lys  Gln  His  Gln  Cys
                       1805                    1810                    1815

GAC  GCG  GAG  TTG  AGG  AAG  GAG  ATT  TCC  GTT  GTG  TGG  GCC  AAT  CTG  CCC        5642
        Asp  Ala  Glu  Leu  Arg  Lys  Glu  Ile  Ser  Val  Val  Trp  Ala  Asn  Leu  Pro
                       1820                    1825                    1830

CAG  AAG  ACT  TTG  GAC  TTG  CTG  GTA  CCA  CCC  CAT  AAG  CCT  GAT  GAG  ATG        5690
        Gln  Lys  Thr  Leu  Asp  Leu  Leu  Val  Pro  Pro  His  Lys  Pro  Asp  Glu  Met
                       1835                    1840                    1845

ACA  GTG  GGG  AAG  GTT  TAT  GCA  GCT  CTG  ATG  ATA  TTT  GAC  TTC  TAC  AAG        5738
        Thr  Val  Gly  Lys  Val  Tyr  Ala  Ala  Leu  Met  Ile  Phe  Asp  Phe  Tyr  Lys
        1850                 1855                    1860                    1865

CAG  AAC  AAA  ACC  ACC  AGA  GAC  CAG  ATG  CAG  CAG  GCT  CCT  GGA  GGC  CTC        5786
        Gln  Asn  Lys  Thr  Thr  Arg  Asp  Gln  Met  Gln  Gln  Ala  Pro  Gly  Gly  Leu
                       1870                    1875                    1880

TCC  CAG  ATG  GGT  CCT  GTG  TCC  CTG  TTC  CAC  CCT  CTG  AAG  GCC  ACC  CTG        5834
        Ser  Gln  Met  Gly  Pro  Val  Ser  Leu  Phe  His  Pro  Leu  Lys  Ala  Thr  Leu
                       1885                    1890                    1895

GAG  CAG  ACA  CAG  CCG  GCT  GTG  CTC  CGA  GGA  GCC  CGG  GTT  TTC  CTT  CGA        5882
        Glu  Gln  Thr  Gln  Pro  Ala  Val  Leu  Arg  Gly  Ala  Arg  Val  Phe  Leu  Arg
                       1900                    1905                    1910

CAG  AAG  AGT  TCC  ACC  TCC  CTC  AGC  AAT  GGC  GGG  GCC  ATA  CAA  AAC  CAA        5930
        Gln  Lys  Ser  Ser  Thr  Ser  Leu  Ser  Asn  Gly  Gly  Ala  Ile  Gln  Asn  Gln
                       1915                    1920                    1925

GAG  AGT  GGC  ATC  AAA  GAG  TCT  GTC  TCC  TGG  GGC  ACT  CAA  AGG  ACC  CAG        5978
        Glu  Ser  Gly  Ile  Lys  Glu  Ser  Val  Ser  Trp  Gly  Thr  Gln  Arg  Thr  Gln
        1930                 1935                    1940                    1945

GAT  GCA  CCC  CAT  GAG  GCC  AGG  CCA  CCC  CTG  GAG  CGT  GGC  CAC  TCC  ACA        6026
```

| | | | | | | | | | | | | | | | | |
|---|---|---|---|---|---|---|---|---|---|---|---|---|---|---|---|---|
| Asp | Ala | Pro | His | Glu | Ala | Arg | Pro | Pro | Leu | Glu | Arg | Gly | His | Ser | Thr | |
| | | | | 1950 | | | | 1955 | | | | | | 1960 | | |

```
GAG  ATC  CCT  GTG  GGG  CGG  TCA  GGA  GCA  CTG  GCT  GTG  GAC  GTT  CAG  ATG      6074
Glu  Ile  Pro  Val  Gly  Arg  Ser  Gly  Ala  Leu  Ala  Val  Asp  Val  Gln  Met
          1965                1970                     1975

CAG  AGC  ATA  ACC  CGG  AGG  GGC  CCT  GAT  GGG  GAG  CCC  CAG  CCT  GGG  CTG      6122
Gln  Ser  Ile  Thr  Arg  Arg  Gly  Pro  Asp  Gly  Glu  Pro  Gln  Pro  Gly  Leu
     1980                     1985                     1990

GAG  AGC  CAG  GGT  CGA  GCG  GCC  TCC  ATG  CCC  CGC  CTT  GCG  GCC  GAG  ACT      6170
Glu  Ser  Gln  Gly  Arg  Ala  Ala  Ser  Met  Pro  Arg  Leu  Ala  Ala  Glu  Thr
1995                     2000                     2005

CAG  CCC  GTC  ACA  GAT  GCC  AGC  CCC  ATG  AAG  CGC  TCC  ATC  TCC  ACG  CTG      6218
Gln  Pro  Val  Thr  Asp  Ala  Ser  Pro  Met  Lys  Arg  Ser  Ile  Ser  Thr  Leu
2010                     2015                     2020                     2025

GCC  CAG  CGG  CCC  CGT  GGG  ACT  CAT  CTT  TGC  AGC  ACC  ACC  CCG  GAC  CGC      6266
Ala  Gln  Arg  Pro  Arg  Gly  Thr  His  Leu  Cys  Ser  Thr  Thr  Pro  Asp  Arg
               2030                     2035                     2040

CCA  CCC  CCT  AGC  CAG  GCG  TCG  TCG  CAC  CAC  CAC  CAC  CAC  CGC  TGC  CAC      6314
Pro  Pro  Pro  Ser  Gln  Ala  Ser  Ser  His  His  His  His  His  Arg  Cys  His
               2045                     2050                     2055

CGC  CGC  AGG  GAC  AGG  AAG  CAG  AGG  TCC  CTG  GAG  AAG  GGG  CCC  AGC  CTG      6362
Arg  Arg  Arg  Asp  Arg  Lys  Gln  Arg  Ser  Leu  Glu  Lys  Gly  Pro  Ser  Leu
          2060                     2065                     2070

TCT  GCC  GAT  ATG  GAT  GGC  GCA  CCA  AGC  AGT  GCT  GTG  GGG  CCG  GGG  CTG      6410
Ser  Ala  Asp  Met  Asp  Gly  Ala  Pro  Ser  Ser  Ala  Val  Gly  Pro  Gly  Leu
     2075                     2080                     2085

CCC  CCG  GGA  GAG  GGG  CCT  ACA  GGC  TGC  CGG  CGG  GAA  CGA  GAG  CGC  CGG      6458
Pro  Pro  Gly  Glu  Gly  Pro  Thr  Gly  Cys  Arg  Arg  Glu  Arg  Glu  Arg  Arg
2090                     2095                     2100                     2105

CAG  GAG  CGG  GGC  CGG  TCC  CAG  GAG  CGG  AGG  CAG  CCC  TCA  TCC  TCC  TCC      6506
Gln  Glu  Arg  Gly  Arg  Ser  Gln  Glu  Arg  Arg  Gln  Pro  Ser  Ser  Ser  Ser
               2110                     2115                     2120

TCG  GAG  AAG  CAG  CGC  TTC  TAC  TCC  TGC  GAC  CGC  TTT  GGG  GGC  CGT  GAG      6554
Ser  Glu  Lys  Gln  Arg  Phe  Tyr  Ser  Cys  Asp  Arg  Phe  Gly  Gly  Arg  Glu
               2125                     2130                     2135

CCC  CCG  AAG  CCC  AAG  CCC  TCC  CTC  AGC  AGC  CAC  CCA  ACG  TCG  CCA  ACA      6602
Pro  Pro  Lys  Pro  Lys  Pro  Ser  Leu  Ser  Ser  His  Pro  Thr  Ser  Pro  Thr
               2140                     2145                     2150

GCT  GGC  CAG  GAG  CCG  GGA  CCC  CAC  CCA  CAG  GCC  GGC  TCA  GCC  GTG  GGC      6650
Ala  Gly  Gln  Glu  Pro  Gly  Pro  His  Pro  Gln  Ala  Gly  Ser  Ala  Val  Gly
          2155                     2160                     2165

TTT  CCG  AAC  ACA  ACG  CCC  TGC  TGC  AGA  GAG  ACC  CCC  TCA  GCC  AGC  CCC      6698
Phe  Pro  Asn  Thr  Thr  Pro  Cys  Cys  Arg  Glu  Thr  Pro  Ser  Ala  Ser  Pro
2170                     2175                     2180                     2185

TGG  CCC  CTG  GCT  CTC  GAA  TTG  GCT  CTG  ACC  CTT  ACC  TGG  GGC  AGC  GTC      6746
Trp  Pro  Leu  Ala  Leu  Glu  Leu  Ala  Leu  Thr  Leu  Thr  Trp  Gly  Ser  Val
               2190                     2195                     2200

TGG  ACA  GTG  AGG  CCT  CTG  TCC  ACG  CCC  TGC  CTG  AGG  ACA  CGC  TCA  CTT      6794
Trp  Thr  Val  Arg  Pro  Leu  Ser  Thr  Pro  Cys  Leu  Arg  Thr  Arg  Ser  Leu
               2205                     2210                     2215

TCG  AGG  AGG  CTG  TGG  CCA  CCA  ACT  CGG  GCC  GCT  CCT  CCA  GGA  CTT  CCT      6842
Ser  Arg  Arg  Leu  Trp  Pro  Pro  Thr  Arg  Ala  Ala  Pro  Pro  Gly  Leu  Pro
               2220                     2225                     2230

ACG  TGT  CCT  CCC  TGACCTCCCA  GTCTCACCCT  CTCCGCCGCG  TGCCCAACGG                  6894
Thr  Cys  Pro  Pro
               2235

TTACCACTGC  ACCCTGGGAC  TCAGCTCGGG  TGGCCGAGCA  CGGCACAGCT  ACCACCACCC              6954

TGACCAAGAC  CACTGGTGCT  AGCTGCACCG  TGACCGCTCA  GACGCCTGCA  TGCAGCAGGC              7014

GTGTGTTCCA  GTGGATGAGT  TTTATCATCC  ACACGGGGCA  GTCGGCCCTC  GGGGGAGGCC              7074
```

-continued

```
TTGCCCACCT TGGTGAGGCT CCTGTGGCCC CTCCCTCCCC CTCCTCCCCT CTTTTACTCT    7134

AGACGACGAA TAAAGCCCTG TTGCTTGAGT GTACGTACCG C                        7175
```

( 2 ) INFORMATION FOR SEQ ID NO:9:

( i ) SEQUENCE CHARACTERISTICS:
        ( A ) LENGTH: 1546 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1437

( i x ) FEATURE:
        ( A ) NAME/KEY: 3'UTR
        ( B ) LOCATION: 1435..1546

( x i ) SEQUENCE DESCRIPTION: SEQ ID NO:9:

```
ATG  GTC  CAG  AAG  ACC  AGC  ATG  TCC  CGG  GGC  CCT  TAC  CCA  CCC  TCC  CAG    48
Met  Val  Gln  Lys  Thr  Ser  Met  Ser  Arg  Gly  Pro  Tyr  Pro  Pro  Ser  Gln
 1                   5                        10                       15

GAG  ATC  CCC  ATG  GAG  GTC  TTC  GAC  CCC  AGC  CCG  CAG  GGC  AAA  TAC  AGC    96
Glu  Ile  Pro  Met  Glu  Val  Phe  Asp  Pro  Ser  Pro  Gln  Gly  Lys  Tyr  Ser
                20                        25                       30

AAG  AGG  AAA  GGG  CGA  TTC  AAA  CGG  TCA  GAT  GGG  AGC  ACG  TCC  TCG  GAT   144
Lys  Arg  Lys  Gly  Arg  Phe  Lys  Arg  Ser  Asp  Gly  Ser  Thr  Ser  Ser  Asp
            35                       40                       45

ACC  ACA  TCC  AAC  AGC  TTT  GTC  CGC  CAG  GGC  TCA  GCG  GAG  TCC  TAC  ACC   192
Thr  Thr  Ser  Asn  Ser  Phe  Val  Arg  Gln  Gly  Ser  Ala  Glu  Ser  Tyr  Thr
       50                       55                       60

AGC  CGT  CCA  TCA  GAC  TCT  GAT  GTA  TCT  CTG  GAG  GAG  GAC  CGG  GAA  GCC   240
Ser  Arg  Pro  Ser  Asp  Ser  Asp  Val  Ser  Leu  Glu  Glu  Asp  Arg  Glu  Ala
 65                      70                       75                       80

TTA  AGG  AAG  GAA  GCA  GAG  CGC  CAG  GCA  TTA  GCG  CAG  CTC  GAG  AAG  GCC   288
Leu  Arg  Lys  Glu  Ala  Glu  Arg  Gln  Ala  Leu  Ala  Gln  Leu  Glu  Lys  Ala
                     85                       90                       95

AAG  ACC  AAG  CCA  GTG  GCA  TTT  GCT  GTG  CGG  ACA  AAT  GTT  GGC  TAC  AAT   336
Lys  Thr  Lys  Pro  Val  Ala  Phe  Ala  Val  Arg  Thr  Asn  Val  Gly  Tyr  Asn
                100                      105                      110

CCG  TCT  CCA  GGG  GAT  GAG  GTG  CCT  GTG  CAG  GGA  GTG  GCC  ATC  ACC  TTC   384
Pro  Ser  Pro  Gly  Asp  Glu  Val  Pro  Val  Gln  Gly  Val  Ala  Ile  Thr  Phe
            115                      120                      125

GAG  CCC  AAA  GAC  TTC  CTG  CAC  ATC  AAG  GAG  AAA  TAC  AAT  AAT  GAC  TGG   432
Glu  Pro  Lys  Asp  Phe  Leu  His  Ile  Lys  Glu  Lys  Tyr  Asn  Asn  Asp  Trp
       130                      135                      140

TGG  ATC  GGG  CGG  CTG  GTG  AAG  GAG  GGC  TGT  GAG  GTT  GGC  TTC  ATT  CCC   480
Trp  Ile  Gly  Arg  Leu  Val  Lys  Glu  Gly  Cys  Glu  Val  Gly  Phe  Ile  Pro
145                      150                      155                      160

AGC  CCC  GTC  AAA  CTG  GAC  AGC  CTT  CGC  CTG  CTG  CAG  GAA  CAG  AAG  CTG   528
Ser  Pro  Val  Lys  Leu  Asp  Ser  Leu  Arg  Leu  Leu  Gln  Glu  Gln  Lys  Leu
                     165                      170                      175

CGC  CAG  AAC  CGC  CTC  GGC  TCC  AGC  AAA  TCA  GGC  GAT  AAC  TCC  AGT  TCC   576
Arg  Gln  Asn  Arg  Leu  Gly  Ser  Ser  Lys  Ser  Gly  Asp  Asn  Ser  Ser  Ser
                180                      185                      190

AGT  CTG  GGA  GAT  GTG  GTG  ACT  GGC  ACC  CGC  CGC  CCC  ACA  CCC  CCT  GCC   624
Ser  Leu  Gly  Asp  Val  Val  Thr  Gly  Thr  Arg  Arg  Pro  Thr  Pro  Pro  Ala
            195                      200                      205

AGT  GCC  AAA  CAG  AAG  CAG  AAG  TCG  ACA  GAG  CAT  GTG  CCC  CCC  TAT  GAC   672
Ser  Ala  Lys  Gln  Lys  Gln  Lys  Ser  Thr  Glu  His  Val  Pro  Pro  Tyr  Asp
```

```
            210                          215                         220
GTG  GTG  CCT  TCC  ATG  AGG  CCC  ATC  ATC  CTG  GTG  GGA  CCG  TCG  CTC  AAG     720
Val  Val  Pro  Ser  Met  Arg  Pro  Ile  Ile  Leu  Val  Gly  Pro  Ser  Leu  Lys
225                      230                      235                      240

GGC  TAC  GAG  GTT  ACA  GAC  ATG  ATG  CAG  AAA  GCT  TTA  TTT  GAC  TTC  TTG     768
Gly  Tyr  Glu  Val  Thr  Asp  Met  Met  Gln  Lys  Ala  Leu  Phe  Asp  Phe  Leu
                    245                      250                      255

AAG  CAT  CGG  TTT  GAT  GGC  AGG  ATC  TCC  ATC  ACT  CGT  GTG  ACG  GCA  GAT     816
Lys  His  Arg  Phe  Asp  Gly  Arg  Ile  Ser  Ile  Thr  Arg  Val  Thr  Ala  Asp
               260                      265                      270

ATT  TCC  CTG  GCT  AAG  CGC  TCA  GTT  CTC  AAC  AAC  CCC  AGC  AAA  CAC  ATC     864
Ile  Ser  Leu  Ala  Lys  Arg  Ser  Val  Leu  Asn  Asn  Pro  Ser  Lys  His  Ile
          275                      280                      285

ATC  ATT  GAG  CGC  TCC  AAC  ACA  CGC  TCC  AGC  CTG  GCT  GAG  GTG  CAG  AGT     912
Ile  Ile  Glu  Arg  Ser  Asn  Thr  Arg  Ser  Ser  Leu  Ala  Glu  Val  Gln  Ser
     290                      295                      300

GAA  ATC  GAG  CGA  ATC  TTC  GAG  CTG  GCC  CGG  ACC  CTT  CAG  TTG  GTC  GCT     960
Glu  Ile  Glu  Arg  Ile  Phe  Glu  Leu  Ala  Arg  Thr  Leu  Gln  Leu  Val  Ala
305                      310                      315                      320

CTG  GAT  GCT  GAC  ACC  ATC  AAT  CAC  CCA  GCC  CAG  CTG  TCC  AAG  ACC  TCG    1008
Leu  Asp  Ala  Asp  Thr  Ile  Asn  His  Pro  Ala  Gln  Leu  Ser  Lys  Thr  Ser
                    325                      330                      335

CTG  GCC  CCC  ATC  ATT  GTT  TAC  ATC  AAG  ATC  ACC  TCT  CCC  AAG  GTA  CTT    1056
Leu  Ala  Pro  Ile  Ile  Val  Tyr  Ile  Lys  Ile  Thr  Ser  Pro  Lys  Val  Leu
               340                      345                      350

CAA  AGG  CTC  ATC  AAG  TCC  CGA  GGA  AAG  TCT  CAG  TCC  AAA  CAC  CTC  AAT    1104
Gln  Arg  Leu  Ile  Lys  Ser  Arg  Gly  Lys  Ser  Gln  Ser  Lys  His  Leu  Asn
          355                      360                      365

GTC  CAA  ATA  GCG  GCC  TCG  GAA  AAG  CTG  GCA  CAG  TGC  CCC  CCT  GAA  ATG    1152
Val  Gln  Ile  Ala  Ala  Ser  Glu  Lys  Leu  Ala  Gln  Cys  Pro  Pro  Glu  Met
     370                      375                      380

TTT  GAC  ATC  ATC  CTG  GAT  GAG  AAC  CAA  TTG  GAG  GAT  GCC  TGC  GAG  CAT    1200
Phe  Asp  Ile  Ile  Leu  Asp  Glu  Asn  Gln  Leu  Glu  Asp  Ala  Cys  Glu  His
385                      390                      395                      400

CTG  GCG  GAG  TAC  TTG  GAA  GCC  TAT  TGG  AAG  GCC  ACA  CAC  CCG  CCC  AGC    1248
Leu  Ala  Glu  Tyr  Leu  Glu  Ala  Tyr  Trp  Lys  Ala  Thr  His  Pro  Pro  Ser
                    405                      410                      415

AGC  ACG  CCA  CCC  AAT  CCG  CTG  CTG  AAC  CGC  ACC  ATG  GCT  ACC  GCA  GCC    1296
Ser  Thr  Pro  Pro  Asn  Pro  Leu  Leu  Asn  Arg  Thr  Met  Ala  Thr  Ala  Ala
               420                      425                      430

CTG  GCT  GCC  AGC  CCT  GCC  CCT  GTC  TCC  AAC  CTC  CAG  GTA  CAG  GTG  CTC    1344
Leu  Ala  Ala  Ser  Pro  Ala  Pro  Val  Ser  Asn  Leu  Gln  Val  Gln  Val  Leu
          435                      440                      445

ACC  TCG  CTC  AGG  AGA  AAC  CTC  GGC  TTC  TGG  GGC  GGG  CTG  GAG  TCC  TCA    1392
Thr  Ser  Leu  Arg  Arg  Asn  Leu  Gly  Phe  Trp  Gly  Gly  Leu  Glu  Ser  Ser
     450                      455                      460

CAG  CGG  GGC  AGT  GTG  GTG  CCC  CAG  GAG  CAG  GAA  CAT  GCC  ATG  TAGTGGGCGC   1444
Gln  Arg  Gly  Ser  Val  Val  Pro  Gln  Glu  Gln  Glu  His  Ala  Met
465                      470                      475

CCTGCCCGTC TTCCCTCCTG CTCTGGGGTC GGAACTGGAG TGCAGGGAAC ATGGAGGAGG                  1504

AAGGGAAGAG CTTTATTTTG TAAAAAAATA AGATGAGCGG CA                                     1546
```

( 2 ) INFORMATION FOR SEQ ID NO:10:

( i ) SEQUENCE CHARACTERISTICS:
        ( A ) LENGTH: 1851 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
    ( A ) NAME/KEY: CDS
    ( B ) LOCATION: 1..1797
    ( D ) OTHER INFORMATION: /standard_name= "Beta1-3"

( i x ) FEATURE:
    ( A ) NAME/KEY: 3'UTR
    ( B ) LOCATION: 1795..1851

( x i ) SEQUENCE DESCRIPTION: SEQ ID NO:10:

| | | | | | | | | | | | | | | | | |
|---|---|---|---|---|---|---|---|---|---|---|---|---|---|---|---|---|
| ATG | GTC | CAG | AAG | ACC | AGC | ATG | TCC | CGG | GGC | CCT | TAC | CCA | CCC | TCC | CAG | 48 |
| Met | Val | Gln | Lys | Thr | Ser | Met | Ser | Arg | Gly | Pro | Tyr | Pro | Pro | Ser | Gln | |
| 1 | | | | 5 | | | | | 10 | | | | | 15 | | |
| GAG | ATC | CCC | ATG | GGA | GTC | TTC | GAC | CCC | AGC | CCG | CAG | GGC | AAA | TAC | AGC | 96 |
| Glu | Ile | Pro | Met | Gly | Val | Phe | Asp | Pro | Ser | Pro | Gln | Gly | Lys | Tyr | Ser | |
| | | | 20 | | | | | 25 | | | | | 30 | | | |
| AAG | AGG | AAA | GGG | CGA | TTC | AAA | CGG | TCA | GAT | GGG | AGC | ACG | TCC | TCG | GAT | 144 |
| Lys | Arg | Lys | Gly | Arg | Phe | Lys | Arg | Ser | Asp | Gly | Ser | Thr | Ser | Ser | Asp | |
| | | 35 | | | | | 40 | | | | | 45 | | | | |
| ACC | ACA | TCC | AAC | AGC | TTT | GTC | CGC | CAG | GGC | TCA | GCG | GAG | TCC | TAC | ACC | 192 |
| Thr | Thr | Ser | Asn | Ser | Phe | Val | Arg | Gln | Gly | Ser | Ala | Glu | Ser | Tyr | Thr | |
| | 50 | | | | | 55 | | | | | 60 | | | | | |
| AGC | CGT | CCA | TCA | GAC | TCT | GAT | GTA | TCT | CTG | GAG | GAG | GAC | CGG | GAA | GCC | 240 |
| Ser | Arg | Pro | Ser | Asp | Ser | Asp | Val | Ser | Leu | Glu | Glu | Asp | Arg | Glu | Ala | |
| 65 | | | | | 70 | | | | | 75 | | | | | 80 | |
| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala | Glu | Arg | Gln | Ala | Leu | Ala | Gln | Leu | Glu | Lys | Ala | |
| | | | | 85 | | | | | 90 | | | | | 95 | | |
| AAG | ACC | AAG | CCA | GTG | GCA | TTT | GCT | GTG | CGG | ACA | AAT | GTT | GGC | TAC | AAT | 336 |
| Lys | Thr | Lys | Pro | Val | Ala | Phe | Ala | Val | Arg | Thr | Asn | Val | Gly | Tyr | Asn | |
| | | | 100 | | | | | 105 | | | | | 110 | | | |
| CCG | TCT | CCA | GGG | GAT | GAG | GTG | CCT | GTG | CAG | GGA | GTG | GCC | ATC | ACC | TTC | 384 |
| Pro | Ser | Pro | Gly | Asp | Glu | Val | Pro | Val | Gln | Gly | Val | Ala | Ile | Thr | Phe | |
| | | 115 | | | | | 120 | | | | | 125 | | | | |
| GAG | CCC | AAA | GAC | TTC | CTG | CAC | ATC | AAG | GAG | AAA | TAC | AAT | AAT | GAC | TGG | 432 |
| Glu | Pro | Lys | Asp | Phe | Leu | His | Ile | Lys | Glu | Lys | Tyr | Asn | Asn | Asp | Trp | |
| | 130 | | | | | 135 | | | | | 140 | | | | | |
| TGG | ATC | GGG | CGG | CTG | GTG | AAG | GAG | GGC | TGT | GAG | GTT | GGC | TTC | ATT | CCC | 480 |
| Trp | Ile | Gly | Arg | Leu | Val | Lys | Glu | Gly | Cys | Glu | Val | Gly | Phe | Ile | Pro | |
| 145 | | | | | 150 | | | | | 155 | | | | | 160 | |
| AGC | CCC | GTC | AAA | CTG | GAC | AGC | CTT | CGC | CTG | CTG | CAG | GAA | CAG | AAG | CTG | 528 |
| Ser | Pro | Val | Lys | Leu | Asp | Ser | Leu | Arg | Leu | Leu | Gln | Glu | Gln | Lys | Leu | |
| | | | | 165 | | | | | 170 | | | | | 175 | | |
| CGC | CAG | AAC | CGC | CTC | GGC | TCC | AGC | AAA | TCA | GGC | GAT | AAC | TCC | AGT | TCC | 576 |
| Arg | Gln | Asn | Arg | Leu | Gly | Ser | Ser | Lys | Ser | Gly | Asp | Asn | Ser | Ser | Ser | |
| | | | 180 | | | | | 185 | | | | | 190 | | | |
| AGT | CTG | GGA | GAT | GTG | GTG | ACT | GGC | ACC | CGC | CGC | CCC | ACA | CCC | CCT | GCC | 624 |
| Ser | Leu | Gly | Asp | Val | Val | Thr | Gly | Thr | Arg | Arg | Pro | Thr | Pro | Pro | Ala | |
| | | 195 | | | | | 200 | | | | | 205 | | | | |
| AGT | GCC | AAA | CAG | AAG | CAG | AAG | TCG | ACA | GAG | CAT | GTG | CCC | CCC | TAT | GAC | 672 |
| Ser | Ala | Lys | Gln | Lys | Gln | Lys | Ser | Thr | Glu | His | Val | Pro | Pro | Tyr | Asp | |
| | 210 | | | | | 215 | | | | | 220 | | | | | |
| GTG | GTG | CCT | TCC | ATG | AGG | CCC | ATC | ATC | CTG | GTG | GGA | CCG | TCG | CTC | AAG | 720 |
| Val | Val | Pro | Ser | Met | Arg | Pro | Ile | Ile | Leu | Val | Gly | Pro | Ser | Leu | Lys | |
| 225 | | | | | 230 | | | | | 235 | | | | | 240 | |
| GGC | TAC | GAG | GTT | ACA | GAC | ATG | ATG | CAG | AAA | GCT | TTA | TTT | GAC | TTC | TTG | 768 |
| Gly | Tyr | Glu | Val | Thr | Asp | Met | Met | Gln | Lys | Ala | Leu | Phe | Asp | Phe | Leu | |
| | | | | 245 | | | | | 250 | | | | | 255 | | |
| AAG | CAT | CGG | TTT | GAT | GGC | AGG | ATC | TCC | ATC | ACT | CGT | GTG | ACG | GCA | GAT | 816 |
| Lys | His | Arg | Phe | Asp | Gly | Arg | Ile | Ser | Ile | Thr | Arg | Val | Thr | Ala | Asp | |
| | | | 260 | | | | | 265 | | | | | 270 | | | |

| | | | | | | | | | | | | | | | | |
|---|---|---|---|---|---|---|---|---|---|---|---|---|---|---|---|---|
| ATT | TCC | CTG | GCT | AAG | CGC | TCA | GTT | CTC | AAC | AAC | CCC | AGC | AAA | CAC | ATC | 864 |
| Ile | Ser | Leu | Ala | Lys | Arg | Ser | Val | Leu | Asn | Asn | Pro | Ser | Lys | His | Ile | |
| | | 275 | | | | | 280 | | | | | 285 | | | | |
| ATC | ATT | GAG | CGC | TCC | AAC | ACA | CGC | TCC | AGC | CTG | GCT | GAG | GTG | CAG | AGT | 912 |
| Ile | Ile | Glu | Arg | Ser | Asn | Thr | Arg | Ser | Ser | Leu | Ala | Glu | Val | Gln | Ser | |
| 290 | | | | | 295 | | | | | 300 | | | | | | |
| GAA | ATC | GAG | CGA | ATC | TTC | GAG | CTG | GCC | CGG | ACC | CTT | CAG | TTG | GTC | GCT | 960 |
| Glu | Ile | Glu | Arg | Ile | Phe | Glu | Leu | Ala | Arg | Thr | Leu | Gln | Leu | Val | Ala | |
| 305 | | | | | 310 | | | | | 315 | | | | | 320 | |
| CTG | GAT | GCT | GAC | ACC | ATC | AAT | CAC | CCA | GCC | CAG | CTG | TCC | AAG | ACC | TCG | 1008 |
| Leu | Asp | Ala | Asp | Thr | Ile | Asn | His | Pro | Ala | Gln | Leu | Ser | Lys | Thr | Ser | |
| | | | | 325 | | | | | 330 | | | | | 335 | | |
| CTG | GCC | CCC | ATC | ATT | GTT | TAC | ATC | AAG | ATC | ACC | TCT | CCC | AAG | GTA | CTT | 1056 |
| Leu | Ala | Pro | Ile | Ile | Val | Tyr | Ile | Lys | Ile | Thr | Ser | Pro | Lys | Val | Leu | |
| | | | 340 | | | | | 345 | | | | | 350 | | | |
| CAA | AGG | CTC | ATC | AAG | TCC | CGA | GGA | AAG | TCT | CAG | TCC | AAA | CAC | CTC | AAT | 1104 |
| Gln | Arg | Leu | Ile | Lys | Ser | Arg | Gly | Lys | Ser | Gln | Ser | Lys | His | Leu | Asn | |
| | | | 355 | | | | | 360 | | | | | 365 | | | |
| GTC | CAA | ATA | GCG | GCC | TCG | GAA | AAG | CTG | GCA | CAG | TGC | CCC | CCT | GAA | ATG | 1152 |
| Val | Gln | Ile | Ala | Ala | Ser | Glu | Lys | Leu | Ala | Gln | Cys | Pro | Pro | Glu | Met | |
| | | 370 | | | | | 375 | | | | | 380 | | | | |
| TTT | GAC | ATC | ATC | CTG | GAT | GAG | AAC | CAA | TTG | GAG | GAT | GCC | TGC | GAG | CAT | 1200 |
| Phe | Asp | Ile | Ile | Leu | Asp | Glu | Asn | Gln | Leu | Glu | Asp | Ala | Cys | Glu | His | |
| 385 | | | | | 390 | | | | | 395 | | | | | 400 | |
| CTG | GCG | GAG | TAC | TTG | GAA | GCC | TAT | TGG | AAG | GCC | ACA | CAC | CCG | CCC | AGC | 1248 |
| Leu | Ala | Glu | Tyr | Leu | Glu | Ala | Tyr | Trp | Lys | Ala | Thr | His | Pro | Pro | Ser | |
| | | | | 405 | | | | | 410 | | | | | 415 | | |
| AGC | ACG | CCA | CCC | AAT | CCG | CTG | CTG | AAC | CGC | ACC | ATG | GCT | ACC | GCA | GCC | 1296 |
| Ser | Thr | Pro | Pro | Asn | Pro | Leu | Leu | Asn | Arg | Thr | Met | Ala | Thr | Ala | Ala | |
| | | | 420 | | | | | 425 | | | | | 430 | | | |
| CTG | GCT | GCC | AGC | CCT | GCC | CCT | GTC | TCC | AAC | CTC | CAG | GGA | CCC | TAC | CTT | 1344 |
| Leu | Ala | Ala | Ser | Pro | Ala | Pro | Val | Ser | Asn | Leu | Gln | Gly | Pro | Tyr | Leu | |
| | | | 435 | | | | | 440 | | | | | 445 | | | |
| GCT | TCC | GGG | GAC | CAG | CCA | CTG | GAA | CGG | GCC | ACC | GGG | GAG | CAC | GCC | AGC | 1392 |
| Ala | Ser | Gly | Asp | Gln | Pro | Leu | Glu | Arg | Ala | Thr | Gly | Glu | His | Ala | Ser | |
| | | 450 | | | | | 455 | | | | | 460 | | | | |
| ATG | CAC | GAG | TAC | CCA | GGG | GAG | CTG | GGC | CAG | CCC | CCA | GGC | CTT | TAC | CCC | 1440 |
| Met | His | Glu | Tyr | Pro | Gly | Glu | Leu | Gly | Gln | Pro | Pro | Gly | Leu | Tyr | Pro | |
| 465 | | | | | 470 | | | | | 475 | | | | | 480 | |
| AGC | AGC | CAC | CCA | CCA | GGC | CGG | GCA | GGC | ACG | CTA | CGG | GCA | CTG | TCC | CGC | 1488 |
| Ser | Ser | His | Pro | Pro | Gly | Arg | Ala | Gly | Thr | Leu | Arg | Ala | Leu | Ser | Arg | |
| | | | | 485 | | | | | 490 | | | | | 495 | | |
| CAA | GAC | ACT | TTT | GAT | GCC | GAC | ACC | CCC | GGC | AGC | CGA | AAC | TCT | GCC | TAC | 1536 |
| Gln | Asp | Thr | Phe | Asp | Ala | Asp | Thr | Pro | Gly | Ser | Arg | Asn | Ser | Ala | Tyr | |
| | | | 500 | | | | | 505 | | | | | 510 | | | |
| ACG | GAG | CTG | GGA | GAC | TCA | TGT | GTG | GAC | ATG | GAG | ACT | GAC | CCC | TCA | GAG | 1584 |
| Thr | Glu | Leu | Gly | Asp | Ser | Cys | Val | Asp | Met | Glu | Thr | Asp | Pro | Ser | Glu | |
| | | 515 | | | | | 520 | | | | | 525 | | | | |
| GGG | CCA | GGG | CTT | GGA | GAC | CCT | GCA | GGG | GGC | GGC | ACG | CCC | CCA | GCC | CGA | 1632 |
| Gly | Pro | Gly | Leu | Gly | Asp | Pro | Ala | Gly | Gly | Gly | Thr | Pro | Pro | Ala | Arg | |
| 530 | | | | | 535 | | | | | 540 | | | | | | |
| CAG | GGA | TCC | TGG | GAG | GAC | GAG | GAA | GAA | GAC | TAT | GAG | GAA | GAG | CTG | ACC | 1680 |
| Gln | Gly | Ser | Trp | Glu | Asp | Glu | Glu | Glu | Asp | Tyr | Glu | Glu | Glu | Leu | Thr | |
| 545 | | | | | 550 | | | | | 555 | | | | | 560 | |
| GAC | AAC | CGG | AAC | CGG | GGC | CGG | AAT | AAG | GCC | CGC | TAC | TGC | GCT | GAG | GGT | 1728 |
| Asp | Asn | Arg | Asn | Arg | Gly | Arg | Asn | Lys | Ala | Arg | Tyr | Cys | Ala | Glu | Gly | |
| | | | | 565 | | | | | 570 | | | | | 575 | | |
| GGG | GGT | CCA | GTT | TTG | GGG | CGC | AAC | AAG | AAT | GAG | CTG | GAG | GGC | TGG | GGA | 1776 |
| Gly | Gly | Pro | Val | Leu | Gly | Arg | Asn | Lys | Asn | Glu | Leu | Glu | Gly | Trp | Gly | |
| | | | 580 | | | | | 585 | | | | | 590 | | | |

```
CGA  GGC  GTC  TAC  ATT  CGC  TGAGAGGCAG  GGGCCACACG  GCGGGAGGAA           1824
Arg  Gly  Val  Tyr  Ile  Arg
          595

GGGCTCTGAG  CCCAGGGGAG  GGGAGGG                                             1851
```

( 2 ) INFORMATION FOR SEQ ID NO:11:

( i ) SEQUENCE CHARACTERISTICS:
        ( A ) LENGTH: 3600 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 35..3310
        ( D ) OTHER INFORMATION: /standard_name= "Alpha-2"

( i x ) FEATURE:
        ( A ) NAME/KEY: 5'UTR
        ( B ) LOCATION: 1..34

( i x ) FEATURE:
        ( A ) NAME/KEY: 3'UTR
        ( B ) LOCATION: 3308..3600

( x i ) SEQUENCE DESCRIPTION: SEQ ID NO:11:

```
GCGGGGGAGG  GGGCATTGAT  CTTCGATCGC  GAAG  ATG  GCT  GCT  GGC  TGC  CTG      52
                                         Met  Ala  Ala  Gly  Cys  Leu
                                          1                       5

CTG  GCC  TTG  ACT  CTG  ACA  CTT  TTC  CAA  TCT  TTG  CTC  ATC  GGC  CCC  TCG   100
Leu  Ala  Leu  Thr  Leu  Thr  Leu  Phe  Gln  Ser  Leu  Leu  Ile  Gly  Pro  Ser
               10                  15                      20

TCG  GAG  GAG  CCG  TTC  CCT  TCG  GCC  GTC  ACT  ATC  AAA  TCA  TGG  GTG  GAT   148
Ser  Glu  Glu  Pro  Phe  Pro  Ser  Ala  Val  Thr  Ile  Lys  Ser  Trp  Val  Asp
          25                       30                  35

AAG  ATG  CAA  GAA  GAC  CTT  GTC  ACA  CTG  GCA  AAA  ACA  GCA  AGT  GGA  GTC   196
Lys  Met  Gln  Glu  Asp  Leu  Val  Thr  Leu  Ala  Lys  Thr  Ala  Ser  Gly  Val
     40                       45                  50

AAT  CAG  CTT  GTT  GAT  ATT  TAT  GAG  AAA  TAT  CAA  GAT  TTG  TAT  ACT  GTG   244
Asn  Gln  Leu  Val  Asp  Ile  Tyr  Glu  Lys  Tyr  Gln  Asp  Leu  Tyr  Thr  Val
55                      60                       65                       70

GAA  CCA  AAT  AAT  GCA  CGC  CAG  CTG  GTA  GAA  ATT  GCA  GCC  AGG  GAT  ATT   292
Glu  Pro  Asn  Asn  Ala  Arg  Gln  Leu  Val  Glu  Ile  Ala  Ala  Arg  Asp  Ile
                    75                  80                       85

GAG  AAA  CTT  CTG  AGC  AAC  AGA  TCT  AAA  GCC  CTG  GTG  AGC  CTG  GCA  TTG   340
Glu  Lys  Leu  Leu  Ser  Asn  Arg  Ser  Lys  Ala  Leu  Val  Ser  Leu  Ala  Leu
               90                  95                       100

GAA  GCG  GAG  AAA  GTT  CAA  GCA  GCT  CAC  CAG  TGG  AGA  GAA  GAT  TTT  GCA   388
Glu  Ala  Glu  Lys  Val  Gln  Ala  Ala  His  Gln  Trp  Arg  Glu  Asp  Phe  Ala
          105                      110                      115

AGC  AAT  GAA  GTT  GTC  TAC  TAC  AAT  GCA  AAG  GAT  GAT  CTC  GAT  CCT  GAG   436
Ser  Asn  Glu  Val  Val  Tyr  Tyr  Asn  Ala  Lys  Asp  Asp  Leu  Asp  Pro  Glu
     120                      125                      130

AAA  AAT  GAC  AGT  GAG  CCA  GGC  AGC  CAG  AGG  ATA  AAA  CCT  GTT  TTC  ATT   484
Lys  Asn  Asp  Ser  Glu  Pro  Gly  Ser  Gln  Arg  Ile  Lys  Pro  Val  Phe  Ile
135                      140                      145                      150

GAA  GAT  GCT  AAT  TTT  GGA  CGA  CAA  ATA  TCT  TAT  CAG  CAC  GCA  GCA  GTC   532
Glu  Asp  Ala  Asn  Phe  Gly  Arg  Gln  Ile  Ser  Tyr  Gln  His  Ala  Ala  Val
               155                      160                      165

CAT  ATT  CCT  ACT  GAC  ATC  TAT  GAG  GGC  TCA  ACA  ATT  GTG  TTA  AAT  GAA   580
His  Ile  Pro  Thr  Asp  Ile  Tyr  Glu  Gly  Ser  Thr  Ile  Val  Leu  Asn  Glu
               170                      175                      180
```

| | | | | | | | | | | | | | | | | |
|---|---|---|---|---|---|---|---|---|---|---|---|---|---|---|---|---|
| CTC | AAC | TGG | ACA | AGT | GCC | TTA | GAT | GAA | GTT | TTC | AAA | AAG | AAT | CGC | GAG | 628 |
| Leu | Asn | Trp | Thr | Ser | Ala | Leu | Asp | Glu | Val | Phe | Lys | Lys | Asn | Arg | Glu | |
| | | 185 | | | | | 190 | | | | | 195 | | | | |
| GAA | GAC | CCT | TCA | TTA | TTG | TGG | CAG | GTT | TTT | GGC | AGT | GCC | ACT | GGC | CTA | 676 |
| Glu | Asp | Pro | Ser | Leu | Leu | Trp | Gln | Val | Phe | Gly | Ser | Ala | Thr | Gly | Leu | |
| | 200 | | | | | 205 | | | | | 210 | | | | | |
| GCT | CGA | TAT | TAT | CCA | GCT | TCA | CCA | TGG | GTT | GAT | AAT | AGT | AGA | ACT | CCA | 724 |
| Ala | Arg | Tyr | Tyr | Pro | Ala | Ser | Pro | Trp | Val | Asp | Asn | Ser | Arg | Thr | Pro | |
| 215 | | | | | 220 | | | | | 225 | | | | | 230 | |
| AAT | AAG | ATT | GAC | CTT | TAT | GAT | GTA | CGC | AGA | AGA | CCA | TGG | TAC | ATC | CAA | 772 |
| Asn | Lys | Ile | Asp | Leu | Tyr | Asp | Val | Arg | Arg | Arg | Pro | Trp | Tyr | Ile | Gln | |
| | | | | 235 | | | | | 240 | | | | | 245 | | |
| GGA | GCT | GCA | TCT | CCT | AAA | GAC | ATG | CTT | ATT | CTG | GTG | GAT | GTG | AGT | GGA | 820 |
| Gly | Ala | Ala | Ser | Pro | Lys | Asp | Met | Leu | Ile | Leu | Val | Asp | Val | Ser | Gly | |
| | | | 250 | | | | | 255 | | | | | 260 | | | |
| AGT | GTT | AGT | GGA | TTG | ACA | CTT | AAA | CTG | ATC | CGA | ACA | TCT | GTC | TCC | GAA | 868 |
| Ser | Val | Ser | Gly | Leu | Thr | Leu | Lys | Leu | Ile | Arg | Thr | Ser | Val | Ser | Glu | |
| | | 265 | | | | | 270 | | | | | 275 | | | | |
| ATG | TTA | GAA | ACC | CTC | TCA | GAT | GAT | GAT | TTC | GTG | AAT | GTA | GCT | TCA | TTT | 916 |
| Met | Leu | Glu | Thr | Leu | Ser | Asp | Asp | Asp | Phe | Val | Asn | Val | Ala | Ser | Phe | |
| | 280 | | | | | 285 | | | | | 290 | | | | | |
| AAC | AGC | AAT | GCT | CAG | GAT | GTA | AGC | TGT | TTT | CAG | CAC | CTT | GTC | CAA | GCA | 964 |
| Asn | Ser | Asn | Ala | Gln | Asp | Val | Ser | Cys | Phe | Gln | His | Leu | Val | Gln | Ala | |
| 295 | | | | | 300 | | | | | 305 | | | | | 310 | |
| AAT | GTA | AGA | AAT | AAA | AAA | GTG | TTG | AAA | GAC | GCG | GTG | AAT | AAT | ATC | ACA | 1012 |
| Asn | Val | Arg | Asn | Lys | Lys | Val | Leu | Lys | Asp | Ala | Val | Asn | Asn | Ile | Thr | |
| | | | | 315 | | | | | 320 | | | | | 325 | | |
| GCC | AAA | GGA | ATT | ACA | GAT | TAT | AAG | AAG | GGC | TTT | AGT | TTT | GCT | TTT | GAA | 1060 |
| Ala | Lys | Gly | Ile | Thr | Asp | Tyr | Lys | Lys | Gly | Phe | Ser | Phe | Ala | Phe | Glu | |
| | | | | 330 | | | | | 335 | | | | | 340 | | |
| CAG | CTG | CTT | AAT | TAT | AAT | GTT | TCC | AGA | GCA | AAC | TGC | AAT | AAG | ATT | ATT | 1108 |
| Gln | Leu | Leu | Asn | Tyr | Asn | Val | Ser | Arg | Ala | Asn | Cys | Asn | Lys | Ile | Ile | |
| | | | 345 | | | | | 350 | | | | | 355 | | | |
| ATG | CTA | TTC | ACG | GAT | GGA | GGA | GAA | GAG | AGA | GCC | CAG | GAG | ATA | TTT | AAC | 1156 |
| Met | Leu | Phe | Thr | Asp | Gly | Gly | Glu | Glu | Arg | Ala | Gln | Glu | Ile | Phe | Asn | |
| | | 360 | | | | | 365 | | | | | 370 | | | | |
| AAA | TAC | AAT | AAA | GAT | AAA | AAA | GTA | CGT | GTA | TTC | AGG | TTT | TCA | GTT | GGT | 1204 |
| Lys | Tyr | Asn | Lys | Asp | Lys | Lys | Val | Arg | Val | Phe | Arg | Phe | Ser | Val | Gly | |
| 375 | | | | | 380 | | | | | 385 | | | | | 390 | |
| CAA | CAC | AAT | TAT | GAG | AGA | GGA | CCT | ATT | CAG | TGG | ATG | GCC | TGT | GAA | AAC | 1252 |
| Gln | His | Asn | Tyr | Glu | Arg | Gly | Pro | Ile | Gln | Trp | Met | Ala | Cys | Glu | Asn | |
| | | | | 395 | | | | | 400 | | | | | 405 | | |
| AAA | GGT | TAT | TAT | TAT | GAA | ATT | CCT | TCC | ATT | GGT | GCA | ATA | AGA | ATC | AAT | 1300 |
| Lys | Gly | Tyr | Tyr | Tyr | Glu | Ile | Pro | Ser | Ile | Gly | Ala | Ile | Arg | Ile | Asn | |
| | | | 410 | | | | | 415 | | | | | 420 | | | |
| ACT | CAG | GAA | TAT | TTG | GAT | GTT | TTG | GGA | AGA | CCA | ATG | GTT | TTA | GCA | GGA | 1348 |
| Thr | Gln | Glu | Tyr | Leu | Asp | Val | Leu | Gly | Arg | Pro | Met | Val | Leu | Ala | Gly | |
| | | 425 | | | | | 430 | | | | | 435 | | | | |
| GAC | AAA | GCT | AAG | CAA | GTC | CAA | TGG | ACA | AAT | GTG | TAC | CTG | GAT | GCA | TTG | 1396 |
| Asp | Lys | Ala | Lys | Gln | Val | Gln | Trp | Thr | Asn | Val | Tyr | Leu | Asp | Ala | Leu | |
| | 440 | | | | | 445 | | | | | 450 | | | | | |
| GAA | CTG | GGA | CTT | GTC | ATT | ACT | GGA | ACT | CTT | CCG | GTC | TTC | AAC | ATA | ACC | 1444 |
| Glu | Leu | Gly | Leu | Val | Ile | Thr | Gly | Thr | Leu | Pro | Val | Phe | Asn | Ile | Thr | |
| 455 | | | | | 460 | | | | | 465 | | | | | 470 | |
| GGC | CAA | TTT | GAA | AAT | AAG | ACA | AAC | TTA | AAG | AAC | CAG | CTG | ATT | CTT | GGT | 1492 |
| Gly | Gln | Phe | Glu | Asn | Lys | Thr | Asn | Leu | Lys | Asn | Gln | Leu | Ile | Leu | Gly | |
| | | | | 475 | | | | | 480 | | | | | 485 | | |
| GTG | ATG | GGA | GTA | GAT | GTG | TCT | TTG | GAA | GAT | ATT | AAA | AGA | CTG | ACA | CCA | 1540 |
| Val | Met | Gly | Val | Asp | Val | Ser | Leu | Glu | Asp | Ile | Lys | Arg | Leu | Thr | Pro | |
| | | | 490 | | | | | 495 | | | | | 500 | | | |

| | | | | | | | | | | | | | | | | |
|---|---|---|---|---|---|---|---|---|---|---|---|---|---|---|---|---|
| CGT | TTT | ACA | CTG | TGC | CCC | AAT | GGG | TAT | TAC | TTT | GCA | ATC | GAT | CCT | AAT | 1588 |
| Arg | Phe | Thr 505 | Leu | Cys | Pro | Asn | Gly 510 | Tyr | Tyr | Phe | Ala | Ile 515 | Asp | Pro | Asn | |
| GGT | TAT | GTT | TTA | TTA | CAT | CCA | AAT | CTT | CAG | CCA | AAG | AAC | CCC | AAA | TCT | 1636 |
| Gly | Tyr 520 | Val | Leu | Leu | His | Pro 525 | Asn | Leu | Gln | Pro | Lys 530 | Asn | Pro | Lys | Ser | |
| CAG | GAG | CCA | GTA | ACA | TTG | GAT | TTC | CTT | GAT | GCA | GAG | TTA | GAG | AAT | GAT | 1684 |
| Gln 535 | Glu | Pro | Val | Thr | Leu 540 | Asp | Phe | Leu | Asp | Ala 545 | Glu | Leu | Glu | Asn | Asp 550 | |
| ATT | AAA | GTG | GAG | ATT | CGA | AAT | AAG | ATG | ATT | GAT | GGG | GAA | AGT | GGA | GAA | 1732 |
| Ile | Lys | Val | Glu | Ile 555 | Arg | Asn | Lys | Met | Ile 560 | Asp | Gly | Glu | Ser 565 | Gly | Glu | |
| AAA | ACA | TTC | AGA | ACT | CTG | GTT | AAA | TCT | CAA | GAT | GAG | AGA | TAT | ATT | GAC | 1780 |
| Lys | Thr | Phe | Arg 570 | Thr | Leu | Val | Lys | Ser 575 | Gln | Asp | Glu | Arg | Tyr 580 | Ile | Asp | |
| AAA | GGA | AAC | AGG | ACA | TAC | ACA | TGG | ACA | CCT | GTC | AAT | GGC | ACA | GAT | TAC | 1828 |
| Lys | Gly | Asn 585 | Arg | Thr | Tyr | Thr | Trp 590 | Thr | Pro | Val | Asn | Gly 595 | Thr | Asp | Tyr | |
| AGT | TTG | GCC | TTG | GTA | TTA | CCA | ACC | TAC | AGT | TTT | TAC | TAT | ATA | AAA | GCC | 1876 |
| Ser | Leu 600 | Ala | Leu | Val | Leu | Pro 605 | Thr | Tyr | Ser | Phe | Tyr 610 | Tyr | Ile | Lys | Ala | |
| AAA | CTA | GAA | GAG | ACA | ATA | ACT | CAG | GCC | AGA | TCA | AAA | AAG | GGC | AAA | ATG | 1924 |
| Lys 615 | Leu | Glu | Glu | Thr | Ile 620 | Thr | Gln | Ala | Arg | Ser 625 | Lys | Lys | Gly | Lys | Met 630 | |
| AAG | GAT | TCG | GAA | ACC | CTG | AAG | CCA | GAT | AAT | TTT | GAA | GAA | TCT | GGC | TAT | 1972 |
| Lys | Asp | Ser | Glu | Thr 635 | Leu | Lys | Pro | Asp | Asn 640 | Phe | Glu | Glu | Ser | Gly 645 | Tyr | |
| ACA | TTC | ATA | GCA | CCA | AGA | GAT | TAC | TGC | AAT | GAC | CTG | AAA | ATA | TCG | GAT | 2020 |
| Thr | Phe | Ile | Ala 650 | Pro | Arg | Asp | Tyr | Cys 655 | Asn | Asp | Leu | Lys | Ile 660 | Ser | Asp | |
| AAT | AAC | ACT | GAA | TTT | CTT | TTA | AAT | TTC | AAC | GAG | TTT | ATT | GAT | AGA | AAA | 2068 |
| Asn | Asn | Thr 665 | Glu | Phe | Leu | Leu | Asn 670 | Phe | Asn | Glu | Phe | Ile 675 | Asp | Arg | Lys | |
| ACT | CCA | AAC | AAC | CCA | TCA | TGT | AAC | GCG | GAT | TTG | ATT | AAT | AGA | GTC | TTG | 2116 |
| Thr | Pro | Asn 680 | Asn | Pro | Ser | Cys | Asn 685 | Ala | Asp | Leu | Ile | Asn 690 | Arg | Val | Leu | |
| CTT | GAT | GCA | GGC | TTT | ACA | AAT | GAA | CTT | GTC | CAA | AAT | TAC | TGG | AGT | AAG | 2164 |
| Leu 695 | Asp | Ala | Gly | Phe | Thr 700 | Asn | Glu | Leu | Val | Gln 705 | Asn | Tyr | Trp | Ser | Lys 710 | |
| CAG | AAA | AAT | ATC | AAG | GGA | GTG | AAA | GCA | CGA | TTT | GTT | GTG | ACT | GAT | GGT | 2212 |
| Gln | Lys | Asn | Ile | Lys 715 | Gly | Val | Lys | Ala | Arg 720 | Phe | Val | Val | Thr | Asp 725 | Gly | |
| GGG | ATT | ACC | AGA | GTT | TAT | CCC | AAA | GAG | GCT | GGA | GAA | AAT | TGG | CAA | GAA | 2260 |
| Gly | Ile | Thr | Arg 730 | Val | Tyr | Pro | Lys | Glu 735 | Ala | Gly | Glu | Asn | Trp 740 | Gln | Glu | |
| AAC | CCA | GAG | ACA | TAT | GAG | GAC | AGC | TTC | TAT | AAA | AGG | AGC | CTA | GAT | AAT | 2308 |
| Asn | Pro | Glu 745 | Thr | Tyr | Glu | Asp | Ser 750 | Phe | Tyr | Lys | Arg | Ser 755 | Leu | Asp | Asn | |
| GAT | AAC | TAT | GTT | TTC | ACT | GCT | CCC | TAC | TTT | AAC | AAA | AGT | GGA | CCT | GGT | 2356 |
| Asp | Asn 760 | Tyr | Val | Phe | Thr | Ala 765 | Pro | Tyr | Phe | Asn | Lys 770 | Ser | Gly | Pro | Gly | |
| GCC | TAT | GAA | TCG | GGC | ATT | ATG | GTA | AGC | AAA | GCT | GTA | GAA | ATA | TAT | ATT | 2404 |
| Ala 775 | Tyr | Glu | Ser | Gly | Ile 780 | Met | Val | Ser | Lys | Ala 785 | Val | Glu | Ile | Tyr | Ile 790 | |
| CAA | GGG | AAA | CTT | CTT | AAA | CCT | GCA | GTT | GTT | GGA | ATT | AAA | ATT | GAT | GTA | 2452 |
| Gln | Gly | Lys | Leu | Leu 795 | Lys | Pro | Ala | Val | Val 800 | Gly | Ile | Lys | Ile | Asp 805 | Val | |
| AAT | TCC | TGG | ATA | GAG | AAT | TTC | ACC | AAA | ACC | TCA | ATC | AGA | GAT | CCG | TGT | 2500 |
| Asn | Ser | Trp | Ile 810 | Glu | Asn | Phe | Thr | Lys 815 | Thr | Ser | Ile | Arg | Asp 820 | Pro | Cys | |

-continued

| | | | | | | | | | | | | | | | | |
|---|---|---|---|---|---|---|---|---|---|---|---|---|---|---|---|---|
| GCT | GGT | CCA | GTT | TGT | GAC | TGC | AAA | AGA | AAC | AGT | GAC | GTA | ATG | GAT | TGT | 2548 |
| Ala | Gly | Pro<br>825 | Val | Cys | Asp | Cys | Lys<br>830 | Arg | Asn | Ser | Asp | Val<br>835 | Met | Asp | Cys | |
| GTG | ATT | CTG | GAT | GAT | GGT | GGG | TTT | CTT | CTG | ATG | GCA | AAT | CAT | GAT | GAT | 2596 |
| Val | Ile<br>840 | Leu | Asp | Asp | Gly | Gly<br>845 | Phe | Leu | Leu | Met | Ala<br>850 | Asn | His | Asp | Asp | |
| TAT | ACT | AAT | CAG | ATT | GGA | AGA | TTT | TTT | GGA | GAG | ATT | GAT | CCC | AGC | TTG | 2644 |
| Tyr<br>855 | Thr | Asn | Gln | Ile | Gly<br>860 | Arg | Phe | Phe | Gly | Glu<br>865 | Ile | Asp | Pro | Ser | Leu<br>870 | |
| ATG | AGA | CAC | CTG | GTT | AAT | ATA | TCA | GTT | TAT | GCT | TTT | AAC | AAA | TCT | TAT | 2692 |
| Met | Arg | His | Leu | Val<br>875 | Asn | Ile | Ser | Val | Tyr<br>880 | Ala | Phe | Asn | Lys | Ser<br>885 | Tyr | |
| GAT | TAT | CAG | TCA | GTA | TGT | GAG | CCC | GGT | GCT | GCA | CCA | AAA | CAA | GGA | GCA | 2740 |
| Asp | Tyr | Gln | Ser<br>890 | Val | Cys | Glu | Pro | Gly<br>895 | Ala | Ala | Pro | Lys | Gln<br>900 | Gly | Ala | |
| GGA | CAT | CGC | TCA | GCA | TAT | GTG | CCA | TCA | GTA | GCA | GAC | ATA | TTA | CAA | ATT | 2788 |
| Gly | His | Arg<br>905 | Ser | Ala | Tyr | Val | Pro<br>910 | Ser | Val | Ala | Asp | Ile<br>915 | Leu | Gln | Ile | |
| GGC | TGG | TGG | GCC | ACT | GCT | GCT | GCC | TGG | TCT | ATT | CTA | CAG | CAG | TTT | CTC | 2836 |
| Gly | Trp<br>920 | Trp | Ala | Thr | Ala | Ala<br>925 | Ala | Trp | Ser | Ile | Leu<br>930 | Gln | Gln | Phe | Leu | |
| TTG | AGT | TTG | ACC | TTT | CCA | CGA | CTC | CTT | GAG | GCA | GTT | GAG | ATG | GAG | GAT | 2884 |
| Leu<br>935 | Ser | Leu | Thr | Phe | Pro<br>940 | Arg | Leu | Leu | Glu | Ala<br>945 | Val | Glu | Met | Glu | Asp<br>950 | |
| GAT | GAC | TTC | ACG | GCC | TCC | CTG | TCC | AAG | CAG | AGC | TGC | ATT | ACT | GAA | CAA | 2932 |
| Asp | Asp | Phe | Thr | Ala<br>955 | Ser | Leu | Ser | Lys | Gln<br>960 | Ser | Cys | Ile | Thr | Glu<br>965 | Gln | |
| ACC | CAG | TAT | TTC | TTC | GAT | AAC | GAC | AGT | AAA | TCA | TTC | AGT | GGT | GTA | TTA | 2980 |
| Thr | Gln | Tyr | Phe<br>970 | Phe | Asp | Asn | Asp | Ser<br>975 | Lys | Ser | Phe | Ser | Gly<br>980 | Val | Leu | |
| GAC | TGT | GGA | AAC | TGT | TCC | AGA | ATC | TTT | CAT | GGA | GAA | AAG | CTT | ATG | AAC | 3028 |
| Asp | Cys | Gly<br>985 | Asn | Cys | Ser | Arg | Ile<br>990 | Phe | His | Gly | Glu | Lys<br>995 | Leu | Met | Asn | |
| ACC | AAC | TTA | ATA | TTC | ATA | ATG | GTT | GAG | AGC | AAA | GGG | ACA | TGT | CCA | TGT | 3076 |
| Thr | Asn | Leu<br>1000 | Ile | Phe | Ile | Met | Val<br>1005 | Glu | Ser | Lys | Gly | Thr<br>1010 | Cys | Pro | Cys | |
| GAC | ACA | CGA | CTG | CTC | ATA | CAA | GCG | GAG | CAG | ACT | TCT | GAC | GGT | CCA | AAT | 3124 |
| Asp | Thr | Arg<br>1015 | Leu | Leu | Ile | Gln<br>1020 | Ala | Glu | Gln | Thr | Ser<br>1025 | Asp | Gly | Pro | Asn<br>1030 | |
| CCT | TGT | GAC | ATG | GTT | AAG | CAA | CCT | AGA | TAC | CGA | AAA | GGG | CCT | GAT | GTC | 3172 |
| Pro | Cys | Asp | Met | Val<br>1035 | Lys | Gln | Pro | Arg | Tyr<br>1040 | Arg | Lys | Gly | Pro<br>1045 | Asp | Val | |
| TGC | TTT | GAT | AAC | AAT | GTC | TTG | GAG | GAT | TAT | ACT | GAC | TGT | GGT | GGT | GTT | 3220 |
| Cys | Phe | Asp | Asn<br>1050 | Asn | Val | Leu | Glu | Asp<br>1055 | Tyr | Thr | Asp | Cys | Gly<br>1060 | Gly | Val | |
| TCT | GGA | TTA | AAT | CCC | TCC | CTG | TGG | TAT | ATC | ATT | GGA | ATC | CAG | TTT | CTA | 3268 |
| Ser | Gly | Leu<br>1065 | Asn | Pro | Ser | Leu | Trp<br>1070 | Tyr | Ile | Ile | Gly | Ile<br>1075 | Gln | Phe | Leu | |
| CTA | CTT | TGG | CTG | GTA | TCT | GGC | AGC | ACA | CAC | CGG | CTG | TTA | TGACCTTCTA | | | 3317 |
| Leu | Leu<br>1080 | Trp | Leu | Val | Ser | Gly<br>1085 | Ser | Thr | His | Arg | Leu<br>1090 | Leu | | | | |

| | | | | | |
|---|---|---|---|---|---|
| AAAACCAAAT | CTGCATAGTT | AAACTCCAGA | CCCTGCCAAA | ACATGAGCCC | TGCCCTCAAT | 3377 |
| TACAGTAACG | TAGGGTCAGC | TATAAAATCA | GACAAACATT | AGCTGGGCCT | GTTCCATGGC | 3437 |
| ATAACACTAA | GGCGCAGACT | CCTAAGGCAC | CCACTGGCTG | CATGTCAGGG | TGTCAGATCC | 3497 |
| TTAAACGTGT | GTGAATGCTG | CATCATCTAT | GTGTAACATC | AAAGCAAAAT | CCTATACGTG | 3557 |
| TCCTCTATTG | GAAAATTTGG | GCGTTTGTTG | TTGCATTGTT | GGT | | 3600 |

( 2 ) INFORMATION FOR SEQ ID NO:12:

( i ) SEQUENCE CHARACTERISTICS:
    ( A ) LENGTH: 323 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:12:

| | | | | | | |
|---|---|---|---|---|---|---|
| CCCCCTGCCA | GTGGCCAAAC | AGAAGCAGAA | GTCGGGTAAT | GAAATGACTA | ACTTAGCCTT | 60 |
| TGAACTAGAC | CCCCTAGAGT | TAGAGGAGGA | AGAGGCTGAG | CTTGGTGAGC | AGAGTGGCTC | 120 |
| TGCCAAGACT | AGTGTTAGCA | GTGTCACCAC | CCCGCCACCC | CATGGCAAAC | GCATCCCCTT | 180 |
| CTTTAAGAAG | ACAGAGCATG | TGCCCCCCTA | TGACGTGGTG | CCTTCCATGA | GGCCCATCAT | 240 |
| CCTGGTGGGA | CCGTCGCTCA | AGGGCTACGA | GGTTACAGAC | ATGATGCAGA | AAGCTTTATT | 300 |
| TGACTTCTTG | AAGCATCGGT | TTG | | | | 323 |

( 2 ) INFORMATION FOR SEQ ID NO:13:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

CCTATTGGTG TAGGTATACC AACAATTAAT TTAAGAAAAA GGAGACCCAA TATCCAG  57

( 2 ) INFORMATION FOR SEQ ID NO:14:

( i ) SEQUENCE CHARACTERISTICS:
        ( A ) LENGTH: 180 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..132

( x i ) SEQUENCE DESCRIPTION: SEQ ID NO:14:

| | | | | | | | | | | | | | | | | |
|---|---|---|---|---|---|---|---|---|---|---|---|---|---|---|---|---|
| TGG | TCC | TTT | GCC | TGC | GCC | TGT | GCC | GCC | TTC | ATC | CTC | CTC | TTT | CTC | GGC | 48 |
| Trp | Ser | Phe | Ala | Cys | Ala | Cys | Ala | Ala | Phe | Ile | Leu | Leu | Phe | Leu | Gly | |
| 1 | | | | 5 | | | | | 10 | | | | | 15 | | |
| GGT | CTC | GCC | CTC | CTG | CTG | TTC | TCC | CTG | CCT | CGA | ATG | CCC | CGG | AAC | CCA | 96 |
| Gly | Leu | Ala | Leu | Leu | Leu | Phe | Ser | Leu | Pro | Arg | Met | Pro | Arg | Asn | Pro | |
| | | | 20 | | | | | 25 | | | | | 30 | | | |
| TGG | GAG | TCC | TGC | ATG | GAT | GCT | GAG | CCC | GAG | CAC | TAACCTCCT | GCGGCCTAG | | | | 149 |
| Trp | Glu | Ser | Cys | Met | Asp | Ala | Glu | Pro | Glu | His | | | | | | |
| | | 35 | | | | | 40 | | | | | | | | | |

CGACCCTCAG GCTTCTTCCC AGGAAGCGGG G  180

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Oligonucleotide ( x i ) SEQUENCE DESCRIPTION: SEQ ID NO:15:

AATTCGGTAC GTACACTCGA GC                                                         22

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Oligonucleotide ( x i ) SEQUENCE DESCRIPTION: SEQ ID NO:16:

GCTCGAGTGT ACGTACCG                                                              18

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Oligonucleotide ( x i ) SEQUENCE DESCRIPTION: SEQ ID NO:17:

CCATGGTACC TTCGTTGACG                                                            20

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Oligonucleotide ( x i ) SEQUENCE DESCRIPTION: SEQ ID NO:18:

AATTCGTCAA CGAAGGTACC ATGG                                                       24

( 2 ) INFORMATION FOR SEQ ID NO:19:

( i ) SEQUENCE CHARACTERISTICS:
        ( A ) LENGTH: 2026 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 58..1509
        ( D ) OTHER INFORMATION: /product="A Beta3 subunit of human
            calcium channel"

( x i ) SEQUENCE DESCRIPTION: SEQ ID NO:19:

AATTCCCGCC TCGGACCCCC TGTCCCGGGG GAGGGGAGA GCCCGCTACC CTGGTCT     57

ATG TCT TTT TCT GAC TCC AGT GCA ACC TTC CTG CTG AAC GAG GGT TCA   105
Met Ser Phe Ser Asp Ser Ser Ala Thr Phe Leu Leu Asn Glu Gly Ser
 1               5                  10                  15

GCC GAC TCC TAC ACC AGC CGC CCA TCT CTG GAC TCA GAC GTC TCC CTG   153
Ala Asp Ser Tyr Thr Ser Arg Pro Ser Leu Asp Ser Asp Val Ser Leu

-continued

```
                        20                            25                              30

GAG  GAG  GAC  CGG  GAG  AGT  GCC  CGG  CGT  GAA  GTA  GAG  AGC  CAG  GCT  CAG         201
Glu  Glu  Asp  Arg  Glu  Ser  Ala  Arg  Arg  Glu  Val  Glu  Ser  Gln  Ala  Gln
          35                      40                          45

CAG  CAG  CTC  GAA  AGG  GCC  AAG  CAC  AAA  CCT  GTG  GCA  TTT  GCG  GTG  AGG         249
Gln  Gln  Leu  Glu  Arg  Ala  Lys  His  Lys  Pro  Val  Ala  Phe  Ala  Val  Arg
     50                      55                          60

ACC  AAT  GTC  AGC  TAC  TGT  GGC  GTA  CTG  GAT  GAG  GAG  TGC  CCA  GTC  CAG         297
Thr  Asn  Val  Ser  Tyr  Cys  Gly  Val  Leu  Asp  Glu  Glu  Cys  Pro  Val  Gln
65                       70                     75                              80

GGC  TCT  GGA  GTC  AAC  TTT  GAG  GCC  AAA  GAT  TTT  CTG  CAC  ATT  AAA  GAG         345
Gly  Ser  Gly  Val  Asn  Phe  Glu  Ala  Lys  Asp  Phe  Leu  His  Ile  Lys  Glu
                         85                     90                          95

AAG  TAC  AGC  AAT  GAC  TGG  TGG  ATC  GGG  CGG  CTA  GTG  AAA  GAG  GGC  GGG         393
Lys  Tyr  Ser  Asn  Asp  Trp  Trp  Ile  Gly  Arg  Leu  Val  Lys  Glu  Gly  Gly
                    100                      105                         110

GAC  ATC  GCC  TTC  ATC  CCC  AGC  CCC  CAG  CGC  CTG  GAG  AGC  ATC  CGG  CTC         441
Asp  Ile  Ala  Phe  Ile  Pro  Ser  Pro  Gln  Arg  Leu  Glu  Ser  Ile  Arg  Leu
               115                      120                    125

AAA  CAG  GAG  CAG  AAG  GCC  AGG  AGA  TCT  GGG  AAC  CCT  TCC  AGC  CTG  AGT         489
Lys  Gln  Glu  Gln  Lys  Ala  Arg  Arg  Ser  Gly  Asn  Pro  Ser  Ser  Leu  Ser
130                      135                         140

GAC  ATT  GGC  AAC  CGA  CGC  TCC  CCT  CCG  CCA  TCT  CTA  GCC  AAG  CAG  AAG         537
Asp  Ile  Gly  Asn  Arg  Arg  Ser  Pro  Pro  Pro  Ser  Leu  Ala  Lys  Gln  Lys
145                      150                         155                    160

CAA  AAG  CAG  GCG  GAA  CAT  GTT  CCC  CCG  TAT  GAC  GTG  GTG  CCC  TCC  ATG         585
Gln  Lys  Gln  Ala  Glu  His  Val  Pro  Pro  Tyr  Asp  Val  Val  Pro  Ser  Met
                    165                      170                         175

CGG  CCT  GTG  GTG  CTG  GTG  GGA  CCC  TCT  CTG  AAA  GGT  TAT  GAG  GTC  ACA         633
Arg  Pro  Val  Val  Leu  Val  Gly  Pro  Ser  Leu  Lys  Gly  Tyr  Glu  Val  Thr
               180                      185                         190

GAC  ATG  ATG  CAG  AAG  GCT  CTC  TTC  GAC  TTC  CTC  AAA  CAC  AGA  TTT  GAT         681
Asp  Met  Met  Gln  Lys  Ala  Leu  Phe  Asp  Phe  Leu  Lys  His  Arg  Phe  Asp
          195                      200                         205

GGC  AGG  ATC  TCC  ATC  ACC  CGA  GTC  ACA  GCC  GAC  CTC  TCC  CTG  GCA  AAG         729
Gly  Arg  Ile  Ser  Ile  Thr  Arg  Val  Thr  Ala  Asp  Leu  Ser  Leu  Ala  Lys
     210                      215                         220

CGA  TCT  GTG  CTC  AAC  AAT  CCG  GGC  AAG  AGG  ACC  ATC  ATT  GAG  CGC  TCC         777
Arg  Ser  Val  Leu  Asn  Asn  Pro  Gly  Lys  Arg  Thr  Ile  Ile  Glu  Arg  Ser
225                      230                         235                    240

TCT  GCC  CGC  TCC  AGC  ATT  GCG  GAA  GTG  CAG  AGT  GAG  ATC  GAG  CGC  ATA         825
Ser  Ala  Arg  Ser  Ser  Ile  Ala  Glu  Val  Gln  Ser  Glu  Ile  Glu  Arg  Ile
                    245                      250                         255

TTT  GAG  CTG  GCC  AAA  TCC  CTG  CAG  CTA  GTA  GTG  TTG  GAC  GCT  GAC  ACC         873
Phe  Glu  Leu  Ala  Lys  Ser  Leu  Gln  Leu  Val  Val  Leu  Asp  Ala  Asp  Thr
               260                      265                         270

ATC  AAC  CAC  CCA  GCA  CAG  CTG  GCC  AAG  ACC  TCG  CTG  GCC  CCC  ATC  ATC         921
Ile  Asn  His  Pro  Ala  Gln  Leu  Ala  Lys  Thr  Ser  Leu  Ala  Pro  Ile  Ile
          275                      280                         285

GTC  TTT  GTC  AAA  GTG  TCC  TCA  CCA  AAG  GTA  CTC  CAG  CGT  CTC  ATT  CGC         969
Val  Phe  Val  Lys  Val  Ser  Ser  Pro  Lys  Val  Leu  Gln  Arg  Leu  Ile  Arg
     290                      295                         300

TCC  CGG  GGG  AAG  TCA  CAG  ATG  AAG  CAC  CTG  ACC  GTA  CAG  ATG  ATG  GCA        1017
Ser  Arg  Gly  Lys  Ser  Gln  Met  Lys  His  Leu  Thr  Val  Gln  Met  Met  Ala
305                      310                         315                    320

TAT  GAT  AAG  CTG  GTT  CAG  TGC  CCA  CCG  GAG  TCA  TTT  GAT  GTG  ATT  CTG        1065
Tyr  Asp  Lys  Leu  Val  Gln  Cys  Pro  Pro  Glu  Ser  Phe  Asp  Val  Ile  Leu
                    325                      330                         335

GAT  GAG  AAC  CAG  CTG  GAG  GAT  GCC  TGT  GAG  CAC  CTG  GCT  GAG  TAC  CTG        1113
Asp  Glu  Asn  Gln  Leu  Glu  Asp  Ala  Cys  Glu  His  Leu  Ala  Glu  Tyr  Leu
```

|  |  |  |  |  |  |  |  |  |  |  |  |  |  |  |  |
|---|---|---|---|---|---|---|---|---|---|---|---|---|---|---|---|
|  | 340 |  |  |  | 345 |  |  |  |  |  | 350 |  |  |  |  |
| GAG | GTT | TAC | TGG | CGG | GCC | ACG | CAC | CAC | CCA | GCC | CCT | GGC | CCC | GGA | CTT | 1161
| Glu | Val | Tyr | Trp | Arg | Ala | Thr | His | His | Pro | Ala | Pro | Gly | Pro | Gly | Leu |
|  |  | 355 |  |  |  |  | 360 |  |  |  |  | 365 |  |  |  |
| CTG | GGT | CCT | CCC | AGT | GCC | ATC | CCC | GGA | CTT | CAG | AAC | CAG | CAG | CTG | CTG | 1209
| Leu | Gly | Pro | Pro | Ser | Ala | Ile | Pro | Gly | Leu | Gln | Asn | Gln | Gln | Leu | Leu |
|  | 370 |  |  |  |  | 375 |  |  |  |  | 380 |  |  |  |  |
| GGG | GAG | CGT | GGC | GAG | GAG | CAC | TCC | CCC | CTT | GAG | CGG | GAC | AGC | TTG | ATG | 1257
| Gly | Glu | Arg | Gly | Glu | Glu | His | Ser | Pro | Leu | Glu | Arg | Asp | Ser | Leu | Met |
| 385 |  |  |  |  | 390 |  |  |  |  | 395 |  |  |  |  | 400 |
| CCC | TCT | GAT | GAG | GCC | AGC | GAG | AGC | TCC | CGC | CAA | GCC | TGG | ACA | GGA | TCT | 1305
| Pro | Ser | Asp | Glu | Ala | Ser | Glu | Ser | Ser | Arg | Gln | Ala | Trp | Thr | Gly | Ser |
|  |  |  |  | 405 |  |  |  |  | 410 |  |  |  |  | 415 |  |
| TCA | CAG | CGT | AGC | TCC | CGC | CAC | CTG | GAG | GAG | GAC | TAT | GCA | GAT | GCC | TAC | 1353
| Ser | Gln | Arg | Ser | Ser | Arg | His | Leu | Glu | Glu | Asp | Tyr | Ala | Asp | Ala | Tyr |
|  |  |  | 420 |  |  |  |  | 425 |  |  |  |  | 430 |  |  |
| CAG | GAC | CTG | TAC | CAG | CCT | CAC | CGC | CAA | CAC | ACC | TCG | GGG | CTG | CCT | AGT | 1401
| Gln | Asp | Leu | Tyr | Gln | Pro | His | Arg | Gln | His | Thr | Ser | Gly | Leu | Pro | Ser |
|  |  | 435 |  |  |  |  | 440 |  |  |  |  | 445 |  |  |  |
| GCT | AAC | GGG | CAT | GAC | CCC | CAA | GAC | CGG | CTT | CTA | GCC | CAG | GAC | TCA | GAA | 1449
| Ala | Asn | Gly | His | Asp | Pro | Gln | Asp | Arg | Leu | Leu | Ala | Gln | Asp | Ser | Glu |
|  | 450 |  |  |  |  | 455 |  |  |  |  | 460 |  |  |  |  |
| CAC | AAC | CAC | AGT | GAC | CGG | AAC | TGG | CAG | CGC | AAC | CGG | CCT | TGG | CCC | AAG | 1497
| His | Asn | His | Ser | Asp | Arg | Asn | Trp | Gln | Arg | Asn | Arg | Pro | Trp | Pro | Lys |
| 465 |  |  |  |  | 470 |  |  |  |  | 475 |  |  |  |  | 480 |
| GAT | AGC | TAC | TGACAGCCTC | CTGCTGCCCT | ACCCTGGCAG | GCACAGGCGC |  |  |  |  |  |  |  |  |  | 1546
| Asp | Ser | Tyr | * |  |  |  |  |  |  |  |  |  |  |  |  |

| AGCTGGCTGG | GGGGCCCACT | CCAGGCAGGG | TGGCGTTAGA | CTGGCATCAG | GCTGGCACTA | 1606 |
|---|---|---|---|---|---|---|
| GGCTCAGCCC | CCAAAACCCC | CTGCCCAGCC | CCAGCTTCAG | GGCTGCCTGT | GGTCCCAAGG | 1666 |
| TTCTGGAGA | AACAGGGGAC | CCCCTCACCT | CCTGGGCAGT | GACCCCTACT | AGGCTCCCAT | 1726 |
| TCCAGGTACT | AGCTGTGTGT | TCTGCACCCC | TGGCACCTTC | CTCTCCTCCC | ACACAGGAAG | 1786 |
| CTGCCCCACT | GGGCAGTGCC | CTCAGGCAG | GATCCCCTTA | GCAGGGTCCT | TCCCACCAGA | 1846 |
| CTCAGGGAAG | GGATGCCCCA | TTAAAGTGAC | AAAAGGGTGG | GTGTGGGCAC | CATGGCATGA | 1906 |
| GGAAGAAACA | AGGTCCCTGA | GCAGGCACAA | GTCCTGACAG | TCAAGGGACT | GCTTTGGCAT | 1966 |
| CCAGGGCCTC | CAGTCACCTC | ACTGCCATAC | ATTAGAAATG | AGACAATTCA | AAGCCCCCC | 2026 |

( 2 ) INFORMATION FOR SEQ ID NO:20:

( i ) SEQUENCE CHARACTERISTICS:
        ( A ) LENGTH: 2144 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 51..1492
        ( D ) OTHER INFORMATION: /product="A Beta3 subunit of human
            calcium channel"

( i i ) MOLECULE TYPE: cDNA ( x i ) SEQUENCE DESCRIPTION: SEQ ID NO:20:

| CGCCCCCGGC | GCCGCTCGTT | CCCCCGACCC | GGACTCCCCC | ATGTATGACG | ACTCCTACGT | 60 |
|---|---|---|---|---|---|---|
| GCCCGGGTTT | GAGGACTCGG | AGGCGGTTTC | AGCCGACTCC | TACACCAGCC | GCCCATCTCT | 120 |
| GGACTCAGAC | GTCTCCCTGG | AGGAGGACCG | GGAGAGTGCC | CGGCGTGAAG | TAGAGAGCCA | 180 |

| | | | | | | |
|---|---|---|---|---|---|---|
| GGCTCAGCAG | CAGCTCGAAA | GGGCCAAGCA | CAAACCTGTG | GCATTTGCGG | TGAGGACCAA | 240 |
| TGTCAGCTAC | TGTGGCGTAC | TGGATGAGGA | GTGCCCAGTC | CAGGGCTCTG | GAGTCAACTT | 300 |
| TGAGGCCAAA | GATTTTCTGC | ACATTAAAGA | GAAGTACAGC | AATGACTGGT | GGATCGGGCG | 360 |
| GCTAGTGAAA | GAGGGCGGGG | ACATCGCCTT | CATCCCCAGC | CCCCAGCGCC | TGGAGAGCAT | 420 |
| CCGGCTCAAA | CAGGAGCAGA | AGGCCAGGAG | ATCTGGGAAC | CCTTCCAGCC | TGAGTGACAT | 480 |
| TGGCAACCGA | CGCTCCCCTC | CGCCATCTCT | AGCCAAGCAG | AAGCAAAAGC | AGGCGGAACA | 540 |
| TGTTCCCCCG | TATGACGTGG | TGCCCTCCAT | GCGGCCTGTG | GTGCTGGTGG | GACCCTCTCT | 600 |
| GAAAGGTTAT | GAGGTCACAG | ACATGATGCA | GAAGGCTCTC | TTCGACTTCC | TCAAACACAG | 660 |
| ATTTGATGGC | AGGATCTCCA | TCACCCGAGT | CACAGCCGAC | CTCTCCCTGG | CAAAGCGATC | 720 |
| TGTGCTCAAC | AATCCGGGCA | AGAGGACCAT | CATTGAGCGC | TCCTCTGCCC | GCTCCAGCAT | 780 |
| TGCGGAAGTG | CAGAGTGAGA | TCGAGCGCAT | ATTTGAGCTG | GCCAAATCCC | TGCAGCTAGT | 840 |
| AGTGTTGGAC | GCTGACACCA | TCAACCACCC | AGCACAGCTG | GCCAAGACCT | CGCTGGCCCC | 900 |
| CATCATCGTC | TTTGTCAAAG | TGTCCTCACC | AAAGGTACTC | CAGCGTCTCA | TTCGCTCCCG | 960 |
| GGGGAAGTCA | CAGATGAAGC | ACCTGACCGT | ACAGATGATG | GCATATGATA | AGCTGGTTCA | 1020 |
| GTGCCCACCG | GAGTCATTTG | ATGTGATTCT | GGATGAGAAC | CAGCTGGAGG | ATGCCTGTGA | 1080 |
| GCACCTGGCT | GAGTACCTGG | AGGTTTACTG | GCGGGCCACG | CACCACCCAG | CCCCTGGCCC | 1140 |
| CGGACTTCTG | GGTCCTCCCA | GTGCCATCCC | CGGACTTCAG | AACCAGCAGC | TGCTGGGGGA | 1200 |
| GCGTGGCGAG | GAGCACTCCC | CCCTTGAGCG | GGACAGCTTG | ATGCCCTCTG | ATGAGGCCAG | 1260 |
| CGAGAGCTCC | CGCCAAGCCT | GGACAGGATC | TTCACAGCGT | AGCTCCCGCC | ACCTGGAGGA | 1320 |
| GGACTATGCA | GATGCCTACC | AGGACCTGTA | CCAGCCTCAC | CGCCAACACA | CCTCGGGGCT | 1380 |
| GCCTAGTGCT | AACGGGCATG | ACCCCCAAGA | CCGGCTTCTA | GCCCAGGACT | CAGAACACAA | 1440 |
| CCACAGTGAC | CGGAACTGGC | AGCGCAACCG | GCCTTGGCCC | AAGGATAGCT | ACTGACAGCC | 1500 |
| TCCTGCTGCC | CTACCCTGGC | AGGCACAGGC | GCAGCTGGCT | GGGGGGCCCA | CTCCAGGCAG | 1560 |
| GGTGGCGTTA | GACTGGCATC | AGGCTGGCAC | TAGGCTCAGC | CCCCAAAACC | CCCTGCCCAG | 1620 |
| CCCCAGCTTC | AGGGCTGCCT | GTGGTCCCAA | GGTTCTGGGA | GAAACAGGGG | ACCCCCTCAC | 1680 |
| CTCCTGGGCA | GTGACCCCTA | CTAGGCTCCC | ATTCCAGGTA | CTAGCTGTGT | GTTCTGCACC | 1740 |
| CCTGGCACCT | TCCTCTCCTC | CCACACAGGA | AGCTGCCCCA | CTGGGCAGTG | CCCTCAGGCC | 1800 |
| AGGATCCCCT | TAGCAGGGTC | CTTCCCACCA | GACTCAGGGA | AGGGATGCCC | CATTAAAGTG | 1860 |
| ACAAAAGGGT | GGGTGTGGGC | ACCATGGCAT | GAGGAAGAAA | CAAGGTCCCT | GAGCAGGCAC | 1920 |
| AAGTCCTGAC | AGTCAAGGGA | CTGCTTTGGC | ATCCAGGGCC | TCCAGTCACC | TCACTGCCAT | 1980 |
| ACATTAGAAA | TGAGACAATT | CAAAGCCCCC | CCAGGGTGGC | ACACCCATCT | GTTGCTGGGG | 2040 |
| TGTGGCAGCC | ACATCCAAGA | CTGGAGCAGC | AGGCTGGCCA | CGCTTGGGCC | AGAGAGAGCT | 2100 |
| CACAGCTGAA | GCTCTTGGAG | GGAAGGGCTC | TCCTCACCCA | ATCG | | 2144 |

( 2 ) INFORMATION FOR SEQ ID NO:21:

( i ) SEQUENCE CHARACTERISTICS:
     ( A ) LENGTH: 28 base pairs
     ( B ) TYPE: nucleic acid
     ( C ) STRANDEDNESS: single
     ( D ) TOPOLOGY: linear ( i i ) MOLECULE TYPE: Other nucleic acid;
     ( A ) DESCRIPTION: Oligonucleotide ( x i ) SEQUENCE DESCRIPTION: SEQ ID NO:21:

CTCAGTACCA TCTCTGATAC CAGCCCCA 28

( 2 ) INFORMATION FOR SEQ ID NO:22:

( i ) SEQUENCE CHARACTERISTICS:
( A ) LENGTH: 7808 base pairs
( B ) TYPE: nucleic acid
( C ) STRANDEDNESS: single
( D ) TOPOLOGY: unknown ( i i ) MOLECULE TYPE: DNA (genomic)

( i x ) FEATURE:
( A ) NAME/KEY: CDS
( B ) LOCATION: 240..7769
( D ) OTHER INFORMATION: /product="Alpha1A-1 subunit of human calcium channel"

( x i ) SEQUENCE DESCRIPTION: SEQ ID NO:22:

| | | | | | |
|---|---|---|---|---|---|
| GATGTCCCGA | GCTGCTATCC | CCGGCTCGGC | CCGGGCAGCC | GCCTTCTGAG | CCCCGACCC 60 |
| GAGGCGCCGA | GCCGCCGCCG | CCCGATGGGC | TGGGCCGTGG | AGCGTCTCCG | CAGTCGTAGC 120 |
| TCCAGCCGCC | GCGCTCCAG | CCCCGGCAGC | CTCAGCATCA | GCGGCGGCGG | CGGCGGCGGC 180 |
| GGCGTCTTCC | GCATCGTTCG | CCGCAGCGTA | ACCCGGAGCC | CTTTGCTCTT | TGCAGAATGG 240 |
| CCCGCTTCGG | AGACGAGATG | CCGGCCCGCT | ACGGGGAGG | AGGCTCCGGG | GCAGCCGCCG 300 |
| GGGTGGTCGT | GGGCAGCGGA | GGCGGGCGAG | GAGCCGGGG | CAGCCGGCAG | GGCGGGCAGC 360 |
| CCGGGGCGCA | AAGGATGTAC | AAGCAGTCAA | TGGCGCAGAG | AGCGCGGACC | ATGGCACTCT 420 |
| ACAACCCCAT | CCCCGTCCGA | CAGAACTGCC | TCACGGTTAA | CCGGTCTCTC | TTCCTCTTCA 480 |
| GCGAAGACAA | CGTGGTGAGA | AAATACGCCA | AAAAGATCAC | CGAATGGCCT | CCCTTTGAAT 540 |
| ATATGATTTT | AGCCACCATC | ATAGCGAATT | GCATCGTCCT | CGCACTGGAG | CAGCATCTGC 600 |
| CTGATGATGA | CAAGACCCCG | ATGTCTGAAC | GGCTGGATGA | CACAGAACCA | TACTTCATTG 660 |
| GAATTTTTTG | TTTCGAGGCT | GGAATTAAAA | TCATTGCCCT | TGGGTTTGCC | TTCCACAAAG 720 |
| GCTCCTACTT | GAGGAATGGC | TGGAATGTCA | TGGACTTTGT | GGTGGTGCTA | ACGGGCATCT 780 |
| TGGCGACAGT | TGGGACGGAG | TTTGACCTAC | GGACGCTGAG | GGCAGTTCGA | GTGCTGCGGC 840 |
| CGCTCAAGCT | GGTGTCTGGA | ATCCCAAGTT | TACAAGTCGT | CCTGAAGTCG | ATCATGAAGG 900 |
| CGATGATCCC | TTTGCTGCAG | ATCGGCCTCC | TCCTATTTTT | TGCAATCCTT | ATTTTTGCAA 960 |
| TCATAGGGTT | AGAATTTTAT | ATGGGAAAAT | TTCATACCAC | CTGCTTTGAA | GAGGGGACAG 1020 |
| ATGACATTCA | GGGTGAGTCT | CCGGCTCCAT | GTGGGACAGA | AGAGCCCGCC | CGCACCTGCC 1080 |
| CCAATGGGAC | CAAATGTCAG | CCCTACTGGG | AAGGGCCCAA | CAACGGGATC | ACTCAGTTCG 1140 |
| ACAACATCCT | GTTTGCAGTG | CTGACTGTTT | TCCAGTGCAT | AACCATGGAA | GGGTGGACTG 1200 |
| ATCTCCTCTA | CAATAGCAAC | GATGCCTCAG | GGAACACTTG | GAACTGGTTG | TACTTCATCC 1260 |
| CCCTCATCAT | CATCGGCTCC | TTTTTATGC | TGAACCTTGT | GCTGGGTGTG | CTGTCAGGGG 1320 |
| AGTTTGCCAA | AGAAAGGGAA | CGGGTGGAGA | ACCGGCGGGC | TTTTCTGAAG | CTGAGGCGGC 1380 |
| AACAACAGAT | TGAACGTGAG | CTCAATGGGT | ACATGGAATG | GATCTCAAAA | GCAGAAGAGG 1440 |
| TGATCCTCGC | CGAGGATGAA | ACTGACGGGG | AGCAGAGGCA | TCCCTTTGAT | GGAGCTCTGC 1500 |
| GGAGAACCAC | CATAAAGAAA | AGCAAGACAG | ATTTGCTCAA | CCCCGAAGAG | GCTGAGGATC 1560 |
| AGCTGGCTGA | TATAGCCTCT | GTGGGTTCTC | CCTTCGCCCG | AGCCAGCATT | AAAAGTGCCA 1620 |
| AGCTGGAGAA | CTCGACCTTT | TTTCACAAAA | AGGAGAGGAG | GATGCGTTTC | TACATCCGCC 1680 |
| GCATGGTCAA | AACTCAGGCC | TTCTACTGGA | CTGTACTCAG | TTTGGTAGCT | CTCAACACGC 1740 |
| TGTGTGTTGC | TATTGTTCAC | TACAACCAGC | CCGAGTGGCT | CTCCGACTTC | CTTTACTATG 1800 |

```
CAGAATTCAT TTTCTTAGGA CTCTTTATGT CCGAAATGTT TATAAAAATG TACGGGCTTG    1860
GGACGCGGCC TTACTTCCAC TCTTCCTTCA ACTGCTTTGA CTGTGGGGTT ATCATTGGGA    1920
GCATCTTCGA GGTCATCTGG GCTGTCATAA AACCTGGCAC ATCCTTTGGA ATCAGCGTGT    1980
TACGAGCCCT CAGGTTATTG CGTATTTTCA AAGTCACAAA GTACTGGGCA TCTCTCAGAA    2040
ACCTGGTCGT CTCTCTCCTC AACTCCATGA AGTCCATCAT CAGCCTGTTG TTTCTCCTTT    2100
TCCTGTTCAT TGTCGTCTTC GCCCTTTTGG GAATGCAACT CTTCGGCGGC CAGTTTAATT    2160
TCGATGAAGG GACTCCTCCC ACCAACTTCG ATACTTTTCC AGCAGCAATA ATGACGGTGT    2220
TTCAGATCCT GACGGGCGAA GACTGGAACG AGGTCATGTA CGACGGGATC AAGTCTCAGG    2280
GGGGCGTGCA GGGCGGCATG GTGTTCTCCA TCTATTTCAT TGTACTGACG CTCTTTGGGA    2340
ACTACACCCT CCTGAATGTG TTCTTGGCCA TCGCTGTGGA CAATCTGGCC AACGCCCAGG    2400
AGCTCACCAA GGTGGAGGCG GACGAGCAAG AGGAAGAAGA AGCAGCGAAC CAGAAACTTG    2460
CCCTACAGAA AGCCAAGGAG GTGGCAGAAG TGAGTCCTCT GTCCGCGGCC AACATGTCTA    2520
TAGCTGTGAA AGAGCAACAG AAGAATCAAA AGCCAGCCAA GTCCGTGTGG GAGCAGCGGA    2580
CCAGTGAGAT GCGAAAGCAG AACTTGCTGG CCAGCCGGGA GGCCCTGTAT AACGAAATGG    2640
ACCCGGACGA GCGCTGGAAG GCTGCCTACA CGCGGCACCT GCGGCCAGAC ATGAAGACGC    2700
ACTTGGACCG GCCGCTGGTG GTGGACCCGC AGGAGAACCG CAACAACAAC ACCAACAAGA    2760
GCCGGGCGGC CGAGCCCACC GTGGACCAGA GCCTCGGCCA GCAGCGCGCC GAGGACTTCC    2820
TCAGGAAACA GGCCCGCTAC CACGATCGGG CCCGGGACCC CAGCGGTTCG GCGGGCCTGG    2880
ACGCACGGAG GCCCTGGGCG GGAAGCCAGG AGGCCGAGCT TAGCCGGGAG GGACCCTACG    2940
GCCGCGAGTC GGACCACCAC GCCCGGGAGG GCAGCCTGGA GCAACCCGGG TTCTGGGAGG    3000
GCGAGGCCGA GCGAGGCAAG GCCGGGGACC CCCACCGGAG GCACGTTCAC CGGCAGGGGG    3060
GCAGCAGGGA GATCCTCAGC GGGTCTCCGC TCACGGGCGC GGACGGGGAC GATCGACGTC    3120
ATCGCGCGCA CCGCAGGCCC GGGGAGGAGG GTCCGGAGGA CAAGGCGGAG CGGAGGGCGC    3180
GGCACCGCGA GGGCAGCCGG CCGGCCCGGG GCGGCGAGGG CGAGGGCGAG GTCCCCGACG    3240
GGGGCGATCG CAGGAGAAGG CACCGGCATG GCGCTCCAGC CACGTACGAG GGGGACGCGC    3300
GGAGGGAGGA CAAGGAGCGG AGGCATCGGA GGAGGAAAGA GAACCAGGGC TCCGGGGTCC    3360
CTGTGTCGGG CCCCAACCTG TCAACCACCC GGCCAATCCA GCAGGACCTG GGCCGCCAAG    3420
ACCCACCCCT GGCAGAGGAT ATTGACAACA TGAAGAACAA CAAGCTGGCC ACCGCGGAGT    3480
CGGCCGCTCC CCACGGCAGC CTTGGCCACG CCGGCCTGCC CCAGAGCCCA GCCAAGATGG    3540
GAAACAGCAC CGACCCCGGC CCCATGCTGG CCATCCCTGC CATGGCCACC AACCCCCAGA    3600
ACGCCGCCAG CCGCCGGACG CCCAACAACC CGGGGAACCC ATCCAATCCC GGCCCCCCCA    3660
AGACCCCCGA GAATAGCCTT ATCGTCACCA ACCCCAGCGG CACCCAGACC AATTCAGCTA    3720
AGACTGCCAG GAAACCCGAC CACACCACAG TGGACATCCC CCAGCCTGC CCACCCCCCC     3780
TCAACCACAC CGTCGTACAA GTGAACAAAA ACGCCAACCC AGACCCACTG CCAAAAAAAG    3840
AGGAAGAGAA GAAGGAGGAG GAGGAAGACG ACCGTGGGGA AGACGGCCCT AAGCCAATGC    3900
CTCCCTATAG CTCCATGTTC ATCCTGTCCA CGACCAACCC CCTTCGCCGC CTGTGCCATT    3960
ACATCCTGAA CCTGCGCTAC TTTGAGATGT GCATCCTCAT GGTCATTGCC ATGAGCAGCA    4020
TCGCCCTGGC CGCCGAGGAC CCTGTGCAGC CCAACGCACC TCGGAACAAC GTGCTGCGAT    4080
ACTTTGACTA CGTTTTTACA GGCGTCTTCA CCTTTGAGAT GGTGATCAAG ATGATTGACC    4140
TGGGGCTCGT CCTGCATCAG GGTGCCTACT TCCGTGACCT CTGGAATATT CTCGACTTCA    4200
```

```
TAGTGGTCAG TGGGGCCCTG GTAGCCTTTG CCTTCACTGG CAATAGCAAA GGAAAAGACA    4260
TCAACACGAT TAAATCCCTC CGAGTCCTCC GGGTGCTACG ACCTCTTAAA ACCATCAAGC    4320
GGCTGCCAAA GCTCAAGGCT GTGTTTGACT GTGTGGTGAA CTCACTTAAA AACGTCTTCA    4380
ACATCCTCAT CGTCTACATG CTATTCATGT TCATCTTCGC CGTGGTGGCT GTGCAGCTCT    4440
TCAAGGGGAA ATTCTTCCAC TGCACTGACG AGTCCAAAGA GTTTGAGAAA GATTGTCGAG    4500
GCAAATACCT CCTCTACGAG AAGAATGAGG TGAAGGCGCG AGACCGGGAG TGGAAGAAGT    4560
ATGAATTCCA TTACGACAAT GTGCTGTGGG CTCTGCTGAC CCTCTTCACC GTGTCCACGG    4620
GAGAAGGCTG GCCACAGGTC CTCAAGCATT CGGTGGACGC CACCTTTGAG AACCAGGGCC    4680
CCAGCCCCGG GTACCGCATG GAGATGTCCA TTTTCTACGT CGTCTACTTT GTGGTGTTCC    4740
CCTTCTTCTT TGTCAATATC TTTGTGGCCT TGATCATCAT CACCTTCCAG GAGCAAGGGG    4800
ACAAGATGAT GGAGGAATAC AGCCTGGAGA AAAATGAGAG GGCCTGCATT GATTTCGCCA    4860
TCAGCGCCAA GCCGCTGACC CGACACATGC CGCAGAACAA GCAGAGCTTC CAGTACCGCA    4920
TGTGGCAGTT CGTGGTGTCT CCGCCTTTCG AGTACACGAT CATGGCCATG ATCGCCCTCA    4980
ACACCATCGT GCTTATGATG AAGTTCTATG GGCTTCTGT TGCTTATGAA AATGCCCTGC    5040
GGGTGTTCAA CATCGTCTTC ACCTCCCTCT TCTCTCTGGA ATGTGTGCTG AAAGTCATGG    5100
CTTTGGGGAT TCTGAATTAT TTCCGCGATG CCTGGAACAT CTTCGACTTT GTGACTGTTC    5160
TGGGCAGCAT CACCGATATC CTCGTGACTG AGTTTGGGAA TCCGAATAAC TTCATCAACC    5220
TGAGCTTTCT CCGCCTCTTC CGAGCTGCCC GGCTCATCAA ACTTCTCCGT CAGGGTTACA    5280
CCATCCGCAT TCTTCTCTGG ACCTTTGTGC AGTCCTTCAA GGCCCTGCCT TATGTCTGTC    5340
TGCTGATCGC CATGCTCTTC TTCATCTATG CCATCATTGG GATGCAGGTG TTTGGTAACA    5400
TTGGCATCGA CGTGGAGGAC GAGGACAGTG ATGAAGATGA GTTCCAAATC ACTGAGCACA    5460
ATAACTTCCG GACCTTCTTC CAGGCCCTCA TGCTTCTCTT CCGGAGTGCC ACCGGGGAAG    5520
CTTGGCACAA CATCATGCTT TCCTGCCTCA GCGGGAAACC GTGTGATAAG AACTCTGGCA    5580
TCCTGACTCG AGAGTGTGGC AATGAATTTG CTTATTTTA CTTTGTTTCC TTCATCTTCC    5640
TCTGCTCGTT TCTGATGCTG AATCTCTTTG TCGCCGTCAT CATGGACAAC TTTGAGTACC    5700
TCACCCGAGA CTCCTCCATC CTGGGCCCCC ACCACCTGGA TGAGTACGTG CGTGTCTGGG    5760
CCGAGTATGA CCCCGCAGCT TGGGGCCGCA TGCCTTACCT GGACATGTAT CAGATGCTGA    5820
GACACATGTC TCCGCCCCTG GGTCTGGGGA AGAAGTGTCC GGCCAGAGTG GCTTACAAGC    5880
GGCTTCTGCG GATGGACCTG CCCGTCGCAG ATGACAACAC CGTCCACTTC AATTCCACCC    5940
TCATGGCTCT GATCCGCACA GCCCTGGACA TCAAGATTGC CAAGGGAGGA GCCGACAAAC    6000
AGCAGATGGA CGCTGAGCTG CGGAAGGAGA TGATGGCGAT TTGGCCCAAT CTGTCCCAGA    6060
AGACGCTAGA CCTGCTGGTC ACACCTCACA AGTCCACGGA CCTCACCGTG GGAAGATCT    6120
ACGCAGCCAT GATGATCATG GAGTACTACC GGCAGAGCAA GGCCAAGAAG CTGCAGGCCA    6180
TGCGCGAGGA GCAGGACCGG ACACCCTCA TGTTCCAGCG CATGGAGCCC CCGTCCCCAA    6240
CGCAGGAAGG GGGACCTGGC CAGAACGCCC TCCCCTCCAC CCAGCTGGAC CAGGAGGAG    6300
CCCTGATGGC TCACGAAAGC GGCCTCAAGG AGAGCCCGTC CTGGGTGACC CAGCGTGCCC    6360
AGGAGATGTT CCAGAAGACG GGCACATGGA GTCCGGAACA AGGCCCCCCT ACCGACATGC    6420
CCAACAGCCA GCCTAACTCT CAGTCCGTGG AGATGCGAGA GATGGGCAGA GATGGCTACT    6480
CCGACAGCGA GCACTACCTC CCCATGGAAG GCCAGGGCCG GGCTGCCTCC ATGCCCCGCC    6540
TCCCTGCAGA GAACCAGAGG AGAAGGGGCC GGCCACGTGG GAATAACCTC AGTACCATCT    6600
```

| | | | | | | |
|---|---|---|---|---|---|---|
|CAGACACCAG|CCCCATGAAG|CGTTCAGCCT|CCGTGCTGGG|CCCCAAGGCC|CGACGCCTGG|6660|
|ACGATTACTC|GCTGGAGCGG|GTCCCGCCCG|AGGAGAACCA|GCGGCACCAC|CAGCGGCGCC|6720|
|GCGACCGCAG|CCACCGCGCC|TCTGAGCGCT|CCCTGGGCCG|CTACACCGAT|GTGGACACAG|6780|
|GCTTGGGGAC|AGACCTGAGC|ATGACCACCC|AATCCGGGGA|CCTGCCGTCG|AAGGAGCGG|6840|
|ACCAGGAGCG|GGGCCGGCCC|AAGGATCGGA|AGCATCGACA|GCACCACCAC|CACCACCACC|6900|
|ACCACCACCA|TCCCCCGCCC|CCCGACAAGG|ACCGCTATGC|CCAGGAACGG|CCGGACCACG|6960|
|GCCGGGCACG|GGCTCGGGAC|CAGCGCTGGT|CCCGCTCGCC|CAGCGAGGGC|CGAGAGCACA|7020|
|TGGCGCACCG|GCAGGGCAGT|AGTTCCGTAA|GTGGAAGCCC|AGCCCCTCA|ACATCTGGTA|7080|
|CCAGCACTCC|GCGGCGGGGC|CGCCGCCAGC|TCCCCAGAC|CCCCTCCACC|CCCCGGCCAC|7140|
|ACGTGTCCTA|TTCCCCTGTG|ATCCGTAAGG|CCGGCGGCTC|GGGGCCCCCG|CAGCAGCAGC|7200|
|AGCAGCAGCA|GCAGCAGCAG|CAGGCGGTGG|CCAGGCCGGG|CCGGGCGGCC|ACCAGCGGCC|7260|
|CTCGGAGGTA|CCCAGGCCCC|ACGGCCGAGC|CTCTGGCCGG|AGATCGGCCG|CCCACGGGGG|7320|
|GCCACAGCAG|CGGCCGCTCG|CCCAGGATGG|AGAGGCGGGT|CCCAGGCCCG|GCCCGGAGCG|7380|
|AGTCCCCCAG|GGCCTGTCGA|CACGGCGGGG|CCCGGTGGCC|GGCATCTGGC|CCGCACGTGT|7440|
|CCGAGGGGCC|CCCGGGTCCC|CGGCACCATG|GCTACTACCG|GGGCTCCGAC|TACGACGAGG|7500|
|CCGATGGCCC|GGGCAGCGGG|GGCGGCGAGG|AGGCCATGGC|CGGGGCCTAC|GACGCGCCAC|7560|
|CCCCCGTACG|ACACGCGTCC|TCGGGCGCCA|CCGGGCGCTC|GCCCAGGACT|CCCCGGGCCT|7620|
|CGGGCCCGGC|CTGCGCCTCG|CCTTCTCGGC|ACGGCCGGCG|ACTCCCCAAC|GGCTACTACC|7680|
|CGGCGCACGG|ACTGGCCAGG|CCCCGCGGGC|CGGGCTCCAG|GAAGGGCCTG|CACGAACCCT|7740|
|ACAGCGAGAG|TGACGATGAT|TGGTGCTAAG|CCCGGGCGAG|GTGGCGCCCG|CCCGGCCCCC|7800|
|CACGCACC| | | | | |7808|

(2) INFORMATION FOR SEQ ID NO:23:

(i) SEQUENCE CHARACTERISTICS:
        (A) LENGTH: 7791 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: CDS
        (B) LOCATION: 240..7037
        (D) OTHER INFORMATION: /product="Alpha1A-2 subunit of human calcium channel"

(xi) SEQUENCE DESCRIPTION: SEQ ID NO:23:

| | | | | | | |
|---|---|---|---|---|---|---|
|GATGTCCCGA|GCTGCTATCC|CCGGCTCGGC|CCGGGCAGCC|GCCTTCTGAG|CCCCCGACCC|60|
|GAGGCGCCGA|GCCGCCGCCG|CCCGATGGGC|TGGGCCGTGG|AGCGTCTCCG|CAGTCGTAGC|120|
|TCCAGCCGCC|GCGCTCCCAG|CCCCGGCAGC|CTCAGCATCA|GCGGCGGCGG|CGGCGGCGGC|180|
|GGCGTCTTCC|GCATCGTTCG|CCGCAGCGTA|ACCCGGAGCC|CTTTGCTCTT|TGCAGAATGG|240|
|CCCGCTTCGG|AGACGAGATG|CCGGCCCGCT|ACGGGGAGG|AGGCTCCGGG|GCAGCCGCCG|300|
|GGGTGGTCGT|GGGCAGCGGA|GGCGGGCGAG|GAGCCGGGG|CAGCCGGCAG|GGCGGGCAGC|360|
|CCGGGGCGCA|AAGGATGTAC|AAGCAGTCAA|TGGCGCAGAG|AGCGCGGACC|ATGGCACTCT|420|
|ACAACCCCAT|CCCCGTCCGA|CAGAACTGCC|TCACGGTTAA|CCGGTCTCTC|TTCCTCTTCA|480|
|GCGAAGACAA|CGTGGTGAGA|AAATACGCCA|AAAAGATCAC|CGAATGGCCT|CCCTTTGAAT|540|

| | | | | | | |
|---|---|---|---|---|---|---|
| ATATGATTTT | AGCCACCATC | ATAGCGAATT | GCATCGTCCT | CGCACTGGAG | CAGCATCTGC | 600 |
| CTGATGATGA | CAAGACCCCG | ATGTCTGAAC | GGCTGGATGA | CACAGAACCA | TACTTCATTG | 660 |
| GAATTTTTTG | TTTCGAGGCT | GGAATTAAAA | TCATTGCCCT | TGGGTTTGCC | TTCCACAAAG | 720 |
| GCTCCTACTT | GAGGAATGGC | TGGAATGTCA | TGGACTTTGT | GGTGGTGCTA | ACGGGCATCT | 780 |
| TGGCGACAGT | TGGGACGGAG | TTTGACCTAC | GGACGCTGAG | GGCAGTTCGA | GTGCTGCGGC | 840 |
| CGCTCAAGCT | GGTGTCTGGA | ATCCCAAGTT | TACAAGTCGT | CCTGAAGTCG | ATCATGAAGG | 900 |
| CGATGATCCC | TTTGCTGCAG | ATCGGCTCC | TCCTATTTTT | TGCAATCCTT | ATTTTGCAA | 960 |
| TCATAGGGTT | AGAATTTTAT | ATGGGAAAAT | TTCATACCAC | CTGCTTTGAA | GAGGGGACAG | 1020 |
| ATGACATTCA | GGGTGAGTCT | CCGGCTCCAT | GTGGGACAGA | AGAGCCCGCC | CGCACCTGCC | 1080 |
| CCAATGGGAC | CAAATGTCAG | CCCTACTGGG | AAGGGCCCAA | CAACGGGATC | ACTCAGTTCG | 1140 |
| ACAACATCCT | GTTTGCAGTG | CTGACTGTTT | TCCAGTGCAT | AACCATGGAA | GGGTGGACTG | 1200 |
| ATCTCCTCTA | CAATAGCAAC | GATGCCTCAG | GGAACACTTG | GAACTGGTTG | TACTTCATCC | 1260 |
| CCCTCATCAT | CATCGGCTCC | TTTTTTATGC | TGAACCTTGT | GCTGGGTGTG | CTGTCAGGGG | 1320 |
| AGTTTGCCAA | AGAAAGGGAA | CGGGTGGAGA | ACCGGCGGGC | TTTTCTGAAG | CTGAGGCGGC | 1380 |
| AACAACAGAT | TGAACGTGAG | CTCAATGGGT | ACATGGAATG | GATCTCAACA | GCAGAAGAGG | 1440 |
| TGATCCTCGC | CGAGGATGAA | ACTGCCGGGG | AGCAGAGGCA | TCCCTTTGAT | GGAGCTCTGC | 1500 |
| GGAGAACCAC | CATAAAGAAA | AGCAAGACAG | ATTTGCTCAA | CCCCGAAGAG | GCTGAGGATC | 1560 |
| AGCTGGCTGA | TATAGCCTCT | GTGGGTTCTC | CCTTCGCCCG | AGCCAGCATT | AAAAGTGCCA | 1620 |
| AGCTGGAGAA | CTCGACCTTT | TTTCACAAAA | AGGAGAGGAG | GATGCGTTTC | TACATCCGCC | 1680 |
| GCATGGTCAA | AACTCAGGCC | TTCTACTGGA | CTGTACTCAG | TGTGGTAGCT | CTCAACACGC | 1740 |
| TGTGTGTTGC | TATTGTTCAC | TACAACCAGC | CCGAGTGGCT | CTCCGACTTC | CTTTACTATG | 1800 |
| CAGAATTCAT | TTTCTTAGGA | CTCTTTATGT | CCGAAATGTT | TATAAAAATG | TACGGGCTTG | 1860 |
| GGACGCGGCC | TTACTTCCAC | TCTTCCTTCA | ACTGCTTTGA | CTGTGGGGTT | ATCATTGGGA | 1920 |
| GCATCTTCGA | GGTCATCTGG | GCTGTCATAA | AACCTGGCAC | ATCCTTTGGA | ATCAGCGTGT | 1980 |
| TACGAGCCCT | CAGGTTATTG | CGTATTTTCA | AAGTCACAAA | GTACTGGGCA | TCTCTCAGAA | 2040 |
| ACCTGGTCGT | CTCTCTCCTC | AACTCCATGA | AGTCCATCAT | CAGCCTGTTG | TTTCTCCTTT | 2100 |
| TCCTGTTCAT | TGTCGTCTTC | GCCCTTTTGG | GAATGCAACT | CTTCGGCGGC | CAGTTTAATT | 2160 |
| TCGATGAAGG | GACTCCTCCC | ACCAACTTCG | ATACTTTTCC | AGCAGCAATA | ATGACGGTGT | 2220 |
| TTCAGATCCT | GACGGGCGAA | GACTGGAACG | AGGTCATGTA | CGACGGGATC | AAGTCTCAGG | 2280 |
| GGGGCGTGCA | GGGCGGCATG | GTGTTCTCCA | TCTATTTCAT | TGTACTGACG | CTCTTTGGGA | 2340 |
| ACTACACCCT | CCTGAATGTG | TTCTTGGCCA | TCGCTGTGGA | CAATCTGGCC | AACGCCCAGG | 2400 |
| AGCTCACCAA | GGTGGAGGCG | GACGAGCAAG | AGGAAGAAGA | AGCAGCGAAC | CAGAAACTTG | 2460 |
| CCCTACAGAA | AGCCAAGGAG | GTGGCAGAAG | TGAGTCCTCT | GTCCGCGGCC | AACATGTCTA | 2520 |
| TAGCTGTGAA | AGAGCAACAG | AAGAATCAAA | AGCCAGCCAA | GTCCGTGTGG | GAGCAGCGGA | 2580 |
| CCAGTGAGAT | GCGAAAGCAG | AACTTGCTGG | CCAGCCGGGA | GGCCCTGTAT | AACGAAATGG | 2640 |
| ACCCGGACGA | GCGCTGGAAG | GCTGCCTACA | CGCGGCACCT | GCGGCCAGAC | ATGAAGACGC | 2700 |
| ACTTGGACCG | GCCGCTGGTG | GTGGACCCGC | AGGAGAACCG | CAACAACAAC | ACCAACAAGA | 2760 |
| GCCGGGCGGC | CGAGYCCACC | GTGGACCAGA | GCCTCGGCCA | GCAGCGCGCC | GAGGACTTCC | 2820 |
| TCAGGAAACA | GGCCCGCTAC | CACGATGGG | CCCGGKAMCC | CAGCGGTTCG | GCGGGCCTGG | 2880 |
| ACGCACGGAG | GCCCTGGGCG | GGAAGCCAGG | AGGCCGAGCT | TAGCCGGGAG | GGACCYWWCG | 2940 |

| | | | | | | |
|---|---|---|---|---|---|---|
| GCCGCGAGTC | GGACCACCAC | GCCCGGGAGG | RCARCCTGGA | GCAWCCCGGG | TTCTGGGAGG | 3000 |
| GCGAKKCCGA | GCGAGRCAAG | TYCGGGGAMC | CCCACCGGAG | GCACGTTCAC | CSGCAGGGGG | 3060 |
| GCAGCAGGGA | GATCCTCAGC | GGGTCTCCGC | TCACGGGCGC | GGACGGGGAC | GATCGACGTC | 3120 |
| ATCGCGCGCA | CCGCAGGCCC | GGGGAGGAGG | GTCCGGAGGA | CAAGGCGGAG | CGGAGGGCGC | 3180 |
| GGCACCGCGA | GGGCAGCCGG | CCGGCCCGGG | GCGGCGAGGG | CGAGGGCGAG | GTCCCCGACG | 3240 |
| GGGGCGATCG | CAGGAGAAGG | CACCGGCATG | GCGCTCCAGC | CACGTACGAG | GGGGACGCGC | 3300 |
| GGAGGGAGGA | CAAGGAGCGG | AGGCATCGGA | GGAGGAAAGA | GAACCAGGGC | TCCGGGGTCC | 3360 |
| CTGTGTCGGG | CCCCAACCTG | TCAACCACCC | GGCCAATCCA | GCAGGACCTG | GGCCGCCAAG | 3420 |
| ACCCACCCCT | GGCAGAGGAT | ATTGACAACA | TGAAGAACAA | CAAGCTGGCC | ACCGCGGAGT | 3480 |
| CGGCCGCTCC | CCACGGCAGC | CTTGGCCACG | CCGGCCTGCC | CCAGAGCCCA | GCCAAGATGG | 3540 |
| GAAACAGCAC | CGACCCCGGC | CCCATGCTGG | CCATCCCTGC | CATGGCCACC | AACCCCCAGA | 3600 |
| ACGCCGCCAG | CCGCCGGACG | CCCAACAACC | CGGGGAACCC | ATCCAATCCC | GGCCCCCCCA | 3660 |
| AGACCCCCGA | GAATAGCCTT | ATCGTCACCA | ACCCCAGCGG | CACCCAGACC | AATTCAGCTA | 3720 |
| AGACTGCCAG | GAAACCCGAC | CACACCACAG | TGGACATCCC | CCCAGCCTGC | CCACCCCCCC | 3780 |
| TCAACCACAC | CGTCGTACAA | GTGAACAAAA | ACGCCAACCC | AGACCCACTG | CCAAAAAAAG | 3840 |
| AGGAAGAGAA | GAAGGAGGAG | GAGGAAGACG | ACCGTGGGGA | AGACGGCCCT | AAGCCAATGC | 3900 |
| CTCCCTATAG | CTCCATGTTC | ATCCTGTCCA | CGACCAACCC | CCTTCGCCGC | CTGTGCCATT | 3960 |
| ACATCCTGAA | CCTGCGCTAC | TTTGAGATGT | GCATCCTCAT | GGTCATTGCC | ATGAGCAGCA | 4020 |
| TCGCCCTGGC | CGCCGAGGAC | CCTGTGCAGC | CAACGCACC | TCGGAACAAC | GTGCTGCGAT | 4080 |
| ACTTTGACTA | CGTTTTTACA | GGCGTCTTCA | CCTTTGAGAT | GGTGATCAAG | ATGATTGACC | 4140 |
| TGGGGCTCGT | CCTGCATCAG | GGTGCCTACT | TCCGTGACCT | CTGGAATATT | CTCGACTTCA | 4200 |
| TAGTGGTCAG | TGGGGCCCTG | GTAGCCTTTG | CCTTCACTGG | CAATAGCAAA | GGAAAAGACA | 4260 |
| TCAACACGAT | TAAATCCCTC | CGAGTCCTCC | GGGTGCTACG | ACCTCTTAAA | ACCATCAAGC | 4320 |
| GGCTGCCAAA | GCTCAAGGCT | GTGTTTGACT | GTGTGGTGAA | CTCACTTAAA | AACGTCTTCA | 4380 |
| ACATCCTCAT | CGTCTACATG | CTATTCATGT | TCATCTTCGC | CGTGGTGGCT | GTGCAGCTCT | 4440 |
| TCAAGGGGAA | ATTCTTCCAC | TGCACTGACG | AGTCCAAAGA | GTTTGAGAAA | GATTGTCGAG | 4500 |
| GCAAATACCT | CCTCTACGAG | AAGAATGAGG | TGAAGGCGCG | AGACCGGGAG | TGGAAGAAGT | 4560 |
| ATGAATTCCA | TTACGACAAT | GTGCTGTGGG | CTCTGCTGAC | CCTCTTCACC | GTGTCCACGG | 4620 |
| GAGAAGGCTG | GCCACAGGTC | CTCAAGCATT | CGGTGGACGC | CACCTTTGAG | AACCAGGGCC | 4680 |
| CCAGCCCCGG | GTACCGCATG | GAGATGTCCA | TTTTCTACGT | CGTCTACTTT | GTGGTGTTCC | 4740 |
| CCTTCTTCTT | TGTCAATATC | TTTGTGGCCT | TGATCATCAT | CACCTTCCAG | GAGCAAGGGG | 4800 |
| ACAAGATGAT | GGAGGAATAC | AGCCTGGAGA | AAAATGAGAG | GGCCTGCATT | GATTTCGCCA | 4860 |
| TCAGCGCCAA | GCCGCTGACC | CGACACATGC | CGCAGAACAA | GCAGAGCTTC | CAGTACCGCA | 4920 |
| TGTGGCAGTT | CGTGGTGTCT | CCGCCTTTCG | AGTACACGAT | CATGGCCATG | ATCGCCCTCA | 4980 |
| ACACCATCGT | GCTTATGATG | AAGTTCTATG | GGCTTCTGT | TGCTTATGAA | AATGCCCTGC | 5040 |
| GGGTGTTCAA | CATCGTCTTC | ACCTCCCTCT | TCTCTCTGGA | ATGTGTGCTG | AAAGTCATGG | 5100 |
| CTTTGGGGAT | TCTGAATTAT | TTCCGCGATG | CCTGGAACAT | CTTCGACTTT | GTGACTGTTC | 5160 |
| TGGGCAGCAT | CACCGATATC | CTCGTGACTG | AGTTTGGGAA | TCCGAATAAC | TTCATCAACC | 5220 |
| TGAGCTTTCT | CCGCCTCTTC | CGAGCTGCCC | GGCTCATCAA | ACTTCTCCGT | CAGGGTTACA | 5280 |
| CCATCCGCAT | TCTTCTCTGG | ACCTTTGTGC | AGTCCTTCAA | GGCCCTGCCT | TATGTCTGTC | 5340 |

| | | | | | | |
|---|---|---|---|---|---|---|
| TGCTGATCGC | CATGCTCTTC | TTCATCTATG | CCATCATTGG | GATGCAGGTG | TTTGGTAACA | 5400 |
| TTGGCATCGA | CGTGGAGGAC | GAGGACAGTG | ATGAAGATGA | GTTCCAAATC | ACTGAGCACA | 5460 |
| ATAACTTCCG | GACCTTCTTC | CAGGCCCTCA | TGCTTCTCTT | CCGGAGTGCC | ACCGGGGAAG | 5520 |
| CTTGGCACAA | CATCATGCTT | TCCTGCCTCA | GCGGGAAACC | GTGTGATAAG | AACTCTGGCA | 5580 |
| TCCTGACTCG | AGAGTGTGGC | AATGAATTTG | CTTATTTTA | CTTTGTTTCC | TTCATCTTCC | 5640 |
| TCTGCTCGTT | TCTGATGCTG | AATCTCTTTG | TCGCCGTCAT | CATGGACAAC | TTTGAGTACC | 5700 |
| TCACCCGAGA | CTCCTCCATC | CTGGGCCCCC | ACCACTGGA | TGAGTACGTG | CGTGTCTGGG | 5760 |
| CCGAGTATGA | CCCCGCAGCT | TGGGGCCGCA | TGCCTTACCT | GGACATGTAT | CAGATGCTGA | 5820 |
| GACACATGTC | TCCGCCCCTG | GGTCTGGGGA | AGAAGTGTCC | GGCCAGAGTG | GCTTACAAGC | 5880 |
| GGCTTCTGCG | GATGGACCTG | CCCGTCGCAG | ATGACAACAC | CGTCCACTTC | AATTCCACCC | 5940 |
| TCATGGCTCT | GATCCGCACA | GCCCTGGACA | TCAAGATTGC | CAAGGGAGGA | GCCGACAAAC | 6000 |
| AGCAGATGGA | CGCTGAGCTG | CGGAAGGAGA | TGATGGCGAT | TTGGCCCAAT | CTGTCCCAGA | 6060 |
| AGACGCTAGA | CCTGCTGGTC | ACACCTCACA | AGTCCACGGA | CCTCACCGTG | GGGAAGATCT | 6120 |
| ACGCAGCCAT | GATGATCATG | GAGTACTACC | GGCAGAGCAA | GGCCAAGAAG | CTGCAGGCCA | 6180 |
| TGCGCGAGGA | GCAGGACCGG | ACACCCCTCA | TGTTCCAGCG | CATGGAGCCC | CCGTCCCCAA | 6240 |
| CGCAGGAAGG | GGGACCTGGC | CAGAACGCCC | TCCCCTCCAC | CCAGCTGGAC | CCAGGAGGAG | 6300 |
| CCCTGATGGC | TCACGAAAGC | GGCCTCAAGG | AGAGCCCGTC | CTGGGTGACC | CAGCGTGCCC | 6360 |
| AGGAGATGTT | CCAGAAGACG | GGCACATGGA | GTCCGGAACA | AGGCCCCCT | ACCGACATGC | 6420 |
| CCAACAGCCA | GCCTAACTCT | CAGTCCGTGG | AGATGCGAGA | GATGGGCAGA | GATGGCTACT | 6480 |
| CCGACAGCGA | GCACTACCTC | CCCATGGAAG | GCCAGGGCCG | GGCTGCCTCC | ATGCCCCGCC | 6540 |
| TCCCTGCAGA | GAACCAGAGG | AGAAGGGGCC | GGCCACGTGG | GAATAACCTC | AGTACCATCT | 6600 |
| CAGACACCAG | CCCCATGAAG | CGTTCAGCCT | CCGTGCTGGG | CCCCAAGGCC | CGACGCCTGG | 6660 |
| ACGATTACTC | GCTGGAGCGG | GTCCCGCCCG | AGGAGAACCA | GCGGCACCAC | CAGCGGCGCC | 6720 |
| GCGACCGCAG | CCACCGCGCC | TCTGAGCGCT | CCCTGGGCCG | CTACACCGAT | GTGGACACAG | 6780 |
| GCTTGGGGAC | AGACCTGAGC | ATGACCACCC | AATCCGGGGA | CCTGCCGTCG | AAGGAGCGGG | 6840 |
| ACCAGGAGCG | GGGCCGGCCC | AAGGATCGGA | AGCATCGACA | GCACCACCAC | CACCACCACC | 6900 |
| ACCACCACCA | TCCCCCGCCC | CCCGACAAGG | ACCGCTATGC | CCAGGAACGG | CCGGACCACG | 6960 |
| GCCGGGCACG | GGCTCGGGAC | CAGCGCTGGT | CCCGCTCGCC | CAGCGAGGGC | CGAGAGCACA | 7020 |
| TGGCGCACCG | GCAGTAGTTC | CGTAAGTGGA | AGCCCAGCCC | CCTCAACATC | TGGTACCAGC | 7080 |
| ACTCCGCKGC | GGGGCCGCCG | CCAGCTCCCC | CAGACCCCCT | CCACCCCCG | GCCACACGTG | 7140 |
| TCCTATTCCC | CTGTGATCCG | TAAGGCCGGC | GGCTCGGGGC | CCCCGCAGCA | GCAGCAGCAG | 7200 |
| CAGCAGGCGG | TGGCCAGGCC | GGGCCGGGCG | GCCACCAGCG | GCCCTCGGAG | GTACCCAGGC | 7260 |
| CCCACGGCCG | AGCCTCTGGC | CGGAGATCGG | CCGCCCACGG | GGGCCACAG | CAGCGGCCGC | 7320 |
| TCGCCCAGGA | TGGAGAGGCG | GGTCCAGGC | CCGGCCCGGA | GCGAGTCCCC | CAGGGCCTGT | 7380 |
| CGACACGGCG | GGGCCCGGTG | GCCGGCATCT | GGCCCGCACG | TGTCCGAGGG | GCCCCGGGT | 7440 |
| CCCCGGCACC | ATGGCTACTA | CCGGGGCTCC | GACTACGACG | AGGCCGATGG | CCCGGGCAGC | 7500 |
| GGGGGCGGCG | AGGAGGCCAT | GGCCGGGGCC | TACGACGCGC | CACCCCCGT | ACGACACGCG | 7560 |
| TCCTCGGGCG | CCACCGGGCG | CTCGCCCAGG | ACTCCCGGG | CCTCGGGCCC | GGCCTGCGCC | 7620 |
| TCGCCTTCTC | GGCACGGCCG | GCGACTCCCC | AACGGCTACT | ACCCGGCGCA | CGGACTGGCC | 7680 |
| AGGCCCCGCG | GGCCGGGCTC | CAGGAAGGGC | CTGCACGAAC | CCTACAGCGA | GAGTGACGAT | 7740 |

GATTGGTGCT AAGCCCGGGC GAGGTGGCGC CCGCCCGGCC CCCCACGCAC C        7791

( 2 ) INFORMATION FOR SEQ ID NO:24:

( i ) SEQUENCE CHARACTERISTICS:
        ( A ) LENGTH: 7032 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 169..6921
        ( D ) OTHER INFORMATION: /product="Alpha1E-1 subunit of
              human calcium channel"

( x i ) SEQUENCE DESCRIPTION: SEQ ID NO:24:

GCTGCTGCTG CCTCTCCGAA GAGCTCGCGG AGCTCCCCAG AGGCGGTGGT CCCCGTGCTT        60

GTCTGGATGC GGCTCTGAGT CTCCGTGTGT CTTTCTGCTT GTTGCTGTGT GCGGGTGTTC        120

GGCCGCGATC ACCTTTGTGT GTCTTCTGTC TGTTTAAACC TCAGGATGGC TCGCTTCGGG        180

GAGGCGGTGG TCGCCAGGCC AGGGTCCGGC GATGGAGACT CGGACCAGAG CAGGAACCGG        240

CAAGGAACCC CCGTGCCGGC CTCGGGGCAG GCGGCCGCCT ACAAGCAGAC GAAAGCACAG        300

AGGGCGCGGA CTATGGCTTT GTACAACCCC ATTCCCGTCC GGCAGAACTG TTTCACCGTC        360

AACAGATCCC TGTTCATCTT CGGAGAAGAT AACATTGTCA GGAAATATGC CAAGAAGCTC        420

ATCGATTGGC CGCCATTTGA GTACATGATC CTGGCCACCA TCATTGCCAA CTGCATCGTC        480

CTGGCCCTGG AGCAGCATCT TCCTGAGGAT GACAAGACCC CCATGTCCCG AAGACTGGAG        540

AAGACAGAAC CTTATTTCAT TGGGATCTTT TGCTTTGAAG CTGGGATCAA AATTGTGGCC        600

CTGGGGTTCA TCTTCCATAA GGGCTCTTAC CTCCGCAATG GCTGGAATGT CATGGACTTC        660

ATCGTGGTCC TCAGTGGCAT CCTGGCCACT GCAGGAACCC ACTTCAATAC TCACGTGGAC        720

CTGAGGACCC TCCGGGCTGT GCGTGTCCTG CGGCCTTTGA AGCTCGTGTC AGGGATACCT        780

AGCCTGCAGA TTGTGTTGAA GTCCATCATG AAGGCCATGG TACCTCTTCT GCAGATTGGC        840

CTTCTGCTCT TCTTTGCCAT CCTGATGTTT GCTATCATTG GTTTGGAGTT CTACAGTGGC        900

AAGTTACATC GAGCRTGCTT CATGAACAAT TCAGGTATTC TAGAAGGATT TGACCCCCCT        960

CACCCATGTG GTGTGCAGGG CTGCCCAGCT GGTTATGAAT GCAAGGACTG GATCGGCCCC        1020

AATGATGGGA TCACCCAGTT TGATAACATC CTTTTTGCTG TGCTGACTGT CTTCCAGTGC        1080

ATCACCATGG AAGGGTGGAC CACTGTGCTG TACAATACCA ATGATGCCTT AGGAGCCACC        1140

TGGAATTGGC TGTACTTCAT CCCCCTCATC ATCATTGGAT CCTTCTTTGT TCTCAACCTA        1200

GTCCTGGGAG TGCTTTCCGG GGAATTTGCC AAAGAGAGAG AGAGTGGAGA GAACCGAAGG        1260

GCTTTCATGA AGCTGCGGCG CCAGCAGCAG ATTGAGCGTG AGCTGAATGG CTACCGTGCC        1320

TGGATAGACA AAGCAGAGGA AGTCATGCTC GCTGAAGAAA ATAAAAATGC TGGAACATCC        1380

GCCTTAGAAG TGCTTCGAAG GGCAACCATC AAGAGGAGCC GGACAGAGGC CATGACTCGA        1440

GACTCCAGTG ATGAGCACTG TGTTGATATC TCCTCTGTGG GCACACCTCT GGCCCGAGCC        1500

AGTATCAAAA GTGCAAAGGT AGACGGGGTC TCTTATTTCC GGCACAAGGA AAGGCTTCTG        1560

CGCATCTCCA TTCGCCACAT GGTTAAATCC CAGGTGTTTT ACTGGATTGT GCTGAGCCTT        1620

GTGGCACTCA ACACTGCCTG TGTGGCCATT GTCCATCACA ACCAGCCCCA GTGGCTCACC        1680

CACCTCCTCT ACTATGCAGA ATTTCTGTTT CTGGGACTCT TCCTCTTGGA GATGTCCCTG        1740

AAGATGTATG GCATGGGGCC TCGCCTTTAT TTTCACTCTT CATTCAACTG CTTTGATTTT        1800

```
GGGGTCACAG TGGGCAGTAT CTTTGAAGTG GTCTGGGCAA TCTTCAGACC TGGTACGTCT   1860
TTTGGAATCA GTGTCTTGCG AGCCCTCCGG CTTCTAAGAA TATTTAAAAT AACCAAGTAT   1920
TGGGCTTCCC TACGGAATTT GGTGGTCTCC TTGATGAGCT CAATGAAGTC TATCATCAGT   1980
TTGCTTTTCC TCCTCTTCCT CTTCATCGTT GTCTTTGCTC TCCTAGGAAT GCAGTTATTT   2040
GGAGGCAGGT TTAACTTTAA TGATGGGACT CCTTCGGCAA ATTTTGATAC CTTCCCTGCA   2100
GCCATCATGA CTGTGTTCCA GATCCTGACG GGTGAGGACT GGAATGAGGT GATGTACAAT   2160
GGGATCCGCT CCCAGGGTGG GGTCAGCTCA GGCATGTGGT CTGCCATCTA CTTCATTGTG   2220
CTCACCTTGT TTGGCAACTA CACGCTACTG AATGTGTTCT TGGCTATCGC TGTGGATAAT   2280
CTCGCCAACG CCCAGGAACT GACCAAGGAT GAACAGGAGG AAGAAGAGGC CTTCAACCAG   2340
AAACATGCAC TGCAGAAGGC CAAGGAGGTC AGCCCGATGT CTGCACCCAA CATGCCTTCG   2400
ATCGAGAGGG AGCGGAGGCG CCGGCACCAC ATGTCCGTGT GGGAGCAGCG TACCAGCCAG   2460
CTGAGGAAGC ACATGCAGAT GTCCAGCCAG GAGGCCCTCA ACAGAGAGGA GGCGCCGACC   2520
ATGAACCCGC TCAACCCCCT CAACCCGCTC AGCTCCCTCA ACCCGCTCAA TGCCCACCCC   2580
AGCCTTTATC GGCGACCCAG GGCCATTGAG GGCCTGGCCC TGGGCCTGGC CCTGGAGAAG   2640
TTCGAGGAGG AGCGCATCAG CCGTGGGGGG TCCCTCAAGG GGGATGGAGG GGACCGATCC   2700
AGTGCCCTGG ACAACCAGAG GACCCCTTTG TCCCTGGGCC AGCGGGAGCC ACCATGGCTG   2760
GCCAGGCCCT GTCATGGAAA CTGTGACCCG ACTCAGCAGG AGGCAGGGGG AGGAGAGGCT   2820
GTGGTGACCT TTGAGGACCG GGCCAGGCAC AGGCAGAGCC AACGGCGCAG CCGGCATCGC   2880
CGCGTCAGGA CAGAAGGCAA GGAGTCCTCT TCAGCCTCCC GGAGCAGGTC TGCCAGCCAG   2940
GAACGCAGTC TGGATGAAGC CATGCCCACT GAAGGGGAGA AGGACCATGA GCTCAGGGGC   3000
AACCATGGTG CCAAGGAGCC AACGATCCAA GAAGAGAGAG CCCAGGATTT AAGGAGGACC   3060
AACAGTCTGA TGGTGTCCAG AGGCTCCGGG CTGGCAGGAG GCCTTGATGA GGCTGACACC   3120
CCCCTAGTCC TGCCCCATCC TGAGCTGGAA GTGGGGAAGC ACGTGGTGCT GACGGAGCAG   3180
GAGCCAGAAG GCAGCAGTGA GCAGGCCCTG CTGGGGAATG TGCAGCTAGA CATGGGCCGG   3240
GTCATCAGCC AGAGCGAGCC TGACCTCTCC TGCATCACGG CCAACACGGA CAAGGCCACC   3300
ACCGAGAGCA CCAGCGTCAC CGTCGCCATC CCCGACGTGG ACCCCTTGGT GGACTCAACC   3360
GTGGTGCACA TTAGCAACAA GACGGATGGG GAAGCCAGTC CCTTGAAGGA GGCAGAGATC   3420
AGAGAGGATG AGGAGGAGGT GGAGAAGAAG AAGCAGAAGA AGGAGAAGCG TGAGACAGGC   3480
AAAGCCATGG TGCCCCACAG CTCAATGTTC ATCTTCAGCA CCACCAACCC GATCCGGAGG   3540
GCCTGCCACT ACATCGTGAA CCTGCGCTAC TTTGAGATGT GCATCCTCCT GGTGATTGCA   3600
GCCAGCAGCA TCGCCCTGGC GGCAGAGGAC CCCGTCCTGA CCAACTCGGA GCGCAACAAA   3660
GTCCTGAGGT ATTTTGACTA TGTGTTCACG GGCGTGTTCA CCTTTGAGAT GGTTATAAAG   3720
ATGATAGACC AAGGCTTGAT CCTGCAGGAT GGGTCCTACT TCCGAGACTT GTGGAACATC   3780
CTGGACTTTG TGGTGGTCGT TGGCGCATTG GTGGCCTTTG CTCTGGCGAA CGCTTTGGGA   3840
ACCAACAAAG GACGGGACAT CAAGACCATC AAGTCTCTGC GGGTGCTCCG AGTTCTAAGG   3900
CCACTGAAAA CCATCAAGCG CTTGCCCAAG CTCAAGGCCG TCTTCGACTG CGTAGTGACC   3960
TCCTTGAAGA ATGTCTTCAA CATACTCATT GTGTACAAGC TCTTCATGTT CATCTTTGCT   4020
GTCATCGCAG TTCAGCTCTT CAAGGGAAAG TTCTTTTATT GCACGGACAG TTCCAAGGAC   4080
ACAGAGAAGG AGTGCATAGG CAACTATGTA GATCACGAGA AAAACAAGAT GGAGGTGAAG   4140
GGCCGGGAAT GGAAGCGCCA TGAATTCCAC TACGACAACA TTATCTGGGC CCTGCTGACC   4200
```

```
CTCTTCACCG  TCTCCACAGG  GGAAGGATGG  CCTCAAGTTC  TGCAGCACTC  TGTAGATGTG    4260
ACAGAGGAAG  ACCGAGGCCC  AAGCCGCAGC  AACCGCATGG  AGATGTCTAT  CTTTTATGTA    4320
GTCTACTTTG  TGGTCTTCCC  CTTCTTCTTT  GTCAATATCT  TTGTGGCTCT  CATCATCATC    4380
ACCTTCCAGG  AGCAAGGGGA  TAAGATGATG  GAGGAGTGCA  GCCTGGAGAA  GAATGAGAGG    4440
GCGTGCATCG  ACTTCGCCAT  CAGCGCCAAA  CCTCTCACCC  GCTACATGCC  GCAGAACAGA    4500
CACACCTTCC  AGTACCGCGT  GTGGCACTTT  GTGGTGTCTC  CGTCCTTTGA  GTACACCATT    4560
ATGGCCATGA  TCGCCTTGAA  TACTGTTGTG  CTGATGATGA  AGTATTATTC  TGCTCCCTGT    4620
ACCTATGAGC  TGGCCCTGAA  GTACCTGAAT  ATCGCCTTCA  CCATGGTGTT  TTCCCTGGAA    4680
TGTGTCCTGA  AGGTCATCGC  TTTTGGCTTT  TTGAACTATT  CCGAGACAC   CTGGAATATC    4740
TTTGACTTCA  TCACCGTGAT  TGGCAGTATC  ACAGAAATTA  TCCTGACAGA  CAGCAAGCTG    4800
GTGAACACCA  GTGGCTTCAA  TATGAGCTTT  CTGAAGCTCT  TCCGAGCTGC  CCGCCTCATA    4860
AAGCTCCTGC  GTCAGGGCTA  TACCATACGC  ATTTTGCTGT  GGACCTTTGT  GCAGTCCTTT    4920
AAGGCCCTCC  CTTATGTCTG  CCTTTTAATT  GCCATGCTTT  TCTTCATTTA  TGCCATCATT    4980
GGGATGCAGG  TATTTGGAAA  CATAAAATTA  GACGAGGAGA  GTCACATCAA  CCGGCACAAC    5040
AACTTCCGGA  GTTTCTTTGG  GTCCCTAATG  CTACTCTTCA  GGAGTGCCAC  AGGTGAGGCC    5100
TGGCAGGAGA  TTATGCTGTC  ATGCCTTGGG  GAGAAGGGCT  GTGAGCCTGA  CACCACCGCA    5160
CCATCAGGGC  AGAACGAGAA  TGAACGCTGC  GGCACCGATC  TGGCCTACGT  GTACTTTGTC    5220
TCCTTCATCT  TCTTCTGCTC  CTTCTTGATG  CTCAACCTGT  TTGTGGCCGT  CATCATGGAC    5280
AACTTTGAGT  ACCTGACTCG  GGACTCCTCC  ATCCTGGGGC  CTCACCACTT  GGACGAGTTT    5340
GTCCGCGTCT  GGGCAGAATA  TGACCGAGCA  GCATGTGGCC  GCATCCATTA  CACTGAGATG    5400
TATGAAATGC  TGACTCTCAT  GTCACCTCCG  CTAGGCCTCG  GCAAGAGATG  TCCCTCCAAA    5460
GTGGCATATA  AGAGGTTGGT  CCTGATGAAC  ATGCCAGTAG  CTGAGGACAT  GACGGTCCAC    5520
TTCACCTCCA  CACTTATGGC  TCTGATCCGG  ACAGCTCTGG  ACATTAAAAT  TGCCAAAGGT    5580
GGTGCAGACA  GGCAGCAGCT  AGACTCAGAG  CTACAAAAGG  AGACCCTAGC  CATCTGGCCT    5640
CACCTATCCC  AGAAGATGCT  GGATCTGCTT  GTGCCCATGC  CCAAAGCCTC  TGACCTGACT    5700
GTGGGCAAAA  TCTATGCAGC  AATGATGATC  ATGGACTACT  ATAAGCAGAG  TAAGGTGAAG    5760
AAGCAGAGGC  AGCAGCTGGA  GGAACAGAAA  AATGCCCCCA  TGTTCCAGCG  CATGGAGCCT    5820
TCATCTCTGC  CTCAGGAGAT  CATTGCTAAT  GCCAAAGCCC  TGCCTTACCT  CCAGCAGGAC    5880
CCCGTTTCAG  GCCTGAGTGG  CCGGAGTGGA  TACCCTTCGA  TGAGTCCACT  CTCTCCCCAG    5940
GATATATTCC  AGTTGGCTTG  TATGGACCCC  GCCGATGACG  GACAGTTCCA  AGAACGGCAG    6000
TCTCTGGTGG  TGACAGACCC  TAGCTCCATG  AGACGTTCAT  TTTCCACTAT  TCGGGATAAG    6060
CGTTCAAATT  CCTCGTGGTT  GGAGGAATTC  TCCATGGAGC  GAAGCAGTGA  AAATACCTAC    6120
AAGTCCCGTC  GCCGGAGTTA  CCACTCCTCC  TTGCGGCTGT  CAGCCCACCG  CCTGAACTCT    6180
GATTCAGGCC  ACAAGTCTGA  CACTCACCCC  TCAGGGGCA   GGGAGCGGCG  ACGATCAAAA    6240
GAGCGAAAGC  ATCTTCTCTC  TCCTGATGTC  TCCCGCTGCA  ATTCAGAAGA  GCGAGGGACC    6300
CAGGCTGACT  GGGAGTCCCC  AGAGCGCCGT  CAATCCAGGT  CACCCAGTGA  GGGCAGGTCA    6360
CAGACGCCCA  ACAGACAGGG  CACAGGTTCC  CTAAGTGAGA  GCTCCATCCC  CTCTGTCTCT    6420
GACACCAGCA  CCCCAAGAAG  AAGTCGTCGG  CAGCTCCCAC  CCGTCCCGCC  AAAGCCCGG    6480
CCCCTCCTTT  CCTACAGCTC  CCTGATTCGA  CACGCGGGCA  GCATCTCTCC  ACCTGCTGAT    6540
GGAAGCGAGG  AGGGCTCCCC  GCTGACCTCC  CAAGCTCTGG  AGAGCAACAA  TGCTTGGCTG    6600
```

| | | | | | |
|---|---|---|---|---|---|
| ACCGAGTCTT | CCAACTCTCC | GCACCCCCAG | CAGAGGCAAC | ATGCCTCCCC | ACAGCGCTAC | 6660
| ATCTCCGAGC | CCTACTTGGC | CCTGCACGAA | GACTCCACG | CCTCAGACTG | TGTTGAGGAG | 6720
| GAGACGCTCA | CTTTCGAAGC | AGCCGTGGCT | ACTAGCCTGG | GCCGTTCCAA | CACCATCGGC | 6780
| TCAGCCCCAC | CCCTGCGGCA | TAGCTGGCAG | ATGCCCAACG | GGCACTATCG | GCGGCGGAGG | 6840
| CGCGGGGGGC | CTGGGCCAGG | CATGATGTGT | GGGGCTGTCA | ACAACCTGCT | AAGTGACACG | 6900
| GAAGAAGATG | ACAAATGCTA | GAGGCTGCTC | CCCCCTCCGA | TGCATGCTCT | TCTCTCACAT | 6960
| GGAGAAAACC | AAGACAGAAT | TGGGAAGCCA | GTGCGGCCCC | GCGGGGAGGA | AGAGGGAAAA | 7020
| GGAAGATGGA | AG | | | | | 7032

( 2 ) INFORMATION FOR SEQ ID NO:25:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 1..57
        ( D ) OTHER INFORMATION: /product="Alpha1E-3 subunit of human
            calcium channel is made upon insertion of this
            sequence into alpha1E-1 between nucleotides 2405 and
            2406"

( x i ) SEQUENCE DESCRIPTION: SEQ ID NO:25:

| | | | | | |
|---|---|---|---|---|---|
| AAGAGACAGA | AGGAGAAGAC | ACCACATGTC | GATGTGGGAG | CCACGCAGCA | GCCACCT | 57

( 2 ) INFORMATION FOR SEQ ID NO:26:

( i ) SEQUENCE CHARACTERISTICS:
        ( A ) LENGTH: 2264 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 2..1951
        ( D ) OTHER INFORMATION: /product="Beta2D subunit of human
            calcium channel"

( x i ) SEQUENCE DESCRIPTION: SEQ ID NO:26:

| | | | | | |
|---|---|---|---|---|---|
| AATTCCGGCG | GCGGCGGTGG | CGCAGGAGAT | CCAGATGGAA | CTGCTAGAGA | ACGTGGCTCC | 60
| CGCGGGGGCG | CTCGGAGCCG | CCGCACAGTC | ATATGGAAAA | GGAGCCAGAA | GGAAAAACAG | 120
| ATTTAAAGGA | TCTGATGGAA | GCACGTCATC | TGATACTACC | TCAAATAGTT | TTGTTCGCCA | 180
| GGGTTCGGCA | GACTCCTACA | CTAGCCGTCC | ATCCGATTCC | GATGTATCTC | TGGAGGAGGA | 240
| CCGGGAGGCA | GTGCGCAGAG | AAGCGGAGCG | GCAGGCCCAG | GCACAGTTGG | AAAAAGCAAA | 300
| GACAAAGCCC | GTTGCATTTG | CGGTTCGGAC | AAATGTCAGC | TACAGTGCGG | CCCATGAAGA | 360
| TGATGTTCCA | GTGCCTGGCA | TGGCCATCTC | ATTCGAAGCA | AAAGATTTTC | TGCATGTTAA | 420
| GGAAAAATTT | AACAATGACT | GGTGGATAGG | GCGATTGGTA | AAAGAAGGCT | GTGAAATCGG | 480
| ATTCATTCCA | AGCCCAGTCA | AACTAGAAAA | CATGAGGCTG | CAGCATGAAC | AGAGAGCCAA | 540
| GCAAGGGAAA | TTCTACTCCA | GTAAATCAGG | AGGAAATTCA | TCATCCAGTT | TGGGTGACAT | 600
| AGTACCTAGT | TCCAGAAAAT | CAACACCTCC | ATCATCTGCT | ATAGACATAG | ATGCTACTGG | 660

| | | | | | |
|---|---|---|---|---|---|
| CTTAGATGCA | GAAGAAAATG | ATATTCCAGC | AAACCACCGC | TCCCCTAAAC | CCAGTGCAAA | 720 |
| CAGTGTAACG | TCACCCCACT | CCAAAGAGAA | AAGAATGCCC | TTCTTTAAGA | AGACAGAGCA | 780 |
| CACTCCTCCG | TATGATGTGG | TACCTTCCAT | GCGACCAGTG | GTCCTAGTGG | GCCCTTCTCT | 840 |
| GAAGGGCTAC | GAGGTCACAG | ATATGATGCA | CAAAGCGCTG | TTTGATTTTT | TAAAACACAG | 900 |
| ATTTGAAGGG | CGGATATCCA | TCACAAGGGT | CACCGCTGAC | ATCTCGCTTG | CCAAACGCTC | 960 |
| GGTATTAAAC | AATCCCAGTA | AGCACGCAAT | AATAGAAAGA | TCCAACACAA | GGTCAAGCTT | 1020 |
| AGCGGAAGTT | CAGAGTGAAA | TCGAAAGGAT | TTTTGAACTT | GCAAGAACAT | TGCAGTTGGT | 1080 |
| GGTCCTTGAC | GCGGATACAA | TTAATCATCC | AGCTCAACTC | AGTAAAACCT | CCTTGGCCCC | 1140 |
| TATTATAGTA | TATGTAAAGA | TTTCTTCTCC | TAAGGTTTTA | CAAAGGTTAA | TAAAATCTCG | 1200 |
| AGGGAAATCT | CAAGCTAAAC | ACCTCAACGT | CCAGATGGTA | GCAGCTGATA | AACTGGCTCA | 1260 |
| GTGTCCTCCA | GAGCTGTTCG | ATGTGATCTT | GGATGAGAAC | CAGCTTGAGG | ATGCCTGTGA | 1320 |
| GCACCTTGCC | GACTATCTGG | AGGCCTACTG | GAAGGCCACC | CATCCTCCCA | GCAGTAGCCT | 1380 |
| CCCCAACCCT | CTCCTTAGCC | GTACATTAGC | CACTTCAAGT | CTGCCTCTTA | GCCCCACCCT | 1440 |
| AGCCTCTAAT | TCACAGGGTT | CTCAAGGTGA | TCAGAGGACT | GATCGCTCCG | CTCCTATCCG | 1500 |
| TTCTGCTTCC | CAAGCTGAAG | AAGAACCTAG | TGTGGAACCA | GTCAAGAAAT | CCCAGCACCG | 1560 |
| CTCTTCCTCC | TCAGCCCCAC | ACCACAACCA | TCGCAGTGGG | ACAAGTCGCG | GCCTCTCCAG | 1620 |
| GCAAGAGACA | TTTGACTCGG | AAACCCAGGA | GAGTCGAGAC | TCTGCCTACG | TAGAGCCAAA | 1680 |
| GGAAGATTAT | TCCCATGACC | ACGTGGACCA | CTATGCCTCA | CACCGTGACC | ACAACCACAG | 1740 |
| AGACGAGACC | CACGGGAGCA | GTGACCACAG | ACACAGGGAG | TCCCGGCACC | GTTCCCGGGA | 1800 |
| CGTGGATCGA | GAGCAGGACC | ACAACGAGTG | CAACAAGCAG | CGCAGCCGTC | ATAAATCCAA | 1860 |
| GGATGGCTAC | TGTGAAAAGG | ATGGAGAAGT | GATATCAAAA | AAACGGAATG | AGGCTGGGGA | 1920 |
| GTGGCACAGG | GATGTTCACA | TCCCCCAATG | AGTGGCGCCC | TCGCGTGTTT | TTTNTTTTTT | 1980 |
| TGGGGGGGNG | TCTTGTTTAT | CTAACAGCAC | CCCCAAAAAA | AAATGTCTGG | GGGGTCTACA | 2040 |
| CTACACACAT | TTGTGCTCTC | TCTTGTAATA | TTGGGTATTA | TTGCTGGCGC | TCGTATAGCA | 2100 |
| ATAGCATGGA | TAGAGTATTG | AGATACTTCC | TCTGGGGCAA | GTGCTACATA | AATTGCCCTG | 2160 |
| GTATGGCTAC | AGCCCTCCGG | GTGCATACTG | CTCTCTACAA | AAACTGGGGG | GGGTCGCTCC | 2220 |
| CACTAGAACA | ACTTCTTGCC | CCCACCCAGG | GCGAATGTTA | AGTG | | 2264 |

( 2 ) INFORMATION FOR SEQ ID NO:27:

( i ) SEQUENCE CHARACTERISTICS:
  ( A ) LENGTH: 894 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: 104..890
  ( D ) OTHER INFORMATION: /product="Beta4 subunit of human calcium channel"

( x i ) SEQUENCE DESCRIPTION: SEQ ID NO:27:

| | | | | | |
|---|---|---|---|---|---|
| TTAAAGCAAA | AGAATTCGGT | ACGTACACTC | GTAGCAGCCC | AGCCTCGGGG | GCCAGCCCCC | 60 |
| TCCGCCCACC | GAACACGGGT | TGGCCATGCG | GCGGTTCTGA | ACGATGTCCT | CCTCCTCCTA | 120 |
| CGCCAAGAAC | GGGACCGCGG | ACGGGCCGCA | CTCCCCCACC | TCGCAGGTGG | CCCGAGGCAC | 180 |

-continued

| | | | | | |
|---|---|---|---|---|---|
| CACAACCCGG | AGGAGCAGGT | TGAAAAGATC | CGATGGCAGC | ACCACTTCGA | CCAGCTTCAT | 240
| CCTCAGACAG | GGTTCAGCGG | ATTCCTACAC | AAGCAGGCCG | CCTGACTCCG | ATGTCTCTTT | 300
| GGAAGAGGAC | CGGGAAGCAA | TTCGACAGGA | GAGAGAACAG | CAAGCAGCTA | TCCAGCTTGA | 360
| GAGAGCAAAG | TCCAAACCTG | TAGCATTTGA | CGAGAAGACA | AATGTGAGCT | ACTGCGGCGC | 420
| CCTGGACGAA | GATGTGCCTG | TTCCCAGCAC | AGCTATCTCC | TTTGATGCTA | AGGACTTTCT | 480
| ACATATTAAA | GAGGAATATA | ACCATGATTG | GTGGATAGGA | AGGCTGGTGA | AAGAGGGCTG | 540
| TGAAATTGGC | TTCATTCCAA | GTCCACTCAG | ATTGGAGGAC | ATACGGATCC | AGCNAGAACC | 600
| CCAAAGAGGA | CGTTTTCACG | GAGGGAAATC | AAGTGGAAAT | TCTTCTTCAA | GTCTTGGAGA | 660
| AATGGTATCT | GGGACATTCC | GAGCAACTCC | CACATCGACA | GCCAAACAGA | AGCCAAAAGT | 720
| GGCGGAGCAC | ATTCCTCCTT | ACGATGTTGT | ACCGTCAATG | CGTCCGGTGG | TGTTAGTGGG | 780
| GCCGTCACTG | AAAGGTTACG | AGGTAACAGA | CATGATGCAG | AAAGCCCTCT | TTGATTTCCT | 840
| GAAGCACAGG | TTTGATGGGA | GGATTTCAGT | AACCAGAGTG | ACAGCTGACA | TTTT | 894

(2) INFORMATION FOR SEQ ID NO:28:

(i) SEQUENCE CHARACTERISTICS:
        (A) LENGTH: 263 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:28:

```
Met Ser Ser Ser Ser Tyr Ala Lys Asn Gly Thr Ala Asp Gly Pro His
 1               5                  10                  15

Ser Pro Thr Ser Gln Val Ala Arg Gly Thr Thr Thr Arg Arg Ser Arg
                20                  25                  30

Leu Lys Arg Ser Asp Gly Ser Thr Thr Ser Thr Ser Phe Ile Leu Arg
            35                  40                  45

Gln Gly Ser Ala Asp Ser Tyr Thr Ser Arg Pro Pro Ser Asp Val
        50                  55                  60

Ser Leu Glu Glu Asp Arg Glu Ala Ile Arg Gln Glu Arg Glu Gln Gln
65                  70                  75                  80

Ala Ala Ile Gln Leu Glu Arg Ala Lys Ser Lys Pro Val Ala Phe Asp
                85                  90                  95

Glu Lys Thr Asn Val Ser Tyr Cys Gly Ala Leu Asp Glu Asp Val Pro
               100                 105                 110

Val Pro Ser Thr Ala Ile Ser Phe Asp Ala Lys Asp Phe Leu His Ile
            115                 120                 125

Lys Glu Glu Tyr Asn His Asp Trp Trp Ile Gly Arg Leu Val Lys Glu
130                 135                 140

Gly Cys Glu Ile Gly Phe Ile Pro Ser Pro Leu Arg Leu Glu Asp Ile
145                 150                 155                 160

Arg Ile Gln Xaa Glu Pro Gln Arg Gly Arg Phe His Gly Gly Lys Ser
                165                 170                 175

Ser Gly Asn Ser Ser Ser Ser Leu Gly Glu Met Val Ser Gly Thr Phe
            180                 185                 190

Arg Ala Thr Pro Thr Ser Thr Ala Lys Gln Lys Pro Lys Val Ala Glu
        195                 200                 205

His Ile Pro Pro Tyr Asp Val Val Pro Ser Met Arg Pro Val Val Leu
    210                 215                 220

Val Gly Pro Ser Leu Lys Gly Tyr Glu Val Thr Asp Met Met Gln Lys
```

|   |   |   |   |   | 225 |   |   |   |   | 230 |   |   |   |   | 235 |   |   |   |   | 240 |
|---|---|---|---|---|---|---|---|---|---|---|---|---|---|---|---|---|---|---|---|---|

Ala Leu Phe Asp Phe Leu Lys His Arg Phe Asp Gly Arg Ile Ser Val
                        245                   250                   255

Thr Arg Val Thr Ala Asp Ile (2) INFORMATION FOR SEQ ID NO:29:

(i) SEQUENCE CHARACTERISTICS:
        (A) LENGTH: 1681 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1437
        (D) OTHER INFORMATION: /standard_name= "Beta1-1"

(ix) FEATURE:
        (A) NAME/KEY: 3'UTR
        (B) LOCATION: 1435..1681

(xi) SEQUENCE DESCRIPTION: SEQ ID NO:29:

```
ATG GTC CAG AAG ACC AGC ATG TCC CGG GGC CCT TAC CCA CCC TCC CAG         48
Met Val Gln Lys Thr Ser Met Ser Arg Gly Pro Tyr Pro Pro Ser Gln
 1               5                  10                  15

GAG ATC CCC ATG GAG GTC TTC GAC CCC AGC CCG CAG GGC AAA TAC AGC         96
Glu Ile Pro Met Glu Val Phe Asp Pro Ser Pro Gln Gly Lys Tyr Ser
             20                  25                  30

AAG AGG AAA GGG CGA TTC AAA CGG TCA GAT GGG AGC ACG TCC TCG GAT        144
Lys Arg Lys Gly Arg Phe Lys Arg Ser Asp Gly Ser Thr Ser Ser Asp
         35                  40                  45

ACC ACA TCC AAC AGC TTT GTC CGC CAG GGC TCA GCG GAG TCC TAC ACC        192
Thr Thr Ser Asn Ser Phe Val Arg Gln Gly Ser Ala Glu Ser Tyr Thr
     50                  55                  60

AGC CGT CCA TCA GAC TCT GAT GTA TCT CTG GAG GAG GAC CGG GAA GCC        240
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCG CAG CTC GAG AAG GCC        288
Leu Arg Lys Glu Ala Glu Arg Gln Ala Leu Ala Gln Leu Glu Lys Ala
                 85                  90                  95

AAG ACC AAG CCA GTG GCA TTT GCT GTG CGG ACA AAT GTT GGC TAC AAT        336
Lys Thr Lys Pro Val Ala Phe Ala Val Arg Thr Asn Val Gly Tyr Asn
            100                 105                 110

CCG TCT CCA GGG GAT GAG GTG CCT GTG CAG GGA GTG GCC ATC ACC TTC        384
Pro Ser Pro Gly Asp Glu Val Pro Val Gln Gly Val Ala Ile Thr Phe
        115                 120                 125

GAG CCC AAA GAC TTC CTG CAC ATC AAG GAG AAA TAC AAT AAT GAC TGG        432
Glu Pro Lys Asp Phe Leu His Ile Lys Glu Lys Tyr Asn Asn Asp Trp
    130                 135                 140

TGG ATC GGG CGG CTG GTG AAG GAG GGC TGT GAG GTT GGC TTC ATT CCC        480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG        528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC        576
Arg Gln Asn Arg Leu Gly Ser Ser Lys Ser Gly Asp Asn Ser Ser Ser
            180                 185                 190

AGT CTG GGA GAT GTG GTG ACT GGC ACC CGC CGC CCC ACA CCC CCT GCC        624
Ser Leu Gly Asp Val Val Thr Gly Thr Arg Arg Pro Thr Pro Pro Ala
        195                 200                 205
```

| | | | | | | | | | | | | | | | | |
|---|---|---|---|---|---|---|---|---|---|---|---|---|---|---|---|---|
| AGT | GGT | AAT | GAA | ATG | ACT | AAC | TTA | GCC | TTT | GAA | CTA | GAC | CCC | CTA | GAG | 672 |
| Ser | Gly | Asn | Glu | Met | Thr | Asn | Leu | Ala | Phe | Glu | Leu | Asp | Pro | Leu | Glu | |
| 210 | | | | | 215 | | | | | 220 | | | | | | |
| TTA | GAG | GAG | GAA | GAG | GCT | GAG | CTT | GGT | GAG | CAG | AGT | GGC | TCT | GCC | AAG | 720 |
| Leu | Glu | Glu | Glu | Glu | Ala | Glu | Leu | Gly | Glu | Gln | Ser | Gly | Ser | Ala | Lys | |
| 225 | | | | | 230 | | | | | 235 | | | | | 240 | |
| ACT | AGT | GTT | AGC | AGT | GTC | ACC | ACC | CCG | CCA | CCC | CAT | GGC | AAA | CGC | ATC | 768 |
| Thr | Ser | Val | Ser | Ser | Val | Thr | Thr | Pro | Pro | Pro | His | Gly | Lys | Arg | Ile | |
| | | | | 245 | | | | | 250 | | | | | 255 | | |
| CCC | TTC | TTT | AAG | AAG | ACA | GAG | CAT | GTG | CCC | CCC | TAT | GAC | GTG | GTG | CCT | 816 |
| Pro | Phe | Phe | Lys | Lys | Thr | Glu | His | Val | Pro | Pro | Tyr | Asp | Val | Val | Pro | |
| | | | | 260 | | | | | 265 | | | | | 270 | | |
| TCC | ATG | AGG | CCC | ATC | ATC | CTG | GTG | GGA | CCG | TCG | CTC | AAG | GGC | TAC | GAG | 864 |
| Ser | Met | Arg | Pro | Ile | Ile | Leu | Val | Gly | Pro | Ser | Leu | Lys | Gly | Tyr | Glu | |
| | | 275 | | | | | 280 | | | | | 285 | | | | |
| GTT | ACA | GAC | ATG | ATG | CAG | AAA | GCT | TTA | TTT | GAC | TTC | TTG | AAG | CAT | CGG | 912 |
| Val | Thr | Asp | Met | Met | Gln | Lys | Ala | Leu | Phe | Asp | Phe | Leu | Lys | His | Arg | |
| | | 290 | | | | | 295 | | | | | 300 | | | | |
| TTT | GAT | GGC | AGG | ATC | TCC | ATC | ACT | CGT | GTG | ACG | GCA | GAT | ATT | TCC | CTG | 960 |
| Phe | Asp | Gly | Arg | Ile | Ser | Ile | Thr | Arg | Val | Thr | Ala | Asp | Ile | Ser | Leu | |
| 305 | | | | | 310 | | | | | 315 | | | | | 320 | |
| GCT | AAG | CGC | TCA | GTT | CTC | AAC | AAC | CCC | AGC | AAA | CAC | ATC | ATC | ATT | GAG | 1008 |
| Ala | Lys | Arg | Ser | Val | Leu | Asn | Asn | Pro | Ser | Lys | His | Ile | Ile | Ile | Glu | |
| | | | | 325 | | | | | 330 | | | | | 335 | | |
| CGC | TCC | AAC | ACA | CGC | TCC | AGC | CTG | GCT | GAG | GTG | CAG | AGT | GAA | ATC | GAG | 1056 |
| Arg | Ser | Asn | Thr | Arg | Ser | Ser | Leu | Ala | Glu | Val | Gln | Ser | Glu | Ile | Glu | |
| | | | 340 | | | | | 345 | | | | | 350 | | | |
| CGA | ATC | TTC | GAG | CTG | GCC | CGG | ACC | CTT | CAG | TTG | GTC | GCT | CTG | GAT | GCT | 1104 |
| Arg | Ile | Phe | Glu | Leu | Ala | Arg | Thr | Leu | Gln | Leu | Val | Ala | Leu | Asp | Ala | |
| | | 355 | | | | | 360 | | | | | 365 | | | | |
| GAC | ACC | ATC | AAT | CAC | CCA | GCC | CAG | CTG | TCC | AAG | ACC | TCG | CTG | GCC | CCC | 1152 |
| Asp | Thr | Ile | Asn | His | Pro | Ala | Gln | Leu | Ser | Lys | Thr | Ser | Leu | Ala | Pro | |
| | 370 | | | | | 375 | | | | | 380 | | | | | |
| ATC | ATT | GTT | TAC | ATC | AAG | ATC | ACC | TCT | CCC | AAG | GTA | CTT | CAA | AGG | CTC | 1200 |
| Ile | Ile | Val | Tyr | Ile | Lys | Ile | Thr | Ser | Pro | Lys | Val | Leu | Gln | Arg | Leu | |
| 385 | | | | | 390 | | | | | 395 | | | | | 400 | |
| ATC | AAG | TCC | CGA | GGA | AAG | TCT | CAG | TCC | AAA | CAC | CTC | AAT | GTC | CAA | ATA | 1248 |
| Ile | Lys | Ser | Arg | Gly | Lys | Ser | Gln | Ser | Lys | His | Leu | Asn | Val | Gln | Ile | |
| | | | | 405 | | | | | 410 | | | | | 415 | | |
| GCG | GCC | TCG | GAA | AAG | CTG | GCA | CAG | TGC | CCC | CCT | GAA | ATG | TTT | GAC | ATC | 1296 |
| Ala | Ala | Ser | Glu | Lys | Leu | Ala | Gln | Cys | Pro | Pro | Glu | Met | Phe | Asp | Ile | |
| | | | | 420 | | | | | 425 | | | | | 430 | | |
| ATC | CTG | GAT | GAG | AAC | CAA | TTG | GAG | GAT | GCC | TGC | GAG | CAT | CTG | GCG | GAG | 1344 |
| Ile | Leu | Asp | Glu | Asn | Gln | Leu | Glu | Asp | Ala | Cys | Glu | His | Leu | Ala | Glu | |
| | | 435 | | | | | 440 | | | | | 445 | | | | |
| TAC | TTG | GAA | GCC | TAT | TGG | AAG | GCC | ACA | CAC | CCG | CCC | AGC | AGC | ACG | CCA | 1392 |
| Tyr | Leu | Glu | Ala | Tyr | Trp | Lys | Ala | Thr | His | Pro | Pro | Ser | Ser | Thr | Pro | |
| | 450 | | | | | 455 | | | | | 460 | | | | | |
| CCC | AAT | CCG | CTG | CTG | AAC | CGC | ACC | ATG | GCT | ACC | GCA | GCC | CTG | GCT | | 1437 |
| Pro | Asn | Pro | Leu | Leu | Asn | Arg | Thr | Met | Ala | Thr | Ala | Ala | Leu | Ala | | |
| 465 | | | | | 470 | | | | | 475 | | | | | | |

| | | | | | |
|---|---|---|---|---|---|
| GCCAGCCCTG | CCCCTGTCTC | CAACCTCCAG | GTACAGGTGC | TCACCTCGCT | CAGGAGAAAC | 1497 |
| CTCGGCTTCT | GGGGCGGGCT | GGAGTCCTCA | CAGCGGGGCA | GTGTGGTGCC | CCAGGAGCAG | 1557 |
| GAACATGCCA | TGTAGTGGGC | GCCCTGCCCG | TCTTCCCTCC | TGCTCTGGGG | TCGGAACTGG | 1617 |
| AGTGCAGGGA | ACATGGAGGA | GGAAGGGAAG | AGCTTTATTT | TGTAAAAAAA | TAAGATGAGC | 1677 |
| GGCA | | | | | | 1681 |

( 2 ) INFORMATION FOR SEQ ID NO:30:

( i ) SEQUENCE CHARACTERISTICS:
        ( A ) LENGTH: 1526 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..651
        ( D ) OTHER INFORMATION: /standard_name= "Beta1-4"

( x i ) SEQUENCE DESCRIPTION: SEQ ID NO:30:

```
ATG GTC CAG AAG ACC AGC ATG TCC CGG GGC CCT TAC CCA CCC TCC CAG     48
Met Val Gln Lys Thr Ser Met Ser Arg Gly Pro Tyr Pro Pro Ser Gln
 1               5                  10                  15

GAG ATC CCC ATG GAG GTC TTC GAC CCC AGC CCG CAG GGC AAA TAC AGC     96
Glu Ile Pro Met Glu Val Phe Asp Pro Ser Pro Gln Gly Lys Tyr Ser
                20                  25                  30

AAG AGG AAA GGG CGA TTC AAA CGG TCA GAT GGG AGC ACG TCC TCG GAT    144
Lys Arg Lys Gly Arg Phe Lys Arg Ser Asp Gly Ser Thr Ser Ser Asp
            35                  40                  45

ACC ACA TCC AAC AGC TTT GTC CGC CAG GGC TCA GCG GAG TCC TAC ACC    192
Thr Thr Ser Asn Ser Phe Val Arg Gln Gly Ser Ala Glu Ser Tyr Thr
        50                  55                  60

AGC CGT CCA TCA GAC TCT GAT GTA TCT CTG GAG GAG GAC CGG GAA GCC    240
Ser Arg Pro Ser Asp Ser Asp Val Ser Leu Glu Glu Asp Arg Glu Ala
65                  70                  75                  80

TTA AGG AAG GAA GCA GAG CGC CAG GCA TTA GCG CAG CTC GAG AAG GCC    288
Leu Arg Lys Glu Ala Glu Arg Gln Ala Leu Ala Gln Leu Glu Lys Ala
                85                  90                  95

AAG ACC AAG CCA GTG GCA TTT GCT GTG CGG ACA AAT GTT GGC TAC AAT    336
Lys Thr Lys Pro Val Ala Phe Ala Val Arg Thr Asn Val Gly Tyr Asn
               100                 105                 110

CCG TCT CCA GGG GAT GAG GTG CCT GTG CAG GGA GTG GCC ATC ACC TTC    384
Pro Ser Pro Gly Asp Glu Val Pro Val Gln Gly Val Ala Ile Thr Phe
           115                 120                 125

GAG CCC AAA GAC TTC CTG CAC ATC AAG GAG AAA TAC AAT AAT GAC TGG    432
Glu Pro Lys Asp Phe Leu His Ile Lys Glu Lys Tyr Asn Asn Asp Trp
       130                 135                 140

TGG ATC GGG CGG CTG GTG AAG GAG GGC TGT GAG GTT GGC TTC ATT CCC    480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG    528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC    576
Arg Gln Asn Arg Leu Gly Ser Ser Lys Ser Gly Asp Asn Ser Ser Ser
                180                 185                 190

AGT CTG GGA GAT GTG GTG ACT GGC ACC CGC CGC CCC ACA CCC CCT GCC    624
Ser Leu Gly Asp Val Val Thr Gly Thr Arg Arg Pro Thr Pro Pro Ala
            195                 200                 205

AGT GAC AGA GCA TGT GCC CCC CTA TGACGTGGTG CCTTCCATGA GGCCCATCAT   678
Ser Asp Arg Ala Cys Ala Pro Leu
        210                 215

CCTGGTGGGA CCGTCGCTCA AGGGCTACGA GGTTACAGAC ATGATGCAGA AAGCTTTATT   738

TGACTTCTTG AAGCATCGGT TTGATGGCAG GATCTCCATC ACTCGTGTGA CGGCAGATAT   798

TTCCCTGGCT AAGCGCTCAG TTCTCAACAA CCCCAGCAAA CACATCATCA TTGAGCGCTC   858

CAACACACGC TCCAGCCTGG CTGAGGTGCA GAGTGAAATC GAGCGAATCT TCGAGCTGGC   918
```

```
CCGGACCCTT   CAGTTGGTCG   CTCTGGATGC   TGACACCATC   AATCACCCAG   CCCAGCTGTC      978

CAAGACCTCG   CTGGCCCCCA   TCATTGTTTA   CATCAAGATC   ACCTCTCCCA   AGGTACTTCA     1038

AAGGCTCATC   AAGTCCCGAG   GAAAGTCTCA   GTCCAAACAC   CTCAATGTCC   AAATAGCGGC     1098

CTCGGAAAAG   CTGGCACAGT   GCCCCCCTGA   AATGTTTGAC   ATCATCCTGG   ATGAGAACCA     1158

ATTGGAGGAT   GCCTGCGAGC   ATCTGGCGGA   GTACTTGGAA   GCCTATTGGA   AGGCCACACA     1218

CCCGCCCAGC   AGCACGCCAC   CCAATCCGCT   GCTGAACCGC   ACCATGGCTA   CCGCAGCCCT     1278

GGCTGCCAGC   CCTGCCCCTG   TCTCCAACCT   CCAGGTACAG   GTGCTCACCT   CGCTCAGGAG     1338

AAACCTCGGC   TTCTGGGGCG   GGCTGGAGTC   CTCACAGCGG   GGCAGTGTGG   TGCCCCAGGA     1398

GCAGGAACAT   GCCATGTAGT   GGGCGCCCTG   CCCGTCTTCC   CTCCTGCTCT   GGGGTCGGAA     1458

CTGGAGTGCA   GGGAACATGG   AGGAGGAAGG   GAAGAGCTTT   ATTTGTAAA   AAAATAAGAT      1518

GAGCGGCA                                                                        1526
```

( 2 ) INFORMATION FOR SEQ ID NO:31:

( i ) SEQUENCE CHARACTERISTICS:
        ( A ) LENGTH: 1393 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..660
        ( D ) OTHER INFORMATION: /standard_name= "Beta1-5"

( x i ) SEQUENCE DESCRIPTION: SEQ ID NO:31:

```
ATG  GTC  CAG  AAG  ACC  AGC  ATG  TCC  CGG  GGC  CCT  TAC  CCA  CCC  TCC  CAG       48
Met  Val  Gln  Lys  Thr  Ser  Met  Ser  Arg  Gly  Pro  Tyr  Pro  Pro  Ser  Gln
 1              5                        10                       15

GAG  ATC  CCC  ATG  GAG  GTC  TTC  GAC  CCC  AGC  CCG  CAG  GGC  AAA  TAC  AGC       96
Glu  Ile  Pro  Met  Glu  Val  Phe  Asp  Pro  Ser  Pro  Gln  Gly  Lys  Tyr  Ser
                 20                       25                       30

AAG  AGG  AAA  GGG  CGA  TTC  AAA  CGG  TCA  GAT  GGG  AGC  ACG  TCC  TCG  GAT      144
Lys  Arg  Lys  Gly  Arg  Phe  Lys  Arg  Ser  Asp  Gly  Ser  Thr  Ser  Ser  Asp
         35                       40                       45

ACC  ACA  TCC  AAC  AGC  TTT  GTC  CGC  CAG  GGC  TCA  GCG  GAG  TCC  TAC  ACC      192
Thr  Thr  Ser  Asn  Ser  Phe  Val  Arg  Gln  Gly  Ser  Ala  Glu  Ser  Tyr  Thr
     50                       55                       60

AGC  CGT  CCA  TCA  GAC  TCT  GAT  GTA  TCT  CTG  GAG  GAG  GAC  CGG  GAA  GCC      240
Ser  Arg  Pro  Ser  Asp  Ser  Asp  Val  Ser  Leu  Glu  Glu  Asp  Arg  Glu  Ala
 65                       70                       75                       80

TTA  AGG  AAG  GAA  GCA  GAG  CGC  CAG  GCA  TTA  GCG  CAG  CTC  GAG  AAG  GCC      288
Leu  Arg  Lys  Glu  Ala  Glu  Arg  Gln  Ala  Leu  Ala  Gln  Leu  Glu  Lys  Ala
                 85                       90                       95

AAG  ACC  AAG  CCA  GTG  GCA  TTT  GCT  GTG  CGG  ACA  AAT  GTT  GGC  TAC  AAT      336
Lys  Thr  Lys  Pro  Val  Ala  Phe  Ala  Val  Arg  Thr  Asn  Val  Gly  Tyr  Asn
                100                      105                      110

CCG  TCT  CCA  GGG  GAT  GAG  GTG  CCT  GTG  CAG  GGA  GTG  GCC  ATC  ACC  TTC      384
Pro  Ser  Pro  Gly  Asp  Glu  Val  Pro  Val  Gln  Gly  Val  Ala  Ile  Thr  Phe
         115                      120                      125

GAG  CCC  AAA  GAC  TTC  CTG  CAC  ATC  AAG  GAG  AAA  TAC  AAT  AAT  GAC  TGG      432
Glu  Pro  Lys  Asp  Phe  Leu  His  Ile  Lys  Glu  Lys  Tyr  Asn  Asn  Asp  Trp
     130                      135                      140

TGG  ATC  GGG  CGG  CTG  GTG  AAG  GAG  GGC  TGT  GAG  GTT  GGC  TTC  ATT  CCC      480
Trp  Ile  Gly  Arg  Leu  Val  Lys  Glu  Gly  Cys  Glu  Val  Gly  Phe  Ile  Pro
145                      150                      155                      160
```

```
AGC  CCC  GTC  AAA  CTG  GAC  AGC  CTT  CGC  CTG  CTG  CAG  GAA  CAG  AAG  CTG        528
Ser  Pro  Val  Lys  Leu  Asp  Ser  Leu  Arg  Leu  Leu  Gln  Glu  Gln  Lys  Leu
               165                      170                      175

CGC  CAG  AAC  CGC  CTC  GGC  TCC  AGC  AAA  TCA  GGC  GAT  AAC  TCC  AGT  TCC        576
Arg  Gln  Asn  Arg  Leu  Gly  Ser  Ser  Lys  Ser  Gly  Asp  Asn  Ser  Ser  Ser
               180                      185                      190

AGT  CTG  GGA  GAT  GTG  GTG  ACT  GGC  ACC  CGC  CGC  CCC  ACA  CCC  CCT  GCC        624
Ser  Leu  Gly  Asp  Val  Val  Thr  Gly  Thr  Arg  Arg  Pro  Thr  Pro  Pro  Ala
               195                      200                      205

AGT  GGT  TAC  AGA  CAT  GAT  GCA  GAA  AGC  TTT  ATT  TGACTTCTTG  AAGCATCGGT         677
Ser  Gly  Tyr  Arg  His  Asp  Ala  Glu  Ser  Phe  Ile
               210                      215                 220

TTGATGGCAG  GATCTCCATC  ACTCGTGTGA  CGGCAGATAT  TTCCCTGGCT  AAGCGCTCAG                737

TTCTCAACAA  CCCCAGCAAA  CACATCATCA  TTGAGCGCTC  AACACACGC   TCCAGCCTGG                797

CTGAGGTGCA  GAGTGAAATC  GAGCGAATCT  TCGAGCTGGC  CCGGACCCTT  CAGTTGGTCG                857

CTCTGGATGC  TGACACCATC  AATCACCCAG  CCCAGCTGTC  CAAGACCTCG  CTGGCCCCCA                917

TCATTGTTTA  CATCAAGATC  ACCTCTCCCA  AGGTACTTCA  AAGGCTCATC  AAGTCCCGAG                977

GAAAGTCTCA  GTCCAAACAC  CTCAATGTCC  AAATAGCGGC  CTCGGAAAAG  CTGGCACAGT              1 0 3 7

GCCCCCCTGA  AATGTTTGAC  ATCATCCTGG  ATGAGAACCA  ATTGGAGGAT  GCCTGCGAGC              1 0 9 7

ATCTGGCGGA  GTACTTGGAA  GCCTATTGGA  AGGCCACACA  CCCGCCCAGC  AGCACGCCAC              1 1 5 7

CCAATCCGCT  GCTGAACCGC  ACCATGGCTA  CCGCAGCCCT  GGCTGCCAGC  CCTGCCCCTG              1 2 1 7

TCTCCAACCT  CCAGGTACAG  GTGCTCACCT  CGCTCAGGAG  AAACCTCGGC  TTCTGGGGCG              1 2 7 7

GGCTGGAGTC  CTCACAGCGG  GGCAGTGTGG  TGCCCCAGGA  GCAGGAACAT  GCCATGTAGT              1 3 3 7

GGGCGCCCTG  CCCGTCTTCC  CTCCTGCTCT  GGGGTCGGAA  CTGGAGTGCA  GGGAAC                  1 3 9 3
```

( 2 ) INFORMATION FOR SEQ ID NO:32:

( i ) SEQUENCE CHARACTERISTICS:
        ( A ) LENGTH: 478 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:32:

```
Met  Val  Gln  Lys  Thr  Ser  Met  Ser  Arg  Gly  Pro  Tyr  Pro  Pro  Ser  Gln
 1                  5                      10                      15

Glu  Ile  Pro  Met  Glu  Val  Phe  Asp  Pro  Ser  Pro  Gln  Gly  Lys  Tyr  Ser
               20                      25                      30

Lys  Arg  Lys  Gly  Arg  Phe  Lys  Arg  Ser  Asp  Gly  Ser  Thr  Ser  Ser  Asp
               35                      40                      45

Thr  Thr  Ser  Asn  Ser  Phe  Val  Arg  Gln  Gly  Ser  Ala  Glu  Ser  Tyr  Thr
     50                      55                      60

Ser  Arg  Pro  Ser  Asp  Ser  Asp  Val  Ser  Leu  Glu  Glu  Asp  Arg  Glu  Ala
65                       70                      75                      80

Leu  Arg  Lys  Glu  Ala  Glu  Arg  Gln  Ala  Leu  Ala  Gln  Leu  Glu  Lys  Ala
                    85                      90                      95
```

| | | | | | | | | | | | | | | |
|---|---|---|---|---|---|---|---|---|---|---|---|---|---|---|
|Lys|Thr|Lys|Pro 100|Val|Ala|Phe|Ala|Val|Arg 105|Thr|Asn|Val|Gly 110|Tyr|Asn|
|Pro|Ser|Pro 115|Gly|Asp|Glu|Val|Pro 120|Val|Gln|Gly|Val|Ala 125|Ile|Thr|Phe|
|Glu|Pro 130|Lys|Asp|Phe|Leu|His 135|Ile|Lys|Glu|Lys|Tyr 140|Asn|Asn|Asp|Trp|
|Trp 145|Ile|Gly|Arg|Leu|Val 150|Lys|Glu|Gly|Cys|Glu 155|Val|Gly|Phe|Ile|Pro 160|
|Ser|Pro|Val|Lys|Leu 165|Asp|Ser|Leu|Arg|Leu 170|Leu|Gln|Glu|Gln|Lys 175|Leu|
|Arg|Gln|Asn|Arg 180|Leu|Gly|Ser|Ser|Lys 185|Ser|Gly|Asp|Asn|Ser 190|Ser|Ser|
|Ser|Leu|Gly 195|Asp|Val|Val|Thr|Gly 200|Thr|Arg|Arg|Pro|Thr 205|Pro|Pro|Ala|
|Ser|Ala 210|Lys|Gln|Lys|Gln|Lys 215|Ser|Thr|Glu|His|Val 220|Pro|Pro|Tyr|Asp|
|Val 225|Val|Pro|Ser|Met|Arg 230|Pro|Ile|Ile|Leu|Val 235|Gly|Pro|Ser|Leu|Lys 240|
|Gly|Tyr|Glu|Val|Thr 245|Asp|Met|Met|Gln|Lys 250|Ala|Leu|Phe|Asp|Phe 255|Leu|
|Lys|His|Arg|Phe 260|Asp|Gly|Arg|Ile|Ser 265|Ile|Thr|Arg|Val|Thr 270|Ala|Asp|
|Ile|Ser|Leu 275|Ala|Lys|Arg|Ser|Val 280|Leu|Asn|Asn|Pro|Ser 285|Lys|His|Ile|
|Ile|Ile 290|Glu|Arg|Ser|Asn|Thr 295|Arg|Ser|Ser|Leu|Ala 300|Glu|Val|Gln|Ser|
|Glu 305|Ile|Glu|Arg|Ile|Phe 310|Glu|Leu|Ala|Arg|Thr 315|Leu|Gln|Leu|Val|Ala 320|
|Leu|Asp|Ala|Asp|Thr 325|Ile|Asn|His|Pro|Ala 330|Gln|Leu|Ser|Lys|Thr 335|Ser|
|Leu|Ala|Pro|Ile 340|Ile|Val|Tyr|Ile|Lys 345|Ile|Thr|Ser|Pro|Lys 350|Val|Leu|
|Gln|Arg|Leu 355|Ile|Lys|Ser|Arg|Gly 360|Lys|Ser|Gln|Ser|Lys 365|His|Leu|Asn|
|Val|Gln 370|Ile|Ala|Ala|Ser|Glu 375|Lys|Leu|Ala|Gln|Cys 380|Pro|Pro|Glu|Met|
|Phe 385|Asp|Ile|Ile|Leu|Asp 390|Glu|Asn|Gln|Leu|Glu 395|Asp|Ala|Cys|Glu|His 400|
|Leu|Ala|Glu|Tyr|Leu 405|Glu|Ala|Tyr|Trp|Lys 410|Ala|Thr|His|Pro|Pro 415|Ser|
|Ser|Thr|Pro|Pro 420|Asn|Pro|Leu|Leu|Asn 425|Arg|Thr|Met|Ala|Thr 430|Ala|Ala|
|Leu|Ala|Ala 435|Ser|Pro|Ala|Pro|Val 440|Ser|Asn|Leu|Gln|Val 445|Gln|Val|Leu|
|Thr|Ser 450|Leu|Arg|Arg|Asn|Leu 455|Gly|Phe|Trp|Gly|Gly 460|Leu|Glu|Ser|Ser|
|Gln|Arg 465|Gly|Ser|Val|Val 470|Pro|Gln|Glu|Gln|Glu 475|His|Ala|Met| | |

(2) INFORMATION FOR SEQ ID NO:33:

(i) SEQUENCE CHARACTERISTICS:
        (A) LENGTH: 598 amino acids
        (B) TYPE: amino acid
        (C) STRANDEDNESS: single
        (D) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( i x ) FEATURE:
( D ) OTHER INFORMATION: /standard_name= "Beta1-3"

( x i ) SEQUENCE DESCRIPTION: SEQ ID NO:33:

| Met | Val | Gln | Lys | Thr | Ser | Met | Ser | Arg | Gly | Pro | Tyr | Pro | Pro | Ser | Gln |
|---|---|---|---|---|---|---|---|---|---|---|---|---|---|---|---|
| 1 | | | | 5 | | | | | 10 | | | | | 15 | |

| Glu | Ile | Pro | Met | Gly | Val | Phe | Asp | Pro | Ser | Pro | Gln | Gly | Lys | Tyr | Ser |
|---|---|---|---|---|---|---|---|---|---|---|---|---|---|---|---|
| | | | 20 | | | | 25 | | | | | 30 | | | |

| Lys | Arg | Lys | Gly | Arg | Phe | Lys | Arg | Ser | Asp | Gly | Ser | Thr | Ser | Ser | Asp |
|---|---|---|---|---|---|---|---|---|---|---|---|---|---|---|---|
| | | 35 | | | | | 40 | | | | | 45 | | | |

| Thr | Thr | Ser | Asn | Ser | Phe | Val | Arg | Gln | Gly | Ser | Ala | Glu | Ser | Tyr | Thr |
|---|---|---|---|---|---|---|---|---|---|---|---|---|---|---|---|
| | 50 | | | | 55 | | | | | 60 | | | | | |

| Ser | Arg | Pro | Ser | Asp | Ser | Asp | Val | Ser | Leu | Glu | Glu | Asp | Arg | Glu | Ala |
|---|---|---|---|---|---|---|---|---|---|---|---|---|---|---|---|
| 65 | | | | | 70 | | | | | 75 | | | | | 80 |

| Leu | Arg | Lys | Glu | Ala | Glu | Arg | Gln | Ala | Leu | Ala | Gln | Leu | Glu | Lys | Ala |
|---|---|---|---|---|---|---|---|---|---|---|---|---|---|---|---|
| | | | | 85 | | | | | 90 | | | | | 95 | |

| Lys | Thr | Lys | Pro | Val | Ala | Phe | Ala | Val | Arg | Thr | Asn | Val | Gly | Tyr | Asn |
|---|---|---|---|---|---|---|---|---|---|---|---|---|---|---|---|
| | | | 100 | | | | 105 | | | | | 110 | | | |

| Pro | Ser | Pro | Gly | Asp | Glu | Val | Pro | Val | Gln | Gly | Val | Ala | Ile | Thr | Phe |
|---|---|---|---|---|---|---|---|---|---|---|---|---|---|---|---|
| | | 115 | | | | | 120 | | | | | 125 | | | |

| Glu | Pro | Lys | Asp | Phe | Leu | His | Ile | Lys | Glu | Lys | Tyr | Asn | Asn | Asp | Trp |
|---|---|---|---|---|---|---|---|---|---|---|---|---|---|---|---|
| | 130 | | | | | 135 | | | | | 140 | | | | |

| Trp | Ile | Gly | Arg | Leu | Val | Lys | Glu | Gly | Cys | Glu | Val | Gly | Phe | Ile | Pro |
|---|---|---|---|---|---|---|---|---|---|---|---|---|---|---|---|
| 145 | | | | | 150 | | | | | 155 | | | | | 160 |

| Ser | Pro | Val | Lys | Leu | Asp | Ser | Leu | Arg | Leu | Leu | Gln | Glu | Gln | Lys | Leu |
|---|---|---|---|---|---|---|---|---|---|---|---|---|---|---|---|
| | | | | 165 | | | | | 170 | | | | | 175 | |

| Arg | Gln | Asn | Arg | Leu | Gly | Ser | Ser | Lys | Ser | Gly | Asp | Asn | Ser | Ser | Ser |
|---|---|---|---|---|---|---|---|---|---|---|---|---|---|---|---|
| | | | 180 | | | | | 185 | | | | | 190 | | |

| Ser | Leu | Gly | Asp | Val | Val | Thr | Gly | Thr | Arg | Arg | Pro | Thr | Pro | Pro | Ala |
|---|---|---|---|---|---|---|---|---|---|---|---|---|---|---|---|
| | | 195 | | | | | 200 | | | | | 205 | | | |

| Ser | Ala | Lys | Gln | Lys | Gln | Lys | Ser | Thr | Glu | His | Val | Pro | Pro | Tyr | Asp |
|---|---|---|---|---|---|---|---|---|---|---|---|---|---|---|---|
| | 210 | | | | | 215 | | | | | 220 | | | | |

| Val | Val | Pro | Ser | Met | Arg | Pro | Ile | Ile | Leu | Val | Gly | Pro | Ser | Leu | Lys |
|---|---|---|---|---|---|---|---|---|---|---|---|---|---|---|---|
| 225 | | | | | 230 | | | | | 235 | | | | | 240 |

| Gly | Tyr | Glu | Val | Thr | Asp | Met | Met | Gln | Lys | Ala | Leu | Phe | Asp | Phe | Leu |
|---|---|---|---|---|---|---|---|---|---|---|---|---|---|---|---|
| | | | | 245 | | | | | 250 | | | | | 255 | |

| Lys | His | Arg | Phe | Asp | Gly | Arg | Ile | Ser | Ile | Thr | Arg | Val | Thr | Ala | Asp |
|---|---|---|---|---|---|---|---|---|---|---|---|---|---|---|---|
| | | | 260 | | | | | 265 | | | | | 270 | | |

| Ile | Ser | Leu | Ala | Lys | Arg | Ser | Val | Leu | Asn | Asn | Pro | Ser | Lys | His | Ile |
|---|---|---|---|---|---|---|---|---|---|---|---|---|---|---|---|
| | | 275 | | | | | 280 | | | | | 285 | | | |

| Ile | Ile | Glu | Arg | Ser | Asn | Thr | Arg | Ser | Ser | Leu | Ala | Glu | Val | Gln | Ser |
|---|---|---|---|---|---|---|---|---|---|---|---|---|---|---|---|
| | 290 | | | | | 295 | | | | | 300 | | | | |

| Glu | Ile | Glu | Arg | Ile | Phe | Glu | Leu | Ala | Arg | Thr | Leu | Gln | Leu | Val | Ala |
|---|---|---|---|---|---|---|---|---|---|---|---|---|---|---|---|
| 305 | | | | | 310 | | | | | 315 | | | | | 320 |

| Leu | Asp | Ala | Asp | Thr | Ile | Asn | His | Pro | Ala | Gln | Leu | Ser | Lys | Thr | Ser |
|---|---|---|---|---|---|---|---|---|---|---|---|---|---|---|---|
| | | | | 325 | | | | | 330 | | | | | 335 | |

| Leu | Ala | Pro | Ile | Ile | Val | Tyr | Ile | Lys | Ile | Thr | Ser | Pro | Lys | Val | Leu |
|---|---|---|---|---|---|---|---|---|---|---|---|---|---|---|---|

|  |  |  |  |  | 340 |  |  | 345 |  |  |  | 350 |  |  |
|---|---|---|---|---|---|---|---|---|---|---|---|---|---|---|
| Gln | Arg | Leu<br>355 | Ile | Lys | Ser | Arg | Gly<br>360 | Lys | Ser | Gln | Ser | Lys<br>365 | His | Leu | Asn |
| Val | Gln<br>370 | Ile | Ala | Ala | Ser | Glu<br>375 | Lys | Leu | Ala | Gln | Cys<br>380 | Pro | Pro | Glu | Met |
| Phe<br>385 | Asp | Ile | Ile | Leu | Asp<br>390 | Glu | Asn | Gln | Leu | Glu<br>395 | Asp | Ala | Cys | Glu | His<br>400 |
| Leu | Ala | Glu | Tyr | Leu<br>405 | Glu | Ala | Tyr | Trp | Lys<br>410 | Ala | Thr | His | Pro | Pro<br>415 | Ser |
| Ser | Thr | Pro | Pro<br>420 | Asn | Pro | Leu | Leu | Asn<br>425 | Arg | Thr | Met | Ala | Thr<br>430 | Ala | Ala |
| Leu | Ala | Ala<br>435 | Ser | Pro | Ala | Pro | Val<br>440 | Ser | Asn | Leu | Gln | Gly<br>445 | Pro | Tyr | Leu |
| Ala | Ser<br>450 | Gly | Asp | Gln | Pro | Leu<br>455 | Glu | Arg | Ala | Thr | Gly<br>460 | Glu | His | Ala | Ser |
| Met<br>465 | His | Glu | Tyr | Pro | Gly<br>470 | Glu | Leu | Gly | Gln | Pro<br>475 | Pro | Gly | Leu | Tyr | Pro<br>480 |
| Ser | Ser | His | Pro | Pro<br>485 | Gly | Arg | Ala | Gly | Thr<br>490 | Leu | Arg | Ala | Leu | Ser<br>495 | Arg |
| Gln | Asp | Thr | Phe<br>500 | Asp | Ala | Asp | Thr | Pro<br>505 | Gly | Ser | Arg | Asn | Ser<br>510 | Ala | Tyr |
| Thr | Glu | Leu<br>515 | Gly | Asp | Ser | Cys | Val<br>520 | Asp | Met | Glu | Thr | Asp<br>525 | Pro | Ser | Glu |
| Gly | Pro<br>530 | Gly | Leu | Gly | Asp | Pro<br>535 | Ala | Gly | Gly | Thr<br>540 | Pro | Pro | Ala | Arg |
| Gln<br>545 | Gly | Ser | Trp | Glu | Asp<br>550 | Glu | Glu | Glu | Asp<br>555 | Tyr | Glu | Glu | Glu | Leu | Thr<br>560 |
| Asp | Asn | Arg | Asn | Arg<br>565 | Gly | Arg | Asn | Lys | Ala<br>570 | Arg | Tyr | Cys | Ala | Glu<br>575 | Gly |
| Gly | Gly | Pro | Val<br>580 | Leu | Gly | Arg | Asn | Lys<br>585 | Asn | Glu | Leu | Glu | Gly<br>590 | Trp | Gly |
| Arg | Gly | Val<br>595 | Tyr | Ile | Arg |  |  |  |  |  |  |  |  |  |  |

(2) INFORMATION FOR SEQ ID NO:34:

(i) SEQUENCE CHARACTERISTICS:
        (A) LENGTH: 483 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(ix) FEATURE:
        (D) OTHER INFORMATION: /product="A Beta3 subunit of human calcium channel"

(xi) SEQUENCE DESCRIPTION: SEQ ID NO:34:

| Met<br>1 | Ser | Phe | Ser | Asp<br>5 | Ser | Ser | Ala | Thr | Phe<br>10 | Leu | Leu | Asn | Glu | Gly<br>15 | Ser |
|---|---|---|---|---|---|---|---|---|---|---|---|---|---|---|---|
| Ala | Asp | Ser | Tyr<br>20 | Thr | Ser | Arg | Pro | Ser<br>25 | Leu | Asp | Ser | Asp | Val<br>30 | Ser | Leu |

-continued

```
Glu  Glu  Asp  Arg  Glu  Ser  Ala  Arg  Arg  Glu  Val  Glu  Ser  Gln  Ala  Gln
          35                       40                       45

Gln  Gln  Leu  Glu  Arg  Ala  Lys  His  Lys  Pro  Val  Ala  Phe  Ala  Val  Arg
     50                       55                       60

Thr  Asn  Val  Ser  Tyr  Cys  Gly  Val  Leu  Asp  Glu  Glu  Cys  Pro  Val  Gln
65                       70                       75                       80

Gly  Ser  Gly  Val  Asn  Phe  Glu  Ala  Lys  Asp  Phe  Leu  His  Ile  Lys  Glu
                    85                       90                       95

Lys  Tyr  Ser  Asn  Asp  Trp  Trp  Ile  Gly  Arg  Leu  Val  Lys  Glu  Gly  Gly
               100                      105                      110

Asp  Ile  Ala  Phe  Ile  Pro  Ser  Pro  Gln  Arg  Leu  Glu  Ser  Ile  Arg  Leu
          115                      120                      125

Lys  Gln  Glu  Gln  Lys  Ala  Arg  Arg  Ser  Gly  Asn  Pro  Ser  Ser  Leu  Ser
     130                      135                      140

Asp  Ile  Gly  Asn  Arg  Arg  Ser  Pro  Pro  Pro  Ser  Leu  Ala  Lys  Gln  Lys
145                      150                      155                      160

Gln  Lys  Gln  Ala  Glu  His  Val  Pro  Pro  Tyr  Asp  Val  Val  Pro  Ser  Met
                    165                      170                      175

Arg  Pro  Val  Val  Leu  Val  Gly  Pro  Ser  Leu  Lys  Gly  Tyr  Glu  Val  Thr
               180                      185                      190

Asp  Met  Met  Gln  Lys  Ala  Leu  Phe  Asp  Phe  Leu  Lys  His  Arg  Phe  Asp
          195                      200                      205

Gly  Arg  Ile  Ser  Ile  Thr  Arg  Val  Thr  Ala  Asp  Leu  Ser  Leu  Ala  Lys
     210                      215                      220

Arg  Ser  Val  Leu  Asn  Asn  Pro  Gly  Lys  Arg  Thr  Ile  Ile  Glu  Arg  Ser
225                      230                      235                      240

Ser  Ala  Arg  Ser  Ser  Ile  Ala  Glu  Val  Gln  Ser  Glu  Ile  Glu  Arg  Ile
                    245                      250                      255

Phe  Glu  Leu  Ala  Lys  Ser  Leu  Gln  Leu  Val  Val  Leu  Asp  Ala  Asp  Thr
               260                      265                      270

Ile  Asn  His  Pro  Ala  Gln  Leu  Ala  Lys  Thr  Ser  Leu  Ala  Pro  Ile  Ile
          275                      280                      285

Val  Phe  Val  Lys  Val  Ser  Ser  Pro  Lys  Val  Leu  Gln  Arg  Leu  Ile  Arg
     290                      295                      300

Ser  Arg  Gly  Lys  Ser  Gln  Met  Lys  His  Leu  Thr  Val  Gln  Met  Met  Ala
305                      310                      315                      320

Tyr  Asp  Lys  Leu  Val  Gln  Cys  Pro  Pro  Glu  Ser  Phe  Asp  Val  Ile  Leu
                    325                      330                      335

Asp  Glu  Asn  Gln  Leu  Glu  Asp  Ala  Cys  Glu  His  Leu  Ala  Glu  Tyr  Leu
               340                      345                      350

Glu  Val  Tyr  Trp  Arg  Ala  Thr  His  His  Pro  Ala  Pro  Gly  Pro  Gly  Leu
          355                      360                      365

Leu  Gly  Pro  Pro  Ser  Ala  Ile  Pro  Gly  Leu  Gln  Asn  Gln  Gln  Leu  Leu
     370                      375                      380

Gly  Glu  Arg  Gly  Glu  Glu  His  Ser  Pro  Leu  Glu  Arg  Asp  Ser  Leu  Met
385                      390                      395                      400

Pro  Ser  Asp  Glu  Ala  Ser  Glu  Ser  Ser  Arg  Gln  Ala  Trp  Thr  Gly  Ser
                    405                      410                      415

Ser  Gln  Arg  Ser  Ser  Arg  His  Leu  Glu  Glu  Asp  Tyr  Ala  Asp  Ala  Tyr
               420                      425                      430

Gln  Asp  Leu  Tyr  Gln  Pro  His  Arg  Gln  His  Thr  Ser  Gly  Leu  Pro  Ser
          435                      440                      445

Ala  Asn  Gly  His  Asp  Pro  Gln  Asp  Arg  Leu  Leu  Ala  Gln  Asp  Ser  Glu
```

|  | 450 |  |  |  | 455 |  |  |  | 460 |  |  |  |
|---|---|---|---|---|---|---|---|---|---|---|---|---|
| His | Asn | His | Ser | Asp | Arg | Asn | Trp | Gln | Arg | Arg | Pro | Trp | Pro | Lys |
| 465 |  |  |  | 470 |  |  |  |  | 475 |  |  |  | 480 |

Asp Ser Tyr (2) INFORMATION FOR SEQ ID NO:35:

(i) SEQUENCE CHARACTERISTICS:
        (A) LENGTH: 2509 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(ix) FEATURE:
        (D) OTHER INFORMATION: /product="Alpha1A-1 subunit of
        human calcium channel"

(xi) SEQUENCE DESCRIPTION: SEQ ID NO:35:

| Ala | Arg | Phe | Gly | Asp | Glu | Met | Pro | Ala | Arg | Tyr | Gly | Gly | Gly | Gly | Ser |
|---|---|---|---|---|---|---|---|---|---|---|---|---|---|---|---|
| 1 |  |  |  | 5 |  |  |  |  | 10 |  |  |  |  | 15 |  |
| Gly | Ala | Ala | Ala | Gly | Val | Val | Val | Gly | Ser | Gly | Gly | Gly | Arg | Gly | Ala |
|  |  |  | 20 |  |  |  |  | 25 |  |  |  |  | 30 |  |  |
| Gly | Gly | Ser | Arg | Gln | Gly | Gly | Gln | Pro | Gly | Ala | Gln | Arg | Met | Tyr | Lys |
|  |  | 35 |  |  |  |  | 40 |  |  |  |  | 45 |  |  |  |
| Gln | Ser | Met | Ala | Gln | Arg | Ala | Arg | Thr | Met | Ala | Leu | Tyr | Asn | Pro | Ile |
|  | 50 |  |  |  |  | 55 |  |  |  |  | 60 |  |  |  |  |
| Pro | Val | Arg | Gln | Asn | Cys | Leu | Thr | Val | Asn | Arg | Ser | Leu | Phe | Leu | Phe |
| 65 |  |  |  |  | 70 |  |  |  |  | 75 |  |  |  |  | 80 |
| Ser | Glu | Asp | Asn | Val | Val | Arg | Lys | Tyr | Ala | Lys | Lys | Ile | Thr | Glu | Trp |
|  |  |  |  | 85 |  |  |  |  | 90 |  |  |  |  | 95 |  |
| Pro | Pro | Phe | Glu | Tyr | Met | Ile | Leu | Ala | Thr | Ile | Ile | Ala | Asn | Cys | Ile |
|  |  |  | 100 |  |  |  |  | 105 |  |  |  |  | 110 |  |  |
| Val | Leu | Ala | Leu | Glu | Gln | His | Leu | Pro | Asp | Asp | Asp | Lys | Thr | Pro | Met |
|  |  | 115 |  |  |  |  | 120 |  |  |  |  | 125 |  |  |  |
| Ser | Glu | Arg | Leu | Asp | Asp | Thr | Glu | Pro | Tyr | Phe | Ile | Gly | Ile | Phe | Cys |
|  | 130 |  |  |  |  | 135 |  |  |  |  | 140 |  |  |  |  |
| Phe | Glu | Ala | Gly | Ile | Lys | Ile | Ile | Ala | Leu | Gly | Phe | Ala | Phe | His | Lys |
| 145 |  |  |  |  | 150 |  |  |  |  | 155 |  |  |  |  | 160 |
| Gly | Ser | Tyr | Leu | Arg | Asn | Gly | Trp | Asn | Val | Met | Asp | Phe | Val | Val | Val |
|  |  |  |  | 165 |  |  |  |  | 170 |  |  |  |  | 175 |  |
| Leu | Thr | Gly | Ile | Leu | Ala | Thr | Val | Gly | Thr | Glu | Phe | Asp | Leu | Arg | Thr |
|  |  |  | 180 |  |  |  |  | 185 |  |  |  |  | 190 |  |  |
| Leu | Arg | Ala | Val | Arg | Val | Leu | Arg | Pro | Leu | Lys | Leu | Val | Ser | Gly | Ile |
|  |  | 195 |  |  |  |  | 200 |  |  |  |  | 205 |  |  |  |
| Pro | Ser | Leu | Gln | Val | Val | Leu | Lys | Ser | Ile | Met | Lys | Ala | Met | Ile | Pro |
|  | 210 |  |  |  |  | 215 |  |  |  |  | 220 |  |  |  |  |
| Leu | Leu | Gln | Ile | Gly | Leu | Leu | Leu | Phe | Phe | Ala | Ile | Leu | Ile | Phe | Ala |
| 225 |  |  |  |  | 230 |  |  |  |  | 235 |  |  |  |  | 240 |
| Ile | Ile | Gly | Leu | Glu | Phe | Tyr | Met | Gly | Lys | Phe | His | Thr | Thr | Cys | Phe |
|  |  |  |  | 245 |  |  |  |  | 250 |  |  |  |  | 255 |  |

```
Glu Glu Gly Thr Asp Asp Ile Gln Gly Glu Ser Pro Ala Pro Cys Gly
            260             265             270
Thr Glu Glu Pro Ala Arg Thr Cys Pro Asn Gly Thr Lys Cys Gln Pro
        275             280             285
Tyr Trp Glu Gly Pro Asn Asn Gly Ile Thr Gln Phe Asp Asn Ile Leu
    290             295             300
Phe Ala Val Leu Thr Val Phe Gln Cys Ile Thr Met Glu Gly Trp Thr
305             310             315             320
Asp Leu Leu Tyr Asn Ser Asn Asp Ala Ser Gly Asn Thr Trp Asn Trp
            325             330             335
Leu Tyr Phe Ile Pro Leu Ile Ile Ile Gly Ser Phe Phe Met Leu Asn
            340             345             350
Leu Val Leu Gly Val Leu Ser Gly Glu Phe Ala Lys Glu Arg Glu Arg
        355             360             365
Val Glu Asn Arg Arg Ala Phe Leu Lys Leu Arg Arg Gln Gln Gln Ile
    370             375             380
Glu Arg Glu Leu Asn Gly Tyr Met Glu Trp Ile Ser Lys Ala Glu Glu
385             390             395             400
Val Ile Leu Ala Glu Asp Glu Thr Asp Gly Glu Gln Arg His Pro Phe
            405             410             415
Asp Gly Ala Leu Arg Arg Thr Thr Ile Lys Lys Ser Lys Thr Asp Leu
            420             425             430
Leu Asn Pro Glu Glu Ala Glu Asp Gln Leu Ala Asp Ile Ala Ser Val
        435             440             445
Gly Ser Pro Phe Ala Arg Ala Ser Ile Lys Ser Ala Lys Leu Glu Asn
    450             455             460
Ser Thr Phe Phe His Lys Lys Glu Arg Arg Met Arg Phe Tyr Ile Arg
465             470             475             480
Arg Met Val Lys Thr Gln Ala Phe Tyr Trp Thr Val Leu Ser Leu Val
            485             490             495
Ala Leu Asn Thr Leu Cys Val Ala Ile Val His Tyr Asn Gln Pro Glu
            500             505             510
Trp Leu Ser Asp Phe Leu Tyr Tyr Ala Glu Phe Ile Phe Leu Gly Leu
        515             520             525
Phe Met Ser Glu Met Phe Ile Lys Met Tyr Gly Leu Gly Thr Arg Pro
    530             535             540
Tyr Phe His Ser Ser Phe Asn Cys Phe Asp Cys Gly Val Ile Ile Gly
545             550             555             560
Ser Ile Phe Glu Val Ile Trp Ala Val Ile Lys Pro Gly Thr Ser Phe
            565             570             575
Gly Ile Ser Val Leu Arg Ala Leu Arg Leu Leu Arg Ile Phe Lys Val
            580             585             590
Thr Lys Tyr Trp Ala Ser Leu Arg Asn Leu Val Val Ser Leu Leu Asn
        595             600             605
Ser Met Lys Ser Ile Ile Ser Leu Leu Phe Leu Leu Phe Leu Phe Ile
    610             615             620
Val Val Phe Ala Leu Leu Gly Met Gln Leu Phe Gly Gly Gln Phe Asn
625             630             635             640
Phe Asp Glu Gly Thr Pro Pro Thr Asn Phe Asp Thr Phe Pro Ala Ala
            645             650             655
Ile Met Thr Val Phe Gln Ile Leu Thr Gly Glu Asp Trp Asn Glu Val
            660             665             670
Met Tyr Asp Gly Ile Lys Ser Gln Gly Gly Val Gln Gly Gly Met Val
        675             680             685
```

-continued

```
Phe Ser Ile Tyr Phe Ile Val Leu Thr Leu Phe Gly Asn Tyr Thr Leu
        690                 695                 700
Leu Asn Val Phe Leu Ala Ile Ala Val Asp Asn Leu Ala Asn Ala Gln
705                 710                 715                 720
Glu Leu Thr Lys Val Glu Ala Asp Glu Gln Glu Glu Glu Glu Ala Ala
                725                 730                 735
Asn Gln Lys Leu Ala Leu Gln Lys Lys Glu Val Ala Glu Val Ser
            740                 745                 750
Pro Leu Ser Ala Ala Asn Met Ser Ile Ala Val Lys Glu Gln Gln Lys
            755                 760                 765
Asn Gln Lys Pro Ala Lys Ser Val Trp Glu Gln Arg Thr Ser Glu Met
            770                 775                 780
Arg Lys Gln Asn Leu Leu Ala Ser Arg Glu Ala Leu Tyr Asn Glu Met
785                 790                 795                 800
Asp Pro Asp Glu Arg Trp Lys Ala Ala Tyr Thr Arg His Leu Arg Pro
                805                 810                 815
Asp Met Lys Thr His Leu Asp Arg Pro Leu Val Val Asp Pro Gln Glu
            820                 825                 830
Asn Arg Asn Asn Thr Asn Lys Ser Arg Ala Ala Glu Pro Thr Val
            835                 840                 845
Asp Gln Ser Leu Gly Gln Arg Ala Glu Asp Phe Leu Arg Lys Gln
850                 855                 860
Ala Arg Tyr His Asp Arg Ala Arg Asp Pro Ser Gly Ser Ala Gly Leu
865                 870                 875                 880
Asp Ala Arg Arg Pro Trp Ala Gly Ser Gln Glu Ala Glu Leu Ser Arg
                885                 890                 895
Glu Gly Pro Tyr Gly Arg Glu Ser Asp His His Ala Arg Glu Gly Ser
            900                 905                 910
Leu Glu Gln Pro Gly Phe Trp Glu Gly Glu Ala Glu Arg Gly Lys Ala
            915                 920                 925
Gly Asp Pro His Arg Arg His Val His Arg Gln Gly Gly Ser Arg Glu
930                 935                 940
Ile Leu Ser Gly Ser Pro Leu Thr Gly Ala Asp Gly Asp Asp Arg Arg
945                 950                 955                 960
His Arg Ala His Arg Arg Pro Gly Glu Gly Pro Glu Asp Lys Ala
                965                 970                 975
Glu Arg Arg Ala Arg His Arg Glu Gly Ser Arg Pro Ala Arg Gly Gly
            980                 985                 990
Glu Gly Glu Gly Glu Val Pro Asp Gly Gly Asp Arg Arg Arg Arg His
            995                 1000                1005
Arg His Gly Ala Pro Ala Thr Tyr Glu Gly Asp Ala Arg Arg Glu Asp
    1010                1015                1020
Lys Glu Arg Arg His Arg Arg Lys Glu Asn Gln Gly Ser Gly Val
025                 1030                1035                1040
Pro Val Ser Gly Pro Asn Leu Ser Thr Thr Arg Pro Ile Gln Gln Asp
                1045                1050                1055
Leu Gly Arg Gln Asp Pro Pro Leu Ala Glu Asp Ile Asp Asn Met Lys
            1060                1065                1070
Asn Asn Lys Leu Ala Thr Ala Glu Ser Ala Ala Pro His Gly Ser Leu
            1075                1080                1085
Gly His Ala Gly Leu Pro Gln Ser Pro Ala Lys Met Gly Asn Ser Thr
            1090                1095                1100
Asp Pro Gly Pro Met Leu Ala Ile Pro Ala Met Ala Thr Asn Pro Gln
```

```
                1105                    1110                    1115                    1120
Asn   Ala   Ala   Ser   Arg   Arg   Thr   Pro   Asn   Asn   Pro   Gly   Asn   Pro   Ser   Asn
                     1125                    1130                         1135
Pro   Gly   Pro   Pro   Lys   Thr   Pro   Glu   Asn   Ser   Leu   Ile   Val   Thr   Asn   Pro
               1140                    1145                         1150
Ser   Gly   Thr   Gln   Thr   Asn   Ser   Ala   Lys   Thr   Ala   Arg   Lys   Pro   Asp   His
               1155                    1160                         1165
Thr   Thr   Val   Asp   Ile   Pro   Pro   Ala   Cys   Pro   Pro   Pro   Leu   Asn   His   Thr
         1170                    1175                    1180
Val   Val   Gln   Val   Asn   Lys   Asn   Ala   Asn   Pro   Asp   Pro   Leu   Pro   Lys   Lys
1185                         1190                    1195                              1200
Glu   Glu   Glu   Lys   Lys   Glu   Glu   Glu   Glu   Asp   Asp   Arg   Gly   Glu   Asp   Gly
                         1205                    1210                         1215
Pro   Lys   Pro   Met   Pro   Pro   Tyr   Ser   Ser   Met   Phe   Ile   Leu   Ser   Thr   Thr
                    1220                    1225                         1230
Asn   Pro   Leu   Arg   Arg   Leu   Cys   His   Tyr   Ile   Leu   Asn   Leu   Arg   Tyr   Phe
               1235                    1240                         1245
Glu   Met   Cys   Ile   Leu   Met   Val   Ile   Ala   Met   Ser   Ser   Ile   Ala   Leu   Ala
         1250                    1255                         1260
Ala   Glu   Asp   Pro   Val   Gln   Pro   Asn   Ala   Pro   Arg   Asn   Asn   Val   Leu   Arg
1265                         1270                    1275                              1280
Tyr   Phe   Asp   Tyr   Val   Phe   Thr   Gly   Val   Phe   Thr   Phe   Glu   Met   Val   Ile
                    1285                    1290                         1295
Lys   Met   Ile   Asp   Leu   Gly   Leu   Val   Leu   His   Gln   Gly   Ala   Tyr   Phe   Arg
               1300                    1305                         1310
Asp   Leu   Trp   Asn   Ile   Leu   Asp   Phe   Ile   Val   Val   Ser   Gly   Ala   Leu   Val
               1315                    1320                         1325
Ala   Phe   Ala   Phe   Thr   Gly   Asn   Ser   Lys   Gly   Lys   Asp   Ile   Asn   Thr   Ile
          1330                    1335                         1340
Lys   Ser   Leu   Arg   Val   Leu   Arg   Val   Leu   Arg   Pro   Leu   Lys   Thr   Ile   Lys
1345                         1350                    1355                              1360
Arg   Leu   Pro   Lys   Leu   Lys   Ala   Val   Phe   Asp   Cys   Val   Val   Asn   Ser   Leu
                    1365                    1370                         1375
Lys   Asn   Val   Phe   Asn   Ile   Leu   Ile   Val   Tyr   Met   Leu   Phe   Met   Phe   Ile
               1380                    1385                         1390
Phe   Ala   Val   Val   Ala   Val   Gln   Leu   Phe   Lys   Gly   Lys   Phe   Phe   His   Cys
          1395                    1400                         1405
Thr   Asp   Glu   Ser   Lys   Glu   Phe   Glu   Lys   Asp   Cys   Arg   Gly   Lys   Tyr   Leu
          1410                    1415                         1420
Leu   Tyr   Glu   Lys   Asn   Glu   Val   Lys   Ala   Arg   Asp   Arg   Glu   Trp   Lys   Lys
1425                         1430                    1435                              1440
Tyr   Glu   Phe   His   Tyr   Asp   Asn   Val   Leu   Trp   Ala   Leu   Leu   Thr   Leu   Phe
                    1445                    1450                         1455
Thr   Val   Ser   Thr   Gly   Glu   Gly   Trp   Pro   Gln   Val   Leu   Lys   His   Ser   Val
                    1460                    1465                         1470
Asp   Ala   Thr   Phe   Glu   Asn   Gln   Gly   Pro   Ser   Pro   Gly   Tyr   Arg   Met   Glu
               1475                    1480                         1485
Met   Ser   Ile   Phe   Tyr   Val   Val   Tyr   Phe   Val   Val   Phe   Pro   Phe   Phe   Phe
          1490                    1495                         1500
Val   Asn   Ile   Phe   Val   Ala   Leu   Ile   Ile   Ile   Thr   Phe   Gln   Glu   Gln   Gly
1505                         1510                    1515                              1520
Asp   Lys   Met   Met   Glu   Glu   Tyr   Ser   Leu   Glu   Lys   Asn   Glu   Arg   Ala   Cys
                    1525                    1530                         1535
```

```
Ile Asp Phe Ala Ile Ser Ala Lys Pro Leu Thr Arg His Met Pro Gln
            1540                1545                1550
Asn Lys Gln Ser Phe Gln Tyr Arg Met Trp Gln Phe Val Val Ser Pro
    1555                1560                1565
Pro Phe Glu Tyr Thr Ile Met Ala Met Ile Ala Leu Asn Thr Ile Val
    1570                1575                1580
Leu Met Met Lys Phe Tyr Gly Ala Ser Val Ala Tyr Glu Asn Ala Leu
585                 1590                1595                1600
Arg Val Phe Asn Ile Val Phe Thr Ser Leu Phe Ser Leu Glu Cys Val
                1605                1610                1615
Leu Lys Val Met Ala Leu Gly Ile Leu Asn Tyr Phe Arg Asp Ala Trp
            1620                1625                1630
Asn Ile Phe Asp Phe Val Thr Val Leu Gly Ser Ile Thr Asp Ile Leu
            1635                1640                1645
Val Thr Glu Phe Gly Asn Pro Asn Asn Phe Ile Asn Leu Ser Phe Leu
    1650                1655                1660
Arg Leu Phe Arg Ala Ala Arg Leu Ile Lys Leu Leu Arg Gln Gly Tyr
665                 1670                1675                1680
Thr Ile Arg Ile Leu Leu Trp Thr Phe Val Gln Ser Phe Lys Ala Leu
                1685                1690                1695
Pro Tyr Val Cys Leu Leu Ile Ala Met Leu Phe Phe Ile Tyr Ala Ile
                1700                1705                1710
Ile Gly Met Gln Val Phe Gly Asn Ile Gly Ile Asp Val Glu Asp Glu
            1715                1720                1725
Asp Ser Asp Glu Asp Glu Phe Gln Ile Thr Glu His Asn Asn Phe Arg
    1730                1735                1740
Thr Phe Phe Gln Ala Leu Met Leu Leu Phe Arg Ser Ala Thr Gly Glu
745                 1750                1755                1760
Ala Trp His Asn Ile Met Leu Ser Cys Leu Ser Gly Lys Pro Cys Asp
                1765                1770                1775
Lys Asn Ser Gly Ile Leu Thr Arg Glu Cys Gly Asn Glu Phe Ala Tyr
            1780                1785                1790
Phe Tyr Phe Val Ser Phe Ile Phe Leu Cys Ser Phe Leu Met Leu Asn
    1795                1800                1805
Leu Phe Val Ala Val Ile Met Asp Asn Phe Glu Tyr Leu Thr Arg Asp
    1810                1815                1820
Ser Ser Ile Leu Gly Pro His His Leu Asp Glu Tyr Val Arg Val Trp
825             1830                1835                1840
Ala Glu Tyr Asp Pro Ala Ala Trp Gly Arg Met Pro Tyr Leu Asp Met
                1845                1850                1855
Tyr Gln Met Leu Arg His Met Ser Pro Pro Leu Gly Leu Gly Lys Lys
            1860                1865                1870
Cys Pro Ala Arg Val Ala Tyr Lys Arg Leu Leu Arg Met Asp Leu Pro
        1875                1880                1885
Val Ala Asp Asp Asn Thr Val His Phe Asn Ser Thr Leu Met Ala Leu
    1890                1895                1900
Ile Arg Thr Ala Leu Asp Ile Lys Ile Ala Lys Gly Gly Ala Asp Lys
905                 1910                1915                1920
Gln Gln Met Asp Ala Glu Leu Arg Lys Glu Met Met Ala Ile Trp Pro
                1925                1930                1935
Asn Leu Ser Gln Lys Thr Leu Asp Leu Leu Val Thr Pro His Lys Ser
            1940                1945                1950
Thr Asp Leu Thr Val Gly Lys Ile Tyr Ala Ala Met Met Ile Met Glu
        1955                1960                1965
```

```
Tyr Tyr Arg Gln Ser Lys Ala Lys Lys Leu Gln Ala Met Arg Glu Glu
    1970                1975                1980

Gln Asp Arg Thr Pro Leu Met Phe Gln Arg Met Glu Pro Pro Ser Pro
985                 1990                1995                2000

Thr Gln Glu Gly Gly Pro Gly Gln Asn Ala Leu Pro Ser Thr Gln Leu
            2005                2010                2015

Asp Pro Gly Gly Ala Leu Met Ala His Glu Ser Gly Leu Lys Glu Ser
        2020                2025                2030

Pro Ser Trp Val Thr Gln Arg Ala Gln Glu Met Phe Gln Lys Thr Gly
        2035                2040                2045

Thr Trp Ser Pro Glu Gln Gly Pro Pro Thr Asp Met Pro Asn Ser Gln
    2050                2055                2060

Pro Asn Ser Gln Ser Val Glu Met Arg Glu Met Gly Arg Asp Gly Tyr
065             2070                2075                2080

Ser Asp Ser Glu His Tyr Leu Pro Met Glu Gly Gln Gly Arg Ala Ala
            2085                2090                2095

Ser Met Pro Arg Leu Pro Ala Glu Asn Gln Arg Arg Arg Gly Arg Pro
        2100                2105                2110

Arg Gly Asn Asn Leu Ser Thr Ile Ser Asp Thr Ser Pro Met Lys Arg
        2115                2120                2125

Ser Ala Ser Val Leu Gly Pro Lys Ala Arg Arg Leu Asp Asp Tyr Ser
    2130                2135                2140

Leu Glu Arg Val Pro Pro Glu Glu Asn Gln Arg His His Gln Arg Arg
145                 2150                2155                2160

Arg Asp Arg Ser His Arg Ala Ser Glu Arg Ser Leu Gly Arg Tyr Thr
            2165                2170                2175

Asp Val Asp Thr Gly Leu Gly Thr Asp Leu Ser Met Thr Thr Gln Ser
        2180                2185                2190

Gly Asp Leu Pro Ser Lys Glu Arg Asp Gln Glu Arg Gly Arg Pro Lys
        2195                2200                2205

Asp Arg Lys His Arg Gln His His His His His His His His His His
    2210                2215                2220

Pro Pro Pro Pro Asp Lys Asp Arg Tyr Ala Gln Glu Arg Pro Asp His
225                 2230                2235                2240

Gly Arg Ala Arg Ala Arg Asp Gln Arg Trp Ser Arg Ser Pro Ser Glu
            2245                2250                2255

Gly Arg Glu His Met Ala His Arg Gln Gly Ser Ser Val Ser Gly
            2260                2265                2270

Ser Pro Ala Pro Ser Thr Ser Gly Thr Ser Thr Pro Arg Arg Gly Arg
    2275                2280                2285

Arg Gln Leu Pro Gln Thr Pro Ser Thr Pro Arg Pro His Val Ser Tyr
    2290                2295                2300

Ser Pro Val Ile Arg Lys Ala Gly Gly Ser Gly Pro Pro Gln Gln Gln
305                 2310                2315                2320

Gln Gln Gln Gln Gln Gln Gln Gln Ala Val Ala Arg Pro Gly Arg Ala
            2325                2330                2335

Ala Thr Ser Gly Pro Arg Arg Tyr Pro Gly Pro Thr Ala Glu Pro Leu
        2340                2345                2350

Ala Gly Asp Arg Pro Pro Thr Gly Gly His Ser Ser Gly Arg Ser Pro
    2355                2360                2365

Arg Met Glu Arg Arg Val Pro Gly Pro Ala Arg Ser Glu Ser Pro Arg
    2370                2375                2380

Ala Cys Arg His Gly Gly Ala Arg Trp Pro Ala Ser Gly Pro His Val
```

-continued

| 385 | | | | | 2390 | | | | | 2395 | | | | | 2400 |
|---|---|---|---|---|---|---|---|---|---|---|---|---|---|---|---|

Ser Glu Gly Pro Pro Gly Pro Arg His His Gly Tyr Tyr Arg Gly Ser
                2405                    2410                    2415

Asp Tyr Asp Glu Ala Asp Gly Pro Gly Ser Gly Gly Gly Glu Glu Ala
            2420                    2425                2430

Met Ala Gly Ala Tyr Asp Ala Pro Pro Val Arg His Ala Ser Ser
            2435                2440                    2445

Gly Ala Thr Gly Arg Ser Pro Arg Thr Pro Arg Ala Ser Gly Pro Ala
        2450                2455                2460

Cys Ala Ser Pro Ser Arg His Gly Arg Arg Leu Pro Asn Gly Tyr Tyr
465                 2470                    2475                    2480

Pro Ala His Gly Leu Ala Arg Pro Arg Gly Pro Gly Ser Arg Lys Gly
                2485                    2490                    2495

Leu His Glu Pro Tyr Ser Glu Ser Asp Asp Asp Trp Cys
            2500                2505

( 2 ) INFORMATION FOR SEQ ID NO:36:

( i ) SEQUENCE CHARACTERISTICS:
    ( A ) LENGTH: 2265 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( i x ) FEATURE:
    ( D ) OTHER INFORMATION: /product="Alpha1A-2 subunit of
    human calcium channel"

( x i ) SEQUENCE DESCRIPTION: SEQ ID NO:36:

Ala Arg Phe Gly Asp Glu Met Pro Ala Arg Tyr Gly Gly Gly Gly Ser
1                   5                   10                  15

Gly Ala Ala Ala Gly Val Val Val Gly Ser Gly Gly Gly Arg Gly Ala
                20                  25                  30

Gly Gly Ser Arg Gln Gly Gly Gln Pro Gly Ala Gln Arg Met Tyr Lys
            35                  40                  45

Gln Ser Met Ala Gln Arg Ala Arg Thr Met Ala Leu Tyr Asn Pro Ile
        50                  55                  60

Pro Val Arg Gln Asn Cys Leu Thr Val Asn Arg Ser Leu Phe Leu Phe
65                  70                  75                  80

Ser Glu Asp Asn Val Val Arg Lys Tyr Ala Lys Lys Ile Thr Glu Trp
                85                  90                  95

Pro Pro Phe Glu Tyr Met Ile Leu Ala Thr Ile Ile Ala Asn Cys Ile
            100                 105                 110

Val Leu Ala Leu Glu Gln His Leu Pro Asp Asp Asp Lys Thr Pro Met
            115                 120                 125

Ser Glu Arg Leu Asp Asp Thr Glu Pro Tyr Phe Ile Gly Ile Phe Cys
        130                 135                 140

Phe Glu Ala Gly Ile Lys Ile Ile Ala Leu Gly Phe Ala Phe His Lys
145                 150                 155                 160

Gly Ser Tyr Leu Arg Asn Gly Trp Asn Val Met Asp Phe Val Val Val
                165                 170                 175

| | | | | | | | | | | | | | | |
|---|---|---|---|---|---|---|---|---|---|---|---|---|---|---|
|Leu|Thr|Gly|Ile<br>180|Leu|Ala|Thr|Val|Gly<br>185|Thr|Glu|Phe|Asp|Leu<br>190|Arg|Thr|
|Leu|Arg|Ala<br>195|Val|Arg|Val|Leu|Arg<br>200|Pro|Leu|Lys|Leu<br>205|Val|Ser|Gly|Ile|
|Pro|Ser<br>210|Leu|Gln|Val|Val|Leu<br>215|Lys|Ser|Ile|Met|Lys<br>220|Ala|Met|Ile|Pro|
|Leu<br>225|Leu|Gln|Ile|Gly|Leu<br>230|Leu|Leu|Phe|Phe|Ala<br>235|Ile|Leu|Ile|Phe|Ala<br>240|
|Ile|Ile|Gly|Leu|Glu<br>245|Phe|Tyr|Met|Gly|Lys<br>250|Phe|His|Thr|Thr|Cys<br>255|Phe|
|Glu|Glu|Gly|Thr<br>260|Asp|Asp|Ile|Gln|Gly<br>265|Glu|Ser|Pro|Ala|Pro<br>270|Cys|Gly|
|Thr|Glu|Glu<br>275|Pro|Ala|Arg|Thr|Cys<br>280|Pro|Asn|Gly|Thr|Lys<br>285|Cys|Gln|Pro|
|Tyr|Trp<br>290|Glu|Gly|Pro|Asn|Asn<br>295|Gly|Ile|Thr|Gln|Phe<br>300|Asp|Asn|Ile|Leu|
|Phe<br>305|Ala|Val|Leu|Thr|Val<br>310|Phe|Gln|Cys|Ile|Thr<br>315|Met|Glu|Gly|Trp|Thr<br>320|
|Asp|Leu|Leu|Tyr|Asn<br>325|Ser|Asn|Asp|Ala|Ser<br>330|Gly|Asn|Thr|Trp|Asn<br>335|Trp|
|Leu|Tyr|Phe|Ile<br>340|Pro|Leu|Ile|Ile|Ile<br>345|Gly|Ser|Phe|Phe|Met<br>350|Leu|Asn|
|Leu|Val|Leu<br>355|Gly|Val|Leu|Ser|Gly<br>360|Glu|Phe|Ala|Lys|Glu<br>365|Arg|Glu|Arg|
|Val|Glu<br>370|Asn|Arg|Arg|Ala|Phe<br>375|Leu|Lys|Leu|Arg|Arg<br>380|Gln|Gln|Gln|Ile|
|Glu<br>385|Arg|Glu|Leu|Asn|Gly<br>390|Tyr|Met|Glu|Trp|Ile<br>395|Ser|Thr|Ala|Glu|Glu<br>400|
|Val|Ile|Leu|Ala|Glu<br>405|Asp|Glu|Thr|Ala|Gly<br>410|Glu|Gln|Arg|His|Pro<br>415|Phe|
|Asp|Gly|Ala|Leu<br>420|Arg|Arg|Thr|Thr|Ile<br>425|Lys|Lys|Ser|Lys|Thr<br>430|Asp|Leu|
|Leu|Asn|Pro<br>435|Glu|Glu|Ala|Glu|Asp<br>440|Gln|Leu|Ala|Asp|Ile<br>445|Ala|Ser|Val|
|Gly|Ser<br>450|Pro|Phe|Ala|Arg|Ala<br>455|Ser|Ile|Lys|Ser|Ala<br>460|Lys|Leu|Glu|Asn|
|Ser<br>465|Thr|Phe|Phe|His|Lys<br>470|Lys|Glu|Arg|Arg|Met<br>475|Arg|Phe|Tyr|Ile|Arg<br>480|
|Arg|Met|Val|Lys|Thr<br>485|Gln|Ala|Phe|Tyr|Trp<br>490|Thr|Val|Leu|Ser|Val<br>495|Val|
|Ala|Leu|Asn|Thr<br>500|Leu|Cys|Val|Ala|Ile<br>505|Val|His|Tyr|Asn|Gln<br>510|Pro|Glu|
|Trp|Leu|Ser|Asp<br>515|Phe|Leu|Tyr|Tyr|Ala<br>520|Glu|Phe|Ile|Phe|Leu<br>525|Gly|Leu|
|Phe|Met|Ser<br>530|Glu|Met|Phe|Ile|Lys<br>535|Met|Tyr|Gly|Leu|Gly<br>540|Thr|Arg|Pro|
|Tyr|Phe<br>545|His|Ser|Ser|Phe|Asn<br>550|Cys|Phe|Asp|Cys|Gly<br>555|Val|Ile|Ile|Gly<br>560|
|Ser|Ile|Phe|Glu|Val<br>565|Ile|Trp|Ala|Val|Ile<br>570|Lys|Pro|Gly|Thr|Ser<br>575|Phe|
|Gly|Ile|Ser|Val<br>580|Leu|Arg|Ala|Leu|Arg<br>585|Leu|Leu|Arg|Ile|Phe<br>590|Lys|Val|
|Thr|Lys|Tyr|Trp|Ala|Ser|Leu|Arg|Asn|Leu|Val|Val|Ser|Leu|Leu|Asn|

|     |     |     |     | 595 |     |     |     |     | 600 |     |     |     |     | 605 |     |
| --- | --- | --- | --- | --- | --- | --- | --- | --- | --- | --- | --- | --- | --- | --- | --- |
| Ser | Met | Lys | Ser | Ile | Ile | Ser | Leu | Leu | Phe | Leu | Leu | Phe | Leu | Phe | Ile |
|     | 610 |     |     |     | 615 |     |     |     |     | 620 |     |     |     |     |     |
| Val | Val | Phe | Ala | Leu | Leu | Gly | Met | Gln | Leu | Phe | Gly | Gly | Gln | Phe | Asn |
| 625 |     |     |     |     | 630 |     |     |     |     | 635 |     |     |     |     | 640 |
| Phe | Asp | Glu | Gly | Thr | Pro | Pro | Thr | Asn | Phe | Asp | Thr | Phe | Pro | Ala | Ala |
|     |     |     |     | 645 |     |     |     |     | 650 |     |     |     |     | 655 |     |
| Ile | Met | Thr | Val | Phe | Gln | Ile | Leu | Thr | Gly | Glu | Asp | Trp | Asn | Glu | Val |
|     |     |     | 660 |     |     |     |     | 665 |     |     |     |     | 670 |     |     |
| Met | Tyr | Asp | Gly | Ile | Lys | Ser | Gln | Gly | Gly | Val | Gln | Gly | Gly | Met | Val |
|     |     | 675 |     |     |     |     | 680 |     |     |     |     | 685 |     |     |     |
| Phe | Ser | Ile | Tyr | Phe | Ile | Val | Leu | Thr | Leu | Phe | Gly | Asn | Tyr | Thr | Leu |
|     | 690 |     |     |     |     | 695 |     |     |     |     | 700 |     |     |     |     |
| Leu | Asn | Val | Phe | Leu | Ala | Ile | Ala | Val | Asp | Asn | Leu | Ala | Asn | Ala | Gln |
| 705 |     |     |     |     | 710 |     |     |     |     | 715 |     |     |     |     | 720 |
| Glu | Leu | Thr | Lys | Val | Glu | Ala | Asp | Glu | Gln | Glu | Glu | Glu | Glu | Ala | Ala |
|     |     |     |     | 725 |     |     |     |     | 730 |     |     |     |     | 735 |     |
| Asn | Gln | Lys | Leu | Ala | Leu | Gln | Lys | Ala | Lys | Glu | Val | Ala | Glu | Val | Ser |
|     |     |     | 740 |     |     |     |     | 745 |     |     |     |     | 750 |     |     |
| Pro | Leu | Ser | Ala | Ala | Asn | Met | Ser | Ile | Ala | Val | Lys | Glu | Gln | Gln | Lys |
|     |     | 755 |     |     |     |     | 760 |     |     |     |     | 765 |     |     |     |
| Asn | Gln | Lys | Pro | Ala | Lys | Ser | Val | Trp | Glu | Gln | Arg | Thr | Ser | Glu | Met |
|     | 770 |     |     |     |     | 775 |     |     |     |     | 780 |     |     |     |     |
| Arg | Lys | Gln | Asn | Leu | Leu | Ala | Ser | Arg | Glu | Ala | Leu | Tyr | Asn | Glu | Met |
| 785 |     |     |     |     | 790 |     |     |     |     | 795 |     |     |     |     | 800 |
| Asp | Pro | Asp | Glu | Arg | Trp | Lys | Ala | Ala | Tyr | Thr | Arg | His | Leu | Arg | Pro |
|     |     |     |     | 805 |     |     |     |     | 810 |     |     |     |     | 815 |     |
| Asp | Met | Lys | Thr | His | Leu | Asp | Arg | Pro | Leu | Val | Val | Asp | Pro | Gln | Glu |
|     |     |     | 820 |     |     |     |     | 825 |     |     |     |     | 830 |     |     |
| Asn | Arg | Asn | Asn | Asn | Thr | Asn | Lys | Ser | Arg | Ala | Ala | Glu | Xaa | Thr | Val |
|     |     | 835 |     |     |     |     | 840 |     |     |     |     | 845 |     |     |     |
| Asp | Gln | Ser | Leu | Gly | Gln | Gln | Arg | Ala | Glu | Asp | Phe | Leu | Arg | Lys | Gln |
|     | 850 |     |     |     |     | 855 |     |     |     |     | 860 |     |     |     |     |
| Ala | Arg | Tyr | His | Asp | Arg | Ala | Arg | Xaa | Pro | Ser | Gly | Ser | Ala | Gly | Leu |
| 865 |     |     |     |     | 870 |     |     |     |     | 875 |     |     |     |     | 880 |
| Asp | Ala | Arg | Arg | Pro | Trp | Ala | Gly | Ser | Gln | Glu | Ala | Glu | Leu | Ser | Arg |
|     |     |     |     | 885 |     |     |     |     | 890 |     |     |     |     | 895 |     |
| Glu | Gly | Xaa | Xaa | Gly | Arg | Glu | Ser | Asp | His | His | Ala | Arg | Glu | Xaa | Xaa |
|     |     |     | 900 |     |     |     |     | 905 |     |     |     |     | 910 |     |     |
| Leu | Glu | Xaa | Pro | Gly | Phe | Trp | Glu | Gly | Xaa | Xaa | Glu | Arg | Xaa | Lys | Xaa |
|     |     | 915 |     |     |     |     | 920 |     |     |     |     | 925 |     |     |     |
| Gly | Xaa | Pro | His | Arg | Arg | His | Val | His | Xaa | Gln | Gly | Gly | Ser | Arg | Glu |
|     | 930 |     |     |     |     | 935 |     |     |     |     | 940 |     |     |     |     |
| Ile | Leu | Ser | Gly | Ser | Pro | Leu | Thr | Gly | Ala | Asp | Gly | Asp | Asp | Arg | Arg |
| 945 |     |     |     |     | 950 |     |     |     |     | 955 |     |     |     |     | 960 |
| His | Arg | Ala | His | Arg | Arg | Pro | Gly | Glu | Glu | Gly | Pro | Glu | Asp | Lys | Ala |
|     |     |     |     | 965 |     |     |     |     | 970 |     |     |     |     | 975 |     |
| Glu | Arg | Arg | Ala | Arg | His | Arg | Glu | Gly | Ser | Arg | Pro | Ala | Arg | Gly | Gly |
|     |     |     | 980 |     |     |     |     | 985 |     |     |     |     | 990 |     |     |
| Glu | Gly | Glu | Gly | Glu | Val | Pro | Asp | Gly | Gly | Asp | Arg | Arg | Arg | Arg | His |
|     |     | 995 |     |     |     |     | 1000|     |     |     |     | 1005|     |     |     |
| Arg | His | Gly | Ala | Pro | Ala | Thr | Tyr | Glu | Gly | Asp | Ala | Arg | Arg | Glu | Asp |
|     | 1010|     |     |     |     | 1015|     |     |     |     | 1020|     |     |     |     |

```
Lys Glu Arg Arg His Arg Arg Arg Lys Glu Asn Gln Gly Ser Gly Val
1025                1030                1035                     1040

Pro Val Ser Gly Pro Asn Leu Ser Thr Thr Arg Pro Ile Gln Gln Asp
                1045                1050                1055

Leu Gly Arg Gln Asp Pro Pro Leu Ala Glu Asp Ile Asp Asn Met Lys
            1060                1065                1070

Asn Asn Lys Leu Ala Thr Ala Glu Ser Ala Ala Pro His Gly Ser Leu
        1075                1080                1085

Gly His Ala Gly Leu Pro Gln Ser Pro Ala Lys Met Gly Asn Ser Thr
    1090                1095                1100

Asp Pro Gly Pro Met Leu Ala Ile Pro Ala Met Ala Thr Asn Pro Gln
1105                1110                1115                     1120

Asn Ala Ala Ser Arg Arg Thr Pro Asn Asn Pro Gly Asn Pro Ser Asn
                1125                1130                1135

Pro Gly Pro Pro Lys Thr Pro Glu Asn Ser Leu Ile Val Thr Asn Pro
                1140                1145                1150

Ser Gly Thr Gln Thr Asn Ser Ala Lys Thr Ala Arg Lys Pro Asp His
            1155                1160                1165

Thr Thr Val Asp Ile Pro Pro Ala Cys Pro Pro Pro Leu Asn His Thr
    1170                1175                1180

Val Val Gln Val Asn Lys Asn Ala Asn Pro Asp Pro Leu Pro Lys Lys
1185                1190                1195                     1200

Glu Glu Glu Lys Lys Glu Glu Glu Glu Asp Asp Arg Gly Glu Asp Gly
                1205                1210                1215

Pro Lys Pro Met Pro Pro Tyr Ser Ser Met Phe Ile Leu Ser Thr Thr
                1220                1225                1230

Asn Pro Leu Arg Arg Leu Cys His Tyr Ile Leu Asn Leu Arg Tyr Phe
            1235                1240                1245

Glu Met Cys Ile Leu Met Val Ile Ala Met Ser Ser Ile Ala Leu Ala
    1250                1255                1260

Ala Glu Asp Pro Val Gln Pro Asn Ala Pro Arg Asn Asn Val Leu Arg
1265                1270                1275                     1280

Tyr Phe Asp Tyr Val Phe Thr Gly Val Phe Thr Phe Glu Met Val Ile
                1285                1290                1295

Lys Met Ile Asp Leu Gly Leu Val Leu His Gln Gly Ala Tyr Phe Arg
            1300                1305                1310

Asp Leu Trp Asn Ile Leu Asp Phe Ile Val Val Ser Gly Ala Leu Val
    1315                1320                1325

Ala Phe Ala Phe Thr Gly Asn Ser Lys Gly Lys Asp Ile Asn Thr Ile
    1330                1335                1340

Lys Ser Leu Arg Val Leu Arg Val Leu Arg Pro Leu Lys Thr Ile Lys
1345                1350                1355                     1360

Arg Leu Pro Lys Leu Lys Ala Val Phe Asp Cys Val Val Asn Ser Leu
                1365                1370                1375

Lys Asn Val Phe Asn Ile Leu Ile Val Tyr Met Leu Phe Met Phe Ile
            1380                1385                1390

Phe Ala Val Val Ala Val Gln Leu Phe Lys Gly Lys Phe Phe His Cys
    1395                1400                1405

Thr Asp Glu Ser Lys Glu Phe Glu Lys Asp Cys Arg Gly Lys Tyr Leu
    1410                1415                1420

Leu Tyr Glu Lys Asn Glu Val Lys Ala Arg Asp Arg Glu Trp Lys Lys
1425                1430                1435                     1440

Tyr Glu Phe His Tyr Asp Asn Val Leu Trp Ala Leu Leu Thr Leu Phe
                1445                1450                1455
```

```
Thr  Val  Ser  Thr  Gly  Glu  Gly  Trp  Pro  Gln  Val  Leu  Lys  His  Ser  Val
          1460                1465                     1470

Asp  Ala  Thr  Phe  Glu  Asn  Gln  Gly  Pro  Ser  Pro  Gly  Tyr  Arg  Met  Glu
          1475                1480                     1485

Met  Ser  Ile  Phe  Tyr  Val  Val  Tyr  Phe  Val  Val  Phe  Pro  Phe  Phe  Phe
     1490                1495                     1500

Val  Asn  Ile  Phe  Val  Ala  Leu  Ile  Ile  Ile  Thr  Phe  Gln  Glu  Gln  Gly
505                 1510                     1515                     1520

Asp  Lys  Met  Met  Glu  Glu  Tyr  Ser  Leu  Glu  Lys  Asn  Glu  Arg  Ala  Cys
          1525                1530                     1535

Ile  Asp  Phe  Ala  Ile  Ser  Ala  Lys  Pro  Leu  Thr  Arg  His  Met  Pro  Gln
          1540                1545                     1550

Asn  Lys  Gln  Ser  Phe  Gln  Tyr  Arg  Met  Trp  Gln  Phe  Val  Val  Ser  Pro
     1555                1560                     1565

Pro  Phe  Glu  Tyr  Thr  Ile  Met  Ala  Met  Ile  Ala  Leu  Asn  Thr  Ile  Val
     1570                1575                     1580

Leu  Met  Met  Lys  Phe  Tyr  Gly  Ala  Ser  Val  Ala  Tyr  Glu  Asn  Ala  Leu
585                 1590                     1595                     1600

Arg  Val  Phe  Asn  Ile  Val  Phe  Thr  Ser  Leu  Phe  Ser  Leu  Glu  Cys  Val
               1605                1610                     1615

Leu  Lys  Val  Met  Ala  Leu  Gly  Ile  Leu  Asn  Tyr  Phe  Arg  Asp  Ala  Trp
               1620                1625                     1630

Asn  Ile  Phe  Asp  Phe  Val  Thr  Val  Leu  Gly  Ser  Ile  Thr  Asp  Ile  Leu
          1635                1640                     1645

Val  Thr  Glu  Phe  Gly  Asn  Pro  Asn  Asn  Phe  Ile  Asn  Leu  Ser  Phe  Leu
     1650                1655                     1660

Arg  Leu  Phe  Arg  Ala  Ala  Arg  Leu  Ile  Lys  Leu  Leu  Arg  Gln  Gly  Tyr
665                 1670                     1675                     1680

Thr  Ile  Arg  Ile  Leu  Leu  Trp  Thr  Phe  Val  Gln  Ser  Phe  Lys  Ala  Leu
               1685                1690                     1695

Pro  Tyr  Val  Cys  Leu  Leu  Ile  Ala  Met  Leu  Phe  Phe  Ile  Tyr  Ala  Ile
               1700                1705                     1710

Ile  Gly  Met  Gln  Val  Phe  Gly  Asn  Ile  Gly  Ile  Asp  Val  Glu  Asp  Glu
          1715                1720                     1725

Asp  Ser  Asp  Glu  Asp  Glu  Phe  Gln  Ile  Thr  Glu  His  Asn  Asn  Phe  Arg
     1730                1735                     1740

Thr  Phe  Phe  Gln  Ala  Leu  Met  Leu  Leu  Phe  Arg  Ser  Ala  Thr  Gly  Glu
745                 1750                     1755                     1760

Ala  Trp  His  Asn  Ile  Met  Leu  Ser  Cys  Leu  Ser  Gly  Lys  Pro  Cys  Asp
               1765                1770                     1775

Lys  Asn  Ser  Gly  Ile  Leu  Thr  Arg  Glu  Cys  Gly  Asn  Glu  Phe  Ala  Tyr
          1780                1785                     1790

Phe  Tyr  Phe  Val  Ser  Phe  Ile  Phe  Leu  Cys  Ser  Phe  Leu  Met  Leu  Asn
          1795                1800                     1805

Leu  Phe  Val  Ala  Val  Ile  Met  Asp  Asn  Phe  Glu  Tyr  Leu  Thr  Arg  Asp
     1810                1815                     1820

Ser  Ser  Ile  Leu  Gly  Pro  His  His  Leu  Asp  Glu  Tyr  Val  Arg  Val  Trp
825                 1830                     1835                     1840

Ala  Glu  Tyr  Asp  Pro  Ala  Ala  Trp  Gly  Arg  Met  Pro  Tyr  Leu  Asp  Met
               1845                1850                     1855

Tyr  Gln  Met  Leu  Arg  His  Met  Ser  Pro  Pro  Leu  Gly  Leu  Gly  Lys  Lys
          1860                1865                     1870

Cys  Pro  Ala  Arg  Val  Ala  Tyr  Lys  Arg  Leu  Leu  Arg  Met  Asp  Leu  Pro
```

|  |  |  |  |  | 1875 |  |  |  |  | 1880 |  |  |  |  | 1885 |  |  |
|---|---|---|---|---|---|---|---|---|---|---|---|---|---|---|---|---|---|

Val Ala Asp Asp Asn Thr Val His Phe Asn Ser Thr Leu Met Ala Leu
                                 1890                              1895                              1900

Ile Arg Thr Ala Leu Asp Ile Lys Ile Ala Lys Gly Gly Ala Asp Lys
1905                              1910                              1915                              1920

Gln Gln Met Asp Ala Glu Leu Arg Lys Glu Met Met Ala Ile Trp Pro
                    1925                              1930                              1935

Asn Leu Ser Gln Lys Thr Leu Asp Leu Leu Val Thr Pro His Lys Ser
                1940                              1945                              1950

Thr Asp Leu Thr Val Gly Lys Ile Tyr Ala Ala Met Met Ile Met Glu
              1955                              1960                              1965

Tyr Tyr Arg Gln Ser Lys Ala Lys Lys Leu Gln Ala Met Arg Glu Glu
          1970                              1975                              1980

Gln Asp Arg Thr Pro Leu Met Phe Gln Arg Met Glu Pro Pro Ser Pro
985                              1990                              1995                              2000

Thr Gln Glu Gly Gly Pro Gly Gln Asn Ala Leu Pro Ser Thr Gln Leu
                        2005                              2010                              2015

Asp Pro Gly Gly Ala Leu Met Ala His Glu Ser Gly Leu Lys Glu Ser
                2020                              2025                              2030

Pro Ser Trp Val Thr Gln Arg Ala Gln Glu Met Phe Gln Lys Thr Gly
              2035                              2040                              2045

Thr Trp Ser Pro Glu Gln Gly Pro Pro Thr Asp Met Pro Asn Ser Gln
      2050                              2055                              2060

Pro Asn Ser Gln Ser Val Glu Met Arg Glu Met Gly Arg Asp Gly Tyr
065                              2070                              2075                              2080

Ser Asp Ser Glu His Tyr Leu Pro Met Glu Gly Gln Gly Arg Ala Ala
                        2085                              2090                              2095

Ser Met Pro Arg Leu Pro Ala Glu Asn Gln Arg Arg Arg Gly Arg Pro
              2100                              2105                              2110

Arg Gly Asn Asn Leu Ser Thr Ile Ser Asp Thr Ser Pro Met Lys Arg
                  2115                              2120                              2125

Ser Ala Ser Val Leu Gly Pro Lys Ala Arg Arg Leu Asp Asp Tyr Ser
      2130                              2135                              2140

Leu Glu Arg Val Pro Pro Glu Glu Asn Gln Arg His His Gln Arg Arg
145                              2150                              2155                              2160

Arg Asp Arg Ser His Arg Ala Ser Glu Arg Ser Leu Gly Arg Tyr Thr
                        2165                              2170                              2175

Asp Val Asp Thr Gly Leu Gly Thr Asp Leu Ser Met Thr Thr Gln Ser
                  2180                              2185                              2190

Gly Asp Leu Pro Ser Lys Glu Arg Asp Gln Glu Arg Gly Arg Pro Lys
          2195                              2200                              2205

Asp Arg Lys His Arg Gln His His His His His His His His His His
    2210                              2215                              2220

Pro Pro Pro Pro Asp Lys Asp Arg Tyr Ala Gln Glu Arg Pro Asp His
225                              2230                              2235                              2240

Gly Arg Ala Arg Ala Arg Asp Gln Arg Trp Ser Arg Ser Pro Ser Glu
                    2245                              2250                              2255

Gly Arg Glu His Met Ala His Arg Gln
              2260                              2265

(2) INFORMATION FOR SEQ ID NO:37:

(i) SEQUENCE CHARACTERISTICS:
        (A) LENGTH: 649 amino acids
        (B) TYPE: amino acid ( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( i x ) FEATURE:
( D ) OTHER INFORMATION: /product="Beta2D subunit of human calcium channel"

( x i ) SEQUENCE DESCRIPTION: SEQ ID NO:37:

| Ile | Pro | Ala | Ala | Ala | Val | Ala | Gln | Glu | Ile | Gln | Met | Glu | Leu | Leu | Glu |
|---|---|---|---|---|---|---|---|---|---|---|---|---|---|---|---|
| 1 | | | | 5 | | | | | 10 | | | | | 15 | |
| Asn | Val | Ala | Pro | Ala | Gly | Ala | Leu | Gly | Ala | Ala | Ala | Gln | Ser | Tyr | Gly |
| | | | 20 | | | | | 25 | | | | | 30 | | |
| Lys | Gly | Ala | Arg | Arg | Lys | Asn | Arg | Phe | Lys | Gly | Ser | Asp | Gly | Ser | Thr |
| | | 35 | | | | | 40 | | | | | 45 | | | |
| Ser | Ser | Asp | Thr | Thr | Ser | Asn | Ser | Phe | Val | Arg | Gln | Gly | Ser | Ala | Asp |
| | 50 | | | | | 55 | | | | | 60 | | | | |
| Ser | Tyr | Thr | Ser | Arg | Pro | Ser | Asp | Ser | Asp | Val | Ser | Leu | Glu | Glu | Asp |
| 65 | | | | | 70 | | | | | 75 | | | | | 80 |
| Arg | Glu | Ala | Val | Arg | Arg | Glu | Ala | Glu | Arg | Gln | Ala | Gln | Ala | Gln | Leu |
| | | | | 85 | | | | | 90 | | | | | 95 | |
| Glu | Lys | Ala | Lys | Thr | Lys | Pro | Val | Ala | Phe | Ala | Val | Arg | Thr | Asn | Val |
| | | | 100 | | | | | 105 | | | | | 110 | | |
| Ser | Tyr | Ser | Ala | Ala | His | Glu | Asp | Asp | Val | Pro | Val | Pro | Gly | Met | Ala |
| | | 115 | | | | | 120 | | | | | 125 | | | |
| Ile | Ser | Phe | Glu | Ala | Lys | Asp | Phe | Leu | His | Val | Lys | Glu | Lys | Phe | Asn |
| | 130 | | | | | 135 | | | | | 140 | | | | |
| Asn | Asp | Trp | Trp | Ile | Gly | Arg | Leu | Val | Lys | Glu | Gly | Cys | Glu | Ile | Gly |
| 145 | | | | | 150 | | | | | 155 | | | | | 160 |
| Phe | Ile | Pro | Ser | Pro | Val | Lys | Leu | Glu | Asn | Met | Arg | Leu | Gln | His | Glu |
| | | | | 165 | | | | | 170 | | | | | 175 | |
| Gln | Arg | Ala | Lys | Gln | Gly | Lys | Phe | Tyr | Ser | Ser | Lys | Ser | Gly | Gly | Asn |
| | | | 180 | | | | | 185 | | | | | 190 | | |
| Ser | Ser | Ser | Ser | Leu | Gly | Asp | Ile | Val | Pro | Ser | Ser | Arg | Lys | Ser | Thr |
| | | | 195 | | | | | 200 | | | | | 205 | | |
| Pro | Pro | Ser | Ser | Ala | Ile | Asp | Ile | Asp | Ala | Thr | Gly | Leu | Asp | Ala | Glu |
| | 210 | | | | | 215 | | | | | 220 | | | | |
| Glu | Asn | Asp | Ile | Pro | Ala | Asn | His | Arg | Ser | Pro | Lys | Pro | Ser | Ala | Asn |
| 225 | | | | | 230 | | | | | 235 | | | | | 240 |
| Ser | Val | Thr | Ser | Pro | His | Ser | Lys | Glu | Lys | Arg | Met | Pro | Phe | Phe | Lys |
| | | | | 245 | | | | | 250 | | | | | 255 | |
| Lys | Thr | Glu | His | Thr | Pro | Pro | Tyr | Asp | Val | Val | Pro | Ser | Met | Arg | Pro |
| | | | 260 | | | | | 265 | | | | | 270 | | |
| Val | Val | Leu | Val | Gly | Pro | Ser | Leu | Lys | Gly | Tyr | Glu | Val | Thr | Asp | Met |
| | | | 275 | | | | | 280 | | | | | 285 | | |
| Met | His | Lys | Ala | Leu | Phe | Asp | Phe | Leu | Lys | His | Arg | Phe | Glu | Gly | Arg |
| | | 290 | | | | | 295 | | | | | 300 | | | |
| Ile | Ser | Ile | Thr | Arg | Val | Thr | Ala | Asp | Ile | Ser | Leu | Ala | Lys | Arg | Ser |
| 305 | | | | | 310 | | | | | 315 | | | | | 320 |
| Val | Leu | Asn | Asn | Pro | Ser | Lys | His | Ala | Ile | Ile | Glu | Arg | Ser | Asn | Thr |

|   |   |   |   |   | 325 |   |   |   |   | 330 |   |   |   |   | 335 |   |
|---|---|---|---|---|---|---|---|---|---|---|---|---|---|---|---|---|
| Arg | Ser | Ser | Leu | Ala | Glu | Val | Gln | Ser | Glu | Ile | Glu | Arg | Ile | Phe | Glu |
|   |   |   | 340 |   |   |   |   | 345 |   |   |   |   | 350 |   |   |
| Leu | Ala | Arg | Thr | Leu | Gln | Leu | Val | Val | Leu | Asp | Ala | Asp | Thr | Ile | Asn |
|   |   |   | 355 |   |   |   |   | 360 |   |   |   |   | 365 |   |   |
| His | Pro | Ala | Gln | Leu | Ser | Lys | Thr | Ser | Leu | Ala | Pro | Ile | Ile | Val | Tyr |
|   |   |   | 370 |   |   |   |   | 375 |   |   |   |   | 380 |   |   |
| Val | Lys | Ile | Ser | Ser | Pro | Lys | Val | Leu | Gln | Arg | Leu | Ile | Lys | Ser | Arg |
| 385 |   |   |   |   |   | 390 |   |   |   |   | 395 |   |   |   |   | 400 |
| Gly | Lys | Ser | Gln | Ala | Lys | His | Leu | Asn | Val | Gln | Met | Val | Ala | Ala | Asp |
|   |   |   |   | 405 |   |   |   |   | 410 |   |   |   |   | 415 |   |
| Lys | Leu | Ala | Gln | Cys | Pro | Pro | Glu | Leu | Phe | Asp | Val | Ile | Leu | Asp | Glu |
|   |   |   | 420 |   |   |   |   | 425 |   |   |   |   | 430 |   |   |
| Asn | Gln | Leu | Glu | Asp | Ala | Cys | Glu | His | Leu | Ala | Asp | Tyr | Leu | Glu | Ala |
|   |   |   | 435 |   |   |   |   | 440 |   |   |   |   | 445 |   |   |
| Tyr | Trp | Lys | Ala | Thr | His | Pro | Pro | Ser | Ser | Ser | Leu | Pro | Asn | Pro | Leu |
|   | 450 |   |   |   |   | 455 |   |   |   |   | 460 |   |   |   |   |
| Leu | Ser | Arg | Thr | Leu | Ala | Thr | Ser | Ser | Leu | Pro | Leu | Ser | Pro | Thr | Leu |
| 465 |   |   |   |   | 470 |   |   |   |   | 475 |   |   |   |   | 480 |
| Ala | Ser | Asn | Ser | Gln | Gly | Ser | Gln | Gly | Asp | Gln | Arg | Thr | Asp | Arg | Ser |
|   |   |   |   | 485 |   |   |   |   | 490 |   |   |   |   | 495 |   |
| Ala | Pro | Ile | Arg | Ser | Ala | Ser | Gln | Ala | Glu | Glu | Glu | Pro | Ser | Val | Glu |
|   |   |   | 500 |   |   |   |   | 505 |   |   |   |   | 510 |   |   |
| Pro | Val | Lys | Lys | Ser | Gln | His | Arg | Ser | Ser | Ser | Ser | Ala | Pro | His | His |
|   |   | 515 |   |   |   |   | 520 |   |   |   |   | 525 |   |   |   |
| Asn | His | Arg | Ser | Gly | Thr | Ser | Arg | Gly | Leu | Ser | Arg | Gln | Glu | Thr | Phe |
|   | 530 |   |   |   |   | 535 |   |   |   |   | 540 |   |   |   |   |
| Asp | Ser | Glu | Thr | Gln | Glu | Ser | Arg | Asp | Ser | Ala | Tyr | Val | Glu | Pro | Lys |
| 545 |   |   |   |   |   | 550 |   |   |   |   | 555 |   |   |   |   | 560 |
| Glu | Asp | Tyr | Ser | His | Asp | His | Val | Asp | His | Tyr | Ala | Ser | His | Arg | Asp |
|   |   |   |   | 565 |   |   |   |   | 570 |   |   |   |   | 575 |   |
| His | Asn | His | Arg | Asp | Glu | Thr | His | Gly | Ser | Ser | Asp | His | Arg | His | Arg |
|   |   |   | 580 |   |   |   |   | 585 |   |   |   |   | 590 |   |   |
| Glu | Ser | Arg | His | Arg | Ser | Arg | Asp | Val | Asp | Arg | Glu | Gln | Asp | His | Asn |
|   |   | 595 |   |   |   |   | 600 |   |   |   |   | 605 |   |   |   |
| Glu | Cys | Asn | Lys | Gln | Arg | Ser | Arg | His | Lys | Ser | Lys | Asp | Gly | Tyr | Cys |
|   | 610 |   |   |   |   | 615 |   |   |   |   | 620 |   |   |   |   |
| Glu | Lys | Asp | Gly | Glu | Val | Ile | Ser | Lys | Lys | Arg | Asn | Glu | Ala | Gly | Glu |
| 625 |   |   |   |   |   | 630 |   |   |   |   | 635 |   |   |   |   | 640 |
| Trp | His | Arg | Asp | Val | His | Ile | Pro | Gln |   |   |   |   |   |   |   |
|   |   |   |   | 645 |   |   |   |   |   |   |   |   |   |   |   |

( 2 ) INFORMATION FOR SEQ ID NO:38:

( i ) SEQUENCE CHARACTERISTICS:
        ( A ) LENGTH: 479 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( i x ) FEATURE:
      ( D ) OTHER INFORMATION: /standard_name= "Beta1-1"

( x i ) SEQUENCE DESCRIPTION: SEQ ID NO:38:

```
Met Val Gln Lys Thr Ser Met Ser Arg Gly Pro Tyr Pro Pro Ser Gln
 1               5                  10                  15

Glu Ile Pro Met Glu Val Phe Asp Pro Ser Pro Gln Gly Lys Tyr Ser
            20                  25                  30

Lys Arg Lys Gly Arg Phe Lys Arg Ser Asp Gly Ser Thr Ser Ser Asp
         35                  40                  45

Thr Thr Ser Asn Ser Phe Val Arg Gln Gly Ser Ala Glu Ser Tyr Thr
     50              55                  60

Ser Arg Pro Ser Asp Ser Asp Val Ser Leu Glu Glu Asp Arg Glu Ala
65              70                  75                      80

Leu Arg Lys Glu Ala Glu Arg Gln Ala Leu Ala Gln Leu Glu Lys Ala
                 85                  90                  95

Lys Thr Lys Pro Val Ala Phe Ala Val Arg Thr Asn Val Gly Tyr Asn
             100                 105                 110

Pro Ser Pro Gly Asp Glu Val Pro Val Gln Gly Val Ala Ile Thr Phe
         115                 120                 125

Glu Pro Lys Asp Phe Leu His Ile Lys Glu Lys Tyr Asn Asn Asp Trp
     130                 135                 140

Trp Ile Gly Arg Leu Val Lys Glu Gly Cys Glu Val Gly Phe Ile Pro
145                 150                 155                 160

Ser Pro Val Lys Leu Asp Ser Leu Arg Leu Leu Gln Glu Gln Lys Leu
                 165                 170                 175

Arg Gln Asn Arg Leu Gly Ser Ser Lys Ser Gly Asp Asn Ser Ser Ser
             180                 185                 190

Ser Leu Gly Asp Val Val Thr Gly Thr Arg Arg Pro Thr Pro Pro Ala
         195                 200                 205

Ser Gly Asn Glu Met Thr Asn Leu Ala Phe Glu Leu Asp Pro Leu Glu
     210                 215                 220

Leu Glu Glu Glu Glu Ala Glu Leu Gly Glu Gln Ser Gly Ser Ala Lys
225                 230                 235                 240

Thr Ser Val Ser Ser Val Thr Thr Pro Pro Pro His Gly Lys Arg Ile
                 245                 250                 255

Pro Phe Phe Lys Lys Thr Glu His Val Pro Pro Tyr Asp Val Val Pro
             260                 265                 270

Ser Met Arg Pro Ile Ile Leu Val Gly Pro Ser Leu Lys Gly Tyr Glu
         275                 280                 285

Val Thr Asp Met Met Gln Lys Ala Leu Phe Asp Phe Leu Lys His Arg
     290                 295                 300

Phe Asp Gly Arg Ile Ser Ile Thr Arg Val Thr Ala Asp Ile Ser Leu
305                 310                 315                 320

Ala Lys Arg Ser Val Leu Asn Asn Pro Ser Lys His Ile Ile Ile Glu
                 325                 330                 335

Arg Ser Asn Thr Arg Ser Ser Leu Ala Glu Val Gln Ser Glu Ile Glu
             340                 345                 350

Arg Ile Phe Glu Leu Ala Arg Thr Leu Gln Leu Val Ala Leu Asp Ala
         355                 360                 365

Asp Thr Ile Asn His Pro Ala Gln Leu Ser Lys Thr Ser Leu Ala Pro
     370                 375                 380

Ile Ile Val Tyr Ile Lys Ile Thr Ser Pro Lys Val Leu Gln Arg Leu
385                 390                 395                 400
```

|   |   |   |   |   |   |   |   |   |   |   |   |   |   |   |
|---|---|---|---|---|---|---|---|---|---|---|---|---|---|---|
| Ile | Lys | Ser | Arg | Gly<br>405 | Lys | Ser | Gln | Ser | Lys<br>410 | His | Leu | Asn | Val | Gln<br>415 | Ile |
| Ala | Ala | Ser | Glu<br>420 | Lys | Leu | Ala | Gln | Cys<br>425 | Pro | Pro | Glu | Met | Phe<br>430 | Asp | Ile |
| Ile | Leu | Asp<br>435 | Glu | Asn | Gln | Leu | Glu<br>440 | Asp | Ala | Cys | Glu | His<br>445 | Leu | Ala | Glu |
| Tyr | Leu<br>450 | Glu | Ala | Tyr | Trp | Lys<br>455 | Ala | Thr | His | Pro | Pro<br>460 | Ser | Ser | Thr | Pro |
| Pro<br>465 | Asn | Pro | Leu | Leu | Asn<br>470 | Arg | Thr | Met | Ala | Thr<br>475 | Ala | Ala | Leu | Ala |

( 2 ) INFORMATION FOR SEQ ID NO:39:

( i ) SEQUENCE CHARACTERISTICS:
        ( A ) LENGTH: 216 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( i x ) FEATURE:
        ( D ) OTHER INFORMATION: /standard_name= "Beta1-4"

( x i ) SEQUENCE DESCRIPTION: SEQ ID NO:39:

|   |   |   |   |   |   |   |   |   |   |   |   |   |   |   |   |
|---|---|---|---|---|---|---|---|---|---|---|---|---|---|---|---|
| Met<br>1 | Val | Gln | Lys | Thr<br>5 | Ser | Met | Ser | Arg | Gly<br>10 | Pro | Tyr | Pro | Pro | Ser<br>15 | Gln |
| Glu | Ile | Pro | Met<br>20 | Glu | Val | Phe | Asp | Pro<br>25 | Ser | Pro | Gln | Gly | Lys<br>30 | Tyr | Ser |
| Lys | Arg | Lys<br>35 | Gly | Arg | Phe | Lys | Arg<br>40 | Ser | Asp | Gly | Ser | Thr<br>45 | Ser | Ser | Asp |
| Thr | Thr<br>50 | Ser | Asn | Ser | Phe | Val<br>55 | Arg | Gln | Gly | Ser | Ala<br>60 | Glu | Ser | Tyr | Thr |
| Ser<br>65 | Arg | Pro | Ser | Asp | Ser<br>70 | Asp | Val | Ser | Leu | Glu<br>75 | Glu | Asp | Arg | Glu | Ala<br>80 |
| Leu | Arg | Lys | Glu | Ala<br>85 | Glu | Arg | Gln | Ala | Leu<br>90 | Ala | Gln | Leu | Glu | Lys<br>95 | Ala |
| Lys | Thr | Lys | Pro<br>100 | Val | Ala | Phe | Ala | Val<br>105 | Arg | Thr | Asn | Val | Gly<br>110 | Tyr | Asn |
| Pro | Ser | Pro<br>115 | Gly | Asp | Glu | Val | Pro<br>120 | Val | Gln | Gly | Val | Ala<br>125 | Ile | Thr | Phe |
| Glu | Pro<br>130 | Lys | Asp | Phe | Leu | His<br>135 | Ile | Lys | Glu | Lys | Tyr<br>140 | Asn | Asn | Asp | Trp |
| Trp | Ile<br>145 | Gly | Arg | Leu | Val | Lys<br>150 | Glu | Gly | Cys | Glu | Val<br>155 | Gly | Phe | Ile | Pro<br>160 |
| Ser | Pro | Val | Lys | Leu<br>165 | Asp | Ser | Leu | Arg | Leu<br>170 | Leu | Gln | Glu | Gln | Lys<br>175 | Leu |
| Arg | Gln | Asn | Arg<br>180 | Leu | Gly | Ser | Ser | Lys<br>185 | Ser | Gly | Asp | Asn | Ser<br>190 | Ser | Ser |
| Ser | Leu | Gly<br>195 | Asp | Val | Val | Thr | Gly<br>200 | Thr | Arg | Arg | Pro | Thr<br>205 | Pro | Pro | Ala |
| Ser | Asp | Arg | Ala | Cys | Ala | Pro | Leu |   |   |   |   |   |   |   |   |

( 2 ) INFORMATION FOR SEQ ID NO:40:

( i ) SEQUENCE CHARACTERISTICS:
    ( A ) LENGTH: 219 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( i x ) FEATURE:
    ( D ) OTHER INFORMATION: /standard_name= "Beta1-5"

( x i ) SEQUENCE DESCRIPTION: SEQ ID NO:40:

```
Met Val Gln Lys Thr Ser Met Ser Arg Gly Pro Tyr Pro Pro Ser Gln
 1               5                  10                  15
Glu Ile Pro Met Glu Val Phe Asp Pro Ser Pro Gln Gly Lys Tyr Ser
            20                  25                  30
Lys Arg Lys Gly Arg Phe Lys Arg Ser Asp Gly Ser Thr Ser Ser Asp
        35                  40                  45
Thr Thr Ser Asn Ser Phe Val Arg Gln Gly Ser Ala Glu Ser Tyr Thr
    50                  55                  60
Ser Arg Pro Ser Asp Ser Asp Val Ser Leu Glu Glu Asp Arg Glu Ala
65                  70                  75                  80
Leu Arg Lys Glu Ala Glu Arg Gln Ala Leu Ala Gln Leu Glu Lys Ala
            85                  90                  95
Lys Thr Lys Pro Val Ala Phe Ala Val Arg Thr Asn Val Gly Tyr Asn
            100                 105                 110
Pro Ser Pro Gly Asp Glu Val Pro Val Gln Gly Val Ala Ile Thr Phe
        115                 120                 125
Glu Pro Lys Asp Phe Leu His Ile Lys Glu Lys Tyr Asn Asn Asp Trp
    130                 135                 140
Trp Ile Gly Arg Leu Val Lys Glu Gly Cys Glu Val Gly Phe Ile Pro
145                 150                 155                 160
Ser Pro Val Lys Leu Asp Ser Leu Arg Leu Leu Gln Glu Gln Lys Leu
            165                 170                 175
Arg Gln Asn Arg Leu Gly Ser Ser Lys Ser Gly Asp Asn Ser Ser Ser
            180                 185                 190
Ser Leu Gly Asp Val Val Thr Gly Thr Arg Arg Pro Thr Pro Pro Ala
        195                 200                 205
Ser Gly Tyr Arg His Asp Ala Glu Ser Phe Ile
    210                 215
```

DNA ENCODING HUMAN CALCIUM CHANNEL $\alpha_{1A}$, $\beta_1$, $\beta_2$, AND $\beta_4$ SUBUNITS, AND ASSAYS USING CELLS THAT EXPRESS THE SUBUNITS This application is a continuation-in-part of U.S. application Ser. No. 08/105,536, filed Aug. 11, 1993, which is a continuation-in-part of International PCT Application Ser. No. PCT/US92/06903, filed Aug. 14, 1992, which is a continuation-in-part of U.S. application Ser. No. 07/868,354, filed Apr. 10, 1992 now abandoned, which is a continuation-in-part of U.S. application Ser. No. 07/745,206, filed Aug. 15, 1991, U.S. Pat. No. 5,429,921 which is a continuation-in-part of U.S. application Ser. No. 07/620,250, filed Nov. 30, 1990, now abandoned, which is a continuation-in-part of U.S. application Ser. No. 07/176,899, filed April 4, 1988, now abandoned. This application is also a continuation-in-part of U.S. Ser. No. 07/482,384, filed Feb. 20, 1990 now U.S. Pat. No. 5,386,025. This application is also a continuation-in-part of U.S. Ser. No. 07/914,231, filed Jul. 13, 1992, now U.S. Pat. No. 5,402,820 which in turn is a continuation of U.S. Ser. No. 07/603,751, filed Nov. 8, 1990, now abandoned, which was filed as application Ser. No. PCT/U.S.89/01408, on Apr. 4, 1989.

The subject matter of each of U.S. application Ser. No. 08/105,536, International PCT application Ser. No. PCT/92/06903, U.S. Ser. No. 07/914,231, U.S. application Ser. No. 07/868,354, U.S. application Ser. No. 07/745,206 U.S. application Ser. No. 07/620,250, U.S. application Ser. No. 07/603,751, U.S. application Ser. No. 07/482,384, U.S. application Ser. No. 07/176,899 and International application Ser. No. PCT/U.S.89/01408 is incorporated herein in its entirety.

TECHNICAL FIELD

The present invention relates to molecular biology and pharmacology. More particularly, the invention relates to calcium channel compositions and methods of making and using the same.

BACKGROUND OF THE INVENTION

Calcium channels are membrane-spanning, multi-subunit proteins that allow controlled entry of $Ca^{2+}$ ions into cells from the extracellular fluid. Cells throughout the animal kingdom, and at least some bacterial, fungal and plant cells, possess one or more types of calcium channel.

The most common type of calcium channel is voltage dependent. "Opening" of a voltage-dependent channel to allow an influx of $Ca^{2+}$ ions into the cells requires a depolarization to a certain level of the potential difference between the inside of the cell bearing the channel and the extracellular medium bathing the cell. The rate of influx of $Ca^{2+}$ into the cell depends on this potential difference. All "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels.

Multiple types of calcium channels have been identified in mammalian cells from various tissues, including skeletal muscle, cardiac muscle, lung, smooth muscle and brain, [see, e.g., Bean, B. P.(1989) *Ann. Rev. Physiol.* 51:367–384 and Hess, P. (1990) *Ann. Rev. Neurosci.* 56:337]. The different types of calcium channels have been broadly categorized into four classes, L-, T-, N-, and P-type, distinguished by current kinetics, holding potential sensitivity and sensitivity to calcium channel agonists and antagonists.

Calcium channels are multisubunit proteins. For example, rabbit skeletal muscle calcium channel contains two large subunits, designated $\alpha_1$ and $\alpha_2$, which have molecular weights between about 130 and about 200 kilodaltons ("kD"), and one to three different smaller subunits of less than about 60 kD in molecular weight. At least one of the larger subunits and possibly some of the smaller subunits are glycosylated. Some of the subunits are capable of being phosphorylated. The $\alpha_1$ subunit has a molecular weight of about 150 to about 170 kD when analyzed by sodium dodecylsulfate (SDS)-polyacrylamide gel electrophoresis (PAGE) after isolation from mammalian muscle tissue and has specific binding sites for various 1,4-dihydropyridines (DHPs) and phenylalkylamines. Under non-reducing conditions (in the presence of N-ethylmaleimide), the $\alpha_2$ subunit migrates in SDS-PAGE as a band corresponding to a molecular weight of about 160–190 kD. Upon reduction, a large fragment and smaller fragments are released. The $\beta$ subunit of the rabbit skeletal muscle calcium channel is a phosphorylated protein that has a molecular weight of 52–65 kD as determined by SDS-PAGE analysis. This subunit is insensitive to reducing conditions. The $\gamma$ subunit of the calcium channel, which is not observed in all purified preparations, appears to be a glycoprotein with an apparent molecular weight of 30–33 kD, as determined by SDS-PAGE analysis.

In order to study calcium channel structure and function, large amounts of pure channel protein are needed. Because of the complex nature of these multisubunit proteins, the varying concentrations of calcium channels in tissue sources of the protein, the presence of mixed populations of calcium channels in tissues, difficulties in obtaining tissues of interest, and the modifications of the native protein that can occur during the isolation procedure, it is extremely difficult to obtain large amounts of highly purified, completely intact calcium channel protein.

Characterization of a particular type of calcium channel by analysis of whole cells is severely restricted by the presence of mixed populations of different types of calcium channels in the majority of cells. Single-channel recording methods that are used to examine individual calcium channels do not reveal any information regarding the molecular structure or biochemical composition of the channel. Furthermore, in performing this type of analysis, the channel is isolated from other cellular constituents that might be important for natural functions and pharmacological interactions.

Characterization of the gene or genes encoding calcium channels provides another means of characterization of different types of calcium channels. The amino acid sequence determined from a complete nucleotide sequence of the coding region of a gene encoding a calcium channel protein represents the primary structure of the protein. Furthermore, secondary structure of the calcium channel protein and the relationship of the protein to the membrane may be predicted based on analysis of the primary structure. For instance, hydropathy plots of the $\alpha_1$ subunit protein of the rabbit skeletal muscle calcium channel indicate that it contains four internal repeats, each containing six putative transmembrane regions [Tanabe, T. et al. (1987) *Nature* 328:313].

The cDNA and corresponding amino acid sequences of the $\alpha_1$, $\alpha_2$, $\beta$ and $\gamma$ subunits of the rabbit skeletal muscle calcium channel [see, Tanabe et al. (1987) *Nature* 328:313–318; published International Application No. WO 89/09834, which is the same as U.S. application Ser. No. 07/603,751, abandoned which is a continuation-in-part of U.S. application Ser. No. 07/176,899, abandoned; Ruth et al. (1989) *Science* 245:1115–1118; and U.S. patent application Ser. No. 482,384, filed Feb. 20, 1990] have been determined. The cDNA and corresponding amino acid sequences of $\alpha_1$ subunits of rabbit cardiac muscle [Mikami, A. et al. (1989) *Nature* 340:230–233] and lung [Biel, M. (1990) *FEBS Letters* 269:409–412] calcium channels have been determined.

In addition, a cDNA clone encoding a rabbit brain calcium channel (designated the BI channel) has been isolated [Mori, Y. et al. (1991) *Nature* 350:398–402]. Partial cDNA clones encoding portions of several different subtypes, referred to as rat brain class A, B, C and D, of the calcium channel $\alpha_1$ subunit have been isolated from rat brain cDNA libraries [Snutch, T. et al. (1990) *Proc. Natl. Acad. Sci. USA* 87:3391–3395]. More recently full-length rat brain class A [Starr, T. et al. (1991) *Proc. Natl. Acad. Sci. USA* 88:5621–5625] and class C [Snutch, T. et al. (1991) *Neuron* 7:45–57] cDNA clones have been isolated. Although the amino acid sequence encoded by the rat brain class C DNA is approximately 95% identical to that encoded by the rabbit cardiac muscle calcium channel $\alpha_1$ subunit-encoding DNA, the amino acid sequence encoded by the rat brain class A DNA shares only 33% sequence identity with the amino acid sequence encoded by the rabbit skeletal or cardiac muscle $\alpha_1$ subunit-encoding DNA. A cDNA clone encoding another rat brain calcium channel $\alpha_1$ subunit has also been obtained [Hui, A. et al. (1991) *Neuron* 7:35–44]. The amino acid sequence encoded by this clone is ~70% homologous to the proteins encoded by the rabbit skeletal and cardiac muscle calcium channel DNA. A cDNA clone closely related to the rat brain class C $\alpha_1$ subunit-encoding cDNA and sequences of partial cDNA clones closely related to other partial cDNA clones encoding apparently different calcium channel $\alpha_1$ subunits have also been isolated [see Snutch, T. et al. (1991) *Neuron* 7:45–57; Perez-Reyes, E. et al. (1990) *J. Biol. Chem.* 265:20430; and Hui, A. et al. (1991) *Neuron* 7:35–44]. DNA clones encoding other calcium channels have also been identified and isolated.

Expression of cDNA encoding calcium channel subunits has been achieved with several of the different rabbit or rat $\alpha_1$ subunit cDNA clones discussed above. Voltage-dependent calcium currents have been detected in murine L cells transfected with DNA encoding the rabbit skeletal muscle calcium channel $\alpha_1$ subunit [Perez-Reyes et al. (1989) *Nature* 340:233–236 (1989)]. These currents were enhanced in the presence of the calcium channel agonist Bay K 8644. Bay K 8644-sensitive $Ba^{2+}$ currents have been detected in oöcytes injected with in vitro transcripts of the rabbit cardiac muscle calcium channel $\alpha_1$ subunit cDNA [Mikami, A. et al. (1989) *Nature* 340:230–233]. These currents were substantially reduced in the presence of the calcium channel antagonist nifedipine. Barium currents of an oöcyte co-injected with RNA encoding the rabbit cardiac muscle calcium channel $\alpha_1$ subunit and the RNA encoding the rabbit skeletal muscle calcium channel $\alpha_2$ subunit were more than 2-fold larger than those of oöcytes injected with transcripts of the rabbit cardiac calcium channel $\alpha_1$ subunit-encoding cDNA. Similar results were obtained when oöcytes were co-injected with RNA encoding the rabbit lung calcium channel $\alpha_1$ subunit and the rabbit skeletal muscle calcium channel $\alpha_2$ subunit. The barium current was greater than that detected in oöcytes injected only with RNA encoding the rabbit lung calcium channel $\alpha_1$ subunit [Biel, M. et al. (1990) *FEBS Letters* 269:409–412]. Inward barium currents have been detected in oöcytes injected with in vitro RNA transcripts encoding the rabbit brain BI channel [Mori et al. (1991) *Nature* 350:398–402]. These currents were increased by two orders of magnitude when in vitro transcripts of the rabbit skeletal muscle calcium channel $\alpha_2$, $\beta$, or $\alpha_2$, $\beta$ and $\gamma$ subunits were co-injected with transcripts of the BI-encoding cDNA. Barium currents in oöcytes co-injected with transcripts encoding the BI channel and the rabbit skeletal muscle calcium channel $\alpha_2$ and $\beta$ were unaffected by the calcium channel antagonists nifedipine or $\omega$-CgTx and inhibited by Bay K 8644 and crude venom from Agelenopsis aperta.

The results of studies of recombinant expression of rabbit calcium channel $\alpha_1$ subunit-encoding cDNA clones and transcripts of the cDNA clones indicate that the $\alpha_1$ subunit forms the pore through which calcium enters cells. The relevance of the barium currents generated in these recombinant cells to the actual current generated by calcium channels containing as one component the respective $\alpha_1$ subunits in vivo is unclear. In order to completely and accurately characterize and evaluate different calcium channel types, however, it is essential to examine the functional properties of recombinant channels containing all of the subunits as found in vivo.

Although there has been limited success in expressing DNA encoding rabbit and rat calcium channel subunits, far less has been achieved with respect to human calcium channels. Little is known about human calcium channel structure and function and gene expression. An understanding of the structure and function of human calcium channels would permit identification of substances that, in some manner, modulate the activity of calcium channels and that have potential for use in treating such disorders.

Because calcium channels are present in various tissues and have a central role in regulating intracellular calcium ion concentrations, they are implicated in a number of vital processes in animals, including neurotransmitter release, muscle contraction, pacemaker activity, and secretion of hormones and other substances. These processes appear to be involved in numerous human disorders, such as CNS and cardiovascular diseases. Calcium channels, thus, are also implicated in numerous disorders. A number of compounds useful for treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{2+}$ into the cells in response to depolarization of the cell membrane.

An understanding of the pharmacology of compounds that interact with calcium channels in other organ systems, such as the CNS, may aid in the rational design of compounds that specifically interact with subtypes of human calcium channels to have desired therapeutic effects, such as in the treatment of neurodegenerative and cardiovascular disorders. Such understanding and the ability to rationally design therapeutically effective compounds, however, have been hampered by an inability to independently determine the types of human calcium channels and the molecular nature of individual subtypes, particularly in the CNS, and by the unavailability of pure preparations of specific channel subtypes to use for evaluation of the specificity of calcium channel-effecting compounds. Thus, identification of DNA encoding human calcium channel subunits and the use of such DNA for expression of calcium channel subunits and functional calcium channels would aid in screening and designing therapeutically effective compounds.

Therefore, it is an object herein, to provide DNA encoding specific calcium channel subunits and to provide eukaryotic cells bearing recombinant tissue-specific or subtype-specific calcium channels. It is also an object to provide assays for identification of potentially therapeutic compounds that act as calcium channel antagonists and agonists.

SUMMARY OF THE INVENTION

Isolated and purified DNA fragments that encode human calcium channel subunits are provided. DNA encoding $\alpha_1$ subunits of a human calcium channel, and RNA, encoding such subunits, made upon transcription of such DNA are provided. In particular, DNA fragments encoding $\alpha_1$ subunits of voltage-dependent human calcium channels (VDCCs) type A, type B (also referred to as VDCC IV), type C (also referred to as VDCC II) type D (also referred to as VDCC III) and type E are provided.

DNA encoding $\alpha_{1A}$, $\alpha_{1B}$, $\alpha_{1C}$, $\alpha_{1D}$ and $\alpha_{1E}$ subunits is provided. DNA encoding an $\alpha_{1D}$ subunit that includes the amino acids substantially as set forth as residues 10–2161 of SEQ ID No. 1 is provided. DNA encoding an $\alpha_{1D}$ subunit that includes substantially the amino acids set forth as amino acids 1–34 in SEQ ID No. 2 in place of amino acids 373–406 of SEQ ID No. 1 is also provided. DNA encoding an $\alpha_{1C}$ subunit that includes the amino acids substantially as set forth in SEQ ID No. 3 or SEQ ID No. 6 and DNA encoding an $\alpha_{1B}$ subunit that includes an amino acid sequence substantially as set forth in SEQ ID No. 7 or in SEQ ID No. 8 is also provided.

DNA encoding $\alpha_{1A}$ subunits is also provided. Such DNA includes DNA encoding an $\alpha_{1A}$ subunit that has substantially the same sequence of amino acids as that set forth in SEQ ID No. 22 or No. 23 or other splice variants of $\alpha_{1A}$ that include all or part of the sequence set forth in SEQ ID No. 22 or 23. The sequence set forth in SEQ ID NO. 22 is a splice variant designated $\alpha_{1A-1}$; and the sequence set forth in SEQ ID NO. 23 is a splice variant designated $\alpha_{1A-2}$. $\alpha_{1A}$ subunits also include subunits that can be isolated using all or a portion of the DNA having SEQ ID NO. 21, 22 or 23 or DNA obtained from the phage lysate of an *E. coli* host containing DNA encoding an $\alpha_{1A}$ subunit that has been deposited in the American Type Culture Collection, 12301 Parklawn Drive, Rockville, Md. 20852 U.S.A. under Accession No. 75293 in accord with the Budapest Treaty. The DNA in such phage includes a DNA fragment having the sequence set forth in SEQ ID No. 21. This fragment selectively hybridizes under conditions of high stringency to DNA encoding $\alpha_{1A}$ but not to DNA encoding $\alpha_{1B}$ and, thus, can be used to isolate DNA that encodes $\alpha_{1A}$ subunits.

DNA encoding $\alpha_{1E}$ subunits of a human calcium channel is also provided. This DNA includes DNA that encodes an $\alpha_{1E}$ splice variant designated $\alpha_{1E-1}$ encoded by the DNA set forth in SEQ ID No. 24, and a variant designated $\alpha_{1E-3}$ encoded by SEQ. ID No. 24 with the fragment set forth in SEQ ID No. 25 inserted between nucleotides 2405 and 2406. This DNA also includes other splice variants thereof that include sequences of amino acids encoded by all or a portion of the sequences of nucleotides set forth in SEQ ID Nos. 24 and 25 and DNA that hybridizes under conditions of high stringency to the DNA of SEQ ID. No. 24 or 25 and that encodes an $\alpha_{1E}$ splice variant.

DNA encoding $\alpha_2$ subunits of a human calcium channel, and RNA encoding such subunits, made upon transcription of such a DNA are provided. DNA encoding splice variants of the $\alpha_2$ subunit, including tissue specific splice variants, are also provided. In particular, DNA encoding the $\alpha_{2a}$–$\alpha_{2e}$ subunit subtypes is provided. In particularly preferred embodiments, the DNA encoding the $\alpha_2$ subunit is produced by alternative processing of a primary transcript that includes DNA encoding the amino acids set forth in SEQ ID 11 and the DNA of SEQ ID No. 13 inserted between nucleotides 1624 and 1625 of SEQ ID No. 11.

Isolated and purified DNA fragments encoding human calcium channel $\beta$ subunits, including DNA encoding $\beta_1$, $\beta_2$, $\beta_3$ and $\beta_4$ subunits, and splice variants of the $\beta$ subunits are provided. RNA encoding $\beta$ subunits, made upon transcription of the DNA is also provided. In particular, DNA encoding the $\beta_1$, $\beta_2$ and $\beta_3$ subunits, including the $\beta_1$ subunit splice variants $\beta_{1-1}$–$\beta_{1-5}$, described below, the $\beta_2$ subunit splice variants $\beta_{2A}$–$\beta_{2F}$, that include all or a portion of SEQ ID No. 26, $\beta_3$ subunit splice variants, including $\beta_3$ subunits that have the sequences set forth in SEQ ID Nos 19 and 20, and DNA encoding the $\beta_4$ subunit that includes the DNA having the sequence set forth in SEQ ID No. 27 is provided. The sequence of amino acids encoded by the open reading frame of SEQ ID No. 27 is set forth in SEQ ID No. 28.

Also *Escherichia coli* (*E. coli*) host cells harboring plasmids containing DNA encoding $\beta_3$ have been deposited in accord with the Budapest Treaty under Accession No. 69048 at the American Type Culture Collection. The deposited clone encompasses nucleotides 122–457 in SEQ ID No. 19 and 107–443 in SEQ ID No. 20.

DNA encoding $\beta$ subunits that are produced by alternative processing of a primary transcript encoding a $\beta$ subunit, including a transcript that includes DNA encoding the amino acids set forth in SEQ ID No. 9 or including a primary transcript that encodes $\beta_3$ as deposited under ATCC Accession No. 69048, but lacking and including alternative exons are provided or may be constructed from the DNA provided herein. For example, DNA encoding a $\beta_1$ subunit that is produced by alternative processing of a primary transcript that includes DNA encoding the amino acids set forth in SEQ ID No. 9, but including the DNA set forth in SEQ ID No. 12 inserted in place of nucleotides 615–781 of SEQ ID No. 9 is also provided. DNA encoding $\beta_1$ subunits that are encoded by transcripts that have the sequence set forth in SEQ ID No. 9 including the DNA set forth in SEQ ID No. 12 inserted in place of nucleotides 615–781 of SEQ ID No. 9, but that lack one or more of the following sequences of nucleotides: nucleotides 14–34 of SEQ ID No. 12, nucleotides 13–34 of SEQ ID No. 12, nucleotides 35–55 of SEQ ID No 12, nucleotides 56–190 of SEQ ID No. 12 and nucleotides 191–271 of SEQ ID No. 12 are also provided.

DNA encoding $\gamma$ subunits of human calcium channels is also provided. RNA, encoding $\gamma$ subunits, made upon transcription of the DNA are also provided. In particular, DNA containing the sequence of nucleotides set forth in SEQ ID No. 14 is provided.

Full-length DNA clones and corresponding RNA transcripts, encoding the $\alpha_1$, including splice variants of $\alpha_{1A}$, $\alpha_{1D}$, $\alpha_{1B}$, and $\alpha_{1E}$, $\alpha_2$ and $\beta$ subunits, including $\beta_{1-1}$–$\beta_{1-5}$ and $\beta_{2D}$ of human calcium channels are provided. Also provided are DNA clones encoding substantial portions of the $\alpha_{1C}$, $\beta_4$ and $\gamma$ subunits of voltage-dependent human calcium channels for the preparation of full-length DNA clones encoding the corresponding full-length subunits.

Eukaryotic cells containing heterologous DNA encoding one or more calcium channel subunits, particularly human calcium channel subunits, or containing RNA transcripts of DNA clones encoding one or more of the subunits are provided. In preferred embodiments, the cells contain DNA or RNA encoding a human $\alpha_1$ subunit, preferably at least an $\alpha_{1D}$, $\alpha_{1B}$ or $\alpha_{1E}$ subunit. In more preferred embodiments, the cells contain DNA or RNA encoding additional heterologous subunits, including at least one $\beta$, $\alpha_2$ or $\gamma$ subunits. In such embodiments, eukaryotic cells stably or transiently transfected with any combination of one, two, three or four of the subunit-encoding DNA clones, such as DNA encoding any of $\alpha_1$, $\alpha_1+\beta$, $\alpha_1+\beta+\alpha_2$, are provided.

In preferred embodiments, the cells express such heterologous calcium channel subunits and include one or more of the subunits in membrane spanning heterologous calcium channels. In more preferred embodiments, the eukaryotic cells express functional, heterologous calcium channels that are capable of gating the passage of calcium channel selective ions and/or binding compounds that, at physiological concentrations, modulate the activity of the heterologous calcium channel. In certain embodiments, the heterologous calcium channels include at least one heterologous calcium channel subunit. In most preferred embodiments, the calcium channels that are expressed on the surface of the eukaryotic cells are composed substantially or entirely of subunits encoded by the heterologous DNA or RNA. In preferred embodiments, the heterologous calcium channels of such cells are distinguishable from any endogenous calcium channels of the host cell. Such cells provide a means to obtain homogeneous populations of calcium channels.

In certain embodiments the recombinant eukaryotic cells that contain the heterologous DNA encoding the calcium channel subunits are produced by transfection with DNA encoding one or more of the subunits or are injected with RNA transcripts of DNA encoding one or more of the calcium channel subunits. The DNA may be introduced as a linear DNA fragment or may be included in an expression vector for stable or transient expression of the subunit-encoding DNA. Vectors containing DNA encoding human calcium channel subunits are also provided.

The eukaryotic cells that express heterologous calcium channels may be used in assays for calcium channel function or, in the case of cells transformed with fewer subunit-encoding nucleic acids than necessary to constitute a functional recombinant human calcium channel, such cells may be used to assess the effects of additional subunits on calcium channel activity. The additional subunits can be provided by subsequently transfecting such a cell with one or more DNA clones or RNA transcripts encoding human calcium channel subunits.

The recombinant eukaryotic cells that express membrane spanning heterologous calcium channels may be used in methods for identifying compounds that modulate calcium channel activity. In particular, the cells are used in assays that identify agonists and antagonists of calcium channel activity in humans and/or assessing the contribution of the various calcium channel subunits to the transport and regulation of transport of calcium ions. Because the cells constitute homogeneous populations of calcium channels, they provide a means to identify agonists or antagonists of calcium channel activity that are specific for each such population.

The assays that use the eukaryotic cells for identifying compounds that modulate calcium channel activity are also provided. In practicing these assays the eukaryotic cell that expresses a heterologous calcium channel, containing at least on subunit encoded by the DNA provided herein, is in a solution containing a test compound and a calcium channel selective ion, the cell membrane is depolarized, and current flowing into said cell is detected. The current that is detected is different from that produced by depolarizing the same or a substantially identical cell in the presence of the same calcium channel selective ion but in the absence of said compound. In preferred embodiments, prior to the depolarization step, the cell is maintained at a holding potential which substantially inactivates calcium channels which are endogenous to said cell. Also in preferred embodiments, the cells are mammalian cells, most preferably HEK cells, or amphibian oöcytes.

Nucleic acid probes containing at least about 14 contiguous nucleotides of $\alpha_{1D}$, $\alpha_{1C}$, $\alpha_{1B}$, $\alpha_{1A}$ and $\alpha_{1E}$, $\alpha_2$, $\beta$, including $\beta_1$ and $\beta_2$ splice variants and $\beta_3$, and $\gamma$ subunit-encoding DNA are provided. Methods using the probes for the isolation and cloning of calcium channel subunit-encoding DNA, including splice variants within tissues and inter-tissue variants are also provided.

Purified human calcium channel subunits and purified human calcium channels are provided. The subunits and channels can be isolated from a eukaryotic cell transfected with DNA that encodes the subunit.

In another embodiment, immunoglobulins or antibodies obtained from the serum of an animal immunized with a substantially pure preparation of a human calcium channel, human calcium channel subunit or epitope-containing fragment of a human calcium subunit are provided. Monoclonal antibodies produced using a human calcium channel, human calcium channel subunit or epitope-containing fragment thereof as an immunogen are also provided. *E. coli* fusion proteins including a fragment of a human calcium channel subunit may also be used as immunogen. Such fusion proteins may contain a bacterial protein or portion thereof, such as the *E. coli* TrpE protein, fused to a calcium channel subunit peptide. The immunoglobulins that are produced using the calcium channel subunits or purified calcium channels as immunogens have, among other properties, the ability to specifically and preferentially bind to and/or cause the immunoprecipitation of a human calcium channel or a subunit thereof which may be present in a biological sample or a solution derived from such a biological sample. Such antibodies may also be used to selectively isolate cells that express calcium channels that contain the subunit for which the antibodies are specific.

A diagnostic method for determining the presence of Lambert Eaton Syndrome (LES) in a human based on immunological reactivity of LES immunoglobulin G (IgG) with a human calcium channel subunit or a eukaryotic cell which expresses a recombinant human calcium channel or a subunit thereof is also provided. In particular, an immunoassay method for diagnosing Lambert-Eaton Syndrome in a person by combining serum or an IgG fraction from the person (test serum) with calcium channel proteins, including the a and $\beta$ subunits, and ascertaining whether antibodies in the test serum react with one or more of the subunits, or a recombinant cell which expresses one or more of the subunits to a greater extent than antibodies in control serum, obtained from a person or group of persons known to be free of the Syndrome, is provided. Any immunoassay procedure known in the art for detecting antibodies against a given antigen in serum can be employed in the method.

DETAILED DESCRIPTION OF THE INVENTION

Definitions

Unless defined otherwise, all technical and scientific terms used herein have the same meaning as is commonly understood by one of skill in the art to which this invention belongs. All patents and publications referred to herein are incorporated by reference herein.

Reference to each of the calcium channel subunits includes the subunits that are specifically disclosed herein and human calcium channel subunits encoded by DNA that can be isolated by using the DNA disclosed as probes and screening an appropriate human cDNA or genomic library under at least low stringency. Such DNA also includes DNA that encodes proteins that have about 40% homology to any of the subunits proteins described herein or DNA that hybridizes under conditions of at least low stringency to the DNA provided herein and the protein encoded by such DNA exhibits additional identifying characteristics, such as function or molecular weight.

It is understood that subunits that are encoded by transcripts that represent splice variants of the disclosed subunits or other such subunits may exhibit less than 40% overall homology to any single subunit, but will include regions of such homology to one or more such subunits. It is also understood that 40% homology refers to proteins that share approximately 40% of their amino acids in common or that share somewhat less, but include conservative amino acid substitutions, whereby the activity of the protein is not substantially altered.

As used herein, the $\alpha_1$ subunits types, encoded by different genes, are designated as type $\alpha_{1A}$, $\alpha_{1B}$, $\alpha_{1C}$, $\alpha_{1D}$ and $\alpha_{1E}$. These types have also been referred to as VDCC IV for $\alpha_{1B}$, VDCC II for $\alpha_{1C}$ and VDCC III for $\alpha_{1D}$. Subunit subtypes, which are splice variants, are referred to, for example as $\alpha_{1B-1}$, $\alpha_{1B-2}$, $\alpha_{1C-1}$ etc.

Thus, as used herein, DNA encoding the $\alpha_1$ subunit refers to DNA that hybridizes to the DNA provided herein under conditions of at least low stringency or encodes a subunit that has roughly about 40% homology to protein encoded by DNA disclosed herein that encodes an $\alpha_1$ subunit of a human calcium channel. An $\alpha_1$ subunit may be identified by its ability to form a calcium channel. Typically, $\alpha_1$ subunits have molecular weights greater than at least about 120 kD. The activity of a calcium channel may be assessed in vitro by methods known to those of skill in the art, including the electrophysiological and other methods described herein. Typically, $\alpha_1$ subunits include regions to which one or more modulators of calcium channel activity, such as a 1,4 DHP or $\omega$-CgTx, interact directly or indirectly. Types of $\alpha_1$ subunits may be distinguished by any method known to those of skill in the art, including on the basis of binding specificity. For example, it has been found herein that $\alpha_{1B}$ subunits participate in the formation channels that have previously been referred to as N-type channels, $\alpha_{1D}$ subunits participate in the formation of channels that had previously been referred to as L-type channels, and $\alpha_{1A}$ subunits appear to participate in the formation of channels that exhibit characteristics typical of channels that had previously been designated P-type channels. Thus, for example, the activity of channels that contain the $\alpha_{1B}$ subunit are insensitive to 1,4 DHPs; whereas the activity of channels that contain the $\alpha_{1D}$ subunit are modulated or altered by a 1,4 DHP. It is presently preferable to refer to calcium channels based on pharmacological characteristics and current kinetics and to avoid historical designations. Types and subtypes of $\alpha_1$ subunits may be characterized on the basis of the effects of such modulators on the subunit or a channel containing the subunit as well as differences in currents and current kinetics produced by calcium channels containing the subunit.

As used herein, an $\alpha_2$ subunit is encoded by DNA that hybridizes to the DNA provided herein under conditions of low stringency or encodes a protein that has about 40% homology with that disclosed herein. Such DNA encodes a protein that typically has a molecular weight greater than about 120 kD, but does not form a calcium channel in the absence of an $\alpha_1$ subunit, and may alter the activity of a calcium channel that contains an $\alpha_1$ subunit. Subtypes of the $\alpha_2$ subunit that arise as splice variants are designated by lower case letter, such as $\alpha_{2a}$, ... $\alpha_{2e}$. In addition, the $\alpha_2$ subunit and the large fragment produced under reducing conditions appear to be glycosylated with at least N-linked sugars and do not specifically bind to the 1,4-DHPs and phenylalkylamines that specifically bind to the $\alpha_1$ subunit. The smaller fragment, the C-terminal fragment, is referred to as the $\delta$ subunit and includes amino acids from about 946 (SEQ ID No. 11) through about the C-terminus. This fragment may dissociate from the remaining portion of $\alpha_2$ when the $\alpha_2$ subunit is exposed to reducing conditions.

As used herein, a $\beta$ subunit is encoded by DNA that hybridizes to the DNA provided herein under conditions of low stringency or encodes a protein that has about 40% homology with that disclosed herein and is a protein that typically has a molecular weight lower than the a subunits and on the order of about 50–80 kD, does not form a detectable calcium channel in the absence of an $\alpha_1$ subunit, but may alter the activity of a calcium channel that contains an $\alpha_1$ subunit or that contains an $\alpha_1$ and $\alpha_2$ subunit.

Types of the $\beta$ subunit that are encoded by different genes are designated with subscripts, such as $\beta 1$, $\beta_2$, $\beta_3$ and $\beta_4$. Subtypes of $\beta$ subunits that arise as splice variants of a particular type are designated with a numerical subscript referring to the subtype and to the variant. Such subtypes include, but are not limited to the $\beta$ splice variants, including $\beta_{1-1}$–$\beta_{1-5}$ and $\beta$ variants, including $\beta_{2A}$–$\beta_{2E}$.

As used herein, a $\gamma$ subunit is a subunit encoded by DNA disclosed herein as encoding the $\gamma$ subunit and may be isolated and identified using the DNA disclosed herein as a probe by hybridization or other such method known to those of skill in the art, whereby full-length clones encoding a $\gamma$ subunit may be isolated or constructed. A $\gamma$ subunit will be encoded by DNA that hybridizes to the DNA provided herein under conditions of low stringency or exhibits sufficient sequence homology to encode a protein that has about 40% homology with the $\gamma$ subunit described herein.

Thus, one of skill in the art, in light of the disclosure herein, can identify DNA encoding $\alpha_1$, $\alpha_2$, $\beta$, $\delta$ and $\gamma$ calcium channel subunits, including types encoded by different genes and subtypes that represent splice variants. For example, DNA probes based on the DNA disclosed herein may be used to screen an appropriate library, including a genomic or cDNA library, and obtain DNA in one or more clones that includes an open reading fragment that encodes an entire protein. Subsequent to screening an appropriate library with the DNA disclosed herein, the isolated DNA can be examined for the presence of an open reading frame from which the sequence of the encoded protein may be deduced. Determination of the molecular weight and comparison with the sequences herein should reveal the identity of the subunit as an $\alpha_1$, $\alpha_2$ etc. subunit. Functional assays may, if necessary, be used to determine whether the subunit is an $\alpha_1$, $\alpha_2$ subunit or $\beta$ subunit.

For example, DNA encoding an $\alpha_{1A}$ subunit may be isolated by screening an appropriate library with DNA, encoding all or a portion of the human $\alpha_{1A}$ subunit. Such DNA includes the DNA in the phage deposited under ATCC Accession No. 75293 that encodes an $\alpha_1$ subunit. DNA encoding an $\alpha_{1A}$ subunit may obtained from an appropriate library by screening with an oligonucleotide having all or a portion of the sequence set forth in SEQ ID No. 21, 22 and/or 23 or with the DNA in the deposited phage. Alternatively, such DNA may have a sequence that encodes an $\alpha_{1A}$ subunit that is encoded by SEQ ID NO. 22 or 23.

Similarly, DNA encoding $\beta_3$ may be isolated by screening a human cDNA library with DNA probes prepared from the plasmid β1.42 deposited under ATCC Accession No. 69048 or obtained from an appropriate library using probes having sequences prepared according to the sequences set forth in SEQ ID Nos. 19 and/or 20. Also, DNA encoding $\beta_4$ may be isolated by screening a human cDNA library with DNA probes prepared according to DNA set forth in SEQ ID No. 27. Any method known to those of skill in the art for isolation and identification of DNA and preparation of full-length genomic or cDNA clones, including methods exemplified herein, may be used.

The subunit encoded by isolated DNA may be identified by comparison with the DNA and amino acid sequences of the subunits provided herein. Splice variants share extensive regions of homology, but include non-homologous regions, subunits encoded by different genes share a uniform distribution of non-homologous sequences.

As used herein, a splice variant refers to a variant produced by differential processing of a primary transcript of genomic DNA that results in more than one type of mRNA. Splice variants may occur within a single tissue type or among tissues (tissue-specific variants). Thus, cDNA clones that encode calcium channel subunit subtypes that have regions of identical amino acids and regions of different amino acid sequences are referred to herein as "splice variants".

As used herein, a "calcium channel selective ion" is an ion that is capable of flowing through, or being blocked from flowing through, a calcium channel which spans a cellular membrane under conditions which would substantially similarly permit or block the flow of $Ca^{2+}$. $Ba^{2+}$ is an example of an ion which is a calcium channel selective ion.

As used herein, a compound that modulates calcium channel activity is one that affects the ability of the calcium channel to pass calcium channel selective ions or affects other detectable calcium channel features, such as current kinetics. Such compounds include calcium channel antagonists and agonists and compounds that exert their effect on the activity of the calcium channel directly or indirectly.

As used herein, a "substantially pure" subunit or protein is a subunit or protein that is sufficiently free of other polypeptide contaminants to appear homogeneous by SDS-PAGE or to be unambiguously sequenced.

As used herein, selectively hybridize means that a DNA fragment hybridizes to second fragment with sufficient specificity to permit the second fragment to be identified or isolated from among a plurality of fragments. In general, selective hybridization occurs at conditions of high stringency.

As used herein, heterologous or foreign DNA and RNA are used interchangeably and refer to DNA or RNA that does not occur naturally as part of the genome in which it is present or which is found in a location or locations in the genome that differ from that in which it occurs in nature. It is DNA or RNA that is not endogenous to the cell and has been artificially introduced into the cell. Examples of heterologous DNA include, but are not limited to, DNA that encodes a calcium channel subunit and DNA that encodes RNA or proteins that mediate or alter expression of endogenous DNA by affecting transcription, translation, or other regulatable biochemical processes. The cell that expresses the heterologous DNA, such as DNA encoding the calcium channel subunit, may contain DNA encoding the same or different calcium channel subunits. The heterologous DNA need not be expressed and may be introduced in a manner such that it is integrated into the host cell genome or is maintained episomally.

As used herein, operative linkage of heterologous DNA to regulatory and effector sequences of nucleotides, such as promoters, enhancers, transcriptional and translational stop sites, and other signal sequences, refers to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art [see, e.g., Maniatis et al. (1982) *Molecular Cloning*: A Laboratory Manual, Cold Spring Harbor Laboratory Press, Cold Spring Harbor, NY].

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or may integrate into the host cell genome.

As used herein, a promoter region refers to the portion of DNA of a gene that controls transcription of DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, a recombinant eukaryotic cell is a eukaryotic cell that contains heterologous DNA or RNA.

As used herein, a recombinant or heterologous calcium channel refers to a calcium channel that contains one or more subunits that are encoded by heterologous DNA that has been introduced into and expressed in a eukaryotic cells that expresses the recombinant calcium channel. A recombinant calcium channel may also include subunits that are produced by DNA endogenous to the cell. In certain embodiments, the recombinant or heterologous calcium channel may contain only subunits that are encoded by heterologous DNA.

As used herein, "functional" with respect to a recombinant or heterologous calcium channel means that the channel is able to provide for and regulate entry of calcium channel selective ions, including, but not limited to, $Ca^{2+}$ or $Ba^{2+}$, in response to a stimulus and/or bind ligands with affinity for the channel. Preferably such calcium channel activity is distinguishable, such as electrophysiological, pharmacological and other means known to those of skill in the art, from any endogenous calcium channel activity that in the host cell.

As used herein, a peptide having an amino acid sequence substantially as set forth in a particular SEQ ID No. includes peptides that have the same function but may include minor variations in sequence, such as conservative amino acid changes or minor deletions or insertions that do not alter the activity of the peptide. The activity of a calcium channel receptor subunit peptide refers to its ability to form functional calcium channels with other such subunits.

As used herein, a physiological concentration of a compound is that which is necessary and sufficient for a biological process to occur. For example, a physiological concentration of a calcium channel selective ion is a concentration of the calcium channel selective ion necessary and sufficient to provide an inward current when the channels open.

As used herein, activity of a calcium channel refers to the movement of a calcium selective ion through a calcium channel. Such activity may be measured by any method known to those of skill in the art, including, but not limited to, measurement of the amount of current which flows through the recombinant channel in response to a stimulus.

As used herein, a "functional assay" refers to an assay that identifies functional calcium channels. A functional assay, thus, is an assay to assess function.

As understood by those skilled in the art, assay methods for identifying compounds, such as antagonists and agonists, that modulate calcium channel activity, generally requires comparison to a control. One type of a "control" cell or "control" culture is a cell or culture that is treated substantially the same as the cell or culture exposed to the test compound except that the control culture is not exposed to the test compound. Another type of a "control" cell or "control" culture may be a cell or a culture of cells which are identical to the transfected cells except the cells employed for the control culture do not express functional calcium channels. In this situation, the response of test cell to the test compound compared to the response (or lack of response) of the receptor-negative cell to the test compound, when cells or cultures of each type of cell are exposed to substantially the same reaction conditions in the presence of the compound being assayed. For example, in methods that use patch clamp electrophysiological procedures, the same cell can be tested in the presence and absence of the test compound, by changing the external solution bathing the cell as known in the art.

It is also understood that each of the subunits disclosed herein may be modified by making conservative amino acid substitutions and the resulting modified subunits are contemplated herein. Suitable conservative substitutions of amino acids are known to those of skill in this art and may be made generally without altering the biological activity, as defined herein, of the resulting molecule. Such substitutions are preferably, although not exclusively, made in accordance with those set forth in Table 1 as follows:

TABLE 1

| Original residue | Conservative substitution |
|---|---|
| Ala (A) | Gly; Ser |
| Arg (R) | Lys |

TABLE 1-continued

| Original residue | Conservative substitution |
|---|---|
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

It is also understood that such substitutions can be made empirically,

Identification and isolation of DNA encoding human calcium channel subunits

Methods for identifying and isolating DNA encoding $\alpha_1$, $\alpha_2$, $\beta$ and $\gamma$ subunits of human calcium channels are provided.

Identification and isolation of such DNA may be accomplished by hybridizing, under appropriate conditions, at least low stringency whereby DNA that encodes the desired subunit is isolated, restriction enzyme-digested human DNA with a labeled probe having at least 14 nucleotides and derived from any contiguous portion of DNA having a sequence of nucleotides set forth herein by sequence identification number. Once a hybridizing fragment is identified in the hybridization reaction, it can be cloned employing standard cloning techniques known to those of skill in the art. Full-length clones may be identified by the presence of a complete open reading frame and the identity of the encoded protein verified by sequence comparison with the subunits provided herein and by functional assays to assess calcium channel forming ability or other function. This method can be used to identify genomic DNA encoding the subunit or cDNA encoding splice variants of human calcium channel subunits generated by alternative splicing of the primary transcript of genomic subunit DNA. For instance, DNA, cDNA or genomic DNA, encoding a calcium channel subunit may be identified by hybridization to a DNA probe and characterized by methods known to those of skill in the art, such as restriction mapping and DNA sequencing, and compared to the DNA provided herein in order to identify heterogeneity or divergence in the sequences the DNA. Such sequence differences may indicate that the transcripts from which the cDNA was produced result from alternative splicing of a primary transcript, if the non-homologous and homologous regions are clustered, or from a different gene if the non-homologous regions are distributed throughout the cloned DNA.

Any suitable method for isolating genes using the DNA provided herein may be used. For example, oligonucleotides corresponding to regions of sequence differences have been used to isolate, by hybridization, DNA encoding the full-length splice variant and can be used to isolate genomic clones. A probe, based on a nucleotide sequence disclosed herein, which encodes at least a portion of a subunit of a human calcium channel, such as a tissue-specific exon, may be used as a probe to clone related DNA, to clone a full-length cDNA clone or genomic clone encoding the human calcium channel subunit.

Labeled, including, but not limited to, radioactively or enzymatically labeled, RNA or single-stranded DNA of at least 14 substantially contiguous bases, preferably at least 30 contiguous bases of a nucleic acid which encodes at least a portion of a human calcium channel subunit, the sequence of which nucleic acid corresponds to a segment of a nucleic acid sequence disclosed herein by reference to a SEQ ID No. are provided. Such nucleic acid segments may be used as probes in the methods provided herein for cloning DNA encoding calcium channel subunits. See, generally, Sambrook et al. (1989) *Molecular Cloning*: A Laboratory Manual, 2nd Edition, Cold Spring Harbor Laboratory Press.

In addition, nucleic acid amplification techniques, which are well known in the art, can be used to locate splice variants of calcium channel subunits by employing oligonucleotides based on DNA sequences surrounding the divergent sequence primers for amplifying human RNA or genomic DNA. Size and sequence determinations of the amplification products can reveal splice variants. Furthermore, isolation of human genomic DNA sequences by hybridization can yield DNA containing multiple exons, separated by introns, that correspond to different splice variants of transcripts encoding human calcium channel subunits.

DNA encoding types and subtypes of each of the $\alpha_1$, $\alpha_2$, $\beta$ and $\gamma$ subunit of voltage-dependent human calcium channels has been cloned herein by screening human cDNA libraries prepared from isolated poly A+ mRNA from cell lines or tissue of human origin having such calcium channels. Among the sources of such cells or tissue for obtaining mRNA are human brain tissue or a human cell line of neural origin, such as a neuroblastoma cell line, human skeletal muscle or smooth muscle cells, and the like. Methods of preparing cDNA libraries are well known in the art [see generally Ausubel et al. (1987) *Current Protocols in Molecular Biology*, Wiley-Interscience, New York; and Davis et al. (1986) *Basic Methods in Molecular Biology*, Elsevier Science Publishing Co., New York].

With respect to each of the respective subunits of a human calcium channel ($\alpha_1$, $\alpha_2$, $\beta$ or $\gamma$), once the DNA encoding the channel subunit was identified by a nucleic acid screening method, the isolated clone was used for further screening to identify overlapping clones. Some of the cloned DNA fragments can and have been subcloned into an appropriate vector such as pIBI24/25 (IBI, New Haven, Conn.), M13mp18/19, pGEM4, pGEM3, pGEM7Z, pSP72 and other such vectors known to those of skill in this art, and characterized by DNA sequencing and restriction enzyme mapping. A sequential series of overlapping clones may thus be generated for each of the subunits until a full-length clone can be prepared by methods, known to those of skill in the art, that include identification of translation initiation (start) and translation termination (stop) codons. For expression of the cloned DNA, the 5═ noncoding region and other transcriptional and translational control regions of such a clone may be replaced with an efficient ribosome binding site and other regulatory regions as known in the art. Other modifications of the 5' end, known to those of skill in the art, that may be required to optimize translation and/or transcription efficiency may also be effected, if deemed necessary.

Examples II–VI, below, describe in detail the cloning of each of the various subunits of a human calcium channel as well as subtypes and splice variants, including tissue-specific variants thereof. In the few instances in which partial sequences of a subunit are disclosed, it is well within the skill of the art, in view of the teaching herein, to obtain the corresponding full-length clones and sequence thereof encoding the subunit, subtype or splice variant thereof.

Identification and isolation of DNA encoding α1 subunits

A number of voltage-dependent calcium channel $\alpha_1$ subunit genes, which are expressed in the human CNS and in other tissues, have been identified and have been designated as $\alpha_{1A}$, $\alpha_{1B}$ (or VDCC IV), $\alpha_{1C}$ (or VDCC II), $\alpha_{1D}$ (or VDCC III) and $\alpha_{1E}$. DNA, isolated from a human neuronal cDNA library, that encodes each of the subunit types has been isolated. DNA encoding subtypes of each of the types, which arise as splice variants are also provided. Subtypes are herein designated, for example, as $\alpha_{1B-1}$, $\alpha_{1B-2}$.

The $\alpha_1$ subunits types A B, C, D and E of voltage-dependent calcium channels, and subtypes thereof, differ with respect to sensitivity to known classes of calcium channel agonists and antagonists, such as DHPs, phenylalkylamines, omega conotoxin (ω-CgTx), the funnel web spider toxin ω-Aga-IV, and pyrazonoylguanidines. They also appear to differ in the holding potential and ion the kinetics of currents produced upon depolarization of cell membranes containing calcium channels that include different types of $\alpha_1$ subunits.

DNA that encodes an $\alpha_1$-subunit that binds to at least one compound selected from among dihydropyridines, phenylalkylamines, ω-CgTx, components of funnel web spider toxin, and pyrazonoylguanidines is provided. For example, the $\alpha_{1B}$ subunit provided herein appears to specifically interact with ω-CgTx in N-type channels, and the $\alpha_1$ subunit provided herein specifically interacts with DHPs in L-type channels.

Identification and isolation of DNA encoding the $\alpha_{1D}$ human calcium channel subunit The $\alpha_{1D}$ subunit cDNA has been isolated using fragments of the rabbit skeletal muscle calcium channel $\alpha_1$ subunit cDNA as a probe to screen a cDNA library of a human neuroblastoma cell line, IMR32, to obtain clone α1.36. This clone was used as a probe to screen additional IMR32 cell cDNA libraries to obtain overlapping clones, which were then employed for screening until a sufficient series of clones to span the length of the nucleotide sequence encoding the human $\alpha_{1D}$ subunit were obtained. Full-length clones encoding $\alpha_{1D}$ were constructed by ligating portions of partial $\alpha_{1D}$ clones as described in Example II. SEQ ID No. 1 shows the 7,635 nucleotide sequence of the cDNA encoding the $\alpha_{1D}$ subunit. There is a 6,483 nucleotide sequence reading frame which encodes a sequence of 2,161 amino acids (as set forth in SEQ ID No. 1).

SEQ ID No. 2 provides the sequence of an alternative exon encoding the IS6 transmembrane domain [see Tanabe, T., et al. (1987) *Nature* 328:313–318 for a description of transmembrane domain terminology] of the $\alpha_{1D}$ subunit.

SEQ ID No. 1 also shows the 2,161 amino acid sequence deduced from the human neuronal calcium channel $\alpha_{1D}$ subunit DNA. Based on the amino acid sequence, the $\alpha_{1D}$ protein has a calculated Mr of 245,163. The $\alpha_{1D}$ subunit of the calcium channel contains four putative internal repeated sequence regions. Four internally repeated regions represent 24 putative transmembrane segments, and the amino- and carboxyl-termini extend intracellularly.

The $\alpha_{1D}$ subunit has been shown to mediate DHP-sensitive, high-voltage-activated, long-lasting calcium channel activity. This calcium channel activity was detected when oocytes were co-injected with RNA transcripts encoding an $\alpha_{1D}$ and $\beta_1$ or $\alpha_{1D}$, $\alpha_2$ and $\beta_1$ subunits. This activity was distinguished from $Ba^{2+}$ currents detected when oocytes were injected with RNA transcripts encoding the $\beta_1$ ±$\alpha_2$ subunits. These currents pharmacologically and biophysically resembled $Ca^{2+}$ currents reported for uninjected oocytes.

Identification and isolation DNA encoding the $\alpha_{1A}$ human calcium channel subunit Biological material containing DNA encoding the $\alpha_{1A}$ subunit had been deposited in the American Type Culture Collection, 12301 Parklawn Drive, Rockville, Md. 20852 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of said Treaty and Regulations and otherwise in compliance with the patent laws and regulations of the U.S. of America and all other nations or international organizations in which this application, or an application claiming priority of this application, is filed or in which any patent granted on any such application is granted.

An $\alpha_{1A}$ subunit is encoded by an approximately 3 kb insert in $\lambda$.gt10 phage designated $\alpha$1.254 in *E. coli* host strain NM514. A phage lysate of this material has been deposited as at the American Type Culture Collection under ATCC Accession No. 75293, as described above. DNA encoding $\alpha_{1A}$ may also be identified by screening with a probe prepared from DNA that has SEQ ID No. 21:

5' CTCAGTACCATCTCTGATACCAGCCCCA 3'.

$\alpha_{1A}$ splice variants have been obtained. The sequences of two $\alpha_{1A}$ splice variants, $\alpha_{1a-1}$ and $\alpha_{1a-2}$ are set forth in SEQ. ID Nos. 22 and 23. Other splice variants may be obtained by screening a human library as described above or using all or a portion of the sequences set forth in SEQ ID Nos. 22 and 23.

Identification and isolation of DNA encoding the $\alpha_{1B}$ human calcium channel subunit DNA encoding the $\alpha_{1B}$ subunit was isolated by screening a human basal ganglia cDNA library with fragments of the rabbit skeletal muscle calcium channel $\alpha_1$ subunit-encoding cDNA. A portion of one of the positive clones was used to screen an IMR32 cell cDNA library. Clones that hybridized to the basal ganglia DNA probe were used to further screen an IMR32 cell cDNA library to identify overlapping clones that in turn were used to screen a human hippocampus cDNA library. In this way, a sufficient series of clones to span nearly the entire length of the nucleotide sequence encoding the human $\alpha_{1B}$ subunit was obtained. PCR amplification of specific regions of the IMR32 cell $\alpha_{1B}$ mRNA yielded additional segments of the $\alpha_{1B}$ coding sequence.

A full-length $\alpha_{1B}$ DNA clone was constructed by ligating portions of the partial cDNA clones as described in Example II.C. SEQ ID Nos. 7 and 8 show the nucleotide sequences of DNA clones encoding the $\alpha_{1B}$ subunit as well as the deduced amino acid sequences. The $\alpha_{1B}$ subunit encoded by SEQ ID No. 7 is referred to as the $\alpha_{1B-1}$ subunit to distinguish it from another $\alpha_{1B}$ subunit, $\alpha_{1B-2}$, encoded by the nucleotide sequence shown as SEQ ID No. 8, which is derived from alternative splicing of the $\alpha_{1B}$ subunit transcript.

PCR amplification of IMR32 cell mRNA using oligonucleotide primers designed according to nucleotide sequences within the $\alpha_{1B-1}$-encoding DNA has identified variants of the $\alpha_{1B}$ transcript that appear to be splice variants because they contain divergent coding sequences.

Identification and isolation of DNA encoding the $\alpha_{1C}$ human calcium channel subunit Numerous $\alpha_{1C}$-specific DNA clones were isolated. Characterization of the sequence revealed the $\alpha_{1C}$ coding sequence, the $\alpha_{1C}$ initiation of translation sequence, and an alternatively spliced region of $\alpha_{1C}$. Alternatively spliced variants of the $\alpha_{1C}$ subunit have been identified. SEQ ID No. 3 sets forth DNA encoding an $\alpha_{1C}$ subunit. The DNA sequences set forth in SEQ ID No. 4 and No. 5 encode two possible amino terminal ends of the $\alpha_{1C}$ protein. SEQ ID No. 6 encodes an alternative exon for the IV S3 transmembrane domain.

The isolation and identification of DNA clones encoding portions of the $\alpha_{1C}$ subunit is described in detail in Example II.

Identification and isolation of DNA encoding the $\alpha_{1E}$ human calcium channel subunit DNA encoding $\alpha_{1E}$ human calcium channel subunits have been isolated from an oligo dT-primed human hippocampus library. The resulting clones, which are splice variants, were designated $\alpha_{1E-1}$ and $\alpha_{1E-2}$. The subunit designated $\alpha_{1E-1}$ has the amino acid sequence encoded by the nucleotide sequence set forth in SEQ ID No. 24, and a subunit designated $\alpha_{1E-3}$ has the amino acid sequence set forth by SEQ. ID No. 24 with the fragment encoded by the DNA set forth in SEQ ID No. 25 inserted between nucleotides 2405 and 2406.7.

The $\alpha_{1E}$ subunits provided herein appear to participate in the formation of calcium channels that have properties of high-voltage activated calcium channels and low-voltage activated channels. These channels are rapidly inactivating compared to other high voltage-activated calcium channels. In addition these channels exhibit pharmacological profiles that are similar to voltage-activated channels, but are also sensitive to DHPs and $\omega$-Aga-IVA, which block certain high voltage activated channels. Additional details regarding the electrophysiology and pharmacology of channels containing $\alpha_{1E}$ subunits is provided in Example VII. F.

Identification and isolation of DNA encoding the other $\alpha_1$ human calcium channel subunit types and subtypes DNA encoding other $\alpha_1$ subunits has also been isolated. Additional such subunits may also be isolated and identified using the DNA provided herein as described for the $\alpha_{1B}, \alpha_{1C}$ and $\alpha_{1D}$ subunits or using other methods known to those of skill in the art. In particular, the DNA provided herein may be used to screen appropriate libraries to isolate related DNA. Full-length clones can be constructed using methods, such as those described herein, and the resulting subunits characterized by comparison of their sequences and electrophysiological and pharmacological properties with the subunits exemplified herein.

Identification and isolation DNA encoding a human calcium channel subunits

DNA encoding $\beta_1$

To isolate DNA encoding the $\beta_1$ subunit, a human hippocampus cDNA library was screened by hybridization to a DNA fragment encoding a rabbit skeletal muscle calcium channel $\beta$ subunit. A hybridizing clone was selected and was in turn used to isolate overlapping clones until the overlapping clones encompassing DNA encoding the entire the human calcium channel $\beta$ subunit were isolated and sequenced.

Five alternatively spliced forms of the human calcium channel $\beta_1$ subunit have been identified and DNA encoding a number of forms have been isolated. These forms are designated $\beta_{1-1}$, expressed in skeletal muscle, $\beta_{1-2}$, expressed in the CNS, $\beta_{1-3}$, also expressed in the in the CNS, $\beta_{1-4}$, expressed in aorta tissue and HEK 293 cells, and $\beta_{1-5}$, expressed in HEK 293 cells. A full-length DNA clone encoding the $\beta_{1-2}$ subunit has been constructed. The subunits $\beta_{1-1}, \beta_{1-2}, \beta_{1-4}$ and $\beta_{1-5}$ have been identified by PCR analysis as alternatively spliced forms of the a subunit.

The alternatively spliced variants were identified by comparison of amino acid sequences encoded by the human neuronal and rabbit skeletal muscle calcium channel β subunit-encoding DNA. This comparison revealed a 45-amino acid deletion in the human β subunit compared to the rabbit β subunit. Using DNA from the region as a probe for DNA cloning, as well as PCR analysis and DNA sequencing of this area of sequence divergence, alternatively spliced forms of the human calcium channel β subunit transcript were identified. For example, the sequence of DNA encoding one splice variant $β_{1-2}$ is set forth in SEQ ID No. 9. SEQ ID No. 10 sets forth the sequence of the $β_{1-3}$ subunit (nt 1-1851, including 3' untranslated sequence nt 1795–1851), which is another splice variant of the : subunit primary transcript. $β_{1-2}$ and $β_{1-3}$ are human neuronal β subunits. DNA distinctive for a portion of a β subunit ($β_{1-4}$) of a human aortic calcium channel and also human embryonic kidney (HEK) cells is set forth in SEQ ID No. 12 (nt 1–13 and 191–271). The sequence of DNA encoding a portion of a human calcium channel β subunit expressed in skeletal muscle ($β_{1-1}$) is shown in SEQ ID No. 12 (nt 1–13 and 35–271).

DNA encoding $β_2$

DNA encoding the $β_2$ splice variants has been obtained. These splice variants include $β_{2A}$–$β_{2F}$. Splice variants $β_{2C}$–$β_{2F}$ include all of sequence set forth in SEQ ID No. 26, except for the portion at the 5' end (up to nucleotide 182), which differs among splice variants. The sequence set forth in SEQ ID No. 26 encodes at least about 90% of $β_{2D}$. Additional splice variants may be isolated using the methods described herein and oligonucleotides including all or portions of the DNA set forth in SEQ ID. No. 26 or may be prepared or obtained as described in the Examples.

DNA encoding $β_3$

DNA encoding the $β_3$ subunit and any splice variants thereof may be isolated by screening a library, as described above for the $β_1$ subunit, using DNA probes prepared according to SEQ ID Nos. 19, 20 or using all or a portion of the deposited $β_3$ clone plasmid β1.42 (ATCC Accession No. 69048).

The *E. coli* host containing plasmid β1.42 that includes DNA encoding a $β_3$ subunit has been deposited as ATCC Accession No. 69048 in the American Type Culture Collection, 12301 Parklawn Drive, Rockville, Md. 20852 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of said Treaty and Regulations and otherwise in compliance with the patent laws and regulations of the U.S. of America and all other nations or international organizations in which this application, or an application claiming priority of this application, is filed or in which any patent granted on any such application is granted.

The $β_3$ encoding plasmid is designated β1.42. The plasmid contains a 2.5 kb EcoRI fragment encoding $β_3$ inserted into vector pGem®7zF(+) and has been deposited in *E. coli* host strain DN5α. A partial DNA sequence of the 5' and 3' ends of $β_3$ are set forth in SEQ ID Nos. 19 and 20, respectively.

Identification and isolation DNA encoding the α2 human calcium channel subunit

DNA encoding a human neuronal calcium channel $α_2$ subunit was isolated in a manner substantially similar to that used for isolating DNA encoding an $α_1$ subunit, except that a human genomic DNA library was probed under low and high stringency conditions with a fragment of DNA encoding the rabbit skeletal muscle calcium channel $α_2$ subunit. The fragment included nucleotides having a sequence corresponding to the nucleotide sequence between nucleotides 43 and 272 inclusive of rabbit back skeletal muscle calcium channel $α_2$ subunit cDNA as disclosed in published PCT International Patent Application Publication No. WO 89/09834, which corresponds to U.S. application Ser. No. 07/620,250, now abandoned which is a continuation-in-part of U.S. Ser. No. 176,899, filed Apr. 4, 1988, also abandoned which applications have been incorporated herein by reference.

Example IV describes the isolation of DNA clones encoding α2 subunits of a human calcium channel from a human DNA library using genomic DNA and cDNA clones, identified by hybridization to the genomic DNA, as probes.

SEQ ID No. 11 shows the sequence of DNA encoding an $α_2$ subunit. As described in Example V, PCR analysis of RNA from human skeletal muscle, brain tissue and aorta using oligonucleotide primers specific for a region of the human neuronal $α_2$ subunit cDNA that diverges from the rabbit skeletal muscle calcium channel $α_2$ subunit cDNA identified splice variants of the human calcium channel $α_2$ subunit transcript.

Identification and isolation of DNA encoding γ human calcium channel subunits

DNA encoding a human neuronal calcium channel γ subunit has been isolated as described in detail in Example VI. SEQ ID No. 14 shows the nucleotide sequence at the 3'-end of this DNA which includes a reading frame encoding a sequence of 43 amino acid residues.

Preparation of recombinant eukaryotic cells containing DNA encoding heterologous calcium channel subunits DNA encoding one or more of the calcium channel subunits or a portion of a calcium channel subunit may be introduced into a host cell for expression or replication of the DNA. Such DNA may be introduced using methods described in the following examples or using other procedures well known to those skilled in the art. Incorporation of cloned DNA into a suitable expression vector, transfection of eukaryotic cells with a plasmid vector or a combination of plasmid vectors, each encoding one or more distinct genes or with linear DNA, and selection of transfected cells are also well known in the art [see, e.g., Sambrook et al. (1989) *Molecular Cloning*: A Laboratory Manual, Second Edition, Cold Spring Harbor Laboratory Press]. Cloned full-length DNA encoding any of the subunits of a human calcium channel may be introduced into a plasmid vector for expression in a eukaryotic cell. Such DNA may be genomic DNA or cDNA. Host cells may be transfected with one or a combination of said plasmids, each of which encodes at least one calcium channel subunit. Alternatively, host cells may be transfected with linear DNA using methods well known to those of skill in the art.

While the DNA provided herein may be expressed in any eukaryotic cell, including yeast cells such as *P. pastoris* [see, e.g., Cregg et al. (1987) *Bio/Technology* 5:479], mammalian expression systems for expression of the DNA encoding the human calcium channel subunits provided herein are preferred.

The heterologous DNA may be introduced by any method known to those of skill in the art, such as transfection with a vector encoding the heterologous DNA. Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCMV or pCDNA1, and MMTV promoter-based vectors. DNA encoding the human calcium channel subunits has been inserted in the vector pCDNA1 at a position immediately following the CMV promoter.

Stably or transiently transfected mammalian cells may be prepared by methods known in the art by transfecting cells with an expression vector having a selectable marker gene such as the gene for thymidine kinase, dihydrofolate reductase, neomycin resistance or the like, and, for transient transfection, growing the transfected cells under conditions selective for cells expressing the marker gene. Functional voltage-dependent calcium channels have been produced in HEK 293 cells transfected with a derivative of the vector pCDNA1 that contains DNA encoding a human calcium channel subunit.

The heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Eukaryotic cells in which DNA or RNA may be introduced, include any cells that are transfectable by such DNA or RNA or into which such DNA may be injected. Virtually any eukaryotic cell can serve as a vehicle for heterologous DNA. Preferred cells are those that can also express the DNA and RNA and most preferred cells are those that can form recombinant or heterologous calcium channels that include one or more subunits encoded by the heterologous DNA. Such cells may be identified empirically or selected from among those known to be readily transfected or injected. Preferred cells for introducing DNA include those that can be transiently or stably transfected and include, but are not limited to cells of mammalian origin, such as COS cells, mouse L cells, CHO cells, human embryonic kidney cells, African green monkey cells and other such cells known to those of skill in the art, amphibian cells, such as *Xenopus laevis* oöcytes, or those of yeast such as *Saccharomyces cerevisiae* or *Pichia pastoris*. Preferred cells for expressing injected RNA transcripts include *Xenopus laevis* oöcytes. Cells that are preferred for transfection of DNA are those that can be readily and efficiently transfected. Such cells are known to those of skill in the art or may be empirically identified. Preferred cells include DG44 cells and HEK 293 cells, particularly HEK 293 cells that have been adapted for growth in suspension and that can be frozen in liquid nitrogen and then thawed and regrown. Such HEK 293 cells are described, for example in U.S. Pat. No. 5,024,939 to Gorman [see, also Stillman et al. (1985) *Mol. Cell.Biol.* 5:2051–2060].

The cells may be used as vehicles for replicating heterologous DNA introduced therein or for expressing the heterologous DNA introduced therein. In certain embodiments, the cells are used as vehicles for expressing the heterologous DNA as a means to produce substantially pure human calcium channel subunits or heterologous calcium channels. Host cells containing the heterologous DNA may be cultured under conditions whereby the calcium channels are expressed. The calcium channel subunits may be purified using protein purification methods known to those of skill in the art. For example, antibodies, such as those provided herein, that specifically bind to one or more of the subunits may be used for affinity purification of the subunit or calcium channels containing the subunits.

Substantially pure subunits of a human calcium channel $\alpha_1$ subunits of a human calcium channel, $\alpha_2$ subunits of a human calcium channel, $\beta$ subunits of a human calcium channel and $\gamma$ subunits of a human calcium channel are provided. Substantially pure isolated calcium channels that contain at least one of the human calcium channel subunits are also provided. Substantially pure calcium channels that contain a mixture of one or more subunits encoded by the host cell and one or more subunits encoded by heterologous DNA or RNA that has been introduced into the cell are also provided. Substantially pure subtype- or tissue-type specific calcium channels are also provided.

In other embodiments, eukaryotic cells that contain heterologous DNA encoding at least one of an $\alpha_1$ subunit of a human calcium channel, an $\alpha_2$ subunit of a human calcium channel, a $\beta$ subunit of a human calcium channel and a $\gamma$ subunit of a human calcium channel are provided. In accordance with one preferred embodiment, the heterologous DNA is expressed in the eukaryotic cell and preferably encodes a human calcium channel $\alpha_1$ subunit.

Expression of heterologous calcium channels: electrophysiology and pharmacology

Electrophysiological methods for measuring calcium channel activity are known to those of skill in the art and are exemplified herein. Any such methods may be used in order to detect the formation of functional calcium channels and to characterize the kinetics and other characteristics of the resulting currents. Pharmacological studies may be combined with the electrophysiological measurements in order to further characterize the calcium channels.

With respect to measurement of the activity of functional heterologous calcium channels, preferably, endogenous ion channel activity and, if desired, heterologous channel activity of channels that do not contain the desired subunits, of a host cell can be inhibited to a significant extent by chemical, pharmacological and electrophysiological means, including the use of differential holding potential, to increase the S/N ratio of the measured heterologous calcium channel activity.

Thus, various combinations of subunits encoded by the DNA provided herein are introduced into eukaryotic cells. The resulting cells can be examined to ascertain whether functional channels are expressed and to determine the properties of the channels. In particularly preferred aspects, the eukaryotic cell which contains the heterologous DNA expresses it and forms a recombinant functional calcium channel activity. In more preferred aspects, the recombinant calcium channel activity is readily detectable because it is a type that is absent from the untransfected host cell or is of a magnitude not exhibited in the untransfected cell.

The eukaryotic cells can be transfected with various combinations of the subunit subtypes provided herein. The resulting cells will provide a uniform population of calcium channels for study of calcium channel activity and for use in the drug screening assays provided herein. Experiments that have been performed have demonstrated the inadequacy of prior classification schemes.

Preferred among transfected cells is a recombinant eukaryotic cell with a functional heterologous calcium channel. The recombinant cell can be produced by introduction of and expression of heterologous DNA or RNA transcripts encoding an $\alpha_1$ subunit of a human calcium channel, more preferably also expressing, a heterologous DNA encoding a $\beta$ subunit of a human calcium channel and/or heterologous DNA encoding an $\alpha_2$ subunit of a human calcium channel. Especially preferred is the expression in such a recombinant cell of each of the $\alpha_1$, $\beta$ and $\alpha_2$ subunits encoded by such heterologous DNA or RNA transcripts, and optionally expression of heterologous DNA or an RNA transcript encoding a $\gamma$ subunit of a human calcium channel.

The functional calcium channels may preferably include at least an $\alpha_1$ subunit and a $\beta$ subunit of a human calcium channel. Eukaryotic cells expressing these two subunits and also cells expressing additional subunits, have been prepared by transfection of DNA and by injection of RNA transcripts. Such cells have exhibited voltage-dependent calcium channel activity attributable to calcium channels that contain one or more of the heterologous human calcium channel subunits. For example, eukaryotic cells expressing heterologous calcium channels containing an $\alpha_2$ subunit in addition to the $\alpha_1$ subunit and a $\beta$ subunit have been shown to exhibit increased calcium selective ion flow across the cellular membrane in response to depolarization, indicating that the $\alpha_2$ subunit may potentiate calcium channel function.

Eukaryotic cells which express heterologous calcium channels containing at least a human $\alpha_1$ subunit, a human $\beta$ subunit and a human $\alpha_2$ subunit are preferred. Eukaryotic cells transformed with a composition containing cDNA or an RNA transcript that encodes an $\alpha_1$ subunit alone or in combination with a $\beta$ and/or an $\alpha_2$ subunit may be used to produce cells that express functional calcium channels. Since recombinant cells expressing human calcium channels containing all of the of the human subunits encoded by the heterologous cDNA or RNA are especially preferred, it is desirable to inject or transfect such host cells with a sufficient concentration of the subunit-encoding nucleic acids to form calcium channels that contain the human subunits encoded by heterologous DNA or RNA. The precise amounts and ratios of DNA or RNA encoding the subunits may be empirically determined and optimized for a particular combination of subunits, cells and assay conditions.

In particular, mammalian cells have been transiently and stably transfected with DNA encoding one or more human calcium channel subunits. Such cells express heterologous calcium channels that exhibit pharmacological and electrophysiological properties characteristic that can be ascribed to human calcium channels. Such cells, however, represent homogeneous populations and the pharmacological and electrophysiological data provides insights into human calcium channel activity heretofore unattainable. For example, HEK cells that have been transiently transfected with DNA encoding the $\alpha_{1E-1}$, $\alpha_{2b}$, and $\beta_{1-3}$ subunits. The resulting cells transiently express these subunits, which form a calcium channels that appear to exhibit properties of L-, N-, T- and P-type channels.

HEK cells that have been transiently transfected with DNA encoding $\alpha_{1B-1}$ $\alpha_{2b}$ and $\beta_{1-2}$ express heterologous calcium channels that exhibit sensitivity to $\omega$-conotoxin and currents typical of N-type channels. It has been found that alteration of the molar ratios of $\alpha_{1B-1}$, $\alpha_{2b}$ and $\beta_{1-2}$ introduced into the cells into to achieve equivalent mRNA levels significantly increased the number of receptors per cell, the current density, and affected the $K_d$ for $\omega$-conotoxin.

The electrophysiology of these channels produced from $\alpha_{1B-1}$ $\alpha_{2b}$, and $\beta_{1-2}$ was compared with channels produced by transiently transfecting HEK cells with DNA encoding $\alpha_{1B-1}$ $\alpha_{2b}$, and $\beta_{1-3}$. The channels exhibited similar voltage dependence of activation, substantially identical voltage dependence, similar kinetics of activation and tail currents that could be fit by a single exponential. The voltage dependence of the kinetics of inactivation was significantly different at all voltages examined.

In certain embodiments, the eukaryotic cell with a heterologous calcium channel is produced by introducing into the cell a first composition, which contains at least one RNA transcript that is translated in the cell into a subunit of a human calcium channel. In preferred embodiments, the subunits that are translated include an $\alpha_1$ subunit of a human calcium channel. More preferably, the composition that is introduced contains an RNA transcript which encodes an $\alpha_1$ subunit of a human calcium channel and also contains (1) an RNA transcript which encodes a $\beta$ subunit of a human calcium channel and/or (2) an RNA transcript which encodes an $\alpha_2$ subunit of a human calcium channel. Especially preferred is the introduction of RNA encoding an $\alpha_1$, a $\beta$ and an $\alpha_2$ human calcium channel subunit, and, optionally, a $\gamma$ subunit of a human calcium channel.

Methods for in vitro transcription of a cloned DNA and injection of the resulting RNA into eukaryotic cells are well known in the art. Transcripts of any of the full-length DNA encoding any of the subunits of a human calcium channel may be injected alone or in combination with other transcripts into eukaryotic cells for expression in the cells. Amphibian oöcytes are particularly preferred for expression of in vitro transcripts of the human calcium channel subunit cDNA clones provided herein. Amphibian oocytes that express functional heterologous calcium channels have been produced by this method.

Assays

Assays for identifying compounds that modulate calcium channel activity

Among the uses for eukaryotic cells which recombinantly express one or more subunits are assays for determining whether a test compound has calcium channel agonist or antagonist activity. These eukaryotic cells may also be used to select from among known calcium channel agonists and antagonists those exhibiting a particular calcium channel subtype specificity and to thereby select compounds that have potential as disease- or tissue-specific therapeutic agents.

In vitro methods for identifying compounds, such as calcium channel agonist and antagonists, that modulate the activity of calcium channels using eukaryotic cells that express heterologous human calcium channels are provided.

In particular, the assays use eukaryotic cells that express heterologous human calcium channel subunits encoded by heterologous DNA provided herein, for screening potential calcium channel agonists and antagonists which are specific for human calcium channels and particularly for screening for compounds that are specific for particular human calcium channel subtypes. Such assays may be used in conjunction with methods of rational drug design to select among agonists and antagonists, which differ slightly in structure, those particularly useful for modulating the activity of human calcium channels, and to design or select compounds that exhibit subtype- or tissue-specific calcium channel antagonist and agonist activities.

These assays should accurately predict the relative therapeutic efficacy of a compound for the treatment of certain disorders in humans. In addition, since subtype-and tissue-specific calcium channel subunits are provided, cells with tissue-specific or subtype-specific recombinant calcium channels may be prepared and used in assays for identification of human calcium channel tissue- or subtype-specific drugs.

Desirably, the host cell for the expression of calcium channel subunits does not produce endogenous calcium channel subunits of the type or in an amount that substantially interferes with the detection of heterologous calcium channel subunits in ligand binding assays or detection of heterologous calcium channel function, such as generation of calcium current, in functional assays. Also, the host cells preferably should not produce endogenous calcium channels which detectably interact with compounds having, at physiological concentrations (generally nanomolar or picomolar concentrations), affinity for calcium channels that contain one or all of the human calcium channel subunits provided herein.

With respect to ligand binding assays for identifying a compound which has affinity for calcium channels, cells are employed which express, preferably, at least a heterologous $\alpha_1$ subunit. Transfected eukaryotic cells which express at least an $\alpha_1$ subunit may be used to determine the ability of a test compound to specifically alter the activity of a calcium channel. Such ligand binding assays may be performed on intact transfected cells or membranes prepared therefrom.

The capacity of a test compound to bind to or otherwise interact with membranes that contain heterologous calcium channels or subunits thereof may be determined by using any appropriate method, such as competitive binding analysis, such as Scatchard plots, in which the binding capacity of such membranes is determined in the presence and absence of one or more concentrations of a compound having known affinity for the calcium channel. Where necessary, the results may be compared to a control experiment designed in accordance with methods known to those of skill in the art. For example, as a negative control, the results may be compared to those of assays of an identically treated membrane preparation from host cells which have not been transfected with one or more subunit-encoding nucleic acids.

The assays involve contacting the cell membrane of a recombinant eukaryotic cell which expresses at least one subunit of a human calcium channel, preferably at least an $\alpha_1$ subunit of a human calcium channel, with a test compound and measuring the ability of the test compound to specifically bind to the membrane or alter or modulate the activity of a heterologous calcium channel on the membrane.

In preferred embodiments, the assay uses a recombinant cell that has a calcium channel containing an $\alpha_1$ subunit of a human calcium channel in combination with a $\beta$-subunit of a human calcium channel and/or an $\alpha_2$ subunit of a human calcium channel. Recombinant cells expressing heterologous calcium channels containing each of the $\alpha_1$, $\beta$ and $\alpha_2$ human subunits, and, optionally, a $\gamma$ subunit of a human calcium channel are especially preferred for use in such assays.

In certain embodiments, the assays for identifying compounds that modulate calcium channel activity are practiced by measuring the calcium channel activity of a eukaryotic cell having a heterologous, functional calcium channel when such cell is exposed to a solution containing the test compound and a calcium channel selective ion and comparing the measured calcium channel activity to the calcium channel activity of the same cell or a substantially identical control cell in a solution not containing the test compound. The cell is maintained in a solution having a concentration of calcium channel selective ions sufficient to provide an inward current when the channels open. Especially preferred for use, is a recombinant cell expressing calcium channels that include each of the $\alpha_1$, $\beta$ and $\alpha_2$ human subunits, and, optionally, a $\gamma$ subunit of a human calcium channel. Methods for practicing such assays are known to those of skill in the art. For example, for similar methods applied with *Xenopus laevis* oöcytes and acetylcholine receptors, see, Mishina et al. [(1985) *Nature* 313:364] and, with such oöcytes and sodium channels [see, Noda et al. (1986) *Nature* 322:826–828]. For similar studies which have been carried out with the acetylcholine receptor, see, e.g., Claudio et al. [(1987) *Science* 238:1688–1694].

Functional recombinant or heterologous calcium channels may be identified by any method known to those of skill in the art. For example, electrophysiological procedures for measuring the current across an ion-selective membrane of a cell, which are well known, may be used. The amount and duration of the flow of calcium selective ions through heterologous calcium channels of a recombinant cell containing DNA encoding one or more of the subunits provided herein has been measured using electrophysiological recordings using a two electrode and the whole-cell patch clamp techniques. In order to improve the sensitivity of the assays, known methods can be used to eliminate or reduce non-calcium currents and calcium currents resulting from endogenous calcium channels, when measuring calcium currents through recombinant channels. For example, the DHP Bay K 8644 specifically enhances L-type calcium channel function by increasing the duration of the open state of the channels [see, e.g., Hess, J. B., et al. (1984) *Nature* 311:538–544]. Prolonged opening of the channels results in calcium currents of increased magnitude and duration. Tail currents can be observed upon repolarization of the cell membrane after activation of ion channels by a depolarizing voltage command. The opened channels require a finite time to close or "deactivate" upon repolarization, and the current that flows through the channels during this period is referred to as a tail current. Because Bay K 8644 prolongs opening events in calcium channels, it tends to prolong these tail currents and make them more pronounced.

In practicing these assays, stably or transiently transfected cells or injected cells that express voltage-dependent human calcium channels containing one or more of the subunits of a human calcium channel desirably may be used in assays to identify agents, such as calcium channel agonists and antagonists, that modulate calcium channel activity. Functionally testing the activity of test compounds, including compounds having unknown activity, for calcium channel agonist or antagonist activity to determine if the test compound potentiates, inhibits or otherwise alters the flow of calcium through a human calcium channel can be accomplished by (a) maintaining a eukaryotic cell which is transfected or injected to express a heterologous functional calcium channel capable of regulating the flow of calcium channel selective ions into the cell in a medium containing calcium channel selective ions (i) in the presence of and (ii) in the absence of a test compound; (b) maintaining the cell under conditions such that the heterologous calcium channels are substantially closed and endogenous calcium channels of the cell are substantially inhibited (c) depolarizing the membrane of the cell maintained in step (b) to an extent and for an amount of time sufficient to cause (preferably, substantially only) the heterologous calcium channels to become permeable to the calcium channel selective ions; and (d) comparing the amount and duration of current flow into the cell in the presence of the test compound to that of the current flow into the cell, or a substantially similar cell, in the absence of the test compound.

The assays thus use cells, provided herein, that express heterologous functional calcium channels and measure functionally, such as electrophysiologically, the ability of a test compound to potentiate, antagonize or otherwise modulate the magnitude and duration of the flow of calcium channel selective ions, such as $Ca^{++}$ or $Ba^{++}$, through the heterologous functional channel. The amount of current which flows through the recombinant calcium channels of a cell may be determined directly, such as electrophysiologically, or by monitoring an independent reaction which occurs intracellularly and which is directly influenced in a calcium (or other) ion dependent manner.

Any method for assessing the activity of a calcium channel may be used in conjunction with the cells and assays provided herein. For example, in one embodiment of the method for testing a compound for its ability to modulate calcium channel activity, the amount of current is measured by its modulation of a reaction which is sensitive to calcium channel selective ions and uses a eukaryotic cell which expresses a heterologous calcium channel and also contains a transcriptional control element operatively linked for expression to a structural gene that encodes an indicator protein. The transcriptional control element used for transcription of the indicator gene is responsive in the cell to a calcium channel selective ion, such as $Ca^{2+}$ and $Ba^+$. The details of such transcriptional based assays are described in commonly owned PCT International Patent Application No. PCT/US91/5625, filed Aug. 7, 1991, published as WO 92/02639, which claims priority to copending commonly owned U.S. application Ser. No. 07/ 563,751, filed Aug. 7, 1990, now U.S. Pat. No. 5,401,629 the contents of which applications are herein incorporated by reference thereto.

Assays for diagnosis of LES

LES is an autoimmune disease characterized by an insufficient release of acetylcholine from motor nerve terminals which normally are responsive to nerve impulses. Immunoglobulins (IgG) from LES patients block individual voltage-dependent calcium channels and thus inhibit calcium channel activity [Kim and Neher, *Science* 239:405–408 (1988)]. A diagnostic assay for Lambert Eaton Syndrome (LES) is provided herein. The diagnostic assay for LES relies on the immunological reactivity of LES IgG with the human calcium channels or particular subunits alone or in combination or expressed on the surface of recombinant cells. For example, such an assay may be based on immunoprecipitation of LES IgG by the human calcium channel subunits and cells that express such subunits provided herein.

EXAMPLES

The following examples are included for illustrative purposes only and are not intended to limit the scope of the invention.

EXAMPLE I
PREPARATION OF LIBRARIES USED FOR ISOLATION OF DNA ENCODING HUMAN NEURONAL VOLTAGE-DEPENDENT CALCIUM CHANNEL SUBUNITS

A. RNA Isolation

1. IMR32 cells

IMR32 cells were obtained from the American Type Culture Collection (ATCC Accession No. CCL127, Rockville, Md.) and grown in DMEM, 10% fetal bovine serum, 1% penicillin/streptomycin (GIBCO, Grand Island, NY) plus 1.0 mM dibutyryl cAMP (dbcAMP) for ten days. Total RNA was isolated from the cells according to the procedure described by H. C. Birnboim [(1988) *Nucleic Acids Research* 16:1487–1497]. Poly($A^+$) RNA was selected according to standard procedures [see, e.g., Sambrook et al. (1989) *Molecular Cloning, A Laboratory Manual*, Cold Spring Harbor Laboratory Press; pg. 7.26–7.29].

2. Human thalamus tissue

Human thalamus tissue (2.34 g), obtained from the National Neurological Research Bank, Los Angeles, Calif., that had been stored frozen at −70° C. was pulverized using a mortar and pestle in the presence of liquid nitrogen and the cells were lysed in 12 ml of lysis buffer (5M guanidinium isothiocyanate, 50 mM TRIS, pH 7.4, 10 mM EDTA, 5% β-mercaptoethanol). Lysis buffer was added to the lysate to yield a final volume of 17 ml. N-laurylsarcosine and CsCl were added to the mixture to yield final concentrations of 4% and 0.01 g/ml, respectively, in a final volume of 18 ml.

The sample was centrifuged at 9,000 rpm in a Sorvall SS34 rotor for 10 min at room temperature to remove the insoluble material as a pellet. The supernatant was divided into two equal portions and each was layered onto a 2-ml cushion of a solution of 5.7M CsCl, 0.1M EDTA contained in separate centrifuge tubes to yield approximately 9 ml per tube. The samples were centrifuged in an SW41 rotor at 37,000 rpm for 24 h at 20° C.

After centrifugation, each RNA pellet was resuspended in 3 ml ETS (10 mM TRIS, pH 7.4, 10 mM EDTA, 0.2% SDS) and combined into a single tube. The RNA was precipitated with 0.25M NaCl and two volumes of 95% ethanol.

The precipitate was collected by centrifugation and resuspended in 4 ml PK buffer (0.05M TRIS, pH 8.4, 0.14M NaCl, 0.01M EDTA, 1% SDS). Proteinase K was added to the sample to a final concentration of 200 μg/ml. The sample was incubated at 22° C. for 1 h, followed by extraction with an equal volume of phenol:chloroform:isoamylalcohol (50:48:2) two times, followed by one extraction with an equal volume of chloroform: isoamylalcohol (24:1). The RNA was precipitated with ethanol and NaCl. The precipitate was resuspended in 400 μl of ETS buffer. The yield of total RNA was approximately 1.0 mg. Poly $A^+$ RNA (30 μg) was isolated from the total RNA according to standard methods as stated in Example I.A.1.

B. Library Construction

Double-stranded cDNA was synthesized according to standard methods [see, e.g., Sambrook et al. (1989) IN: *Molecular Cloning, A Laboratory Manual*, Cold Spring Harbor Laboratory Press, Chapter 8]. Each library was prepared in substantially the same manner except for differences in: 1) the oligonucleotide used to prime the first strand cDNA synthesis, 2) the adapters that were attached to the double-stranded cDNA, 3) the method used to remove the free or unused adapters, and 4) the size of the fractionated cDNA ligated into the λ phage vector.

1. IMR32 cDNA library #1

Single-stranded cDNA was synthesized using IMR32 poly($A^+$) RNA (Example I.A.1.) as a template and was primed using oligo $(dT)_{12-18}$ (Collaborative Research Inc., Bedford, Mass.). The single-stranded cDNA was converted to double-stranded cDNA and the yield was approximately 2 μg. EcoI adapters:

5'-AATTCGGTACGTACACTCGAGC-3' = 22-mer (SEQ ID No. 15)
3'-    GCCATGCATGTGAGCTCG-5' = 18-mer (SEQ ID No. 16)

also containing SnaBI and XhoI restriction sites were then added to the double-stranded cDNA according to the following procedure.

a. Phosphorylation of 18-mer

The 18-mer was phosphorylated using standard methods [see, e.g., Sambrook et al. (1989) IN: *Molecular Cloning, A Laboratory Manual*, Cold Spring Harbor Laboratory Press, Chapter 8] by combining in a 10 μl total volume the 18-mer (225 pmoles) with [$^{32}P$]γ-ATP (7000 Ci/mmole; 1.0 μl) and kinase (2 U) and incubating at 37° C. for 15 minutes. After incubation, 1 μl 10 mN ATP and an additional 2 U of kinase were added and incubated at 37° C. for 15 minutes. Kinase was then inactivated by boiling for 10 minutes.

b. Hybridization of 22-mer

The 22-mer was hybridized to the phosphorylated 18-mer by addition of 225 pmoles of the 22-mer (plus water to bring volume to 15 μl), and incubation at 65° C. for 5 minutes. The reaction was then allowed to slow cool to room temperature.

The adapters were thus present at a concentration of 15 pmoles/μl, and were ready for cDNA-adapter ligation.

c. Ligation of adapters to cDNA

After the EcoRI, SnaBI, XhoI adapters were ligated to the double-stranded cDNA using a standard protocol [see, e.g., Sambrook et al. (1989) IN: *Molecular Cloning, A Laboratory Manual*, Cold Spring Harbor Laboratory Press, Chapter 8], the ligase was inactivated by heating the mixture to 72° C. for 15 minutes. The following reagents were added to the cDNA ligation reaction and heated at 37° C. for 30 minutes: cDNA ligation reaction (20 µl), water (24 µl), lox kinase buffer (3 µl), 10 mM ATP (1 µl) and kinase (2 µl of 2 U/µl). The reaction was stopped by the addition of 2 µl 0.5M EDTA, followed by one phenol/chloroform extraction and one chloroform extraction.

d. Size Selection and Packaging of cDNA

The double-stranded cDNA with the EcoRI, SnaBI, XhoI adapters ligated was purified away from the free or unligated adapters using a 5 ml Sepharose CL-4B column (Sigma, St. Louis, Mo.). 100 µl fractions were collected and those containing the cDNA, determined by monitoring the radioactivity, were pooled, ethanol precipitated, resuspended in TE buffer and loaded onto a 1% agarose gel. After the electrophoresis, the gel was stained with ethidium bromide and the 1 to 3 kb fraction was cut from the gel. The cDNA embedded in the agarose was eluted using the "Geneluter Electroelution System" (Invitrogen, San Diego, Calif.). The eluted cDNA was collected by ethanol precipitation and resuspended in TE buffer at 0.10 pmol/µl. The cDNA was ligated to 1 µg of EcoRI digested, dephosphorylated λgt11 in a 5 µl reaction volume at a 2- to 4-fold molar excess ratio of cDNA over the λgt11 vector. The ligated λgt11 containing the cDNA insert was packaged into λ phage virions in vitro using the Gigapack (Stratagene, La Jolla, Calif.) kit. The packaged phage were plated on an *E. coli* Y1088 bacterial lawn in preparation for screening.

2. IMR32 cDNA library #2

This library was prepared as described (Example I.B.1.) with the exception that 3 to 9 kb cDNA fragments were ligated into the λgt11 phage vector rather than the 1 to 3 kb fragments.

3. IMR32 cDNA library #3

IMR32 cell poly($A^+$) RNA (Example I.A.1.) was used as a template to synthesize single-stranded cDNA. The primers for the first strand cDNA synthesis were random primers (hexadeoxy-nucleotides [pd(N)$_6$] Cat #5020-1, Clontech, Palo Alto, Calif.). The double-stranded cDNA was synthesized, EcoRI, SnaBI, XhoI adapters were added to the cDNA, the unligated adapters were removed, and the double-stranded cDNA with the ligated adapters was fractionated on an agarose gel, as described in Example I.B.1. The cDNA fraction greater than 1.8 kb was eluted from the agarose, ligated into λgt11, packaged, and plated into a bacterial lawn of Y1088 (as described in Example I.B.1.).

4. IMR32 cDNA library #4

IMR32 cell poly($A^+$) RNA (Example I.A.1.) was used as a template to synthesize single-stranded cDNA. The primers for the first strand cDNA synthesis were oligonucleotides: 89–365a specific for the $\alpha_{1D}$ (VDCC III) type $\alpha_1$-subunit (see Example II.A.) coding sequence (the complementary sequence of nt 2927 to 2956, SEQ ID No. 1), 89–495 specific for the $\alpha_{1C}$ (VDCC II) type $\alpha_1$-subunit (see Example II.B.) coding sequence (the complementary sequence of nt 852 to 873, SEQ ID No. 3), and 90-12 specific for the $\alpha_{1C}$-subunit coding sequence (the complementary sequence of nt 2496 to 2520, SEQ ID No. 3). The cDNA library was then constructed as described (Example I.B.3), except that the cDNA size-fraction greater than 1.5 kb was eluted from the agarose rather than the greater than 1.8 kb fraction.

5. IMR32 cDNA library #5

The cDNA library was constructed as described (Example I.B.3.) with the exception that the size-fraction greater than 1.2 kb was eluted from the agarose rather than the greater than 1.8 kb fraction.

6. Human thalamus cDNA library #6

Human thalamus poly ($A^+$) RNA (Example I.A.2.) was used as a template to synthesize single-stranded cDNA. Oligo (dT) was used to prime the first strand synthesis (Example I.B.1.). The double-stranded cDNA was synthesized (Example I.B.1.) and EcoRI, KpnI, NcoI adapters of the following sequence:

5' CCATGGTACCTTCGTTGACG 3' = 20-mer (SEQ ID NO. 17)
3' GGTACCATGGAAGCAACTGCTTAA 5' = 24-mer (SEQ ID NO. 18)

were ligated to the double-stranded cDNA as described (Example I.B.1.) with the 20-mer replacing the 18-mer and the 24-mer replacing the 22-mer. The unligated adapters were removed by passing the cDNA-adapter mixture through a 1 ml Bio Gel A-50 (Bio-Rad Laboratories, Richmond, Calif.) column. Fractions (30 µl) were collected and 1 µl of each fraction in the first peak of radioactivity was electrophoresed on a 1% agarose gel. After electrophoresis, the gel was dried on a vacuum gel drier and exposed to x-ray film. The fractions containing cDNA fragments greater than 600 bp were pooled, ethanol precipitated, and ligated into λgt11 (Example I.B.1.). The construction of the cDNA library was completed as described (Example I.B.1.).

C. Hybridization and Washing Conditions

Hybridization of radiolabelled nucleic acids to immobilized DNA for the purpose of screening cDNA libraries, DNA Southern transfers, or northern transfers was routinely performed in standard hybridization conditions [hybridization: 50% deionized formamide, 200 µg/ml sonicated herring sperm DNA (Cat #223646, Boehringer Mannheim Biochemicals, Indianapolis, Ind.), 5×SSPE, 5×Denhardt's, 42° C.; wash :0.2×SSPE, 0.1% SDS, 65° C.]. The recipes for SSPE and Denhardt's and the preparation of deionized formamide are described, for example, in Sambrook et al. (1989) *Molecular Cloning*, A Laboratory Manual, Cold Spring Harbor Laboratory Press, Chapter 8). In some hybridizations, lower stringency conditions were used in that 10% deionized formamide replaced 50% deionized formamide described for the standard hybridization conditions.

The washing conditions for removing the non-specific probe from the filters was either high, medium, or low stringency as described below:

1) high stringency: 0.1×SSPE, 0.1% SDS, 65° C.

2) medium stringency: 0.2×SSPE, 0.1% SDS, 50° C.

3) low stringency: 1.0×SSPE, 0.1% SDS, 50° C.

It is understood that equivalent stringencies may be achieved using alternative buffers, salts and temperatures.

EXAMPLE II
ISOLATION OF DNA ENCODING THE HUMAN NEURONAL CALCIUM CHANNEL $\alpha_1$ SUBUNIT A. Isolation of DNA encoding the $\alpha_{1D}$ subunit 1. Reference list of partial $\alpha_{1D}$ cDNA clones Numerous $\alpha_{1D}$-specific cDNA clones were isolated in order to characterize the complete $\alpha_{1D}$ coding sequence plus portions of the 5' and 3' untranslated sequences. SEQ ID No.

1 shows the complete $\alpha_{1D}$ DNA coding sequence, plus 510 nucleotides of $\alpha_{1D}$ 5' untranslated sequence ending in the guanidine nucleotide adjacent to the adenine nucleotide of the proposed initiation of translation as well as 642 nucleotides of 3' untranslated sequence. Also shown in SEQ ID No. 1 is the deduced amino acid sequence. A list of partial cDNA clones used to characterize the $\alpha_{1D}$ sequence and the nucleotide position of each clone relative to the full-length $\alpha_{1D}$ cDNA sequence, which is set forth in SEQ ID No. 1, is shown below. The isolation and characterization of these clones are described below (Example II.A.2.).

| IMR32 | 1.144 | nt 1 to 510 of 5' untranslated sequence, nt 511 to 2431, | SEQ ID No. 1 SEQ ID No. 1 |
|---|---|---|---|
| IMR32* | 1.136 | nt 1627 to 2988, nt 1 to 104 of SEQ ID No. 2 additional exon, | SEQ ID No. 1 |
| IMR32@ | 1.80 | nt 2083 to 6468, | SEQ ID No. 1 |
| IMR32# | 1.36 | nt 2857 to 4281, | SEQ ID No. 1 |
| IMR32 | 1.163 | nt 5200 to 7635, | SEQ ID NO. 1 |

*5' of nt 1627, IMR32 1.136 encodes an intron and an additional exon described in Example II.A.2.d.
@IMR32 1.80 contains two deletions, nt 2984 to 3131 and nt 5303 to 5349 (SEQ ID No. 1). The 148 nt deletion (nt 2984 to 3131) was corrected by performing a polymerase chain reaction described in Example II.A.3.b.
IMR32 1.36 contains a 132 nt deletion (nt 3081 to 3212).

2. Isolation and characterization of individual clones listed in Example II.A.1.
a. IMR32 1.36

Two million recombinants of the IMR32 cDNA library #1 (Example I.B.1.) were screened in duplicate at a density of approximately 200,000 plaques per 150 mm plate using a mixture of radiolabelled fragments of the coding region of the rabbit skeletal muscle calcium channel $\alpha_1$ cDNA [for the sequence of the rabbit skeletal muscle calcium channel $\alpha_1$ subunit cDNA, see, Tanabe et al. (1987). Nature 328:313–318]:

| Fragment | Nucleotides |
|---|---|
| KpnI-EcoRI | −78 to 1006 |
| EcoRI-XhoI | 1006 to 2653 |
| ApaI-ApaI | 3093 to 4182 |
| BglII-sacI | 4487 to 5310 |

The hybridization was performed using low stringency hybridization conditions (Example I.C.) and the filters were washed under low stringency (Example I.C.). Only one $\alpha_{1D}$-specific recombinant (IMR32 1.36) of the 2×10⁶ screened was identified. IMR32 1.36 was plaque purified by standard methods (J. Sambrook et al. (1989) *Molecular Cloning*, A Laboratory Manual, Cold Spring Harbor Laboratory Press, Chapter 8) subcloned into pGEM3 (Promega, Madison, Wis.) and characterized by DNA sequencing.
b. IMR32 1.80

Approximately 1×10⁶ recombinants of the IMR32 cDNA library #2 (Example I.B.2.) were screened in duplicate at a density of approximately 100,000 plaques per 150 mm plate using the IMR32 1.36 cDNA fragment (Example II.A.1) as a probe. Standard hybridization conditions were used, and the filters were washed under high stringency (Example I.C.). Three positive plaques were identified one of which was IMR32 1.80. IMR32 1.80 was plaque purified by standard methods, restriction mapped, subcloned, and characterized by DNA sequencing.
C. IMR32 1.144

Approximately 1×10⁶ recombinants of the IMR32 cDNA library #3 (Example I.B.3) were screened with the EcoRI-PvuII fragment (nt 2083 to 2518, SEQ ID No. 1) of IMR32 1.80. The hybridization was performed using standard hybridization conditions (Example I.C.) and the filters were washed under high stringency (Example I.C.). Three positive plaques were identified one of which was IMR32 1.144. IMR32 1.144 was plaque purified, restriction mapped, and the cDNA insert was subcloned into pGEM7Z (Promega, Madison, Wis.) and characterized by DNA sequencing. This characterization revealed that IMR32 1.144 has a series of ATG codons encoding seven possible initiating methionines (nt 511 to 531, SEQ ID No. 1). PCR analysis, and DNA sequencing of cloned PCR products encoding these seven ATG codons confirmed that this sequence is present in the $\alpha_{1D}$ transcript expressed in dbcAMP-induced IMR32 cells.
d. IMR32 1.136

Approximately 1×10⁶ recombinants of the IMR32 cDNA library #4 (Example I.B.4) were screened with the EcoRI-PvuII fragment (nt 2083 to 2518, SEQ ID No. 1) of IMR32 1.80 (Example II.A.1.). The hybridization was performed using standard hybridization conditions (Example I.C.) and the filters were washed under high stringency (Example I.C.). Six positive plaques were identified one of which was IMR32 1.136. IMR32 1.136 was plaque purified, restriction mapped, and the cDNA insert was subcloned into a standard plasmid vector, pSP72 (Promega, Madison, Wis.), and characterized by DNA sequencing. This characterization revealed that IMR32 1.136 encodes an incompletely spliced $\alpha_{1D}$ transcript. The clone contains nucleotides 1627 to 2988 of SEQ ID No. 1 preceded by an approximate 640 bp intron. This intron is then preceded by a 104 nt exon (SEQ ID No. 2) which is an alternative exon encoding the IS6 transmembrane domain [see, e.g., Tanabe et al. (1987) *Nature* 328:313–318 for a description of the IS1 to IVS6 transmembrane terminology] of the $\alpha_{1D}$ subunit and can replace nt 1627 to 1730, SEQ ID No. 1, to produce a completely spliced $\alpha_{1D}$ transcript.
e. IMR32 1.163

Approximately 1×10⁶ recombinants of the IMR32 cDNA library #3 (Example I.B.3.) were screened with the NcoI-XhoI fragment of IMR32 1.80 (Example II.A.1.) containing nt 5811 to 6468 (SEQ ID No. 1). The hybridization was performed using standard hybridization conditions (Example I.C.) and the filters were washed under high stringency (Example I.C.). Three positive plaques were identified one of which was IMR32 1.163. IMR32 1.163 was plaque purified, restriction mapped, and the cDNA insert was subcloned into a standard plasmid vector, pSP72 (Promega, Madison, Wis.), and characterized by DNA sequencing. This characterization revealed that IMR32 1.163 contains the $\alpha_{1D}$ termination codon, nt 6994 to 6996 (SEQ ID No. 1).

3. Construction of a full-length $\alpha_{1D}$ cDNA [pVDCCIII (A)]

$\alpha_{1D}$ cDNA clones IMR32 1.144, IMR32 1.136, IMR32 1.80, and IMR32 1.163 (Example II.A.2.) overlap and include the entire $\alpha_{1D}$ coding sequence, nt 511 to 6993 (SEQ ID No. 1), with the exception of a 148 bp deletion, nt 2984 to 3131 (SEQ ID No. 1). Portions of these partial cDNA clones were ligated to generate a full-length $\alpha_{1D}$ cDNA in a eukaryotic expression vector. The resulting vector was called pVDCCIII(A). The construction of pVDCCIII(A) was performed in four steps described in detail below: (1) the construction of pVDCCIII/5' using portions of IMR32 1.144, IMR32 1.136, and IMR32 1.80, (2) the construction of pVDCCIII/5'.3 that corrects the 148 nt deletion in the IMR32 1.80 portion of pVDCCIII/5', (3) the construction of pVDCCIII/3'.1 using portions of IMR32 1.80 and IMR32 1.163, and (4) the ligation of a portion of the pVDCCIII/5'.3 insert, the insert of pVDCCIII/3'.1, and pcDNA1 (Invitrogen, San Diego, Calif.) to form pVDCCIII(A). The vector pcDNA1 is a eukaryotic expression vector containing a cytomegalovirus (CMV) promoter which is a constitutive promoter recognized by mammalian host cell RNA polymerase II.

Each of the DNA fragments used in preparing the full-length construct was purified by electrophoresis through an agarose gel onto DE81 filter paper (Whatman, Clifton, N.J.) and elution from the filter paper using 1.0M NaCl, 10 mM TRIS, pH 8.0, 1 mM EDTA. The ligations typically were performed in a 10 μl reaction volume with an equal molar ratio of insert fragment and a two-fold molar excess of the total insert relative to the vector. The amount of DNA used was normally about 50 ng to 100 ng.

a. pVDCCIII/5'

To construct pVDCCIII/5', IMR32 1.144 (Example II.A.2.c.) was digested with XhoI and EcoRI and the fragment containing the vector (pGEM7Z), $\alpha_{1D}$ nt 1 to 510 (SEQ ID No. 1), and $\alpha_{1D}$ nt 511 to 1732 (SEQ ID No. 1) was isolated by gel electrophoresis. The EcoRI-ApaI fragment of IMR32 1.136 (Example II.A.2.d.) nucleotides 1733 to 2671 (SEQ ID No. 1) was isolated, and the ApaI-HindIII fragment of IMR32 1.80 (Example II.A.2.b.), nucleotides 2672 to 4492 (SEQ ID No. 1) was isolated. The three DNA clones were ligated to form pVDCCIII/5' containing nt 1 to 510 (5' untranslated sequence; SEQ ID No. 1) and nt 511 to 4492 (SEQ ID No. 1).

b. pVDCCIII/5'.3

Comparison of the IMR32 1.36 and IMR32 1.80 DNA sequences revealed that these two cDNA clones differ through the $\alpha_{1D}$ coding sequence, nucleotides 2984 to 3212. PCR analysis of IMR32 1.80 and dbcAMP-induced (1.0 mM, 10 days) IMR32 cytoplasmic RNA (isolated according to Ausubel, F. M. et al. (Eds) (1988) *Current Protocols in Molecular Biology*, John Wiley and Sons, New York) revealed that IMR32 1.80 had a 148 nt deletion, nt 2984 to 3131 (SEQ ID No. 1), and that IMR32 1.36 had a 132 nt deletion, nt 3081 to 3212. To perform the PCR analysis, amplification was primed with $\alpha_{1D}$-specific oligonucleotides 112 (nt 2548 to 2572, SEQ ID No. 1) and 311 (the complementary sequence of nt 3928 to 3957, SEQ ID No. 1). These products were then reamplified using $\alpha_{1D}$-specific oligonucleotides 310 (nt 2583 to 2608 SEQ ID No. 1) and 312 (the complementary sequence of nt 3883 to 3909). This reamplified product, which contains AccI and BglII restriction sites, was digested with AccI and BglII and the AccI-BglII fragment, nt 2765 to 3890 (SEQ ID No. 1) was cloned into AccI-BglII digested pVDCCIII/5' to replace the AccI-BglII pVDCCIII/5' fragment that had the deletion. This new construct was named pVDCCIII/5'.3. DNA sequence determination of pVDCCIII/5'.3 through the amplified region confirmed the 148 nt deletion in IMR32 1.80.

c. pVDCCIII/3'.1

To construct pVDCCIII/3'.1, the cDNA insert of IMR32 1.163 (Example II.A.2.e.) was subcloned into pBluescript II (Stratagene, La Jolla, Calif.) as an XhoI fragment. The XhoI sites on the cDNA fragment were furnished by the adapters used to construct the cDNA library (Example I.B.3.). The insert was oriented such that the translational orientation of the insert of IMR32 1.163 was opposite to that of the lacZ gene present in the plasmid, as confirmed by analysis of restriction enzyme digests of the resulting plasmid. This was done to preclude the possibility of expression of $\alpha_{1D}$ sequences in DH5α cells transformed with this plasmid due to fusion with the lacZ gene. This plasmid was then digested with HindIII and BglII and the HindIII-BglII fragment (the HindIII site comes from the vector and the BglII site is at nt 6220, SEQ ID No. 1) was eliminated, thus deleting nt 5200 to 6220 (SEQ ID No. 1) of the IMR32 1.163 clone and removing this sequence from the remainder of the plasmid which contained the 3' BglII-XhoI fragment, nt 6221 to 7635 (SEQ ID No. 1). pVDCCIII/3'.1 was then made by splicing together the HindIII-PvuII fragment from IMR32 1.80 (nucleotides 4493–5296, SEQ ID No. 1), the PvuII-BglII fragment of IMR32 1.163 (nucleotides 5294 to 6220, SEQ ID No. 1) and the HindIII-BglII-digested pBluescript plasmid containing the 3' BglII/XhoI IMR32 1.163 fragment (nt 6221 to 7635, SEQ ID No. 1).

d. pVDCCIII(A): the full-length $\alpha_{1D}$ construct

To construct pVDCCIII(A), the DraI-HindIII fragment (5' untranslated sequence nt 330 to 510, SEQ ID No. 1 and coding sequence nt 511 to 4492, SEQ ID No. 1) of pVDCCIII/5'.3 (Example II.A.3.b.) was isolated; the HindIII-XhoI fragment of pVDCCIII/3'.1 (containing nt 4493 to 7635, SEQ ID No. 1, plus the XhoI site of the adapter) (Example II.A.3.c.) was isolated; and the plasmid vector, pcDNA1, was digested with EcoRV and XhoI and isolated on an agarose gel. The three DNA fragments were ligated and MC1061-P3 (Invitrogen, San Diego, Calif.) was transformed. Isolated clones were analyzed by restriction mapping and DNA sequencing and pVDCCIII (A) was identified which had the fragments correctly ligated together: DraI-HindIII, HindIII-XhoI, XhoI-EcoRV with the blunt-end DraI and EcoRV site ligating together to form the circular plasmid.

The amino-terminus of the $\alpha_{1D}$ subunit is encoded by the seven consecutive 5' methionine codons (nt 511 to 531, SEQ ID No. 1). This 5' portion plus nt 532 to 537, encoding two lysine residues, were deleted from pVDCCIII(A) and replaced with an efficient ribosomal binding site (5'-ACCACC-3') to form pVDCCIII.RBS(A). Expression experiments in which transcripts of this construct were injected into *Xenopus laevis* oöcytes did not result in an enhancement in the recombinant voltage-dependent calcium channel expression level relative to the level of expression in oöcytes injected with transcripts of pVDCCIII(A).

B. Isolation of DNA encoding the $\alpha_{1C}$ subunit

1. Reference List of Partial $\alpha_{1C}$ cDNA clones

Numerous $\alpha_{1C}$-specific cDNA clones were isolated in order to characterize the $\alpha_{1C}$ coding sequence, the $\alpha_{1C}$ initiation of translation, and an alternatively spliced region of $\alpha_{1C}$. SEQ ID No. 3 sets forth the characterized $\alpha_{1C}$ coding sequence (nt 1 to 5904) and deduced amino acid sequence. SEQ ID No. 4 and No. 5 encode two possible amino terminal ends of the $\alpha_{1C}$ protein. SEQ ID No. 6 encodes an alternative exon for the IV S3 transmembrane domain. Shown below is a list of clones used to characterize the $\alpha_{1C}$ sequence and the nucleotide position of each clone relative to the characterized $\alpha_{1C}$ sequence (SEQ ID No. 3). The isolation and characterization of these cDNA clones are described below (Example II.B.2).

| IMR32 | 1.66 | nt 1 to 916, SEQ ID No. 3 |
|---|---|---|
|  |  | nt 1 to 132, SEQ ID No. 4 |

-continued

| IMR32 | 1.157 | nt 1 to 873, SEQ ID No. 3 |
| | | nt 1 to 89, SEQ ID No. 5 |
| IMR32 | 1.67 | nt 50 to 1717, SEQ ID No. 3 |
| *IMR32 | 1.86 | nt 1366 to 2583, SEQ ID No. 3 |
| @1.16G | | nt 758 to 867, SEQ ID No. 3 |
| IMR32 | 1.37 | nt 2804 to 5904, SEQ ID No. 3 |
| CNS | 1.30 | nt 2199 to 3903, SEQ ID No. 3 |
| | | nt 1 to 84 of alternative exon, SEQ ID No. 6 |
| IMR32 | 1.38 | nt 2448 to 4702, SEQ ID No. 3 |
| | | nt 1 to 84 of alternative exon, SEQ ID No. 6 |

*IMR32 1.86 has a 73 nt deletion compared to the rabbit cardiac muscle calcium channel $\alpha_1$ subunit cDNA sequence.
@1.16G is an $\alpha_{1C}$ genomic clone.

2. Isolation and characterization of clones described in Example II.B.1.

a. CNS 1.30

Approximately $1 \times 10^6$ recombinants of the human thalamus cDNA library No. 6 (Example I.B.6.) were screened with fragments of the rabbit skeletal muscle calcium channel $\alpha_1$ cDNA described in Example II.A.2.a. The hybridization was performed using standard hybridization conditions (Example I.C.) and the filters were washed under low stringency (Example I.C.). Six positive plaques were identified, one of which was CNS 1.30. CNS 1.30 was plaque purified, restriction mapped, subcloned, and characterized by DNA sequencing. CNS 1.30 encodes $\alpha_{1C}$-specific sequence nt 2199 to 3903 (SEQ ID No. 3) followed by nt 1 to 84 of one of two identified alternative $\alpha_{1C}$ exons (SEQ ID No. 6). 3' of SEQ ID No. 6, CNS 1.30 contains an intron and, thus, CNS 1.30 encodes a partially spliced $\alpha_{1C}$ transcript.

b. 1.16G

Approximately $1 \times 10^6$ recombinants of a λEMBL3-based human genomic DNA library (Cat #HL1006d Clontech Corp., Palo Alto, Calif.) were screened using a rabbit skeletal muscle cDNA fragment (nt −78 to 1006, Example II.A.2.a.). The hybridization was performed using standard hybridization conditions (Example I.C.) and the filters were washed under low stringency (Example I.C.). Fourteen positive plaques were identified, one of which was 1.16G. Clone 1.16G was plaque purified, restriction mapped, subcloned, and portions were characterized by DNA sequencing. DNA sequencing revealed that 1.16G encodes $\alpha_{1C}$-specific sequence as described in Example II.B.1.

a. IMR32 1.66 and IMR32 1.67

Approximately $1 \times 10^6$ recombinants of IMR32 cDNA library #5 (Example I.B.5.) were screened with a 151 bp KpnI-SacI fragment of 1.16G (Example II.B.2.b.) encoding $\alpha_{1C}$ sequence (nt 758 to 867, SEQ ID No. 3). The hybridization was performed using standard hybridization conditions (Example I.C.). The filters were then washed in 0.5× SSPE at 65° C. Of the positive plaques, IMR32 1.66 and IMR32 1.67 were identified. The hybridizing plaques were purified, restriction mapped, subcloned, and characterized by DNA sequencing. Two of these cDNA clones, IMR32 1.66 and 1.67, encode $\alpha_{1C}$ subunits as described (Example II.B.1.). In addition, IMR32 1.66 encodes a partially spliced $\alpha_{1C}$ transcript marked by a GT splice donor dinucleotide beginning at the nucleotide 3' of nt 916 (SEQ ID No. 3). The intron sequence within 1.66 is 101 nt long. IMR32 1.66 encodes the $\alpha_{1C}$ initiation of translation, nt 1 to 3 (SEQ ID No. 3) and 132 nt of 5' untranslated sequence (SEQ ID No. 4) precede the start codon in IMR32 1.66.

d. IMR32 1.37 and IMR32 1.38

Approximately $2 \times 10^6$ recombinants of IMR32 cDNA library #1 (Example I.B.1.) were screened with the CNS 1.30 cDNA fragment (Example II.B.2.a.). The hybridization was performed using low stringency hybridization conditions (Example I.C.) and the filters were washed under low stringency (Example I.C.). Four positive plaques were identified, plaque purified, restriction mapped, subcloned, and characterized by DNA sequencing. Two of the clones, IMR32 1.37 and IMR32 1.38 encode $\alpha_{1C}$-specific sequences as described in Example II.B.1.

DNA sequence comparison of IMR32 1.37 and IMR32 1.38 revealed that the $\alpha_{1C}$ transcript includes two exons that encode the IVS3 transmembrane domain. IMR32 1.37 has a single exon, nt 3904 to 3987 (SEQ ID No. 3) and IMR32 1.38 appears to be anomalously spliced to contain both exons juxtaposed, nt 3904 to 3987 (SEQ ID No. 3) followed by nt 1 to 84 (SEQ ID No. 6). The alternative splice of the $\alpha_{1C}$ transcript to contain either of the two exons encoding the IVS3 region was confirmed by comparing the CNS 1.30 sequence to the IMR32 1.37 sequence. CNS 1.30 contains nt 1 to 84 (SEQ ID No. 6) preceded by the identical sequence contained in IMR32 1.37 for nt 2199 to 3903 (SEQ ID No. 3). As described in Example II.B.2.a., an intron follows nt 1 to 84 (SEQ ID No. 6). Two alternative exons have been spliced adjacent to nt 3903 (SEQ ID No. 3) represented by CNS 1.30 and IMR32 1.37.

e. IMR32 1.86

IMR32 cDNA library #1 (Example I.B.1.) was screened in duplicate using oligonucleotide probes 90–9 (nt 1462 to 1491, SEQ ID No. 3) and 90–12 (nt 2496 to 2520, SEQ ID No. 3). These oligonucleotide probes were chosen in order to isolate a clone that encodes the $\alpha_{1C}$ subunit between the 3' end of IMR32 1.67 (nt 1717, SEQ ID No. 3) and the 5' end of CNS 1.30 (nt 2199, SEQ ID No. 3). The hybridization conditions were standard hybridization conditions (Example I.C.) with the exception that the 50% deionized formamide was reduced to 20%. The filters were washed under low stringency (Example I.C.). Three positive plaques were identified one of which was IMR32 1.86. IMR32 1.86 was plaque purified, subcloned, and characterized by restriction mapping and DNA sequencing. IMR32 1.86 encodes $\alpha_{1C}$ sequences as described in Example II.B.1. Characterization by DNA sequencing revealed that IMR32 1.86 contains a 73 nt deletion compared to the DNA encoding rabbit cardiac muscle calcium channel $\alpha_1$ subunit [Mikami et al. (1989) Nature 340:230], nt 2191 to 2263. These missing nucleotides correspond to nt 2176–2248 of SEQ ID No. 3. Because the 5'-end of CNS 1.30 overlaps the 3'-end of IMR32 1.86, some of these missing nucleotides, i.e., nt 2205–2248 of SEQ ID No. 3, are accounted for by CNS 1.30. The remaining missing nucleotides of the 73 nucleotide deletion in IMR32 1.86 (i.e., nt 2176–2204 SEQ ID No. 3) were determined by PCR analysis of dbcAMP-induced IMR32 cell RNA. The 73 nt deletion is a frame-shift mutation and, thus, needs to be corrected. The exact human sequence through this region, (which has been determined by the DNA sequence of CNS 1.30 and PCR analysis of IMR32 cell RNA) can be inserted into IMR32 1.86 by standard methods, e.g., replacement of a restriction fragment or site-directed mutagenesis.

f. IMR32 1.157

One million recombinants of IMR32 cDNA library #4 (Example I.B.4.) were screened with an XhoI-EcoRI fragment of IMR32 1.67 encoding $\alpha_{1C}$ nt 50 to 774 (SEQ ID No. 3). The hybridization was performed using standard hybridization conditions (Example I.C.). The filters were washed under high stringency (Example I.C.). One of the positive plaques identified was IMR32 1.157. This plaque was purified, the insert was restriction mapped and subcloned to a standard plasmid vector pGEM7Z (Promega, Madison, Wis.). The DNA was characterized by sequencing. IMR32 1.157 appears to encodes an alternative 5' portion of the $\alpha_{1C}$ sequence beginning with nt 1 to 89 (SEQ ID No. 5) and followed by nt 1 to 873 (SEQ ID No. 3). Analysis of the 1.66 and 1.157 5' sequence is described below (Example II.B.3.).

3. Characterization of the $\alpha_{1C}$ initiation of translation site

Portions of the sequences of IMR32 1.157 (nt 57 to 89, SEQ ID No. 5; nt 1 to 67, SEQ ID No. 3), IMR32 1.66 (nt 100 to 132, SEQ ID No. 4; nt 1 to 67, SEQ ID No. 3), were compared to the rabbit lung CaCB-receptor cDNA sequence, nt −33 to 67 [Biel et al. (1990) *FEBS Lett.* 269:409]. The human sequences are possible alternative 5' ends of the $\alpha_{1C}$ transcript encoding the region of initiation of translation. IMR32 1.66 closely matches the CaCB receptor cDNA sequence and diverges from the CaCB receptor cDNA sequence in the 5' direction beginning at nt 122 (SEQ ID No. 4). The start codon identified in the CaCB receptor cDNA sequence is the same start codon used to describe the $\alpha_{1C}$ coding sequence, nt 1 to 3 (SEQ ID No. 3). The functional significance of the IMR32 1.157 sequence, nt 1 to 89 (SEQ ID No. 5), is not clear. Chimeras containing sequence between 1.157 and the $\alpha_{1C}$ coding sequence can be constructed and functional differences can be tested.

C. Isolation of partial cDNA clones encoding the $\alpha_{1B}$ subunit and construction of a full-length clone A human basal ganglia cDNA library was screened with the rabbit skeletal muscle $\alpha_1$ subunit cDNA fragments (see Example II.A.2.a for description of fragments) under low stringency conditions. One of the hybridizing clones was used to screen an IMR32 cell cDNA library to obtain additional partial $\alpha_{1B}$ cDNA clones, which were in turn used to further screen an IMR32 cell cDNA library for additional partial cDNA clones. One of the partial IMR32 $\alpha_{1B}$ clones was used to screen a human hippocampus library to obtain a partial $\alpha_{1B}$ clone encoding the 3' end of the $\alpha_{1B}$ coding sequence. The sequence of some of the regions of the partial cDNA clones was compared to the sequence of products of PCR analysis of IMR32 cell RNA to determine the accuracy of the cDNA sequences.

PCR analysis of IMR32 cell RNA and genomic DNA using oligonucleotide primers corresponding to sequences located 5' and 3' of the STOP codon of the DNA encoding the $\alpha_{1B}$ subunit revealed an alternatively spliced $\alpha_{1B}$-encoding mRNA in IMR32 cells. This second mRNA product is the result of differential splicing of the $\alpha_{1B}$ subunit transcript to include another exon that is not present in the mRNA corresponding to the other 3$\alpha_{1B}$ cDNA sequence that was initially isolated. To distinguish these splice variants of the $\alpha_{1B}$ subunit, the subunit encoded by a DNA sequence corresponding to the form containing the additional exon is referred to as $\alpha_{1B-1}$ (SEQ ID No. 7), whereas the subunit encoded by a DNA sequence corresponding to the form lacking the additional exon is referred to as $\alpha_{1B-2}$ (SEQ ID No. 8). The sequence of $\alpha_{1B-1}$ diverges from that of $\alpha_{1B-2}$ beginning at nt 6633 (SEQ ID No. 7). Following the sequence of the additional exon in $\alpha_{1B-1}$ (nt 6633–6819; SEQ ID No. 7), the $\alpha_{1B-1}$ and $\alpha_{1B-2}$ sequences are identical (i.e., nt 6820–7362 in SEQ ID No. 7 and nt 6633–7175 in SEQ ID No. 8). SEQ ID No. 7 and No. 8 set forth 143 nt of 5' untranslated sequence (nt 1–143) as well as 202 nt of 3' untranslated sequence (nt 7161–7362, SEQ ID No. 7) of the DNA encoding $\alpha_{1B-1}$ and 321 nt of 3' untranslated sequence (nt 6855–7175, SEQ ID No. 8) of the DNA encoding $\alpha_{1B-2}$.

PCR analysis of the IS6 region of the $\alpha_{1B}$ transcript revealed what appear to be additional splice variants based on multiple fragment sizes seen on an ethidium bromide-stained agarose gel containing the products of the PCR reaction.

A full-length $\alpha_{1B-1}$ cDNA clone designated pcDNA-$\alpha_{1B-1}$ was prepared in an eight-step process as follows.

STEP 1: The SacI restriction site of pGEM3 (Promega, Madison, Wis.) was destroyed by digestion at the SacI site, producing blunt ends by treatment with T4 DNA polymerase, and religation. The new vector was designated pGEMΔSac.

STEP 2: Fragment 1 (HindIII/KpnI; nt 2337 to 4303 of SEQ ID No. 7) was ligated into HindIII/KpnI digested pGEM3ΔSac to produce pα1.177HK.

STEP 3: Fragment 1 has a 2 nucleotide deletion (nt 3852 and 3853 of SEQ ID No. 7). The deletion was repaired by inserting a PCR fragment (fragment 2) of IMR32 RNA into pa1.177HK. Thus, fragment 2 (NarI/KpnI; nt 3828 to 4303 of SEQ ID No. 7) was inserted into NarI/KpnI digested pα1.177HK replacing the NarI/KpnI portion of fragment 1 and producing pα1.177HK/PCR.

STEP 4: Fragment 3 (KpnI/KpnI; nt 4303 to 5663 of SEQ ID No. 7) was ligated into KpnI digested pα1.177HK/PCR to produce pα1B5'K.

STEP 5: Fragment 4 (EcoRI/HindIII; EcoRI adaptor plus nt 1 to 2337 of SEQ ID No. 7) and fragment 5 (HindIII/XhoI fragment of pα1B5'K; nt 2337 to 5446 of SEQ ID No. 7) were ligated together into EcoRI/XhoI digested pcDNA1 (Invitrogen, San Diego, Calif.) to produce pα1B5'.

STEP 6: Fragment 6 (EcoRI/EcoRI; EcoRI adapters on both ends plus nt 5749 to 7362 of SEQ ID No. 7) was ligated into EcoRI digested pBluescript II KS (Stratagene, La Jolla, Calif.) with the 5' end of the fragment proximal to the KpnI site in the polylinker to produce pα1.230.

STEP 7: Fragment 7 (KpnI/XhoI; nt 4303 to 5446 of SEQ ID No. 7), and fragment 8 (XhoI/CspI; nt 5446 to 6259 of SEQ ID No. 7) were ligated into KpnI/CspI digested pα1.230 (removes nt 5749 to 6259 of SEQ ID No. 7 that was encoded in pα1.230 and maintains nt 6259 to 7362 of SEQ ID No. 7) to produce pα1B3'.

STEP 8: Fragment 9 (SphI/XhoI; nt 4993 to 5446 of SEQ ID No. 7) and fragment 10 (XhoI/XbaI of pα1B3'; nt 5446 to 7319 of SEQ ID No. 7) were ligated into SphI/XbaI digested pα1B5' (removes nt 4993 to 5446 of SEQ ID No. 7 that were encoded in pα1B5' and maintains nt 1 to 4850 of SEQ ID No. 7) to produce pcDNA$\alpha_{1B-1}$.

The resulting construct, pcDNA$\alpha_{1B-1}$, contains, in pCDNA1, a full-length coding region encoding $\alpha_{1B-1}$ (nt 144–7362, SEQ ID No. 7), plus 5' untranslated sequence (nt 1–143, SEQ ID No. 7) and 3' untranslated sequence (nt 7161–7319, SEQ ID No. 7) under the transcriptional control of the CMV promoter.

D. Isolation of DNA encoding human calcium channel $\alpha_{1A}$ subunits

1. Isolation of partial clones

DNA clones encoding portions of human calcium channel $\alpha_{1A}$ subunits were obtained by hybridization screening of human cerebellum cDNA libraries and nucleic acid amplification of human cerebellum RNA. Clones corresponding to the 3' end of the $\alpha_{1A}$ coding sequence were isolated by screening 1×10$^6$ recombinants of a randomly primed cerebellum cDNA library (size-selected for inserts greater than 2.8 kb in length) under low stringency conditions (6×SSPE, 5×Denhart's solution, 0.2% SDS, 200 µg/ml sonicated herring sperm DNA, 42° C.) with oligonucleotide 704 containing nt 6190–6217 of the rat $\alpha_{1A}$ coding sequence [Starr et al. (1992) *Proc. Natl. Acad. Sci. U.S.A.* 88:5621–5625]. Washes were performed under low stringency conditions. Several clones that hybridized to the probe (clones $\alpha$1.251–$\alpha$1.259 and $\alpha$1.244) were purified and characterized by restriction enzyme mapping and DNA sequence analysis. At least two of the clones, $\alpha$1.244 and $\alpha$1.254, contained a translation termination codon. Although clones $\alpha$1.244 and $\alpha$1.254 are different lengths, they both contain a sequence of nucleotides that corresponds to the extreme 3' end of the $\alpha_{1A}$ transcript, i.e., the two clones overlap. These two clones are identical in the region of overlap, except, clone $\alpha$1.244 contains a sequence of 5 and a sequence of 12 nucleotides that are not present in $\alpha$1.254.

To obtain additional $\alpha_{1A}$-encoding clones, 1×10$^6$ recombinants of a randomly primed cerebellum cDNA library (size-selected for inserts ranging from 1.0 to 2.8 kb in length) was screened for hybridization to three oligonucleotides: oligonucleotide 701 (containing nucleotides 2288–2315 of the rat $\alpha_{1A}$ coding sequence), oligonucleotide 702 (containing nucleotides 3559–3585 of the rat $\alpha_{1A}$ coding sequence) and oligonucleotide 703 (containing nucleotides 4798–4827 of the rat $\alpha_{1A}$ coding sequence). Hybridization and washes were performed using the same conditions as used for the first screening with oligonucleotide 704, except that washes were conducted at 45° C. Twenty clones (clones $\alpha$1.269–$\alpha$1.288) hybridized to the probe. Several clones were plaque-purified and characterized by restriction enzyme mapping and DNA sequence analysis. One clone, $\alpha$1.279, contained a sequence of about 170 nucleotides that is not present in other clones corresponding to the same region of the coding sequence. This region may be present in other splice variants. None of the clones contained a translation initiation codon.

To obtain clones corresponding to the 5' end of the human $\alpha_{1A}$ coding sequence, another cerebellum cDNA library was prepared using oligonucleotide 720 (containing nucleotides 2485–2510 of SEQ ID No. 22) to specifically prime first-strand cDNA synthesis. The library (8×10$^5$ recombinants) was screened for hybridization to three oligonucleotides: oligonucleotide 701, oligonucleotide 726 (containing nucleotides 2333–2360 of the rat $\alpha_{1A}$ coding sequence) and oligonucleotide 700 (containing nucleotides 767–796 of the rat $\alpha_{1A}$ coding sequence) under low stringency hybridization and washing conditions. Approximately 50 plaques hybridized to the probe. Hybridizing clones $\alpha$1.381–$\alpha$1.390 were plaque-purified and characterized by restriction enzyme mapping and DNA sequence analysis. At least one of the clones, $\alpha$1.381, contained a translation initiation codon.

Alignment of the sequences of the purified clones revealed that the sequences overlapped to comprise the entire $\alpha_{1A}$ coding sequence. However, not all the overlapping sequences of partial clones contained convenient enzyme restriction sites for use in ligating partial clones to construct a full-length $\alpha_{1A}$ coding sequence. To obtain DNA fragments containing convenient restriction enzyme sites that could be used in constructing a full-length $\alpha_{1A}$ DNA, cDNA was synthesized from RNA isolated from human cerebellum tissue and subjected to nucleic acid amplification. The oligonucleotides used as primers corresponded to human $\alpha_{1A}$ coding sequence located 5' and 3' of selected restriction enzyme sites. Thus, in the first amplification reaction, oligonucleotides 753 (containing nucleotides 2368–2391 of SEQ ID No. 22) and 728 (containing nucleotides 3179–3202 of SEQ ID No. 22) were used as the primer pair. To provide a sufficient amount of the desired DNA fragment, the product of this amplification was reamplified using oligonucleotides 753 and 754 (containing nucleotides 3112–3135 of SEQ ID No. 22 as the primer pair. The resulting product was 768 bp in length. In the second amplification reaction, oligonucleotides 719 (containing nucleotides 4950–4975 of SEQ ID No. 22 and 752 (containing nucleotides 5647–5670 of SEQ ID No. 22) were used as the primer pair. To provide a sufficient amount of the desired second DNA fragment, the product of this amplification was reamplified using oligonucleotides 756 (containing nucleotides 5112–5135 of SEQ ID No. 22) and 752 as the primer pair. The resulting product was 559 bp in length.

2. Construction of full-Length $\alpha_{1A}$ coding sequences

Portions of clone $\alpha$1.381, the 768-bp nucleic acid amplification product, clone $\alpha$1.278, the 559-bp nucleic acid amplification product, and clone $\alpha$1.244 were ligated at convenient restriction sites to generate a full-length $\alpha_{1A}$ coding sequence referred to as $\alpha_{1A-1}$.

Comparison of the results of sequence analysis of clones $\alpha$1.244 and $\alpha$1.254 indicated that the primary transcript of the $\alpha_{1A}$ subunit gene is alternatively spliced to yield at least two variant mRNAs encoding different forms of the $\alpha_{1A}$ subunit. One form, $\alpha_{1A-1}$, is encoded by the sequence shown in SEQ ID No. 22. The sequence encoding a second form, $\alpha_{1A-2}$, differs from the $\alpha_{1A-1}$-encoding sequence at the 3' end in that it lacks a 5-nt sequence found in clone $\alpha$1.244 (nucleotides 7035–7039 of SEQ ID No. 22). This deletion shifts the reading frame and introduces a translation termination codon resulting in an $\alpha_{1A-2}$ coding sequence that encodes a shorter $\alpha_{1A}$ subunit than that encoded by the $\alpha_{1A-1}$ splice variant. Consequently, a portion of the 3' end of the $\alpha_{1A-2}$ coding sequence is actually 3' untranslated sequence in the $\alpha_{1A-2}$ DNA. The complete sequence of $\alpha_{1A-2}$, which can be constructed by ligating portions of clone $\alpha$1.381, the 768-bp nucleic acid amplification product, clone $\alpha$1.278, the 559-bp nucleic acid amplification product and clone $\alpha$1.254, is set forth in SEQ ID No. 23.

E. Isolation of DNA Encoding the $\alpha_{1E}$ Subunit

DNA encoding $\alpha_{1E}$ subunits of the human calcium channel were isolated from human hippocampus libraries. The selected clones sequenced. DNA sequence analysis of DNA clones encoding the $\alpha_{1E}$ subunit indicated that at least two alternatively spliced forms of the same $\alpha_{1E}$ subunit primary transcript are expressed. One form has the sequence set forth in SEQ ID No. 24 and was designated $\alpha_{1E-1}$ and the other was designated $\alpha_{1E-3}$, which has the sequence obtained by inserting SEQ ID No. 25 between nucleotides 2405 and 2406 of SEQ ID No. 24.

The subunit designated $\alpha_{1E-1}$ has a calculated molecular weight of 254,836 and the subunit designated $\alpha_{1E-3}$ has a calculated molecular weight of 257,348. $\alpha_{1E-3}$ has a 19 amino acid insertion (encoded by SEQ ID No. 25) relative to $\alpha_{1E-1}$ in the region that appears to be the cytoplasmic loop between transmembrane domains IIS6 and IIIS1.

EXAMPLE III

ISOLATION OF cDNA CLONES ENCODING THE HUMAN NEURONAL CALCIUM CHANNEL $\beta_1$ subunit A. Isolation of partial cDNA clones encoding the $\beta$ subunit and construction of a full-length clone encoding the $\beta_1$ subunit A human hippocampus cDNA library was screened with the rabbit skeletal muscle calcium channel $\beta_1$ subunit cDNA fragment (nt 441 to 1379) [for isolation and sequence of the rabbit skeletal muscle calcium channel $\beta$ subunit cDNA, see U.S. patent application Ser. NO. 482,384 or Ruth et al. (1989) *Science* 245:1115] using standard hybridization conditions (Example I.C.). A portion of one of the hybridizing clones was used to rescreen the hippocampus library to obtain additional cDNA clones. The cDNA inserts of hybridizing clones were characterized by restriction mapping and DNA sequencing and compared to the rabbit skeletal muscle calcium channel $\beta_1$ subunit cDNA sequence.

Portions of the partial $\beta_1$ subunit cDNA clones were ligated to generate a full-length clone encoding the entire $\beta_1$ subunit. SEQ ID No. 9 shows the $\beta_1$ subunit coding sequence (nt 1–1434) as well as a portion of the 3' untranslated sequence (nt 1435–1546). The deduced amino acid sequence is also provided in SEQ ID No. 9. In order to perform expression experiments, full-length $\beta$ subunit cDNA clones were constructed as follows.

Step 1: DNA fragment 1 (~800 bp of 5' untranslated sequence plus nt 1–277 of SEQ ID No. 9) was ligated to DNA fragment 2 (nt 277–1546 of SEQ ID No. 9 plus 448 bp of intron sequence) and cloned into pGEM7Z. The resulting plasmid, p$\beta$1-1.18, contained a full-length $\beta_1$ subunit clone that included a 448-bp intron.

Step 2: To replace the 5' untranslated sequence of p$\beta$1-1.18 with a ribosome binding site, a double-stranded adapter was synthesized that contains an EcoRI site, sequence encoding a ribosome binding site (5'-ACCACC-3') and nt 1–25 of SEQ ID No. 9. The adapter was ligated to SmaI-digested p$\beta$1-1.18, and the products of the ligation reaction were digested with EcoRI.

Step 3: The EcoRI fragment from step 2 containing the EcoRI adapter, efficient ribosome binding site and nt 1–1546 of SEQ ID No. 9 plus intron sequence was cloned into a plasmid vector and designated p$\beta$1-1.18RBS. The EcoRI fragment of p$\beta$1-1.18RBS was subcloned into EcoRI-digested pcDNA1 with the initiation codon proximal to CMV promoter to form pHBCaCH$\beta_{1a}$RBS(A).

Step 4: To generate a full-length clone encoding the $\beta_1$ subunit lacking intron sequence, DNA fragment 3 (nt 69–1146 of SEQ ID No. 9 plus 448 bp of intron sequence followed by nt 1147–1546 of SEQ ID No. 9), was subjected to site-directed mutagenesis to delete the intron sequence, thereby yielding p$\beta$1 (–). The EcoRI-XhoI fragment of p$\beta$1–1.18RBS (containing of the ribosome binding site and nt 1–277 of SEQ ID No. 9) was ligated to the XhoI-EcoRI fragment of p$\beta_1$ (–) (containing of nt 277–1546 of SEQ ID No. 9) and cloned into pcDNA1 with the initiation of translation proximal to the CMV promoter. The resulting expression plasmid was designated pHBCaCH$\beta_{1b}$RBS(A).

B. Splice Variant $\beta_{1-3}$

DNA sequence analysis of the DNA clones encoding the $\beta_1$ subunit indicated that in the CNS at least two alternatively spliced forms of the same human $\beta_1$ subunit primary transcript are expressed. One form is represented by the sequence shown in SEQ ID No. 9 and is referred to as $\beta_{1-2}$. The sequences of $\beta_{1-2}$ and the alternative form, $\beta_{1-3}$, diverge at nt 1334 (SEQ ID No. 9). The complete $\beta_{1-3}$ sequence (nt 1–1851), including 3' untranslated sequence (nt 1795–1851), is set forth in SEQ ID No. 10.

EXAMPLE IV

ISOLATION OP cDNA CLONES ENCODING THE HUMAN NEURONAL CALCIUM CHANNEL $\alpha_2$-subunit A. Isolation of cDNA clones The complete human neuronal $\alpha_2$ coding sequence (nt 35–3307) plus a portion of the 5' untranslated sequence (nt 1 to 34) as well as a portion of the 3' untranslated sequence (nt 3308–3600) is set forth in SEQ ID No. 11.

To isolate DNA encoding the human neuronal $\alpha_2$ subunit, human $\alpha_2$ genomic clones first were isolated by probing human genomic Southern blots using a rabbit skeletal muscle calcium channel $\alpha_2$ subunit cDNA fragment [nt 43 to 272, Ellis et al. (1988) *Science* 240:1661]. Human genomic DNA was digested with EcoRI, electrophoresed, blotted, and probed with the rabbit skeletal muscle probe using standard hybridization conditions (Example I.C.) and low stringency washing conditions (Example I.C.). Two restriction fragments were identified, 3.5 kb and 3.0 kb. These EcoRI restriction fragments were cloned by preparing a $\lambda$gt11 library containing human genomic EcoRI fragments ranging from 2.2 kb to 4.3 kb. The library was screened as described above using the rabbit $\alpha_2$ probe, hybridizing clones were isolated and characterized by DNA sequencing. HGCaCH$\alpha$2.20 contained the 3.5 kb fragment and HGCaCH$\alpha$2.9 contained the 3.0 kb fragment.

Restriction mapping and DNA sequencing revealed that HGCaCH$\alpha$2.20 contains an 82 bp exon (nt 130 to 211 of the human $\alpha_2$ coding sequence, SEQ ID No. 11) on a 650 bp PstI-XbaI restriction fragment and that HGCaCH$\alpha$2.9 contains 105 bp of an exon (nt 212 to 316 of the coding sequence, SEQ ID No. 11) on a 750 bp XbaI-BglII restriction fragment. These restriction fragments were used to screen the human basal ganglia cDNA library (Example II.C.2.a.). HBCaCH$\alpha$2.1 was isolated (nt 29 to 1163, SEQ ID No. 11) and used to screen a human brain stem cDNA library (ATCC Accession No. 37432) obtained from the American Type Culture Collection, 12301 Parklawn Drive, Rockville, Md. 20852. Two clones were isolated, HBCaCH$\alpha$2.5 (nt 1 to 1162, SEQ ID No. 11) and HBCaCH$\alpha$2.8 (nt 714 to 1562, SEQ ID No. 11, followed by 1600 nt of intervening sequence). A 2400 bp fragment of HBCaCH$\alpha$2.8 (beginning at nt 759 of SEQ ID No. 11 and ending at a SmaI site in the intron) was used to rescreen the brain stem library and to isolate HBCaCH$\alpha$2.11 (nt 879 to 3600, SEQ ID No. 11). Clones HBCaCH$\alpha$2.5 and HBCaCH$\alpha$2.11 overlap to encode an entire human brain $\alpha_2$ protein.

B. Construction of pHBCaCH$\alpha_2$A

To construct pHBCaCH$\alpha_2$A containing DNA encoding a full-length human calcium channel $\alpha_2$ subunit, an (EcoRI)-PvuII fragment of HBCaCH$\alpha$2.5 (nt 1 to 1061, SEQ ID No. 11, EcoRI adapter, PvuII partial digest) and a PvuII-PstI fragment of HBCaCH$\alpha$2.11 (nt 1061 to 2424 SEQ ID No. 11; PvuII partial digest) were ligated into EcoRI-PstI-digested pIBI24 (Stratagene, La Jolla, Calif.). Subsequently, an (EcoRI)-PstI fragment (nt 1 to 2424 SEQ ID No. 11) was isolated and ligated to a PstI-(EcoRI) fragment (nt 2424 to 3600 SEQ ID No. 11) of HBCaCH$\alpha$2.11 in EcoRI-digested pIBI24 to produce DNA, HBCaCH$\alpha$2, encoding a full-length human brain $\alpha_2$ subunit. The 3600 bp EcoRI insert of HBCaCH$\alpha_2$ (nt 1 to 3600, SEQ ID No. 11) was subcloned into pcDNA1 (pHBCaCH$\alpha$2A) with the methionine initiating codon proximal to the CMV promoter. The 3600 bp EcoRI insert of HBCaCH$\alpha_2$ was also subcloned into pSV2dHFR [Subramani et al. (1981). *Mol. Cell. Biol.*

1:854–864] which contains the SV40 early promoter, mouse dihydrofolate reductase (dhfr) gene, SV40 polyadenylation and splice sites and sequences required for maintenance of the vector in bacteria.

EXAMPLE V
DIFFERENTIAL PROCESSING OF THE HUMAN $\beta_1$ TRANSCRIPT AND THE HUMAN $\alpha_2$ TRANSCRIPT A. Differential processing of the $\beta_1$ transcript PCR analysis of the human $\beta_1$ transcript present in skeletal muscle, aorta, hippocampus and basal ganglia, and HEK 293 cells revealed differential processing of the region corresponding to nt 615–781 of SEQ ID No. 9 in each of the tissues. Four different sequences that result in five different processed $\beta_1$ transcripts through this region were identified. The $\beta_1$ transcripts from the different tissues contained different combinations of the four sequences, except for one of the $\beta$ transcripts expressed in HEK 293 cells ($\beta_{1-5}$) which lacked all four sequences.

None of the $\beta_1$ transcripts contained each of the four sequences; however, for ease of reference, all four sequences are set forth end-to-end as a single long sequence in SEQ ID No. 12. The four sequences that are differentially processed are sequence 1 (nt 14–34 in SEQ ID No. 12), sequence 2 (nt 35–55 in SEQ ID No. 12), sequence 3 (nt 56–190 in SEQ ID No. 12) and sequence 4 (nt 191–271 in SEQ ID No. 12). The forms of the $\beta_1$ transcript that have been identified include: (1) a form that lacks sequence 1 called $\beta_{1-1}$ (expressed in skeletal muscle), (2) a form that lacks sequences 2 and 3 called $\beta_{1-2}$ (expressed in CNS), (3) a form that lacks sequences 1, 2 and 3 called $\beta_{1-4}$ (expressed in aorta and HEK cells) and (4) a form that lacks sequences 1–4 called $\beta_{1-5}$ (expressed in HEK cells). Additionally, the $\beta_{1-4}$ and $\beta_{1-5}$ forms contain the guanine nucleotide (nt 13 in SEQ ID No. 12) which is absent in the $\beta_{1-1}$ and $\beta_{1-2}$ forms The sequences of these splice variants designated $\beta_{1-1}$, $\beta_{1-2}$, $\beta_{1-3}$, $\beta_{1-4}$ and $\beta_{1-5}$ are forth in sequence ID Nos. 29, 9, 10, 30 and 31, respectively.

B. Differential processing of transcripts encoding the $\alpha_2$ subunit.

The complete human neuronal $\alpha_2$ coding sequence (nt 35–3307) plus a portion of the 5' untranslated sequence (nt 1 to 34) as well as a portion of the 3' untranslated sequence (nt 3308–3600) is set forth as SEQ ID No. 11.

PCR analysis of the human $\alpha_2$ transcript present in skeletal muscle, aorta, and CNS revealed differential processing of the region corresponding to nt 1595–1942 of SEQ ID No. 11 in each of the tissues.

The analysis indicated that the primary transcript of the genomic DNA that includes the nucleotides corresponding to nt 1595–1942 also includes an additional sequence (SEQ ID No. 13: 5'CCTATTGGTGTAGGTATACCAACAAT- TAATTT AAGAAAAAGGAGACCCAATATCCAG 3') inserted between nt 1624 and 1625 of SEQ ID No. 11. Five alternatively spliced variant transcripts that differ in the presence or absence of one to three different portions of the region of the primary transcript that includes the region of nt 1595–1942 of SEQ ID No. 11 plus SEQ ID No. 13 inserted between nt 1624 and 1625 have been identified. The five $\alpha_2$-encoding transcripts from the different tissues include different combinations of the three sequences, except for one of the $\alpha_2$ transcripts expressed in aorta which lacks all three sequences. None of the $\alpha_2$ transcripts contained each of the three sequences. The sequences of the three regions that are differentially processed are sequence 1 (SEQ ID No. 13), sequence 2 (5'AACCCCAAATCTCAG 3', which is nt 1625–1639 of SEQ ID No. 11), and sequence 3 (5'CAAAAAAGGGCAAAATGAAGG 3', which is nt 1908–1928 of SEQ ID No. 11). The five $\alpha_2$ forms identified are (1) a form that lacks sequence 3 called $\alpha_{2a}$ (expressed in skeletal muscle), (2) a form that lacks sequence 1 called $\alpha_{2b}$ (expressed in CNS), (3) a form that lacks sequences 1 and 2 called $\alpha_{2c}$ expressed in aorta), (4) a form that lacks sequences 1, 2 and 3 called $\alpha_{2d}$ (expressed in aorta) and (5) a form that lacks sequences 1 and 3 called $\alpha_{2e}$ (expressed in aorta).

EXAMPLE VI
ISOLATION OF DNA ENCODING A CALCIUM CHANNEL $\gamma$ SUBUNIT FROM A HUMAN BRAIN cDNA LIBRARY A. Isolation of DNA encoding the $\gamma$ subunit Approximately $1 \times 10^6$ recombinants from a $\lambda$gt11-based human hippocampus cDNA library (Clontech catalog #HL1088b, Palo Alto, Calif.) were screened by hybridization to a 484 bp sequence of the rabbit skeletal muscle calcium channel $\gamma$ subunit cDNA (nucleotides 621–626 of the coding sequence plus 438 nucleotides of 3'-untranslated sequence) contained in vector 7J10 [Jay, S. et al. (1990). *Science* 248:490–492]. Hybridization was performed using moderate stringency conditions (20% deionized formamide, 5×Denhardt's, 6×SSPE, 0.2% SDS, 20 $\mu$g/ml herring sperm DNA, 42° C.) and the filters were washed under low stringency (see Example I.C.). A plaque that hybridized to this probe was purified and insert DNA was subcloned into pGEM7Z. This cDNA insert was designated $\gamma$1.4.

B. Characterization of $\gamma$1.4

$\gamma$1.4 was confirmed by DNA hybridization and characterized by DNA sequencing. The 1500 bp SstI fragment of $\gamma$1.4 hybridized to the rabbit skeletal muscle calcium channel $\gamma$ subunit cDNA $\gamma$J10 on a Southern blot. SEQ analysis of this fragment revealed that it contains of approximately 500 nt of human DNA sequence and ~1000 nt of $\lambda$gt11 sequence (included due to apparent destruction of one of the EcoRI cloning sites in $\lambda$gt11). The human DNA sequence contains of 129 nt of coding sequence followed immediately by a translational STOP codon and 3' untranslated sequence (SEQ ID No. 14).

To isolate the remaining 5' sequence of the human $\gamma$ subunit cDNA, human CNS cDNA libraries and/or preparations of mRNA from human CNS tissues can first be assayed by PCR methods using oligonucleotide primers based on the $\gamma$ cDNA-specific sequence of $\gamma$1.4. Additional human neuronal $\gamma$ subunit-encoding DNA can be isolated from cDNA libraries that, based on the results of the PCR assay, contain $\gamma$-specific amplifiable cDNA. Alternatively, cDNA libraries can be constructed from mRNA preparations that, based on the results of PCR assays, contain $\gamma$-specific amplifiable transcripts. Such libraries are constructed by standard methods using oligo dT to prime first-strand cDNA synthesis from poly $A^+$ RNA (see Example I.B.). Alternatively, first-strand cDNA can be specified by priming first-strand cDNA synthesis with a $\gamma$ cDNA-specific oligonucleotide based on the human DNA sequence in $\gamma$1.4. A cDNA library can then be constructed based on this first-strand synthesis and screened with the $\gamma$-specific portion of $\gamma$1.4.

EXAMPLE VII
ISOLATION OF cDNA CLONES ENCODING THE HUMAN NEURONAL Ca CHANNEL $\beta_2$ SUBUNIT Isolation of DNA Encoding human calcium channel $\beta_2$ subunits Sequencing of clones isolated as described in Example III revealed a clone encoding a substantial portion of a human neuronal calcium channel $\beta_2$ subunit (designated $\beta_{2D}$ D see, nucleotides 1–1866 SEQ ID No. 26). An oligonucleotide based on the 5' end of this clone was used to prime a human hippocampus cDNA library. The library was screened with this $\beta_2$ clone under conditions of low to medium stringency (final wash 0.5×SSPE, 50° C.). Several hybridizing clones were isolated and sequenced. Among these clones were those that encode $\beta_{2C}$, $\beta_{2E}$ and $\beta_{2F}$.

A randomly primed hippocampus library was then screened using a combination of the clone encoding $\beta_{2D}$ and a portion of the $\beta_3$ clone deposited under ATCC Accession No. 69048. Multiple hybridizing clones were isolated. Among these were clones designated β101, β102 and β104. β101 appears to encodes the 5' end of a splice variant of $\beta_2$, designated $\beta_{2E}$. β102 and β104 encode portions of the 3' end of $\beta_2$.

It appears that the $\beta_2$ splice variants include nucleotide 182–2264 of SEQ ID No. 26 and differ only between the start codon and nucleotides that correspond to 182 of SEQ. ID No. 26.

EXAMPLE VIII
ISOLATION OF cDNA CLONES ENCODING HUMAN CALCIUM CHANNEL $\beta_4$ and $\beta_3$ SUBUNITS A. Isolation of cDNA Clones Encoding a Human $\beta_4$ Subunit A clone containing a translation initiation codon and approximately 60% of the $\beta_4$ coding sequence (see Sequence ID No. 27) was obtained from a human cerebellum cDNA library. To obtain DNA encoding the remaining 3' portion of the $\beta_4$ coding sequence, a human cerebellum cDNA library was screened for hybridization a nucleic acid amplification product under high stringency hybridization and wash conditions. Hybridizing clones are purified and characterized by restriction enzyme mapping and DNA sequence analysis to identify those that contain sequence corresponding to the 3' end of the $\beta_4$ subunit coding sequence and a termination codon. Selected clones are ligated to the clone containing the 5' half of the $\beta_4$ coding sequence at convenient restriction sites to generate a full-length cDNA encoding a $\beta_4$ subunit.

B. Isolation of cDNA Clones Encoding a Human $\beta_3$ Subunit

Sequencing of clones isolated as described in Example III also revealed a clone encoding a human neuronal calcium channel $\beta_3$ subunit. This clone includes nucleotides having the sequence set forth in SEQ ID Nos. 19 and 20 and also includes DNA that has been deposited as plasmid β1.42 (ATCC Accession No. 69048).

To isolate a full-length cDNA clone encoding a complete $\beta_3$ subunit, a human hippocampus cDNA library (Stratagene, La Jolla, Calif.) was screened for hybridization to a 5' EcoRI-PstI fragment of the cDNA encoding $\beta_{1-2}$ using lower stringency hybridization conditions (20% deionized formamide, 200 μg/ml sonicated herring sperm DNA, 5×SSPE, 5×Denhardt's solution, 42° C.) and wash conditions. One of the hybridizing clones contained both translation initiation and termination codons and encodes a complete $\beta_3$ subunit (nucleotides 58–1509 of Sequence ID No. 19). The clone also contained 57 nucleotides of 5' untranslated sequence (nucleotides 1–57 of Sequence ID No. 19) and 649 bp of 3' untranslated sequence (including nucleotides 1510–2026 of Sequence ID No. 19). In vitro transcripts of the cDNA were prepared and injected into Xenopus oocytes along with transcripts of the $\alpha_{1B-1}$ and $\alpha_{2b}$ cDNAs using methods similar to those described in Example IX.D. Two-electrode voltage clamp recordings of the oocytes revealed significant voltage-dependent inward Ba$^{2+}$ currents.

An additional $\beta_3$ subunit-encoding cDNA was obtained by screening a human cerebellum cDNA library for hybridization to the nucleic acid amplification product referred to in Example VIII.A. under lower stringency (20% deionized formamide, 200 μg/ml sonicated herring sperm DNA, 5×SSPE, 5×Denhardt's solution, 42° C.) hybridization and wash conditions. The 5' ends of this clone (Sequence ID No. 20) and the first $\beta_3$ subunit cDNA (Sequence ID No. 19) differ at the 5' end and are splice variants of the $\beta_3$ gene.

EXAMPLE IX
RECOMBINANT EXPRESSION OF HUMAN NEURONAL CALCIUM CHANNEL SUBUNIT-ENCODING cDNA AND RNA TRANSCRIPTS IN MAMMALIAN CELLS

A. Recombinant Expression of the Human Neuronal Calcium Channel $\alpha_2$ subunit cDNA in DG44 Cells 1. Stable transfection of DG44 cells DG44 cells [dhfr$^-$ Chinese hamster ovary cells; see, e.g., Urlaub, G. et al. (1986) *Som. Cell Molec. Genet.* 12:555–566] obtained from Lawrence Chasin at Columbia University were stably transfected by CaPO$_4$ precipitation methods [Wigler et al. (1979) *Proc. Natl. Acad. Sci. USA* 76:1373–1376] with pSV2dhfr vector containing the human neuronal calcium channel $\alpha_2$-subunit cDNA (see Example IV) for polycistronic expression/selection in transfected cells. Transfectants were grown on 10% DMEM medium without hypoxanthine or thymidine in order to select cells that had incorporated the expression vector. Twelve transfectant cell lines were established as indicated by their ability to survive on this medium.

2. Analysis of $\alpha_2$ subunit cDNA expression in transfected DG44 cells

Total RNA was extracted according to the method of Birnboim [(1988) *Nuc. Acids Res.* 16:1487–1497] from four of the DG44 cell lines that had been stably transfected with pSV2dhfr containing the human neuronal calcium channel $\alpha_2$ subunit cDNA. RNA (~15 μg per lane) was separated on a 1% agarose formaldehyde gel, transferred to nitrocellulose and hybridized to the random-primed human neuronal calcium channel $\alpha_2$ cDNA (hybridization: 50% formamide, 5×SSPE, 5 ×Denhardt's, 42° C.; wash :0.2×SSPE, 0.1% SDS, 65° C.). Northern blot analysis of total RNA from four of the DG44 cell lines that had been stably transfected with pSV2dhfr containing the human neuronal calcium channel $\alpha_2$ subunit cDNA revealed that one of the four cell lines contained hybridizing mRNA the size expected for the transcript of the $\alpha_2$ subunit cDNA (5000 nt based on the size of the cDNA) when grown in the presence of 10 mM sodium butyrate for two days. Butyrate nonspecifically induces transcription and is often used for inducing the SV40 early promoter [Gorman, C. and Howard, B. (1983) *Nucleic Acids Res.* 11:1631]. This cell line, 44'$_2$-9, also produced mRNA species smaller (several species) and larger (6800 nt) than the size expected for the transcript of the $\alpha_2$ cDNA (5000 nt) that hybridized to the $\alpha_2$ cDNA-based probe. The 5000- and 6800-nt transcripts produced by this transfectant should contain the entire $\alpha_2$ subunit coding sequence and therefore should yield a full-length $\alpha_2$ subunit protein. A weakly hybridizing 8000-nucleotide transcript was present in untransfected and transfected DG44 cells. Apparently, DG44 cells transcribe a calcium channel $\alpha_2$ subunit or similar gene at low levels. The level of expression of this endogenous $\alpha_2$ subunit transcript did not appear to be affected by exposing the cells to butyrate before isolation of RNA for northern analysis.

Total protein was extracted from three of the DG44 cell lines that had been stably transfected with pSV2dhfr containing the human neuronal calcium channel $\alpha_2$ subunit cDNA. Approximately 10$^7$ cells were sonicated in 300 μl of a solution containing 50 mM HEPES, 1 mM EDTA, 1 mM PMSF. An equal volume of 2× loading dye [Laemmli, U.K. (1970). *Nature* 227:680] was added to the samples and the protein was subjected to electrophoresis on an 8% polyacrylamide gel and then electrotransferred to nitrocellulose. The nitrocellulose was incubated with polyclonal guinea pig antisera (1:200 dilution) directed against the rabbit skeletal muscle calcium channel $\alpha_2$ subunit (obtained from K. Campbell, University of Iowa) followed by incubation with [$^{125}$I]-protein A. The blot was exposed to X-ray film at −70° C. Reduced samples of protein from the transfected cells as well as from untransfected DG44 cells contained immunoreactive protein of the size expected for the $\alpha_2$ subunit of the human neuronal calcium channel (130–150 kDa). The level of this immunoreactive protein was higher in 44$\alpha_2$-9 cells that had been grown in the presence of 10 mM sodium butyrate than in 44$\alpha_2$-9 cells that were grown in the absence of sodium butyrate. These data correlate well with those obtained in northern analyses of total RNA from 44$\alpha_2$-9 and untransfected DG44 cells. Cell line 44$\alpha_2$-9 also produced a 110 kD immunoreactive protein that may be either a product of proteolytic degradation of the full-length $\alpha_2$ subunit or a product of translation of one of the shorter (<5000 nt) mRNAs produced in this cell line that hybridized to the $\alpha_2$ subunit cDNA probe.

B. Expression of DNA encoding human neuronal calcium channel $\alpha_1$, $\alpha_2$ and $\beta_1$ subunits in HEK cells Human embryonic kidney cells (HEK 293 cells) were transiently and stably transfected with human neuronal DNA encoding calcium channel subunits. Individual transfectants were analyzed electrophysiologically for the presence of voltage-activated barium currents and functional recombinant voltage-dependent calcium channels were.

1. Transfection of HEK 293 cells

Separate expression vectors containing DNA encoding human neuronal calcium channel $\alpha_{1D}$, $\alpha_2$ and $\beta_1$ subunits, plasmids pVDCCIII(A), pHBCaCH$\alpha_2$A, and pHBCaCH$\beta_{1a}$RBS(A), respectively, were constructed as described in Examples II.A.3, IV.B. and III.B.3., respectively. These three vectors were used to transiently co-transfect HEK 293 cells. For stable transfection of HEK 293 cells, vector pHBCaCH$\beta_{1b}$RBS(A) (Example III.B.3.) was used in place of pHBCaCH$\beta_{1a}$RBS (A) to introduce the DNA encoding the $\beta_1$ subunit into the cells along with pVDCCIII(A) and pHBCaCH$\alpha_2$A.

a. Transient transfection

Expression vectors pVDCCIII(A), pHBCaCH$\alpha_2$A and pHBCaCH$\beta_{1a}$RBS(A) were used in two sets of transient transfections of HEK 293 cells (ATCC Accession No. CRL1573). In one transfection procedure, HEK 293 cells were transiently cotransfected with the $\alpha_1$ subunit cDNA expression plasmid, the $\alpha_2$ subunit cDNA expression plasmid, the $\beta_1$ subunit cDNA expression plasmid and plasmid pCMVβgal (Clontech Laboratories, Palo Alto, Calif.). Plasmid pCMVβgal contains the lacZ gene (encoding *E. coli* β-galactosidase) fused to the cytomegalovirus (CMV) promoter and was included in this transfection as a marker gene for monitoring the efficiency of transfection. In the other transfection procedure, HEK 293 cells were transiently co-transfected with the $\alpha_1$ subunit cDNA expression plasmid pVDCCIII(A) and pCMVβgal. In both transfections, 2–4×10$^6$ HEK 293 cells in a 10-cm tissue culture plate were transiently co-transfected with 5 µg of each of the plasmids included in the experiment according to standard CaPO$_4$ precipitation transfection procedures (Wigler et al. (1979) *Proc. Natl. Acad. Sci. USA* 76:1373–1376). The transfectants were analyzed for β-galactosidase expression by direct staining of the product of a reaction involving β-galactosidase and the X-gal substrate [Jones, J. R. (1986) EMBO 5:3133–3142] and by measurement of β-galactosidase activity [Miller, J. H. (1972) Experiments in Molecular Genetics, pp. 352–355, Cold Spring Harbor Press]. To evaluate subunit cDNA expression in these transfectants, the cells were analyzed for subunit transcript production (northern analysis), subunit protein production (immunoblot analysis of cell lysates) and functional calcium channel expression (electrophysiological analysis).

b. Stable transfection

HEK 293 cells were transfected using the calcium phosphate transfection procedure [Current Protocols in *Molecular Biology*, Vol. 1, Wiley Inter-Science, Supplement 14, Unit 9.1.1–9.1.9 (1990)]. Ten-cm plates, each containing one-to-two million HEK 293 cells, were transfected with 1 ml of DNA/calcium phosphate precipitate containing 5 µg pVDCCIII(A), 5 µg pHBCaCH$\alpha$2A, 5 µg pHBCaCH$\beta_{1b}$RBS(A), 5 µg pCMVBgal and 1 µg pSV2neo (as a selectable marker). After 10–20 days of growth in media containing 500 µg G418, colonies had formed and were isolated using cloning cylinders.

2. Analysis of HEK 293 cells transiently transfected with DNA encoding human neuronal calcium channel subunits a. Analysis of β-galactosidase expression Transient transfectants were assayed for β-galactosidase expression by β-galactosidase activity assays (Miller, J. H., (1972) Experiments in Molecular Genetics, pp. 352–355, Cold Spring Harbor Press) of cell lysates (prepared as described in Example VII.A.2) and staining of fixed cells (Jones, J. R. (1986) *EMBO* 5:3133–3142). The results of these assays indicated that approximately 30% of the HEK 293 cells had been transfected.

b. Northern analysis

PolyA+ RNA was isolated using the Invitrogen Fast Trak Kit (InVitrogen, San Diego, Calif.) from HEK 293 cells transiently transfected with DNA encoding each of the $\alpha_1$, $\alpha_2$ and $\beta_1$ subunits and the lacZ gene or the $\alpha_1$ subunit and the lacZ gene. The RNA was subjected to electrophoresis on an agarose gel and transferred to nitrocellulose. The nitrocellulose was then hybridized with one or more of the following radiolabeled probes: the lacZ gene, human neuronal calcium channel $\alpha_{1D}$ subunit-encoding cDNA, human neuronal calcium channel $\alpha_2$ subunit-encoding cDNA or human neuronal calcium channel $\beta_1$ subunit-encoding cDNA. Two transcripts that hybridized with the $\alpha_1$ subunit-encoding cDNA were detected in HEK 293 cells transfected with the DNA encoding the $\alpha_1$, $\alpha_2$, and $\beta_1$ subunits and the lacZ gene as well as in HEK 293 cells transfected with the $\alpha_1$ subunit cDNA and the lacZ gene. One mRNA species was the size expected for the transcript of the $\alpha_1$ subunit cDNA (8000 nucleotides). The second RNA species was smaller (4000 nucleotides) than the size expected for this transcript. RNA of the size expected for the transcript of the lacZ gene was detected in cells transfected with the $\alpha_1$, $\alpha_2$ and $\beta_1$ subunit-encoding cDNA and the lacZ gene and in cells transfected with the $\alpha_1$ subunit cDNA and the lacZ gene by hybridization to the lacZ gene sequence.

RNA from cells transfected with the $\alpha_1$, $\alpha_2$ and $\beta_1$ subunit-encoding cDNA and the lacZ gene was also hybridized with the $\alpha_2$ and $\beta_1$ subunit cDNA probes. Two mRNA species hybridized to the $\alpha_2$ subunit cDNA probe. One species was the size expected for the transcript of the $\alpha_2$ subunit cDNA (4000 nucleotides). The other species was larger (6000 nucleotides) than the expected size of this transcript. Multiple RNA species in the cells co-transfected with $\alpha_1$, $\alpha_2$ and $\beta_1$ subunit-encoding cDNA and the lacZ gene hybridized to the $\beta_1$ subunit cDNA probe. Multiple β-subunit transcripts of varying sizes were produced since the β subunit cDNA expression vector contains two potential polyA$^+$ addition sites.

c. Electrophysiological analysis

Individual transiently transfected HEK 293 cells were assayed for the presence of voltage-dependent barium currents using the whole-cell variant of the patch clamp technique [Hamill et al. (1981). *Pflugers Arch.* 391:85–100]. HEK 293 cells transiently transfected with pCMVβgal only were assayed for barium currents as a negative control in these experiments. The cells were placed in a bathing solution that contained barium ions to serve as the current carrier. Choline chloride, instead of NaCl or KCl, was used as the major salt component of the bath solution to eliminate currents through sodium and potassium channels. The bathing solution contained 1 MM $MgCl_2$ and was buffered at pH 7.3 with 10 mM HEPES (pH adjusted with sodium or tetraethylammonium hydroxide). Patch pipettes were filled with a solution containing 135 mM CsCl, 1 mM $MgCl_2$, 10 MM glucose, 10 mM EGTA, 4 mM ATP and 10 mM HEPES (pH adjusted to 7.3 with tetraethylammonium hydroxide). Cesium and tetraethylammonium ions block most types of potassium channels. Pipettes were coated with Sylgard (Dow-Corning, Midland, Mich.) and had resistances of 1–4 megohm. Currents were measured through a 500 megohm headstage resistor with the Axopatch IC (Axon Instruments, Foster City, Calif.) amplifier, interfaced with a Labmaster (Scientific Solutions, Solon, Ohio) data acquisition board in an IBM-compatible PC. PClamp (Axon Instruments) was used to generate voltage commands and acquire data. Data were analyzed with pClamp or Quattro Professional (Borland International, Scotts Valley, Calif.) programs.

To apply drugs, "puffer" pipettes positioned within several micrometers of the cell under study were used to apply solutions by pressure application. The drugs used for pharmacological characterization were dissolved in a solution identical to the bathing solution. Samples of a 10 mM stock solution of Bay K 8644 (RBI, Natick, Mass.), which was prepared in DMSO, were diluted to a final concentration of 1 μM in 15 mM $Ba^{2+}$-containing bath solution before they were applied.

Twenty-one negative control HEK 293 cells (transiently transfected with the lacZ gene expression vector pCMVβgal only) were analyzed by the whole-cell variant of the patch clamp method for recording currents. Only one cell displayed a discernable inward barium current; this current was not affected by the presence of 1 μM Bay K 8644. In addition, application of Bay K 8644 to four cells that did not display $Ba^{2+}$ currents did not result in the appearance of any currents.

Two days after transient transfection of HEK 293 cells with $\alpha_1$, $\alpha_2$ and $\beta_1$ subunit-encoding cDNA and the lacZ gene, individual transfectants were assayed for voltage-dependent barium currents. The currents in nine transfectants were recorded. Because the efficiency of transfection of one cell can vary from the efficiency of transfection of another cell, the degree of expression of heterologous proteins in individual transfectants varies and some cells do not incorporate or express the foreign DNA. Inward barium currents were detected in two of these nine transfectants. In these assays, the holding potential of the membrane was −90 mV. The membrane was depolarized in a series of voltage steps to different test potentials and the current in the presence and absence of 1 μM Bay K 8644 was recorded. The inward barium current was significantly enhanced in magnitude by the addition of Bay K 8644. The largest inward barium current (∼160 pA) was recorded when the membrane was depolarized to 0 mV in the presence of 1 μM Bay K 8644. A comparison of the I–V curves, generated by plotting the largest current recorded after each depolarization versus the depolarization voltage, corresponding to recordings conducted in the absence and presence of Bay K 8644 illustrated the enhancement of the voltage-activated current in the presence of Bay K 8644.

Pronounced tail currents were detected in the tracings of currents generated in the presence of Bay K 8644 in HEK 293 cells transfected with $\alpha_1$, $\alpha_2$ and $\beta_1$ subunit-encoding cDNA and the lacZ gene, indicating that the recombinant calcium channels responsible for the voltage-activated barium currents recorded in this transfected appear to be DHP-sensitive.

The second of the two transfected cells that displayed inward barium currents expressed a ∼50 pA current when the membrane was depolarized from ∼90 mV. This current was nearly completely blocked by 200 μM cadmium, an established calcium channel blocker.

Ten cells that were transiently transfected with the DNA encoding the $\alpha_1$ subunit and the lacZ gene were analyzed by whole-cell patch clamp methods two days after transfection. One of these cells displayed a 30 pA inward barium current. This current amplified 2-fold in the presence of 1 μM Bay K 8644. Furthermore, small tail currents were detected in the presence of Bay K 8644. These data indicate that expression of the human neuronal calcium channel $\alpha_{1D}$ subunit-encoding cDNA in HEK 293 yields a functional DHP-sensitive calcium channel.

3. Analysis of HEK 293 cells stably transfected with DNA encoding human neuronal calcium channel subunits Individual stably transfected HEK 293 cells were assayed electrophysiologically for the presence of voltage-dependent barium currents as described for electrophysiological analysis of transiently transfected HEK 293 cells (see Example VII.B.2.c). In an effort to maximize calcium channel activity via cyclic-AMP-dependent kinase-mediated phosphorylation [Pelzer, et al. (1990) *Rev. Physiol. Biochem. Pharmacol.* 114:107–207], cAMP (Na salt, 250 μM) was added to the pipet solution and forskolin (10 μM) was added to the bath solution in some of the recordings. Qualitatively similar results were obtained whether these compounds were present or not.

Barium currents were recorded from stably transfected cells in the absence and presence of Bay K 8644 (1 μM). When the cell was depolarized to −10 mV from a holding potential of −90 mV in the absence of Bay K 8644, a current of approximately 35 pA with a rapidly deactivating tail current was recorded. During application of Bay K 8644, an identical depolarizing protocol elicited a current of approximately 75 pA, accompanied by an augmented and prolonged tail current. The peak magnitude of currents recorded from this same cell as a function of a series of depolarizing voltages were assessed. The responses in the presence of Bay K 8644 not only increased, but the entire current-voltage relation shifted about −10 mV. Thus, three typical hallmarks of Bay K 8644 action, namely increased current magnitude, prolonged tail currents, and negatively shifted activation voltage, were observed, clearly indicating the expression of a DHP-sensitive calcium channel in these stably transfected cells. No such effects of Bay K 8644 were observed in untransfected HEK 293 cells, either with or without cAMP or forskolin.

C. Use of pCMV-based vectors and pcDNA1-based vectors for expression of DNA encoding human neuronal calcium channel subunits 1. Preparation of constructs To determine if the levels of recombinant expression of human calcium channel subunit-encoding DNA in host cells could be enhanced by using pCMV-based instead of pcDNA1-based expression vectors, additional expression vectors were constructed. The full-length $\alpha_{1D}$ cDNA from pVDCCIII (A) (see Example II.A.3.d), the full-length $\alpha_2$ cDNA, contained on a 3600 bp EcoRI fragment from HBCaCH$\alpha_2$ (see Example IV.B) and a full-length $\beta_1$ subunit cDNA from pHBCaCH$\beta_{1b}$RBS(A) (see Example III.B.3) were separately subcloned into plasmid pCMV$\beta$gal. Plasmid pCMV$\beta$gal was digested with NotI to remove the lacZ gene. The remaining vector portion of the plasmid, referred to as pCMV, was blunt-ended at the NotI sites. The full-length $\alpha_2$-encoding DNA and $\beta_1$-encoding DNA, contained on separate EcoRI fragments, were isolated, blunt-ended and separately ligated to the blunt-ended vector fragment of pCMV locating the cDNAs between the CMV promoter and SV40 polyadenylation sites in pCMV. To ligate the $\alpha_{1D}$-encoding cDNA with pCMV, the restriction sites in the polylinkers immediately 5' of the CMV promoter and immediately 3' of the SV40 polyadenylation site were removed from pCMV. A polylinker was added at the NotI site. The polylinker had the following sequence of restriction enzyme recognition sites:

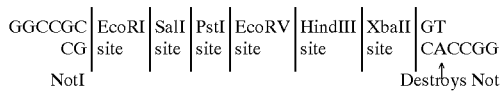

The $\alpha_{1D}$-encoding DNA, isolated as a BamHI/XhoI fragment from pVDCCIII(A), was then ligated to XbaII/SalI-digested pCMV to place it between the CMV promoter and SV40 polyadenylation site.

Plasmid pCMV contains the CMV promoter as does pcDNA1, but differs from pcDNA1 in the location of splice donor/splice acceptor sites relative to the inserted subunit-encoding DNA. After inserting the subunit-encoding DNA into pCMV, the splice donor/splice acceptor sites are located 3' of the CMV promoter and 5' of the subunit-encoding DNA start codon. After inserting the subunit-encoding DNA into pcDNA1, the splice donor/splice acceptor sites are located 3' of the subunit cDNA stop codon.

2. Transfection of HEK 293 cells

HEK 293 cells were transiently co-transfected with the $\alpha_{1D}$, $\alpha_2$ and $\beta_1$ subunit-encoding DNA in pCMV or with the $\alpha_{1D}$, $\alpha_2$ and $\beta$ subunit-encoding DNA in pcDNA1 (vectors pVDCCIII(A), pHBCaCH$\alpha_2$A and pHBCaCH$\beta_{1b}$RBS(A), respectively), as described in Example VII.B.1.a. Plasmid pCMV$\beta$gal was included in each transfection to as a measure of transfection efficiency. The results of $\beta$-galactosidase assays of the transfectants (see Example VII.B.2.), indicated that HEK 293 cells were transfected equally efficiently with pCMV- and pcDNA1-based plasmids.

3. Northern analysis

Total and polyA$^+$ RNA were isolated from the transiently transfected cells as described in Examples VII.A.2 and VII.B.2.b. Northern blots of the RNA were hybridized with the following radiolabeled probes: $\alpha_{1D}$ cDNA, human neuronal calcium channel $\alpha_2$ subunit cDNA and DNA encoding the human neuronal calcium channel $\beta_1$ subunit. Messenger RNA of sizes expected for $\alpha_{1D}$, $\alpha_2$ and $\beta_1$ subunit transcripts were detected in all transfectants. A greater amount of the $\alpha_{1D}$ transcript was present in cells that were co-transfected with pCMV-based plasmids then in cells that were co-transfected with pcDNA1-based plasmids. Equivalent amounts of $\alpha_2$ and $\beta_1$ subunit transcripts were detected in all transfectants.

D. Expression in *Xenopus laevis* oöcytes of RNA encoding human neuronal calcium channel subunits Various combinations of the transcripts of DNA encoding the human neuronal $\alpha_{1D}$, $\alpha_2$ and $\beta_1$ subunits prepared in vitro were injected into *Xenopus laevis* oöcytes. Those injected with combinations that included $\alpha_{1D}$ exhibited voltage-activated barium currents.

1. Preparation of transcripts

Transcripts encoding the human neuronal calcium channel $\alpha_{1D}$, $\alpha_2$ and $\beta_1$ subunits were synthesized according to the instructions of the mCAP mRNA CAPPING KIT (Strategene, La Jolla, Calif. catalog #200350). Plasmids pVDCC III.RBS(A), containing of pcDNA1 and the $\alpha_{1D}$ cDNA that begins with a ribosome binding site and the eighth ATG codon of the coding sequence (see Example III.A.3.d), plasmid pHBCaCH$\alpha_1$A containing of pcDNA1 and an $\alpha_2$ subunit cDNA (see Example IV), and plasmid pHBCaCH$\beta_{1b}$RBS(A) containing pcDNA1 and the $\beta_1$ DNA lacking intron sequence and containing a ribosome binding site (see Example III), were linearized by restriction digestion. The $\alpha_{1D}$ cDNA- and $\alpha_2$ subunit-encoding plasmids were digested with XhoI, and the $\beta_1$ subunit-encoding plasmid was digested with EcoRV. The DNA insert was transcribed with T7 RNA polymerase.

2. Injection of oöcytes

*Xenopus laevis* oöcytes were isolated and defolliculated by collagenase treatment and maintained in 100 mM NaCl, 2 mM KCl, 1.8 mM CaCl$_2$, 1 mM MgCl$_2$, 5 mM HEPES, pH 7.6, 20 µg/ml ampicillin and 25 µg/ml streptomycin at 19–25° C. for 2 to 5 days after injection and prior to recording. For each transcript that was injected into the oöcyte, 6 ng of the specific mRNA was injected per cell in a total volume of 50 nl.

3. Intracellular voltage recordings

Injected oöcytes were examined for voltage-dependent barium currents using two-electrode voltage clamp methods [Dascal, N. (1987) CRC Crit. *Rev. Biochem.* 22:317]. The pClamp (Axon Instruments) software package was used in conjunction with a Labmaster 125 kHz data acquisition interface to generate voltage commands and to acquire and analyze data. Quattro Professional was also used in this analysis. Current signals were digitized at 1–5 kHz, and filtered appropriately. The bath solution contained of the following: 40 mM BaCl$_2$, 36 mM tetraethylammonium chloride (TEA-Cl), 2 mM KCl, 5 mM 4-aminopyridine, 0.15 mM niflumic acid, 5 mM HEPES, pH 7.6.

a. Electrophysiological analysis of oöcytes injected with transcripts encoding the human neuronal calcium channel $\alpha_1$, $\alpha_2$ and $\beta_1$-subunits Uninjected oöcytes were examined by two-electrode voltage clamp methods and a very small (25 nA) endogenous inward Ba$^{2+}$ current was detected in only one of seven analyzed cells.

Oöcytes coinjected with $\alpha_{1D}$, $\alpha_2$ and $\beta_1$ subunit transcripts expressed sustained inward barium currents upon depolarization of the membrane from a holding potential of −90 mV or −50 mV (154±129 nA, n=21). These currents typically showed little inactivation when test pulses ranging from 140 to 700 msec. were administered. Depolarization to a series of voltages revealed currents that first appeared at approximately −30 mV and peaked at approximately 0 mV.

Application of the DHP Bay K 8644 increased the magnitude of the currents, prolonged the tail currents present upon repolarization of the cell and induced a hyperpolarizing shift in current activation. Bay K 8644 was prepared fresh from a stock solution in DMSO and introduced as a 10× concentrate directly into the 60 µl bath while the perfusion pump was turned off. The DMSO concentration of the final diluted drug solutions in contact with the cell never exceeded 0.1%. Control experiments showed that 0.1% DMSO had no effect on membrane currents.

Application of the DHP antagonist nifedipine (stock solution prepared in DMSO and applied to the cell as described for application of Bay K 8644) blocked a substantial fraction (91±6%, n=7) of the inward barium current in oocytes coinjected with transcripts of the $\alpha_{1D}$, $\alpha_2$ and $\beta_1$ subunits. A residual inactivating component of the inward barium current typically remained after nifedipine application. The inward barium current was blocked completely by 50 µM $Cd^{2+}$, but only approximately 15% by 100 µM $Ni^{2+}$.

The effect of ωCgTX on the inward barium currents in oocytes co-injected with transcripts of the $\alpha_{1D}$, $\alpha_2$, and β subunits was investigated. ωCgTX (Bachem, Inc., Torrance Calif.) was prepared in the 15 mM $BaCl_2$ bath solution plus 0.1% cytochrome C (Sigma) to serve as a carrier protein. Control experiments showed that cytochrome C had no effect on currents. A series of voltage pulses from a −90 mV holding potential to 0 mV were recorded at 20 msec. intervals. To reduce the inhibition of ωCgTX binding by divalent cations, recordings were made in 15 mM $BaCl_2$, 73.5 mM tetraethylammonium chloride, and the remaining ingredients identical to the 40 mM $Ba^{2+}$ recording solution. Bay K 8644 was applied to the cell prior to addition to ωCgTX in order to determine the effect of ωCgTX on the DHP-sensitive current component that was distinguished by the prolonged tail currents. The inward barium current was blocked weakly (54±29%, n=7) and reversibly by relatively high concentrations (10–15 µM) of ωCgTX. The test currents and the accompanying tail currents were blocked progressively within two to three minutes after application of ωCgTX, but both recovered partially as the ωCgTX was flushed from the bath.

b. Analysis of oocytes injected with only a transcripts encoding the human neuronal calcium channel $\alpha_{1D}$ or transcripts encoding an $\alpha_{1D}$ and other subunits The contribution of the $\alpha_2$ and $\beta_1$ subunits to the inward barium current in oocytes injected with transcripts encoding the $\alpha_{1D}$, $\alpha_2$ and $\beta_1$ subunits was assessed by expression of the $\alpha_{1D}$ subunit alone or in combination with either the $\beta_1$ subunit or the $\alpha_2$ subunit. In oocytes injected with only the transcript of a $\alpha_{1D}$ cDNA, no $Ba^{2+}$ currents were detected (n=3). In oocytes injected with transcripts of $\alpha_{1D}$ and $\beta_1$ cDNAs, small (108±39 nA) $Ba^{2+}$ currents were detected upon depolarization of the membrane from a holding potential of −90 mV that resembled the currents observed in cells injected with transcripts of $\alpha_{1D}$, $\alpha_2$ and $\beta_1$ cDNAs, although the magnitude of the current was less. In two of the four oocytes injected with transcripts of the $\alpha_{1D}$-encoding and $\beta_1$-encoding DNA, the $Ba^{2+}$ currents exhibited a sensitivity to Bay K 8644 that was similar to the Bay K 8644 sensitivity of $Ba^{2+}$ currents expressed in oocytes injected with transcripts encoding the $\alpha_{1D}$ $\alpha_1$-, $\alpha_2$- and β subunits.

Three of five oocytes injected with transcripts encoding the $\alpha_{1D}$ and $\alpha_2$ subunits exhibited very small $Ba^{2+}$ currents (15–30 nA) upon depolarization of the membrane from a holding potential of −90 mV. These barium currents showed little or no response to Bay K 8644.

c. Analysis of oocytes injected with transcripts encoding the human neuronal calcium channel $\alpha_2$ and/or $\beta_1$ subunit To evaluate the contribution of the $\alpha_{1D}$ $\alpha_1$-subunit to the inward barium currents detected in oocytes co-injected with transcripts encoding the $\alpha_{1D}$, $\alpha_2$ and $\beta_1$ subunits, oocytes injected with transcripts encoding the human neuronal calcium channel $\alpha_2$ and/or $\beta_1$ subunits were assayed for barium currents. Oocytes injected with transcripts encoding the $\alpha_2$ subunit displayed no detectable inward barium currents (n=5). Oocytes injected with transcripts encoding a $\beta_1$ subunit displayed measurable (54±23 nA, n=5) inward barium currents upon depolarization and oocytes injected with transcripts encoding the $\alpha_2$ and $\beta_1$ subunits displayed inward barium currents that were approximately 50% larger (80±61 nA, n=18) than those detected in oocytes injected with transcripts of the $\beta_1$-encoding DNA only.

The inward barium currents in oocytes injected with transcripts encoding the $\beta_1$ subunit or $\alpha_2$ and $\beta_1$ subunits typically were first observed when the membrane was depolarized to −30 mV from a holding potential of −90 mV and peaked when the membrane was depolarized to 10 to 20 mV. Macroscopically, the currents in oocytes injected with transcripts encoding the $\alpha_2$ and $\beta_1$ subunits or with transcripts encoding the $\beta_1$ subunit were indistinguishable. In contrast to the currents in oocytes co-injected with transcripts of $\alpha_{1D}$, $\alpha_2$ and $\beta_1$ subunit cDNAs, these currents showed a significant inactivation during the test pulse and a strong sensitivity to the holding potential. The inward barium currents in oocytes co-injected with transcripts encoding the $\alpha_2$ and $\beta_1$ subunits usually inactivated to 10–60% of the peak magnitude during a 140-msec pulse and were significantly more sensitive to holding potential than those in oocytes co-injected with transcripts encoding the $\alpha_{1D}$, $\alpha_2$ and $\beta_1$ subunits. Changing the holding potential of the membranes of oocytes co-injected with transcripts encoding the $\alpha_2$ and $\beta_1$ subunits from −90 to −50 mV resulted in an approximately 81% (n=11) reduction in the magnitude of the inward barium current of these cells. In contrast, the inward barium current measured in oocytes co-injected with transcripts encoding the $\alpha_{1D}$, $\alpha_2$ and $\beta_1$ subunits were reduced approximately 24% (n=11) when the holding potential was changed from −90 to −50 mV.

The inward barium currents detected in oocytes injected with transcripts encoding the $\alpha_2$ and $\beta_1$ subunits were pharmacologically distinct from those observed in oocytes co-injected with transcripts encoding the $\alpha_{1D}$, $\alpha_2$ and $\beta_1$ subunits. Oocytes injected with transcripts encoding the $\alpha_2$ and $\beta_1$ subunits displayed inward barium currents that were insensitive to Bay K 8644 (n=11). Nifedipine sensitivity was difficult to measure because of the holding potential sensitivity of nifedipine and the current observed in oocytes injected with transcripts encoding the $\alpha_2$ and $\beta_1$ subunits. Nevertheless, two oocytes that were co-injected with transcripts encoding the $\alpha_2$ and, subunits displayed measurable (25 to 45 nA) inward barium currents when depolarized from a holding potential of −50 mV. These currents were insensitive to nifedipine (5 to 10 µM). The inward barium currents in oöcytes injected with transcripts encoding the $\alpha_2$ and $\beta_1$ subunits showed the same sensitivity to heavy metals as the currents detected in oöcytes injected with transcripts encoding the $\alpha_{1D}$, $\alpha_2$ and $\beta_1$ subunits.

The inward barium current detected in oöcytes injected with transcripts encoding the human neuronal $\alpha_2$ and $\beta_1$ subunits has pharmacological and biophysical properties that resemble calcium currents in uninjected *Xenopus oöcytes*. Because the amino acids of this human neuronal calcium channel $\beta_1$ subunit lack hydrophobic segments capable of forming transmembrane domains, it is unlikely that recombinant $\beta_1$ subunits alone can form an ion channel. It is more probable that a homologous endogenous $\alpha_1$ subunit exists in oöcytes and that the activity mediated by such an $\alpha_1$ subunit is enhanced by expression of a human neuronal $\beta_1$ subunit.

E. Expression of DNA encoding human neuronal calcium channel $\alpha_{1B}$, $\alpha_{2B}$ and $\beta_{1-2}$ subunits in HEK cells 1. Transfection of HEK cells The transient expression of the human neuronal $\alpha_{1B-1}$, $\alpha_{2b}$ and $\beta_{1-2}$ subunits was studied in HEK293 cells. The HEK293 cells were grown as a monolayer culture in Dulbecco's modified Eagle's medium (Gibco) containing 5% defined-supplemented bovine calf serum (Hyclone) plus penicillin G (100 U/ml) and streptomycin sulfate (100 µg/ml). HEK293 cell transfections were mediated by calcium phosphate as described above. Transfected cells were examined for inward $Ba^{2+}$ currents ($I_{Ba}$) mediated by voltage-dependent $Ca^{2+}$ channels.

Cells were transfected ($2\times10^6$ per polylysine-coated plate. Standard transfections (10-cm dish) contained 8 µg of pcDNA$\alpha_{1B-1}$, 5 µg of pHBCaCH$\alpha_2$A, 2 µg pHBCaCH$\beta_{1b}$RBS(A) (see, Examples II.A.3, IV.B. and III) and 2 µg of CMV$\beta$ (Clontech) $\beta$-glactosidase expression plasmid, and pUC18 to maintain a constant mass of 20 µg/ml. Cells were analyzed 48 to 72 hours after transfection. Transfection efficiencies (±10%), which were determined by in situ histochemical staining for $\beta$-galactosidase activity (Sanes et al. (1986) *EMBO J.*, 5:3133), generally were greater than 50%.

2. Electrophysiological analysis of transfectant currents

1. Materials and methods

Properties of recombinantly expressed $Ca^{2+}$ channels were studied by whole cell patch-clamp techniques. Recordings were performed on transfected HEK293 cells 2 to 3 days after transfection. Cells were plated at 100,000 to 300,000 cells per polylysine-coated, 35-mm tissue culture dishes (Falcon, Oxnard, Calif.) 24 hours before recordings. Cells were perfused with 15 mM $BaCl_2$, 125 mM choline chloride, 1 mM $MgCl_2$, and 10 mM Hepes (pH=7.3) adjusted with tetraethylammonium hydroxide (bath solution). Pipettes were filled with 135 mM CsCl, 10 mM EGTA, 10 mM Hepes, 4 mM Mg-adenosine triphosphate (pH=7.5) adjusted with tetraethylammonium hydroxide. Sylgard (Dow-Corning, Midland, Mich.) -coated, fire-polished, and filled pipettes had resistances of 1 to 2 megohm before gigohm seals were established to cells.

Bay K 8644 and nifedipine (Research Biochemicals, Natick, Mass.) were prepared from stock solutions (in dimethyl sulfoxide) and diluted into the bath solution. The dimethyl sulfoxide concentration in the final drug solutions in contact with the cells never exceeded 0.1%. Control experiments showed that 0.1% dimethyl sulfoxide had no effect on membrane currents. $\omega$CgTX (Bachem, Inc., Torrance Calif.) was prepared in the 15 mM $BaCl_2$ bath solution plus 0.1% cytochrome C (Sigma, St. Louis Mo.) to serve as a carrier protein. Control experiments showed that cytochrome C had no effect on currents. These drugs were dissolved in bath solution, and continuously applied by means of puffer pipettes as required for a given experiment. Recordings were performed at room temperature (22° to 25° C.). Series resistance compensation (70 to 85%) was employed to minimize voltage error that resulted from pipette access resistance, typically 2 to 3.5 megohm. Current signals were filtered (−3 dB, 4-pole Bessel) at a frequency of ¼ to ⅕ the sampling rate, which ranged from 0.5 to 3 kHz. Voltage commands were generated and data were acquired with CLAMPEX (pClamp, Axon Instruments, Foster City, Calif.). All reported data are corrected for linear leak and capacitive components. Exponential fitting of currents was performed with CLAMPFIT (Axon Instruments, Foster City, Calif.).

2. Results

Transfectants were examined for inward $Ba^{2+}$ currents ($I_{Ba}$). Cells cotransfected with DNA encoding $\alpha_{1B-1}$, $\alpha_{2b}$, and $\beta_{1-2}$ subunits expressed high-voltage-activated $Ca^{2+}$ channels. $I_{Ba}$ first appeared when the membrane was depolarized from a holding potential of −90 mV to −20 mV and peaked in magnitude at 10 mV. Thirty-nine of 95 cells (12 independent transfections) had $I_{Ba}$ that ranged from 30 to 2700 pA, with a mean of 433 pA. The mean current density was 26 pA/pF, and the highest density was 150 pA/pF. The $I_{Ba}$ typically increased by 2- to 20-fold during the first 5 minutes of recording. Repeated depolarizations during long records often revealed rundown of $I_{Ba}$ usually not exceeding 20% within 10 min. $I_{Ba}$ typically activated within 10 ms and inactivated with both a fast time constant ranging from 46 to 105 ms and a slow time constant ranging from 291 to 453 ms (n=3). Inactivation showed a complex voltage dependence, such that $I_{Ba}$ elicited at ≧20 mV inactivated more slowly than $I_{Ba}$ elicited at lower test voltages, possibly a result of an increase in the magnitude of slow compared to fast inactivation components at higher test voltages.

Recombinant $\alpha_{1B-1}\alpha_{2b}\beta_{1-2}$ channels were sensitive to holding potential. Steady-state inactivation of $I_{Ba}$, measured after a 30- to 60-s conditioning at various holding potentials, was approximately 50% at holding potential between −60 and −70 mV and approximately 90% at −40 mV. Recovery of $I_{Ba}$ from inactivation was usually incomplete, measuring 55 to 75% of the original magnitude within 1 min. after the holding potential was returned to more negative potentials, possibly indicating some rundown or a slow recovery rate.

Recombinant $\alpha_{1B-1}\alpha_{2b}\beta_{1-2}$ channels were also blocked irreversibly by $\omega$-CgTx concentrations ranging from 0.5 to 10 µM during the time scale of the experiments. Application of 5 µM toxin (n=7) blocked the activity completely within 2 min., and no recovery of $I_{Ba}$ was observed after washing $\omega$-CgTx from the bath for up to 15 min. $d^{2+}$ blockage (50 µM) was rapid, complete, and reversible; the DHPs Bay K 8644 (1 µM; n=4) or nifedipine (5 µM; n=3) had no discernable effect.

Cells cotransfected with DNA encoding $\alpha_{1B-1}$, $\alpha_{2b}$, and $\beta_{1-2}$ subunits predominantly displayed a single class of saturable, high-affinity $\omega$-CgTx binding sites. The determined dissociation constant ($K_d$) value was 54.6±14.5 pM (n=4). Cells transfected with the vector containing only $\beta$-galactosidase-encoding DNA or $\alpha_{2b}\beta$-encoding DNA showed no specific binding. The binding capacity ($B_{max}$) of the $\alpha_{1B-1}\alpha_{2b}\beta$-transfected cells was 28,710±11,950 sites per cell (n=4).

These results demonstrate that $\alpha_{1B-1}\alpha_{2b}\beta_{1-2}$-transfected cells express high-voltage-activated, inactivating $Ca^{2+}$ channel activity that is irreversibly blocked by $\omega$-CgTx, insensitive to DHPs, and sensitive to holding potential. The activation and inactivation kinetics and voltage sensitivity of the channel formed in these cells are generally consistent with previous characterizations of neuronal N-type $Ca^{2+}$ channels.

F. Expression of DNA encoding human neuronal calcium channel $\alpha_{1B-1}$, $\alpha_{1B-2}$, $\alpha_{2B}$, $\beta_{1-2}$ and $\beta_{1-3}$ subunits in HEX cells Significant $Ba^{2+}$ currents were not detected in untransfected HEK293 cells. Furthermore, untransfected HEK293 cells do not express detectable $\omega$-CgTx GVIA binding sites.

In order to approximate the expression of a homogeneous population of trimeric $\alpha_{1B}$, $\alpha_{2b}$ and $\beta_1$ protein complexes in transfected HEK293 cells, the $\alpha_{1B}$, $\alpha_{2b}$ and $\beta_1$ expression levels were altered. The efficiency of expression and assembly of channel complexes at the cell surface were optimized by adjusting the molar ratio of $\alpha_{1B}$, $\alpha_{2b}$ and $\beta_1$ expression plasmids used in the transfections. The transfectants were analyzed for mRNA levels, $\omega$-CgTx GVIA binding and $Ca^{2+}$ channel current density in order to determine near optimal channel expression in the absence of immunological reagents for evaluating protein expression.

1. Transfections

HEK293 cells were maintained in DMEM (Gibco #320-1965AJ), 5.5% Defined/Supplemented bovine calf serum (Hyclone #A-2151-L), 100 U/ml penicillin G and 100 μg/ml streptomycin. $Ca^{2+}$-phosphate based transient transfections were performed and analyzed as described above. Cells were co-transfected with either 8 μg pcDNA1$\alpha_{1B-1}$ (described in Example II.C), 5 μg pHBCaCH$\alpha_2$A (see, Example IV.B.), 2 μg pHBCaCH$\beta_{1b}$RBS(A) ($\beta_{1-2}$ expression plasmid; see Examples III.A. and IX.E.), and 2 μg pCMVβ-gal [Clontech, Palo Alto, Calif.] (2:1.8:1 molar ratio of $Ca^{2+}$ channel subunit expression plasmids) or with 3 μg pcDNA1$\alpha_{1B-1}$ or pcDNA1$\alpha_{1B-2}$, 11.25 μg pHBCaCH$\alpha_2$A, 0.75 or 1.0 μg pHBCaCH$\beta_{1b}$RBS(A) or pcDNA1$\beta_{1-3}$ and 2 μg pCMVβ-gal (2:10.9:1 molar ratio of $Ca^{2+}$ channel subunit expression plasmids). Plasmid pCMVβ-gal, a β-galactosidase expression plasmid, was included in the transfections as a marker to permit transfection efficiency estimates by histochemical staining. When less than three subunits were expressed, pCMVPL2, a pCMV promoter-containing vector that lacks a cDNA insert, was substituted to maintain equal moles of pCMV-based DNA in the transfection. pUC18 DNA was used to maintain the total mass of DNA in the transfection at 20 μg/plate.

RNA from the transfected cells was analyzed by Northern blot analysis for calcium channel subunit mRNA expression using random primed $^{32}$P-labeled subunit specific probes. HEK293 cells co-transfected with $\alpha_{1B-1}$, $\alpha_{2b}$ and $\beta_{1-2}$ expression plasmids (8, 5 and 2 μg, respectively; molar ratio=2:1.8:1) did not express equivalent levels of each $Ca^{2+}$ channel subunit mRNA. Relatively high levels of $\alpha_{1B-1}$ and $\beta_{1-2}$ mRNAs were expressed, but significantly lower levels of $\alpha_{2b}$ mRNA were expressed. Based on autoradiograph exposures required to produce equivalent signals for all three mRNAs, $\alpha_{2b}$ transcript levels were estimated to be 5 to 10 times lower than $\alpha_{1B-1}$ and $\beta_{1-2}$ transcript levels. Untransfected HEK293 cells did not express detectable levels of $\alpha_{1B-1}$, $\alpha_{2b}$, or $\beta_{1-2}$ mRNAs.

To achieve equivalent $Ca^{2+}$ channel subunit mRNA expression levels, a series of transfections was performed with various amounts of $\alpha_{1B-1}$, $\alpha_{2b}$ and $\beta_{1-2}$ expression plasmids. Because the $\alpha_{1B-1}$ and $\beta_{2b}$ mRNAs were expressed at very high levels compared to $\alpha_{2b}$ mRNA, the mass of $\alpha_{1B-1}$ and $\beta_{1-2}$ plasmids was lowered and the mass of $\alpha_{2b}$ plasmid was increased in the transfection experiments. Co-transfection with 3, 11.25 and 0.75 μg of $\alpha_{1B-1}$, $\alpha_{2b}$ and $\beta_{1-2}$ expression plasmids, respectively (molar ratio= 2:10.9:1), approached equivalent expression levels of each $Ca^{2+}$ channel subunit mRNA. The relative molar quantity of $\alpha_{2b}$ expression plasmid to $\alpha_{1B-1}$ and $\beta_{1-2}$ expression plasmids was increased 6-fold. The mass of $\alpha_{1B-1}$ and $\beta_{1-2}$ plasmids in the transfection was decreased 2.67-fold and the mass of $\alpha_{2b}$ plasmid was increased 2.25-fold. The 6-fold molar increase of $\alpha_{2b}$ relative to $\alpha_{1B-1}$ and $\beta_{1-2}$ required to achieve near equal abundance mRNA levels is consistent with the previous 5- to 10-fold lower estimate of relative $\alpha_{2b}$ mRNA abundance. $\omega$-CgTx GVIA binding to cells transfected with various amounts of expression plasmids indicated that the 3, 11.25 and 0.75 μg of $\alpha_{1B-1}$, $\alpha_{2b}$ and $\beta_{1-2}$ plasmids, respectively, improved the level of cell surface expression of channel complexes. Further increases in the mass of $\alpha_{2b}$ and $\beta_{1-2}$ expression plasmids while $\alpha_{1B-1}$ was held constant, and alterations in the mass of the $\alpha_{1B-1}$ expression plasmid while $\alpha_{2b}$ and $\beta_{1-2}$ were held constant, indicated that the cell surface expression of $\omega$-CgTx GVIA binding sites per cell was nearly optimal. All subsequent transfections were performed with 3, 11.25 and 0.75 μg or 1.0 μg of $\alpha_{1B-1}$ or $\alpha_{1B-2}$, $\alpha_{2b}$ and $\beta_{1-2}$ or $\beta_{1-3}$ expression plasmids, respectively.

2. $^{125}$I-$\omega$-CgTx GVIA binding to transfected cells

Statistical analysis of the $K_d$ and $B_{max}$ values was performed using one-way analysis of variance (ANOVA) followed by the Tukey-Kramer test for multiple pairwise comparisons (p$\geq$0.05).

Combinations of human voltage-dependent $Ca^{2+}$ channel subunits, $\alpha_{1B-1}$, $\alpha_{1B-2}$, $\alpha_{2b}$, and $\beta_{1-2}$ and $\beta_{1-3}$, were analyzed for saturation binding of $^{125}$I-$\omega$-CgTx GVIA. About 200,000 cells were used per assay, except for the $\alpha_{1B-1}$, $\alpha_{1B-2}$, $\alpha_{1B-1}\alpha_{2b}$ and $\alpha_{1B-2}\alpha_{2b}$ combination which wee assayed with $1\times10^6$ cells per tube The transfected cells displayed a single-class of saturable, high-affinity binding sites. The values for the dissociation constants ($K_d$) and binding capacities ($B_{max}$) were determined for the different combinations. The results are summarized as follows:

| Subunit Combination | $K_d$ (pM) | $B_{max}$ (sites/cell) |
|---|---|---|
| $\alpha_{1B-1}\alpha_{2b}\beta_{1-2}$ | 54.9 ± 11.1 (n = 4) | 45,324 ± 15,606 |
| $\alpha_{1B-1}\alpha_{2b}\beta_{1-3}$ | 53.2 ± 3.6 (n = 3) | 91,004 ± 37,654 |
| $\alpha_{1B-1}\beta_{1-2}$ | 17.9 ± 1.9 (n = 3) | 5,756 ± 2,163 |
| $\alpha_{1B-1}\beta_{1-3}$ | 17.9 ± 1.6 (n = 3) | 8,729 ± 2,980 |
| $\alpha_{1B-1}\alpha_{2b}$ | 84.6 ± 15.3 (n = 3) | 2,256 ± 356 |
| $\alpha_{1B-1}$ | 31.7 ± 4.2 (n = 3) | 757 ± 128 |
| $\alpha_{1B-2}\alpha_{2b}\beta_{1-2}$ | 53.0 ± 4.8 (n = 3) | 19,371 ± 3,798 |
| $\alpha_{1B-2}\alpha_{2b}\beta_{1-3}$ | 44.3 ± 8.1 (n = 3) | 37,652 ± 8,129 |
| $\alpha_{1B-2}\beta_{1-2}$ | 16.4 ± 1.2 (n = 3) | 2,126 ± 412 |
| $\alpha_{1B-2}\beta_{1-3}$ | 22.2 ± 5.8 (n = 3) | 2,944 ± 1,168 |
| $\alpha_{1B-2}\alpha_{2b}$ | N.D.* (n = 3) | N.D. |
| $\alpha_{1B-2}$ | N.D. | N.D. |

N.D. = not detectable

Cells transfected with subunit combinations lacking either the $\alpha_{1B-1}$ or the $\alpha_{1B-2}$ subunit did not exhibit any detectable $^{125}$I-$\omega$-CgTx GVIA binding ($\leq$600 sites/cell). $^{125}$I-$\omega$-CgTx GVIA binding to HEK293 cells transfected with $\alpha_{1B-2}$ alone or $\alpha_{1B-2}\alpha_{2b}$ was too low for reliable Scatchard analysis of the data. Comparison of the $K_d$ and $B_{max}$ values revealed several relationships between specific combinations of subunits and the binding affinities and capacities of the transfected cells. In cells transfected with all three subunits, ($\alpha_{1B-1}\alpha_{2b}\beta_{1-2}$-, $\alpha_{1B-1}\alpha_{2b}\beta_{1-3}$-, $\alpha_{1B-2}\alpha_{2b}\beta_{1-2}$-, or $\alpha_{1B-2}\alpha_{2b}\beta_{1-3}$-transfectants) the $K_d$ values were indistinguishable (p>0.05), ranging from 44.3±8.1 pM to 54.9±11.1 pM. In cells transfected with two-subunit combinations lacking the $\alpha_{2b}$ subunit ($\alpha_{1B\text{-}1}\beta_{1\text{-}2}$, $\alpha_{1B\text{-}1}\beta_{1\text{-}3}$, $\alpha_{1B\text{-}2}\beta_{1\text{-}2}$ or $\alpha_{1B\text{-}2}\beta_{1\text{-}2}$) the $K_d$ values were significantly lower than the three-subunit combination (p<0.01), ranging from 16.4±1.2 to 22.2±5.8 pM. Cells transfected with only the $\alpha_{1B\text{-}1}$ subunit had a $K_d$ value of 31.7±4.2 pM, a value that was not different from the two-subunit combinations lacking $\alpha_{2b}$ (p<0.05). As with the comparison between the four $\alpha_{1B}\alpha_{2b}\beta_1$ versus $\alpha_{1B}\beta_1$ combinations, when the $\alpha_{1B\text{-}1}$ was co-expressed with $\alpha_{2b}$, the $K_d$ increased significantly (p<0.05) from 31.7±4.2 to 84.6±5.3 pM. These data demonstrate that co-expression of the $\beta_{2b}$ subunit combinations results in lower binding affinity of the cell surface receptors for $^{125}$I-ω-CgTx GVIA. The $B_{max}$ values of cells transfected with various subunit combinations also differed considerably. Cells transfected with the $\alpha_{1B\text{-}1}$ subunit alone expressed a low but detectable number of binding sites (approximately 750 binding sites/cell). When the $\alpha_{1B\text{-}1}$ subunit was co-expressed with the $\alpha_{2b}$ subunit, the binding capacity increased approximately three-fold while co-expression of a $\beta_{1\text{-}2}$ or $\beta_{1\text{-}3}$ subunit with $\alpha_{1B\text{-}1}$ resulted in 8-to 10-fold higher expression of surface binding. Cells transfected with all three subunits expressed the highest number of cell surface receptors. The binding capacities of cells transfected with $\alpha_{1B\text{-}1}\alpha_{2b}\beta_{1\text{-}3}$ or $\alpha_{1B\text{-}2}\alpha_{2b}\beta_{1\text{-}3}$ combinations were approximately two-fold higher than the corresponding combinations containing the $\beta_{1\text{-}2}$ subunit. Likewise, cells transfected with $\alpha_{1B\text{-}1}\alpha_{2b}\beta_{1\text{-}2}$ or $\alpha_{1B\text{-}1}\alpha_{2b}\beta_{1\text{-}3}$ combinations expressed approximately 2.5-fold more binding sites per cell than the corresponding combinations containing $\alpha_{1B\text{-}2}$. In all cases, co-expression of the $\alpha_{2b}$ subunit with $\alpha_{1B}$ and $\beta_1$ increased the surface receptor density compared to cells transfected with only the corresponding $\alpha_{1B}$ and $\beta_1$ combinations; approximately 8-fold for $\alpha_{1B\text{-}1}\alpha_{2b}\beta_{1\text{-}2}$, 10-fold for $\alpha_{1B\text{-}1}\alpha_{2b}\beta_{1\text{-}3}$, 9-fold for $\alpha_{1B\text{-}2}\alpha_{2b}\beta_{1\text{-}2}$, and 13-fold for $\alpha_{1B\text{-}2}\alpha_{2b}\beta_{1\text{-}3}$. Thus, comparison of the $B_{max}$ values suggests that the toxin-binding subunit, $\alpha_{1B\text{-}1}$ or $\alpha_{1B\text{-}2}$, is more efficiently expressed and assembled on the cell surface when co-expressed with either the $\alpha_{2b}$ or the $\beta_{1\text{-}2}$ or $\beta_{1\text{-}3}$ subunit, and most efficiently expressed when $\alpha_{2b}$ and $\beta_1$ subunits are present.

3. Electrophysiology

Functional expression of $\alpha_{1B\text{-}1}\alpha_{2b}\beta_{1\text{-}2}$ and $\alpha_{1B\text{-}1}\beta_{1\text{-}2}$ subunit combinations was evaluated using the whole-cell recording technique. Transfected cells that had no contacts with surrounding cells and simple morphology were used approximately 48 hours after transfection for recording. The pipette solution was (in mM) 135 CsCl, 10 EGTA, 1 MgCl$_2$, 10 HEPES, and 4 mM Mg-ATP (pH 7.3, adjusted with TEA-OH). The external solution was (in mM) 15 BaCl$_2$, 125 Choline Cl, 1 MgCl$_2$, and 10 HEPES (pH 7.3, adjusted with TEA-OH). ω-CgTx GVIA (Bachem) was prepared in the external solution with 0.1% cytochrome C (Sigma) to serve as a carrier. Control experiments showed that cytochrome C had no effect on the Ba$^{2+}$ current.

The macroscopic electrophysiological properties of Ba$^{2+}$ currents in cells transfected with various amounts of the $\alpha_{2b}$ expression plasmid with the relative amounts of $\alpha_{1B\text{-}1}$ and $\beta_{1\text{-}2}$ plasmids held constant were examined. The amplitudes and densities of the Ba$^{2+}$ currents (15 mM BaCl$_2$) recorded from whole cells of these transfectants differed dramatically. The average currents from 7 to 11 cells of three types of transfections (no $\alpha_{2b}$; 2:1:8:1 [$\alpha_{1B\text{-}1}$:$\alpha_{2b}$:$\beta_{1\text{-}2}$] molar ratio; and 2:10.9:1 [$\alpha_{1B\text{-}1}$:$\alpha_{2b}$:$\beta_{1\text{-}2}$] molar ratio) were determined. The smallest currents (range: 10 to 205 pA) were recorded when $\alpha_{2b}$ was not included in the transfection, and the largest currents (range: 50 to 8300 pA) were recorded with the 2:10.9:1 ratio of $\alpha_{1B\text{-}1}\alpha_{2b}\beta_{1\text{-}2}$ plasmids, the ratio that resulted in near equivalent mRNA levels for each subunit transcript. When the amount of $\alpha_{2b}$ plasmid was adjusted to yield approximately an equal abundance of subunit mRNAs, the average peak Ba$^{2+}$ current increased from 433 pA to 1,824 pA (4.2-fold) with a corresponding increase in average current density from 26 pA/pF to 127 pA/pF (4.9-fold). This increase is in the presence of a 2.7-fold decrease in the mass of $\alpha_{1B\text{-}1}$ and $\beta_{1\text{-}2}$ expression plasmids in the transfections. In all transfections, the magnitudes of the Ba$^{2+}$ currents did not follow a normal distribution.

To compare the subunit combinations and determine the effects of $\alpha_{2b}$, the current-voltage properties of cells transfected with $\alpha_{1B\text{-}1}\beta_{1\text{-}2}$ or with $\alpha_{1B\text{-}1}\alpha_{2b}\beta_{1\text{-}2}$ in either the 2:1.8:1 ($\alpha_{1B\text{-}1}$:$\alpha_{2b}$:$\beta_{1\text{-}2}$) molar ratio or the 2:10.9:1 ($\alpha_{1B\text{-}1}$:$\alpha_{2b}$:$\beta_{1\text{-}2}$) molar ratio transfectants were examined. The extreme examples of no $\alpha_{2b}$ and 11.25 μg $\alpha_{2b}$ (2:10.9:1 molar ratio) showed no significant differences in the current voltage plot at test potentials between 0 mV and +40 mV (p<0.05). The slight differences observed at either side of the peak region of the current voltage plot were likely due to normalization. The very small currents observed in the $\alpha_{1B\text{-}1}\beta_{1\text{-}2}$ transfected cells have a substantially higher component of residual leak relative to the barium current that is activated by the test pulse. When the current voltage plots are normalized, this leak is a much greater component than in the $\alpha_{1B\text{-}1}\alpha_{2b}\beta_{1\text{-}2}$ transfected cells and as a result, the current-voltage plot appears broader. This is the most likely explanation of the apparent differences in the current voltage plots, especially given the fact that the current-voltage plot for the $\alpha_{1B\text{-}1}\beta_{1\text{-}2}$ transfected cells diverge on both sides of the peak. Typically, when the voltage-dependence activation is shifted, the entire current-voltage plot is shifted, which was not observed. To qualitatively compare the kinetics of each, the average responses of test pulses from −90 mV to 10 mV were normalized and plotted. No significant differences in activation or inactivation kinetics of whole-cell Ba$^{2+}$ currents were observed with any combination.

G. Expression of DNA encoding human neuronal calcium channel $\alpha_{1E\text{-}3}\alpha_{2B}\beta_{1\text{-}3}$ and $\alpha_{1E\text{-}1}\alpha_{2B}\beta_{1\text{-}3}$ subunits in HEK cells Functional expression of the $\alpha_{1E\text{-}1}\alpha_{2B}\beta_{1\text{-}3}$ and $\alpha_{1E\text{-}3}\alpha_{2B}\beta_{1\text{-}3}$, as well as $\alpha_{1E\text{-}3}$ was evaluated using the whole cell recording technique.

1. Methods

Recordings were performed on transiently transfected HEK 293 cells two days following the transfection, from cells that had no contacts with surrounding cells and which had simple morphology.

The internal solution used to fill pipettes for recording the barium current from the transfected recombinant calcium channels was (in mM) 135 CsCl, 10 EGTA, 1 MgCl$_2$, 10 HEPES, and 4 mM Mg-ATP (pH 7.4–7.5, adjusted with TEA-OH). The external solution for recording the barium current was (in mM) 15 BaCl$_2$, 150 Choline Cl, 1 MgCl$_2$, and 10 HEPES and 5 TEA-OH (pH 7.3, adjusted with TEA-OH). In experiments in which Ca$^{2+}$ was replaced for Ba$^{2+}$, a Laminar flow chamber was used in order to completely exchange the extracellular solution and prevent any mixing of Ba$^{2+}$ and Ca$^{2+}$. ω-CgTx GVIA was prepared in the external solution with 0.1% cytochrome C to serve as a carrier, the toxin was applied by pressurized puffer pipette. Series resistance was compensated 70–85% and currents were analyzed only if the voltage error from series resistance was less than 5 mV. Leak resistance and capacitance was corrected by subtracting the scaled current observed with the P/-4 protocol as implemented by pClamp (Axon Instruments).

2. Electrophysiology Results

Cells transfected with $\alpha_{1E-1}\alpha_{2b}\beta_{1-3}$ or $\alpha_{1E-3}\alpha_{2b}\beta_{1-3}$ showed strong barium currents with whole cell patch clamp recordings. Cells expressing $\alpha_{1E-3}\alpha_{2b}\beta_{1-3}$ had larger peak currents than those expressing $\alpha_{1B-1}\alpha_{2b}\beta_{1-3}$. In addition, the kinetics of activation and inactivation are clearly substantially faster in the cells expressing $\alpha_{1E}$ calcium channels. HEK 293 cells expressing $\alpha_{1E-3}$ alone have a significant degree of functional calcium channels, with properties similar to those expressing $\alpha_{1E}\alpha_{2b}\beta_{1-3}$ but with substantially smaller peak barium currents. Thus, with $\alpha_{1E}$, the $\alpha_2$ and $\beta_1$ subunits are not required for functional expression of $\alpha_{1E}$ mediated calcium channels, but do substantially increase the number of functional calcium channels.

Examination of the current voltage properties of $\alpha_{1E}\alpha_{2b}\beta_{1-3}$ expressing cells indicates that $\alpha_{1E-3}\alpha_{2b}\beta_{1-3}$ is a high-voltage activated calcium channel and the peak current is reached at a potential only slightly less positive than other neuronal calcium channels also expressing $\alpha_{1E-1}$ and $\beta_1$, and $\alpha_{1B}$ and $\alpha_{1D}$. Current voltage properties of $\alpha_{1E-1}\alpha_{2b}\beta_{1-3}$ and $\alpha_{1E-3}\alpha_{2b}\beta_{1-3}$ are statistically different from those of $\alpha_{1B-1}\alpha_{2b}\beta_{1-3}$. Current voltage curves for $\alpha_{1E-1}\alpha_{2b}\beta_{1-3}$ and $\alpha_{1E-3}\alpha_{2b}\beta_{1-3}$ peak at approximately +5 mV, as does the current voltage curve for $\alpha_{1E-3}$ alone.

The kinetics and voltage dependence of inactivation using both prepulse (200 ms) and steady-state inactivation was examined. $\alpha_{1E}$ mediated calcium channels are rapidly inactivated relative to previously cloned calcium channels and other high voltage-activated calcium channels. $\alpha_{1E-3}\alpha_{2b}\beta_{1-3}$ mediated calcium channels are inactivated rapidly and are thus sensitive to relatively brief (200 ms) prepulses as well as long prepulses (>20s steady state inactivation), but recover rapidly from steady state inactivation. The kinetics of the rapid inactivation has two components, one with a time constant of approximately 25 ms and the other approximately 400 ms.

To determine whether $\alpha_{1E}$ mediated calcium channels have properties of low voltage activated calcium channels, the details of tail currents activated by a test pulse ranging –60 to +90 mV were measured at –60 mV. Tail currents recorded at –60 mV could be well fit by a single exponential of 150 to 300 μs; at least an order of magnitude faster than those typically observed with low voltage-activated calcium channels.

HEK 293 cells expressing $\alpha_{1E-3}\alpha_{2b}\beta_{1-3}$ flux more current with $Ba^{2+}$ as the charge carrier and currents carried by $Ba^{2+}$ and $Ca^{2+}$ have different current-voltage properties. Furthermore, the time course of inactivation is slower and the amount of prepulse inactivation less with $Ca^{2+}$ as the charge carrier.

While the invention has been described with some specificity, modifications apparent to those with ordinary skill in the art may be made without departing from the scope of the invention. Since such modifications will be apparent to those of skill in the art, it is intended that this invention be limited only by the scope of the appended claims.

---

What is claimed is:

1. An isolated DNA molecule, comprising a sequence of nucleotides that encodes an $\alpha_{1A}$-subunit of a human calcium channel, wherein:
the sequence of nucleotides encoding the $\alpha_{1A}$-subunit is selected from the group consisting of:
  (a) a sequence of nucleotides that encodes a naturally-occurring human $\alpha_{1A}$-subunit and comprises the sequence of nucleotides set forth in SEQ ID No. 22 or 23;
  (b) a sequence of nucleotides that encodes an $\alpha_{1A}$-subunit, wherein a DNA molecule having said sequence hybridizes under conditions of high stringency to DNA that is fully complementary to an mRNA transcript native to a human cell, wherein the transcript (i) encodes an $\alpha_{1A}$-subunit, (ii) comprises the sequence of nucleotides set forth in SEQ ID NO: 22 or 23, wherein T residues are replaced by U, and (iii) hybridizes under conditions of high stringency to any probe containing at least 14 contiguous bases from the coding portion of said sequence of nucleotides that encodes an $\alpha_{1A}$-subunit;
(c) a sequence of nucleotides that encodes an $\alpha_1$-subunit that comprises the sequence of amino acids set forth in SEQ ID No. 35 or 36; and
(d) a sequence of nucleotides degenerate with the $\alpha_{1A}$-subunit-encoding sequence of (b).

2. The DNA molecule of claim 1, wherein the subunit is an $\alpha_{1A-1}$-subunit of a human calcium channel.

3. The DNA molecule of claim 2, comprising the coding sequence set forth in SEQ ID NO: 22.

4. The DNA molecule claim 1, wherein the subunit is an $\alpha_{1A-2}$-subunit of a human calcium channel.

5. The DNA molecule of claim 4, comprising the coding sequence set forth in SEQ ID NO: 23.

6. A mammalian cell comprising heterologous DNA having the nucleotide sequence of the DNA molecule of claim 1 that encodes an $\alpha_{1A}$-subunit of a human calcium channel.

7. The cell of claim 6, further comprising heterologous DNA that encodes a β-subunit of a human calcium channel wherein the β-subunit is selected from the group consisting of:
a β-subunit comprising the sequence of amino acids set forth in SEQ ID No. 32, 33, 37, 38, 39 or 40;
a calcium channel β-subunit comprising a sequence of amino acids encoded by a β-subunit-encoding DNA molecule capable of hybridizing under conditions of high stringency with DNA which is fully complementary to an mRNA transcript native to a human cell and which comprises the sequence of nucleotides set forth in SEQ ID No. 9, 10, 26, 27, 29, 30 or 31, such that any probe that contains at least 14 contiguous bases from the coding portion of the β-subunit-encoding DNA is capable of hybridizing under conditions of high stringency to the mRNA transcript.

8. The eukaryotic cell of claim 6, further comprising heterologous DNA that encodes a β-subunit of a human calcium channel, wherein the β subunit is a $\beta_4$-subunit, comprising the sequence of amino acids set forth in SEQ ID No. 28.

9. The eukaryotic cell of claim 6 selected from the group consisting of a HEK 293 cell, a Chinese hamster ovary cell, an African green monkey cell, and a mouse L cell.

10. The cell of claim 6, wherein the $\alpha_{1A}$ subunit is an $\alpha_{1A-1}$ subunit.

11. The cell of claim 6, wherein the $\alpha_{1A}$ subunit is an $\alpha_{A-2}$ subunit.

12. The cell of claim 7, wherein the β subunit is a $\beta_1$-subunit.

13. The cell of claim 7, wherein the β subunit is a $\beta_2$-subunit.

14. A eukaryotic cell with a functional, heterologous calcium channel, produced by a process comprising:
introducing RNA into a cell that is translatable in said cell to afford an $\alpha_1$-subunit of a human calcium channel, wherein:
the $\alpha_1$-subunit has an amino acid sequence encoded by the DNA molecule of claim 1;
the only heterologous ion channels are calcium channels; and
the cell is an amphibian oocyte.

15. The cell of claim 14, wherein the $\alpha_{1A}$ subunit is an $\alpha_{1A-1}$ subunit.

16. The cell of claim 14, wherein the $\alpha_{1A}$ subunit is an $\alpha_{1A-2}$ subunit.

17. The eukaryotic cell of claim 14, produced by a process further comprising:

introducing RNA that is translatable in said cell into β-subunit of a human calcium channel that is a β-subunit selected from the group consisting of:
a β-subunit comprising the sequence of amino acids set forth in SEQ ID NOs: 32, 33, 37, 38, 39, or 40;
a β-subunit encoded by DNA comprising the sequence of nucleotides set forth in SEQ ID NO: 19; and
a calcium channel β-subunit comprising a sequence of amino acids encoded by a DNA molecule capable of hybridizing under conditions of high stringency with DNA which is fully complementary to an mRNA transcript native to a human cell and which comprises the sequence of nucleotides set forth in SEQ ID NO: 9, 10, 26, 29, 30, or 31, such that any probe that contains at least 14 contiguous bases from the coding portion of the β-subunit-encoding DNA is capable of hybridizing under conditions of high stringency to the mRNA transcript.

18. The eukaryotic cell of claim 17, wherein the β subunit is a $\beta_1$-subunit.

19. The eukaryotic cell of claim 17, wherein the β subunit is a $\beta_2$-subunit.

20. An isolated DNA molecule, comprising a sequence of nucleotides that encodes a $\beta_1$-subunit of a human calcium channel, wherein:
the sequence of nucleotides encoding the $\beta_1$-subunit is selected from the group consisting of:
(a) a sequence of nucleotides that encodes a naturally-occurring human $\beta_1$-subunit and that comprises the sequence of nucleotides set forth in SEQ ID No. 9, 10, 29, 30 or 31;
(b) a sequence of nucleotides that encodes a $\beta_1$-subunit, wherein a DNA molecule having said sequence hybridizes under conditions of high stringency to DNA that is fully complementary to an mRNA transcript native to a human cell, wherein the transcript (i) encodes a β-subunit and (ii) hybridizes under conditions of high stringency to any probe containing at least 14 contiguous bases from the coding portion of said sequence of nucleotides that encodes a β-subunit;
(c) a sequence of nucleotides that encodes a $\beta_1$-subunit that comprises the sequence of amino acids set forth in SEQ ID Nos. 32, 33, 38, 39 or 40; and
(d) a sequence of nucleotides degenerate with the $\beta_1$-subunit encoding sequence of (b).

21. A method for identifying a compound that modulates the activity of a calcium channel, comprising;
suspending a eukaryotic cell that has a functional, heterologous calcium channel, in a solution containing a test compound and a calcium channel selective ion:
depolarizing the cell membrane of said cell; and
detecting the current flowing into said cell, whereby test compounds that modulate the activity of a calcium channel are identified, wherein:
the heterologous calcium channel comprises at least one human calcium channel subunit encoded by DNA or RNA that is heterologous to said cell;
the current that is detected is different from that produced by depolarizing the same or a substantially identical cell in the presence of the same calcium channel selective ion but in the absence of said compound or the heterologous channels;
the heterologous calcium channels are the only heterologous ion channels expressed by the cells;
the human calcium channel subunit encoded by the heterologous DNA is an $\alpha_{1A}$-subunit of a human calcium channel and is selected from the group consisting of:
  (a) a sequence of nucleotides that encodes a naturally-occurring human $\alpha_{1A}$-subunit and comprises the sequence of nucleotides set forth in SEQ ID No. 22 or 23;
  (b) a sequence of nucleotides that encodes an $\alpha_{1A}$-subunit, wherein a DNA molecule having said sequence hybridizes under conditions of high stringency to DNA that is fully complementary to an mRNA transcript native to a human cell, wherein the transcript (i) encodes an $\alpha_{1A}$-subunit, (ii) comprises the sequence of nucleotides set forth in SEQ ID NO: 22 or 23, wherein T residues are replaced by U, and (iii) hybridizes under conditions of high stringency to any probe containing at least 14 contiguous bases from the coding portion of said sequence of nucleotides that encodes an $\alpha_{1A}$-subunit;
  (c) a sequence of nucleotides that encodes an $\alpha_1$-subunit that comprises a sequence of amino acids encoded by SEQ ID No. 35 or 36; and
  (d) a sequence of nucleotides degenerate with the $\alpha_{1A}$-subunit-encoding sequence of (b).

22. The method of claim 21, wherein the heterologous calcium channel also comprises a β-subunit selected from the group consisting of:
  a β-subunit comprising the sequence of amino acids set forth in SEQ ID NOs: 32, 33, 37, 38, 39, or 40;
  a β-subunit encoded by DNA comprising the sequence of nucleotides set forth in SEQ ID NO: 19; and
  a calcium channel β-subunit comprising a sequence of amino acids encoded by a DNA molecule capable of hybridizing under conditions of high stringency with DNA which is fully complementary to an mRNA transcript native to a human cell and which comprises the sequence of nucleotides set forth in SEQ ID NO: 9, 10, 26, 29, 30, or 31, such that any probe that contains at least 14 contiguous bases from the coding portion of the β-subunit-encoding DNA is capable of hybridizing under conditions of high stringency to the mRNA transcript.

23. The method of claim 22, wherein the β-subunit is a $\beta_1$-subunit.

24. The method of claim 22, wherein the β-subunit is a $\beta_2$-subunit.

25. The method of claim 22, wherein the β-subunit is a $\beta_4$-subunit.

26. A plasmid having all of the identifying characteristics of the plasmid harbored in the *Escherichia coli* (*E. coli*) host cells having ATCC Accession No. 75293.

27. An isolated DNA molecule, comprising the sequence of nucleotides set forth in SEQ ID NO: 22 or 23.

28. An isolated oligonucleotide, comprising the sequence of nucleotides set forth in SEQ ID NO: 21.

29. An isolated DNA molecule that encodes an naturally-occurring $\beta_1$-subunit of a human calcium channel.

30. An isolated nucleic acid molecule that encodes a full-length $\beta_1$-subunit of a human calcium channel, wherein the nucleic acid molecule is fully complementary to nucleic acid that is native to a human cell.

31. An isolated DNA molecule, comprising the sequence of nucleotides set forth in SEQ ID NO: 9, 10, 26, 27, 29, 30 or 31.

32. An isolated DNA probe, comprising the sequence of nucleotides set forth as nucleotides 191–271 in SEQ ID NO: 12.

33. An isolated DNA probe, comprising the sequence of nucleotides set forth as nucleotides 35–271 in SEQ ID NO: 12.

34. An isolated DNA molecule, comprising the sequence of nucleotides set forth as nucleotides 182–2264 of SEQ ID NO: 26.

35. A DNA molecule according to claim 34, comprising the sequence of nucleotides set forth in SEQ ID NO: 26.

36. An isolated DNA molecule, comprising a sequence of nucleotides encoding the sequence of amino acids set forth in SEQ ID NO: 28.

37. A DNA molecule according to claim 36, comprising the sequence of nucleotides set forth in SEQ ID NO: 27.

* * * * *